US 11,267,801 B2

(12) United States Patent
Brizgys et al.

(10) Patent No.: US 11,267,801 B2
(45) Date of Patent: *Mar. 8, 2022

(54) THERAPEUTIC COMPOUNDS

(71) Applicant: Gilead Sciences, Inc., Foster City, CA (US)

(72) Inventors: Gediminas Brizgys, San Carlos, CA (US); Eda Canales, San Mateo, CA (US); Chienhung Chou, Dublin, CA (US); Michael Graupe, Pacifica, CA (US); Jiayao Li, Foster City, CA (US); Roland D. Saito, San Mateo, CA (US); Scott D. Schroeder, Union City, CA (US); Winston C. Tse, Redwood, CA (US); Qiaoyin Wu, Foster City, CA (US); Jennifer R. Zhang, Union City, CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/062,676

(22) Filed: Oct. 5, 2020

(65) Prior Publication Data

US 2021/0171498 A1 Jun. 10, 2021

Related U.S. Application Data

(63) Continuation of application No. 16/275,605, filed on Feb. 14, 2019, now Pat. No. 10,836,746.

(60) Provisional application No. 62/630,955, filed on Feb. 15, 2018.

(51) Int. Cl.
 C07D 401/14 (2006.01)
 A61P 31/18 (2006.01)
 C07D 405/14 (2006.01)
 C07D 413/14 (2006.01)

(52) U.S. Cl.
 CPC ............ *C07D 401/14* (2013.01); *A61P 31/18* (2018.01); *C07D 405/14* (2013.01); *C07D 413/14* (2013.01)

(58) Field of Classification Search
 CPC .. C07D 401/14; C07D 405/14; C07D 413/14; A61P 31/18
 See application file for complete search history.

(56) References Cited

U.S. PATENT DOCUMENTS

| 3,845,770 | A | 11/1974 | Theeuwes et al. |
| 4,326,525 | A | 4/1982 | Swanson et al. |
| 4,816,570 | A | 3/1989 | Farquhar |
| 4,902,514 | A | 2/1990 | Barclay et al. |
| 4,968,788 | A | 11/1990 | Farquhar |
| 4,992,445 | A | 2/1991 | Lawter et al. |
| 5,001,139 | A | 3/1991 | Lawter et al. |
| 5,023,252 | A | 6/1991 | Hseih |
| 5,616,345 | A | 4/1997 | Geoghegan et al. |
| 5,663,159 | A | 9/1997 | Starrett, Jr. et al. |
| 5,792,756 | A | 8/1998 | Starrett, Jr. et al. |
| 5,922,695 | A | 7/1999 | Arimilli et al. |
| 5,935,946 | A | 8/1999 | Munger, Jr. et al. |
| 5,977,089 | A | 11/1999 | Arimilli et al. |
| 7,390,791 | B2 | 6/2008 | Becker et al. |
| 7,803,788 | B2 | 9/2010 | Becker et al. |
| 8,263,627 | B2 | 9/2012 | Barrow et al. |
| 8,748,412 | B2 | 6/2014 | Liao et al. |
| 8,754,065 | B2 | 6/2014 | Liu et al. |

(Continued)

FOREIGN PATENT DOCUMENTS

| CN | 101910133 A | 12/2010 |
| WO | WO 1991/19721 | 12/1991 |

(Continued)

OTHER PUBLICATIONS

Yant et al., (2014) "An Improved PF74 Analog Inhibits Multiple HIV Capsid Functions Independently of Host Cyclophilin A and CPSF6" Poster Presented at the Conference on Retroviruses and Opportunistic Infections (CROI), Boston Massachusetts, 1 page.*

(Continued)

*Primary Examiner* — Kamal A Saeed

(74) *Attorney, Agent, or Firm* — Fish & Richardson P.C.

(57) ABSTRACT

The invention provides compounds having Formula (I):

(I)

or a pharmaceutically acceptable salt thereof, as well as pharmaceutical compositions comprising the same, processes for their preparation, and methods of treating and preventing HIV infection by their administration.

23 Claims, No Drawings

(56) References Cited

U.S. PATENT DOCUMENTS

| | | |
|---|---|---|
| 8,835,488 B2 | 9/2014 | Yamashita et al. |
| 9,012,441 B2 | 4/2015 | Bondy et al. |
| 9,050,344 B2 | 6/2015 | Brizgys et al. |
| 9,220,710 B2 | 12/2015 | Bondy et al. |
| 9,540,343 B2 | 1/2017 | Bondy et al. |
| 9,670,205 B2 | 6/2017 | Aktoudianakis et al. |
| 9,789,089 B2 | 10/2017 | Bondy et al. |
| 9,873,680 B2 | 1/2018 | Brizgys et al. |
| 9,944,619 B2 | 4/2018 | Bondy et al. |
| 9,951,043 B2 | 4/2018 | Brizgys et al. |
| 10,071,985 B2 | 9/2018 | Graupe et al. |
| 10,370,342 B2 | 8/2019 | Chin et al. |
| 10,370,358 B2 | 8/2019 | Bondy et al. |
| 10,640,499 B2 | 5/2020 | Chin et al. |
| 10,654,827 B2 | 5/2020 | Graupe et al. |
| 10,696,657 B2 | 6/2020 | Vandehey |
| 10,836,746 B2 | 11/2020 | Brizgys et al. |
| 10,849,892 B2 | 12/2020 | Houston et al. |
| 11,117,886 B2 | 9/2021 | Vandehey et al. |
| 2005/0282805 A1 | 12/2005 | Hangeland et al. |
| 2007/0083045 A1 | 4/2007 | Di Francesco et al. |
| 2008/0234251 A1 | 9/2008 | Doherty et al. |
| 2008/0306050 A1 | 12/2008 | Doherty et al. |
| 2010/0029585 A1 | 2/2010 | Dietsch et al. |
| 2010/0129306 A1 | 5/2010 | Julien et al. |
| 2010/0143301 A1 | 6/2010 | Desai et al. |
| 2010/0249176 A1 | 9/2010 | Barrow et al. |
| 2011/0092485 A1 | 4/2011 | Burgess et al. |
| 2011/0118235 A1 | 5/2011 | Burgess et al. |
| 2012/0045761 A1 | 2/2012 | Jagannath et al. |
| 2012/0082658 A1 | 4/2012 | Hershberg |
| 2012/0219615 A1 | 8/2012 | Coukos et al. |
| 2013/0165489 A1 | 6/2013 | Cocklin et al. |
| 2013/0251673 A1 | 9/2013 | Flores et al. |
| 2014/0045849 A1 | 2/2014 | McGowan et al. |
| 2014/0066432 A1 | 3/2014 | Burgess et al. |
| 2014/0073642 A1 | 3/2014 | Embrechts et al. |
| 2014/0088085 A1 | 3/2014 | Burgess et al. |
| 2014/0142085 A1 | 5/2014 | Bondy et al. |
| 2014/0221346 A1 | 8/2014 | Halcomb et al. |
| 2014/0221347 A1 | 8/2014 | Brizgys et al. |
| 2014/0221356 A1 | 8/2014 | Jin et al. |
| 2014/0221378 A1 | 8/2014 | Miyazaki et al. |
| 2014/0221380 A1 | 8/2014 | Miyazaki et al. |
| 2014/0221417 A1 | 8/2014 | Halcomb et al. |
| 2014/0221421 A1 | 8/2014 | Bondy et al. |
| 2014/0275167 A1 | 9/2014 | Hartman |
| 2014/0296266 A1 | 10/2014 | Hu et al. |
| 2014/0303164 A1 | 10/2014 | Brizgys et al. |
| 2014/0350031 A1 | 11/2014 | McGowan et al. |
| 2016/0067224 A1 | 3/2016 | Bondy et al. |
| 2016/0083368 A1 | 3/2016 | Brizgys et al. |
| 2016/0108030 A1 | 4/2016 | Brizgys et al. |
| 2016/0250215 A1 | 9/2016 | Baszcynski et al. |
| 2016/0289229 A1 | 10/2016 | Aktoudianakis et al. |
| 2016/0368881 A1 | 12/2016 | Bondy et al. |
| 2017/0137405 A1 | 5/2017 | Bondy et al. |
| 2018/0051005 A1 | 2/2018 | Graupe et al. |
| 2018/0194746 A1 | 7/2018 | Bondy et al. |
| 2018/0273508 A1 | 9/2018 | Brizgys et al. |
| 2018/0370950 A1 | 12/2018 | Graupe et al. |
| 2019/0083478 A1 | 3/2019 | Houston et al. |
| 2019/0084963 A1 | 3/2019 | Shi |
| 2019/0300505 A1 | 10/2019 | Allan et al. |
| 2019/0345136 A1 | 11/2019 | Brizgys et al. |
| 2019/0375726 A1 | 12/2019 | Bondy et al. |
| 2020/0038389 A1 | 2/2020 | Bauer |
| 2020/0262815 A1 | 8/2020 | Graupe et al. |
| 2020/0369647 A1 | 11/2020 | Allan et al. |
| 2020/0397772 A1 | 12/2020 | Houston et al. |
| 2021/0009555 A1 | 1/2021 | Brizgys et al. |
| 2021/0188815 A1 | 6/2021 | Bekerman et al. |

FOREIGN PATENT DOCUMENTS

| | | |
|---|---|---|
| WO | WO 2003/002530 | 1/2003 |
| WO | WO 2003/002553 | 1/2003 |
| WO | WO 2004/050643 | 6/2004 |
| WO | WO 2004/071448 | 8/2004 |
| WO | WO 2004/096286 | 11/2004 |
| WO | WO 2005/087725 | 9/2005 |
| WO | WO 2005/123680 | 12/2005 |
| WO | WO 2006/015261 | 2/2006 |
| WO | WO 2006/110157 | 10/2006 |
| WO | WO 2007/070826 | 8/2007 |
| WO | WO 2008/013622 | 1/2008 |
| WO | WO 2009/005677 | 1/2009 |
| WO | WO 2009/010804 | 1/2009 |
| WO | WO 2009/062285 | 5/2009 |
| WO | WO 2009/114677 | 9/2009 |
| WO | WO 2010/130034 | 11/2010 |
| WO | WO 2011/059887 | 5/2011 |
| WO | WO 2011/143772 | 11/2011 |
| WO | WO 2012/003497 | 1/2012 |
| WO | WO 2012/003498 | 1/2012 |
| WO | WO 2012/065062 | 5/2012 |
| WO | WO 2012/145728 | 10/2012 |
| WO | WO 2013/006738 | 1/2013 |
| WO | WO 2013/006792 | 1/2013 |
| WO | WO 2013/091096 | 6/2013 |
| WO | WO 2013/159064 | 10/2013 |
| WO | WO 2014/016358 | 1/2014 |
| WO | WO 2014/023813 | 2/2014 |
| WO | WO 2014/028931 | 2/2014 |
| WO | WO 2014/056953 | 4/2014 |
| WO | WO 2014/076221 | 5/2014 |
| WO | WO 2014/100323 | 6/2014 |
| WO | WO 2014/110297 | 7/2014 |
| WO | WO 2014/110298 | 7/2014 |
| WO | WO 2014/110323 | 7/2014 |
| WO | WO 2014/128189 | 8/2014 |
| WO | WO 2014/134566 | 9/2014 |
| WO | WO 2015/008097 | 1/2015 |
| WO | WO 2015/061518 | 4/2015 |
| WO | WO 2015/130966 | 9/2015 |
| WO | WO 2016/033243 | 3/2016 |
| WO | WO 2016/040084 | 3/2016 |
| WO | WO 2016/172424 | 10/2016 |
| WO | WO 2016/172425 | 10/2016 |
| WO | WO 2017/007689 | 1/2017 |
| WO | WO 2018/035359 | 2/2018 |
| WO | WO 2018/145021 | 8/2018 |
| WO | WO 2018/203235 | 11/2018 |
| WO | WO 2019/035904 | 2/2019 |
| WO | WO 2019/035973 | 2/2019 |

OTHER PUBLICATIONS

[No Author Listed], "2-[9-(Difluoromethyl)-5,5-difluoro-7,8-diazatricylo[4.4.0.02,4]nona-l(6),8-dien-7-yl]acetic acid," PubChem CID 71186949, Mar. 21, 2013, 18 pages.

[No Author Listed], "3-Methyl-3-methylsulfonylbut-1-yne," PubChem CID 14241469, Feb. 9, 2002, 16 pages.

[No Author Listed], CAS registry No. 1620056-83-8, Aug. 6, 2014, 1 page.

Benzaria, S. et al. (Dec. 6, 1996). "Synthesis, In Vitro Antiviral Evaluation, and Stability Studies of Bis( S-Acyl-2-Thioethyl) Ester Derivatives of 9-[2-(Phosphonomethoxy)Ethyl]adenine (PMEA) as Potential PMEA Prodrugs with Improved Oral Bioavailability," J. Med. Chem. 39(25):4958-4965.

Berge et al., (1977) "Pharmaceutical Salts," J. Pharma. Sci., 66(1): 1-19.

Bhattacharya et al. (2014) Structural Basis of HIV-1 Capsid Recognition by PF74 and CPSF6, PNAS; 111 (52):18625-18630.

Blair et al., (2010) "HIV Capsid is a Tractable Target for Small Molecule Therapeutic Intervention," PLoS Pathog. 6(12): e1001220, 10 pages.

Briggs et al., (2003) "Structural Organization of Authentic, Mature HIV-1 Virions and Cores," The EMBO Journal; vol. 22 No, 7 pp. 1707-1715.

(56) References Cited

OTHER PUBLICATIONS

Brittain, "Polymorphism in pharmaceutical solids," Marcel Dekker, Inc., 1999, 235-238.
Brown, M.K. et al. (2005) "Highly Enantioselective Cu-Catalyzed Conjugate Additions of Dialkylzinc Reagents to Unsaturated Furanones and Pyranones: Preparation of Air-Stable and Catalytically Active Cu-Peptide," Angew. Chem. Int. Ed. Engl. 44(33):5306-5310.
Bundgaard, H. (1991). "Design and Application of Prodrugs," Chapter 5 in A Textbook of Drug Design and Development, Krogsgaard-Larsen, P. et al. eds., Harwood Academic Publishers, Chur, Switzerland, pp. 113-191.
Campbell et al., (2015) "HIV-1 Capsid: The Multifaceted Key Player in HIV-1 Infection," Nat Rev Microbial.; 13(8): 471-483.
Carnes et al., "Inhibitors of the HIV-1 Capsid, A Target of Opportunity," Curr. Opin. HIV AIDS, 2018, 13(4):359-365.
Chin et al. (2015) "Direct Visualization of HIV-1 Replication Intermediates Shows That Capsid and CPSF6 Modulate HIV-1 Intra-Nuclear Invasion and Integration", Cell Repotis 13:1717-1731.
Cos, P. et al. (1998) "Structure-Activity Relationship and Classification of Flavonoids as Inhibitors of Xanthine Oxidase and Superoxide Scavengers," J. Natl. Prod. 61:71-76.
Cossy, J. et al. (Oct. 23, 1995). "Ring Opening of Cyclopropylketones Induced by Photochemical Electron Transfer," Tetrahedron 51 (43):11751-11764.
Curreli et al., (2011) "Virtual Screening Based Identification of Novel Small-molecule Inhibitors Targeted to the HIV-1 Capsid," Bioorganic & Medicinal Chemistry 19:77-90.
De Lombaert, S. et al. (Feb. 18, 1994). "N-Phosphonomethyl Dipeptides and Their Phosphonate Prodrugs, A New Generation of Neutral Endopeptidase (NEP, EC 3.4.24.11) Inhibitors," J. Med. Chem. 37(4):498-511.
Fader et al., (2013) Optimization of a 1,5 dihydrobenzo[b][1,4]diazepine-2,4-dione Series of HIV Capsid Assembly Inhibitors 2: Structure-Activity Relationships (SAR) of the C3-Phenyl Moiety, Bioorganic & Medicinal Chemistry Letters, 23(11):3396-3400.
Farquhar, D. et al. (Mar. 1983). "Biologically Reversible Phosphate-Protective Groups," J. Pharm. Sci. 72(3):324-325.
Fields, G. B. (1994) "Methods for Removing the Fmoc Group," Methods in Molecular Biology, 35: 17-27.
Forshey et al., (2002) "Formation of a Human Immunodeficiency Virus Type 1 Core of Optimal Stability Is Crucial for Viral Replication," J. Virology, 76(11) p. 5667-5677.
Foster, A. B. (1984) "Deuterium Isotope Effects in Studies of Drug Metabolism," Trends Pharmacol. Sci., 5(12):524-527.
Ganser et al., (1999) "Assembly and Analysis of Conical Models for the HIV-1 Core," Science 283, 80-82.
Ganser-Pornillos et al., (2007) "Structure of Full-Length HIV-1 CA: A Model for the Mature Capsid Lattice," Cell.; 131(1):70-9, 29 pages.
Hagmann, W. K. (2008) "The many roles for fluorine in medicinal chemistry," J. Med. Chem., 51(15):4359-4369.
Hammer, S. et al. (Aug. 6, 2008). "Antiretroviral Treatment of Adult HIV Infection. 2008 Recommendations of the International AIDS Society: USA Panel," JAMA 300(5):555-570.
Hanack, M. et al., (1964) "cis—und trans bicyclo [3.1.0] hexano-(2)," Chemische Berichte, 97(6):1669-1672, XP055573746 (with English translation).
Hodgson, D.M. et al. (2004). "Intramolecular Cyclopropanation of Unsaturated Terminal Epoxides," J. Am. Chem. Soc. 126(28):8664-8665.
Hodgson, D.M. et al. (2007) "Intramolecular Cyclopropanation of Unsaturated Terminal Epoxides and Chlorohydrins," J. Am. Chem. Soc., 129(14):4456-4462.
Hung et al. (2013) "Large-Scale Functional Purification of Recombinant HIV-1 Capsid" PLOS One, vol. 8, Issue 3, e58035, 11 pages.
Ishiyama, T. et al., (1995) "Palladium(0)-Catalyzed Cross-Coupling Reaction of Alkoxydiboron with Haloarenes: A Direct Procedure for Aiylboronic Esters," J. Org. Chem., 60(23):7508-7510.

Jeong, .J.U. (2010) "Synthesis of Tetrasubstituted Pyrazones and Pyrazone N-Oxides," Tetrahedron Letters 51 (6):974-976.
Jin et al., (2010) "SAR and Molecular Mechanism Study of Novel Acylhydrazone Compounds Targeting HIV-1 CA," Bioorganic & Medicinal Chemistry, 18: 2135-2140.
Jouvenet et al., (2006) "Plasma Membrane Is the Site of Productive HIV-1 Particle Assembly," PLoS Biol. 4(12):e435, 15 pages.
Kashima, C. et al. (1991). "New Peptide Synthesis Using the Ozonolysate of 2-(1-Phthalimido)alkyl-5-Phenyloxazoles," J. Heterocyclic Chem. 28: 1241-1244.
Kelly, B. N., et al., (2007) "Structure of the Antiviral Assembly Inhibitor CAP-1 Complex with the HIV-1 CA Protein," Journal of Molecular Biology 373(2):355-66.
Khamnei, S. et al. (1996). "Neighboring Group Catalysis in the Design of Nucleotide Prodrugs," J. Med. Chem. 39(20):4109-4115.
Kim, S. et al., (2013) "Discovery of a New HIV-1 Inhibitor Scaffold and Synthesis of Potential Prodrugs of Indazoles," Bioorganic & Medicinal Chemistry Letters, 23(10): 2888-2892.
Kocienski, P.J. (May 1994). "Carbonyl Protecting Groups," Chapter 5 in Protecting Groups, Thieme Publishing Group: New York, NY, pp. 155-184.
Kocienski, P.J. (May 1994). "Carboxyl Protecting Groups," Chapter 4 in Protecting Groups, Thieme Publishing Group: New York, NY, pp. 118-154.
Kocienski, P.J. (May 1994). "Diol Protecting Groups," Chapter 3 in Protecting Groups, Thieme Publishing Group: New York, NY, pp. 95-117.
Kocienski, P.J. (May 1994). "Hydroxyl Protecting Groups," Chapter 2 in Protecting Groups, Thieme Publishing Group: New York, NY, pp. 21-94.
Kocienski, P.J. (May 1994). "Protecting Groups: An Overview," Chapter 1 in Protecting Groups, Thieme Publishing Group: New York, NY, pp. 1-20.
Lad et al., (2015) "Functional Label-Free Assays for Characterizing the in Vitro Mechanism of Action of Small Molecule Modulators of Capsid Assembly" Biochemistry, 54: 2240-2248.
Lamorte et al. (2015) "Discovery of Novel Small-Molecule HIV-1 Replication Inhibitors That Stabilize Capsid Complexes" Antimicrobial Agents and Chemotherapy, 57(10): 4622-4631.
Lazerwith et al., (2017) "New Antiretrovirals for HIV and Antivirals for HBV," in Comprehensive Medicinal Chemistry, 3rd Edition, 1-36.
Lee et al., (2010) "Flexible Use of Nuclear Import Pathways by HIV-1," Cell Host & Microbe 7: 221-233.
Lemke, C.T. et al. (Jun. 2012). "Distinct Effects of Two HIV-1 Capsid Assembly Inhibitor Families That Bind the Same Site Within the N-Terminal Domain of the Viral CA Protein," J. Virol. 86(12):6643-6655.
MacMillan, D. S. et al., (2013) "Evaluation of alternative solvent in common amide coupling reactions: replacement of dicloromethane and N,N-dimethlformamide," Green Chem, 15: 596-600.
Matreyek et al., (2013) "Nucleoporin NUP153 Phenylalanine-Glycine Motifs Engage a Common Binding Pocket within the HIV-1 Capsid Protein to Mediate Lentiviral Infectivity" PLOS Pathogens vol. 9, Issue 10, e1003693. 21 pages.
Mitchell, A.G. et al. (1992). "Bioreversible Protection for the Phospho Group: Bioactivation of the Di(4-Acyloxybenzyl) and Mono(4-acyloxybenzyl) Phosphoesters of Methylphosphonate and Phosphonoacetate," J. Chem. Soc. Perkin Trans. 1, pp. 2345-2353.
Miyaura, N. and Suzuki, A. (1995) "Palladium-Catalyzed Cross-Coupling Reactions of Oganoboron Compounds," Chem Rev, 95:2457-2483.
Montalbetti, C. A. G. N. and Falque, V. (2005) "Amide bond formation and peptide coupling," Tetrahedon, 61:10827-10852.
Nicolaou, K. C. et al. (2005) "Palladium-Catalyzed Cross-Coupling Reactions in Total Synthesis," Angew Chem Int Ed, 44:4442-4489.
Ovais, S. et al. (2013) "Synthesis, antiproliferative and anti-inflammatory activities of some novel 6-aryl-2-(p-(methanesulfonyl)phenyl)-4,5-dihydropyridazi-3(2H)-ones," European Journal of Medicinal Chemistry, 67:352-358.

(56) References Cited

OTHER PUBLICATIONS

Owen, A. et al. (2016) "Strengths, weaknesses, opportunities and challenges for long acting injectable therapies: Insights for applications in HIV therapy," Advances Drug Delivery Reviews 103:144-156.

Palella, F. J. et al. (1998) "Declining morbidity and mortality among patients with advanced human immunodeficiency virus infection," N Engl. J Med., 338:853-860.

Patel, H. R. et al., (2009) "Poloxamers: a pharmaceutical excipients with therapeutic behaviors," International Journal of PharmTech Research, 1(2):299-303.

PCT International Preliminary Report on Patentability in International Appln. No. PCT/US2019/017948, dated Aug. 18, 2020, 6 pages.

PCT International Search Report and Written Opinion in International Appln. No. PCT/US2019/017948, dated Aug. 4, 2019, 11 pages.

PCT Third Party Observation in International Appln. No. PCT/US2019/017948, dated Jun. 15, 2020, 7 pages.

Pornillos et al., (2009) "X-ray Structures of the Hexameric Building Block of the HIV Capsid" Cell 137(7): 1282-92.

Pornillos et al., (2009) Supplemental Data for "X-ray Structures of the Hexameric Building Block of the HIV Capsid" Cell 137(7):1282-92.

Powers, J. J. et al. (2009) "Synthesis of Methyl-, Fluoro-, and Chloro-substituted 6-Hydroxyisoindolin-1-1-Ones" Tetrahedron Letters 50(12):1267-1269.

Price et al. (2012) "CPSF6 Defines a Conserved Capsid Interface That Modulates HIV-1 Replication" PLOS Pathogens, 8(8):e1002896, 14 pages.

Puech, F. et al. (Oct. 1993). "Intracellular Delivery of Nucleoside Monophosphates Through a Reductase-Mediated Activation Process," Antiviral Res. 22(2-3):155-174.

Registry (STN) [online], Mar. 22, 2010 [date of retrieval: Nov. 12, 2018], CAS registry No. 1213065-84-9.

Registry (STN) [online], Mar. 23, 2010 [date of retrieval: Nov. 12, 2018], CAS registry No. 1213495-28-3.

Rihn et al., (2013) "Extreme Genetic Fragility of the HIV-1 Capsid" PLOS One, vol. 9 Issue 6 e1003461, 25 pages.

Shi et al. (2011) "Small-Molecule Inhibition of Human Immunodeficiency Virus Type 1 Capsid Destabilization" Journal of Virology 85(1): 542-549.

Siddiqui, A. et al. (1999) "The Presence of Substituents on the Aryl Moiety of the Aryl Phosphoramidate Derivative of d4T Enhances Anti-HIV Efficacy in Cell Culture: A Structure-Activity Relationship" J. Med. Chem. 42:393-399.

Smith, R.J. et al. (2010) "Evolutionary Dynamics of Complex Networks of HIV Drug-Resistant Strains: The Case of San Francisco," Science 327(5966):697-701.

Sticht et al., (2005) "A peptide inhibitor of HIV-1 assembly in vitro" Nature Structural & Molecular Biology, 12(8): 671-677.

STN Registry No. 137349-29-2, Nov. 15, 1991, 1 page.

Sublocade Product Label, issued: Nov. 2017, 43 pages.

Taiwo, B. (2009). "Understanding Transmitted HIV Resistance Through the Experience in the USA," Int'l. J. of Infectious Diseases 13(5):552-559.

Talele, "The 'Cyclopropyl Fragment' is a Versatile Player that Frequently Appears in Preclinical/Clinical Drug Molecules," Journal of Medicinal Chemistry, 2016, 59(19):8712-8756.

Tanaka, R. et al. (2005) "One-Pot Synthesis of Metalated Pyridines from Two Acetylenes, a Nitrile, and a Titanium(II) Alkoxide," J. Am. Chem. Soc. 127(21):7774-7780.

Tang et al., (2003) "Antiviral Inhibition of the HIV-1 Capsid Protein," J. Mol. Biol., 327: 1013-1020.

Thenin-Houssier et al., "HIV-1 capsid inhibitors as antiretroviral agents," Curr. HIV Res., 2016, 14(3):270-282.

Tse et al., "Discovery of Novel Potent HIV Capsid Inhibitors with Long-Acting Potential," Presentation at the Conference on Retroviruses and Opportunistic Infections (CROI), Seattle, WA, Feb. 14, 2017, 18 pages.

Tse et al., (2017) "Discovery of Novel Potent HIV Capsid Inhibitors with Long-Acting Potential," Abstract for Oral Presentation at the Conference on Retroviruses and Opportunistic Infections (CROI), Seattle, WA, 18 pages.

Tsiang et al., (2012) "A Trimer of Dimers Is the Basic Building Block for Human immunodeficiency Virus-1 Capsid Assembly" Biochemistry, 51: 4416-4428.

Wong et al., (2014) "SPR Assay Development to Characterize Capsid Inhibitors Binding & MOA," Poster Presented at the Developments in Protein Interaction (DiPIA), La Jolla, CA, 1 page.

Wu et al., "Selective Inhibitors of Tumor Progression Loci-2(Tp12) Kinase with Potent Inhibition of TNF-Alpha Production in Human Whole Blood," Bioorg. Med. Chem. Lett., 2009, 19(13):3485-3488.

Xianghui et al., "In Silico Virtual Screening," Biotechnology in the Post-Genome Era, 2003, 16 pages.

Yadav et al., "Co-crystals: a novel approach to modify physicochemical properties of active pharmaceutical ingredients" Indian J. Pharm. Sci., 2009, 71(4):359-370.

Yale, H. L. (1958) "The trifluoromethyl group in medicinal chemistry," J. Med. Chem., 1(2):121-133.

Yant et al., (2014) "PF74 Inhibits Multiple HIV Capsid Functions Independently of Host Cyclophilin A and CPSF6" Abstract for Poster Presented at the Conference on Retroviruses and.

Zheng, J. et al. (2018) "GS-6207: A Novel, Potent and Selective First-In-Class Inhibitor of HIV-1 Capsid Function Displays Nonclinical Pharmacokinetics Supporting Long-Acting Potential," Poster Presented at ID Week 2018, San Francisco, CA, 1 page.

Zhou et al. (2015) "HIV-1 Resistance to the Capsid-Targeting Inhibitor PF74 Results in Altered Dependence on Host Factors Required for Virus Nuclear Entry" Journal of Virology, 89(17): 9068-9079.

Bastin et al., "Salt Selection and Optimisation Procedures for Pharmaceutical New Chemical Entities," Organic Process Research & Development, Jul. 2000, 4(5): 427-435.

Fontes Ferreira da Cunha et al., "4D-QSAR Models of HOE/BAY-793 Analogues as HIV-1 Protease Inhibitors," QSAR & Combinatorial Science, 2005, 24(2): 240-253.

Jarvis et al., "Conquering HIV's capsid", C&EN Chicago, Jul. 2017, 95(31): 23-25.

Molina et al., "On-Demand Preexposure Prophylaxis in Men at High Risk for HIV-1 Infection," N Engl. J Med. 2015, 353:2237-2246.

Morissette et al., "High-throughput crystallization: polymorphs, salts, co-crystals and solvates of pharmaceutical solids," Advanced Drug Delivery Reviews, Feb. 2004, 56(3):275-300.

Pornillos et al., "Atomic level modeling of the HIV capsid," Nature, Jan. 2011, 469(7330):424-427.

Pungpo et al., "Computer-aided molecular design of highly potent HIV-1 RT inhibitors: 3D QSAR and molecular docking strudies of efavirenz derivatives," SAR and QSAR in Environmental Research, 2006, 17(4):353-370.

Silverman, "The Organic Chemistry of Drug Design and Drug Action," Elsevier, 2004, pp. 121-169.

Silvestri et al., "Novel Indolyl Aryl Sulfones Active against HIV-1 Carrying NNRTI Resistance Mutations: Synthesis and SAR Studies," Journal of Medical Chemistry, 2003, 46(12): 2482-2493.

Yang et al., "Design, synthesis and anti-HIV-1 evaluation of hydrazide-based peptidomimetics as selective gelatinase inhibitors," Bioorganic & Medicinal Chemistry, May 2016, 24(9):2125-2136.

Canadian Office Action in CA Appln. No. 3089590, dated Sep. 17, 2021, 3 pages.

Japanese Office Action in JP Appln. No. 2020-543506, dated Sep. 30, 2021, 7 pages (with English translation).

\* cited by examiner

THERAPEUTIC COMPOUNDS

CROSS REFERENCE TO RELATED APPLICATIONS

This Application is a continuation of U.S. Ser. No. 16/275,605 filed on Feb. 14, 2019, which claims the benefit of U.S. Provisional Application 62/630,955 filed on Feb. 15, 2018. The entire contents of these applications are incorporated herein by reference in their entirety.

FIELD

This application relates to chemical compounds that may inhibit human immunodeficiency virus (HIV), to compositions and formulations containing such compounds, and to methods of using and making such compounds.

BACKGROUND

Positive-single stranded RNA viruses comprising the Retroviridae family include those of the subfamily Orthoretrovirinae and genera Alpharetrovirus, Betaretrovirus, Gamaretrovirus, Deltaretrovirus, Epsilonretrovirus, Lentivirus, and Spumavirus which cause many human and animal diseases. Among the Lentivirus, HIV-1 infection in humans leads to depletion of T helper cells and immune dysfunction, producing immunodeficiency and vulnerability to opportunistic infections. Treating HIV-1 infections with highly active antiretroviral therapies (HAART) has proven to be effective at reducing viral load and significantly delaying disease progression (Hammer, S. M., et al.; *JAMA* 2008, 300: 555-570). However, these treatments could lead to the emergence of HIV strains that are resistant to current therapies (Taiwo, B., *International Journal of Infectious Diseases* 2009, 13:552-559; Smith, R. J., et al., *Science* 2010, 327: 697-701). Therefore, there is a pressing need to discover new antiretroviral agents that are active against emerging drug-resistant HIV variants.

SUMMARY

Provided herein are compounds and methods for the treatment or prevention of HIV (i.e., human immunodeficiency virus) infection.

In some embodiments, disclosed herein is a compound of Formula (I):

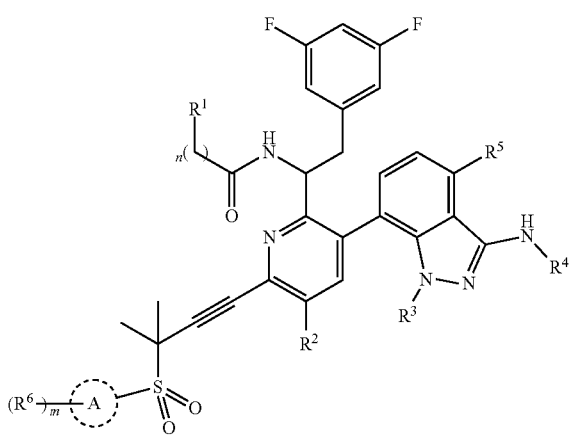

(I)

wherein
A is 3-6 membered carbocycle;
n is 0, 1, or 2;
m is 0, 1, or 2;
$R^1$ is 5-12 membered heteroaryl or 5-12 membered heterocycle, wherein any 5-12 membered heteroaryl or 5-12 membered heterocycle of $R^1$ is unsubstituted or substituted with 1, 2, 3, 4 or 5 $Z^1$ groups, wherein the $Z^1$ groups are the same or different;
each $Z^1$ is independently $(C_1-C_6)$alkyl, $(C_3-C_7)$carbocycle, halogen, or —CN, wherein any $(C_1-C_6)$alkyl or $(C_3-C_7)$ carbocycle of $Z^1$ is unsubstituted or substituted with 1, 2, 3, 4 or 5 $Z^{1a}$ groups, wherein the $Z^{1a}$ groups are the same or different;
each $Z^{1a}$ is independently halogen, $(C_3-C_7)$carbocycle, —OH, or —CN;
$R^2$ is hydrogen, halogen, —OH, or —CN;
$R^3$ is $(C_1-C_6)$alkyl or 3-5 membered heterocycle, wherein the $(C_1-C_6)$alkyl is unsubstituted or substituted with 1, 2, or 3 halogen atoms;
$R^4$ is hydrogen, —S(O)$_2$—$(C_1-C_6)$alkyl, —S(O)$_2$—$(C_3-C_6)$ carbocycle, or 5-6 membered heteroaryl, wherein any —S(O)$_2$—$(C_1-C_6)$ alkyl, —S(O)$_2$—$(C_3-C_6)$carbocycle, or 5-6 membered heteroaryl of $R^4$ is unsubstituted or substituted with 1, 2, or 3 $Z^2$ groups, wherein the $Z^2$ groups are the same or different;
$Z^2$ is $(C_1-C_6)$alkyl or $(C_3-C_6)$carbocycle, wherein any $(C_1-C_6)$alkyl or $(C_3-C_6)$carbocycle is unsubstituted or substituted with 1, 2, or 3 $Z^{2a}$ groups, wherein the $Z^{2a}$ groups are the same or different;
$Z^{2a}$ is hydroxyl or halogen;
$R^5$ is hydrogen or halogen; and
$R^6$ is $(C_1-C_3)$alkyl;
or a pharmaceutically acceptable salt thereof.

In some embodiments, disclosed herein is a compound of Formula (Ia), or a pharmaceutically acceptable salt thereof,

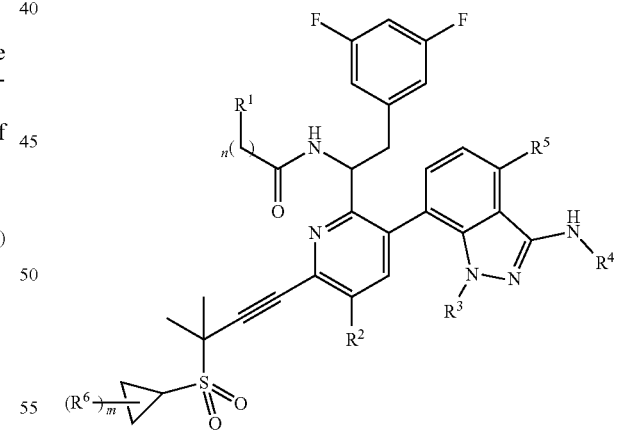

(Ia)

wherein:
n is 0, 1, or 2;
m is 0 or 1;
$R^1$ is 5-9 membered heteroaryl or 5-9 membered heterocycle, wherein any 5-9 membered heteroaryl or 5-9 membered heterocycle of $R^1$ is unsubstituted or substituted with 1, 2, 3, 4 or 5 $Z^1$ groups, wherein the $Z^1$ groups are the same or different;
each $Z^1$ is independently $(C_1-C_6)$alkyl, $(C_3-C_7)$carbocycle, or halogen, wherein any $(C_1-C_6)$alkyl or $(C_3-C_7)$carbocycle of $Z^1$ is unsubstituted or substituted with 1, 2, 3, 4 or 5 $Z^{1a}$ groups, wherein the $Z^{1a}$ groups are the same or different;

each $Z^{1a}$ is independently halogen or $(C_3-C_7)$carbocycle;

$R^2$ is hydrogen or iodide;

$R^3$ is $(C_1-C_2)$alkyl or 3-5 membered heterocycle, wherein the $(C_1-C_2)$alkyl is unsubstituted or substituted with 2 or 3 halogen atoms;

$R^4$ is hydrogen, $—S(O)_2—(C_1-C_2)$alkyl, $—S(O)_2$-cyclopropyl, or 5-membered heteroaryl, wherein any $—S(O)_2—(C_1-C_2)$alkyl, $—S(O)_2$-cyclopropyl, or 5-membered heteroaryl of $R^4$ is unsubstituted or substituted with 1, 2, or 3 $Z^2$ groups, wherein the $Z^2$ groups are the same or different;

$Z^2$ is $(C_1-C_3)$alkyl or cyclopropyl, wherein any $(C_1-C_3)$alkyl or cyclopropyl is unsubstituted or substituted with 1, 2, or 3 $Z^{2a}$ groups, wherein the $Z^{2a}$ groups are the same or different;

$Z^{2a}$ is hydroxyl or fluorine;

$R^5$ is hydrogen, chorine, or fluorine; and $R^6$ is $(C_1-C_3)$alkyl.

In some embodiments, disclosed herein is a compound of Formula (Ia), or a pharmaceutically acceptable salt thereof, wherein: n is 0, 1, or 2;

n is 0, 1, or 2;

m is 0 or 1;

$R^1$ is 5-9 membered heteroaryl that is unsubstituted or substituted with 1, 2, 3, 4 or 5 $Z^1$ groups, wherein the $Z^1$ groups are the same or different;

each $Z^1$ is independently $(C_1-C_6)$alkyl, $(C_3-C_7)$carbocycle, or halogen, wherein any $(C_1-C_6)$alkyl or $(C_3-C_7)$carbocycle of $Z^1$ is unsubstituted or substituted with 1, 2, 3, 4 or 5 $Z^{1a}$ groups, wherein the $Z^{1a}$ groups are the same or different;

each $Z^{1a}$ is independently halogen or $(C_3-C_7)$carbocycle;

$R^2$ is hydrogen or iodide;

$R^3$ is $(C_1-C_2)$alkyl or 3-5 membered heterocycle, wherein the $(C_1-C_2)$alkyl is unsubstituted or substituted with 2 or 3 fluorine atoms;

$R^4$ is hydrogen, $—S(O)_2—(C_1-C_2)$alkyl, $—S(O)_2$-cyclopropyl, or 5-membered heteroaryl, wherein any $—S(O)_2—(C_1-C_2)$alkyl, $—S(O)_2$-cyclopropyl, or 5-membered heteroaryl of $R^4$ is unsubstituted or substituted with 1, 2, or 3 $Z^2$ groups, wherein the $Z^2$ groups are the same or different;

$Z^2$ is $(C_1-C_3)$alkyl or cyclopropyl, wherein any $(C_1-C_3)$alkyl or cyclopropyl is unsubstituted or substituted with 1, 2, or 3 $Z^{2a}$ groups, wherein the $Z^{2a}$ groups are the same or different;

$Z^{2a}$ is hydroxyl or fluorine;

$R^5$ is hydrogen, chorine, or fluorine; and $R^6$ is methyl.

In some embodiments, disclosed herein is a compound of Formula (Ia), or a pharmaceutically acceptable salt thereof, wherein:

n is 0, 1, or 2;

m is 0 or 1;

$R^1$ is 5-9 membered heteroaryl that is unsubstituted or substituted with 1, 2, 3, 4 or 5 $Z^1$ groups, wherein the $Z^1$ groups are the same or different;

each $Z^1$ is independently $(C_1-C_6)$alkyl, $(C_3-C_7)$carbocycle, or halogen, wherein any $(C_1-C_6)$alkyl or $(C_3-C_7)$carbocycle of $Z^1$ is unsubstituted or substituted with 1, 2, 3, 4 or 5 $Z^{1a}$ groups, wherein the $Z^{1a}$ groups are the same or different;

each $Z^{1a}$ is independently halogen or $(C_3-C_7)$carbocycle;

$R^2$ is hydrogen;

$R^3$ is $(C_1-C_2)$alkyl or 4 membered heterocycle, wherein the $(C_1-C_2)$alkyl is unsubstituted or substituted with 2 or 3 fluorine atoms;

$R^4$ is $—S(O)_2—(C_1-C_2)$alkyl, $—S(O)_2$-cyclopropyl, or 5-membered heteroaryl, wherein any $—S(O)_2—(C_1-C_2)$alkyl, $—S(O)_2$-cyclopropyl, or 5-membered heteroaryl of $R^4$ is unsubstituted or substituted with 1, 2, or 3 $Z^2$ groups, wherein the $Z^2$ groups are the same or different;

$Z^2$ is $(C_1-C_3)$alkyl or cyclopropyl, wherein any $(C_1-C_3)$alkyl or cyclopropyl is unsubstituted or substituted with 1, 2, or 3 $Z^{2a}$ groups, wherein the $Z^{2a}$ groups are the same or different;

$Z^2a$ is hydroxyl or fluorine;

$R^5$ is hydrogen, chorine, or fluorine; and $R^6$ is methyl.

In some embodiments, disclosed herein is a compound of Formula (Ib):

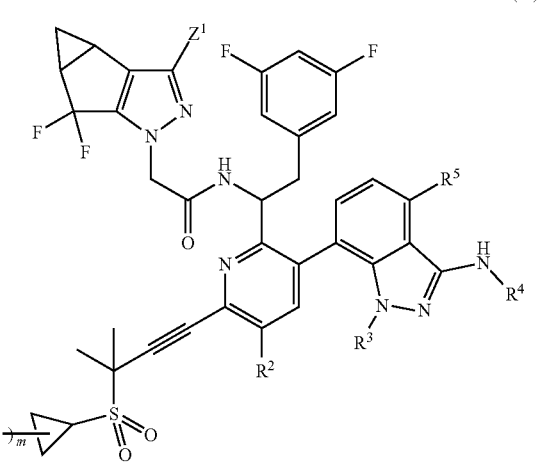

(Ib)

or a pharmaceutically acceptable salt thereof.

In some embodiments, disclosed herein is a compound of Formula (Ic):

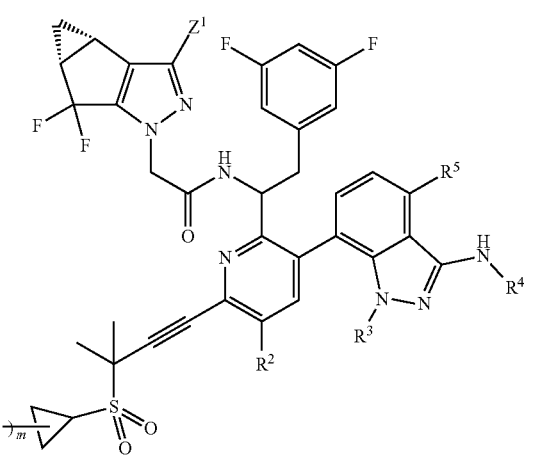

(Ic)

or a pharmaceutically acceptable salt thereof.

In some embodiments, disclosed herein is a compound of Formula (Id):

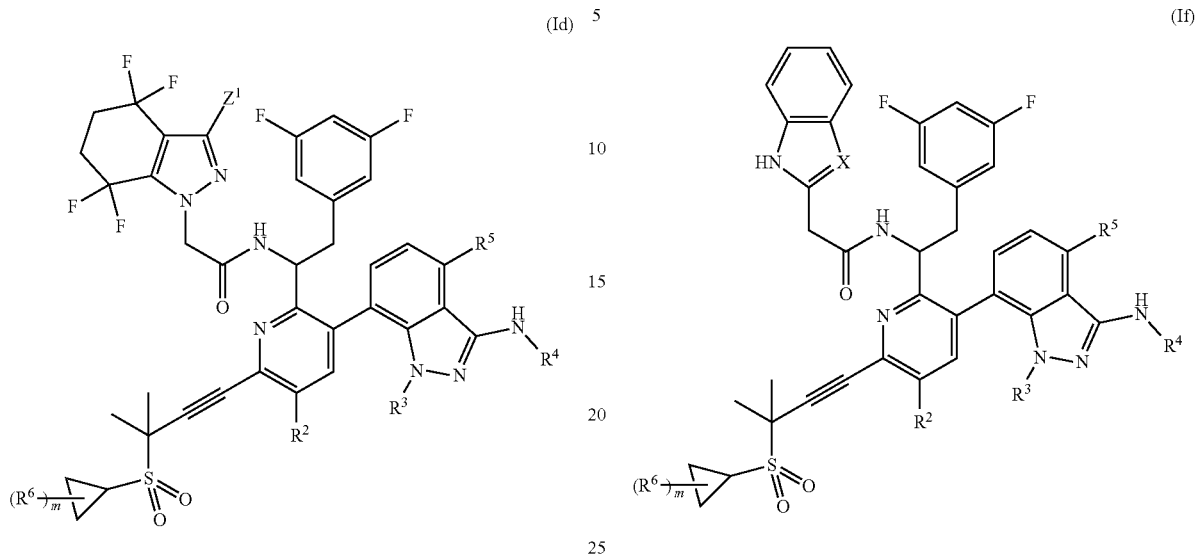

(Id)

or a pharmaceutically acceptable salt thereof.

In some embodiments, disclosed herein is a compound of Formula (Ie):

(Ie)

wherein
each $X^1$ and $X^2$ are independently N or CH;
or a pharmaceutically acceptable salt thereof.

In some embodiments, disclosed herein is a compound of Formula (If):

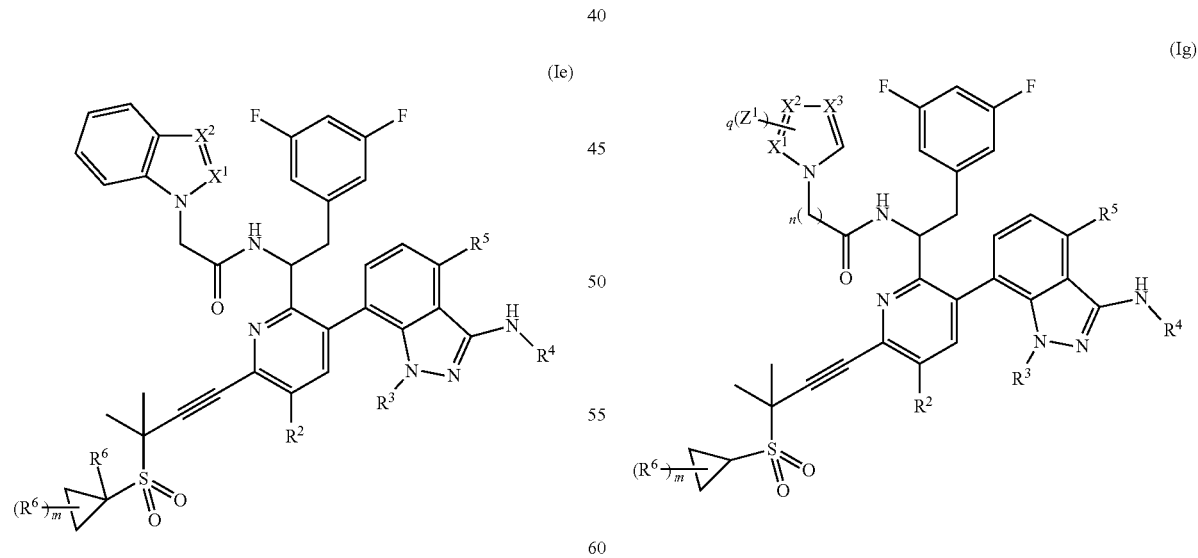

(If)

wherein
X is N or CH;
or a pharmaceutically acceptable salt thereof.

In some embodiments, disclosed herein is a compound of Formula (Ig):

(Ig)

wherein
q is 0, 1, 2, or 3;
each $X^1$, $X^2$, and $X^3$ are independently N or CH;
or a pharmaceutically acceptable salt thereof.

In some embodiments, disclosed herein is a compound of Formula (Ih):

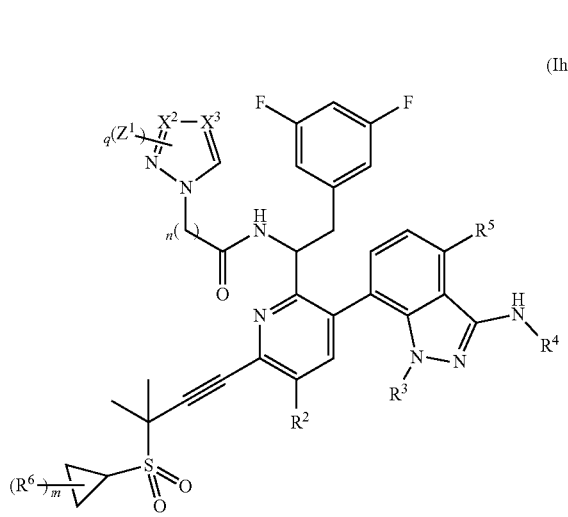

(Ih)

wherein
q is 0, 1, 2, or 3;
each $X^2$ and $X^3$ are independently N or CH;
or a pharmaceutically acceptable salt thereof.

In some embodiments, disclosed herein is a compound of Formula (Ii):

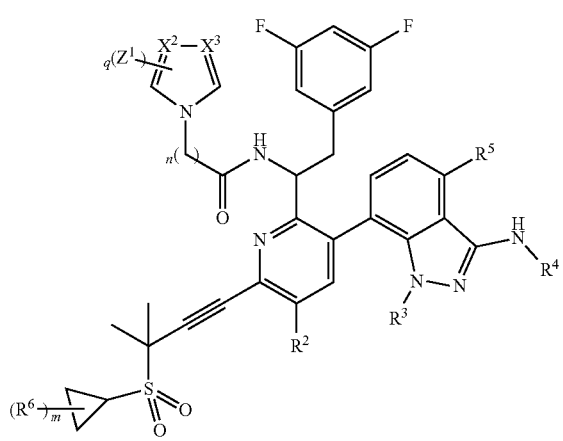

(Ii)

wherein
q is 0, 1, 2, or 3;
each $X^2$ and $X^3$ are independently N or CH;
or a pharmaceutically acceptable salt thereof.

In some embodiments, disclosed herein is a compound of Formula (Ij):

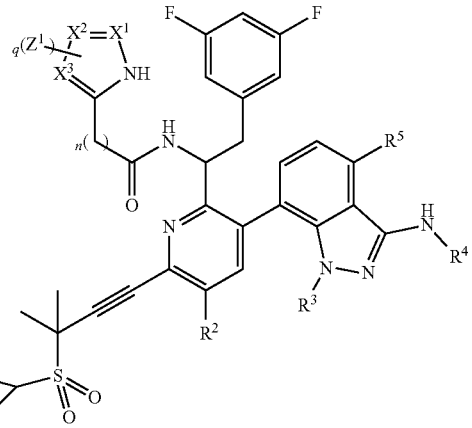

(Ij)

wherein
q is 0, 1, 2, or 3;
each $X^1$, $X^2$, and $X^3$ are independently N or CH;
or a pharmaceutically acceptable salt thereof.

In some embodiments, disclosed herein is a compound of Formula (Ik):

(Ik)

wherein
each $X^2$ and $X^3$ are independently N or CH;
or a pharmaceutically acceptable salt thereof.

In some embodiments, provided herein is a pharmaceutical composition comprising a compound of disclosed herein or a pharmaceutically acceptable salt thereof, and a pharmaceutically acceptable carrier. Another embodiment provides a pharmaceutical composition comprising a compound as disclosed herein, including a compound of any one of formulas I, Ia, Ib, Ic, Id, Ie, If, Ig, Ih, Ii, Ij and Ik, or a pharmaceutically acceptable salt thereof, and a pharmaceutically acceptable carrier.

In some embodiments, provided herein is a pharmaceutical composition comprising a compound of formula I (e.g., a compound of any one of formulas I, Ia, Ib, Ic, Id, Ie, If, Ig, Ih, Ii, Ij and Ik) or a pharmaceutically acceptable salt thereof; and an additional therapeutic agent, wherein the additional therapeutic agent is an HIV protease inhibitor, a HIV non-nucleoside or non-nucleotide inhibitor of reverse transcriptase, a HIV nucleoside or nucleotide inhibitor of reverse transcriptase, a HIV integrase inhibitor, a HIV non-catalytic site (or allosteric) integrase inhibitor, an HIV entry inhibitor, an HIV maturation inhibitor, a latency reversing agent, a compound that targets the HIV capsid, an immune-based therapy, a phosphatidylinositol 3-kinase (PI3K) inhibitor, a HIV antibody, a bispecific antibody and/or "antibody-like" therapeutic protein, a HIV p17 matrix protein inhibitor, a IL-13 antagonist, a peptidyl-prolyl cis-trans isomerase A modulator, a protein disulfide isomerase inhibitor, a complement C5a receptor antagonist, a DNA methyltransferase inhibitor, a HIV vif gene modulator, a Vif dimerization antagonist, a HIV-1 viral infectivity factor inhibitor, a TAT protein inhibitor, a HIV-1 Nef modulator, a Hck tyrosine kinase modulator, a mixed lineage kinase-3 (MLK-3) inhibitor, a HIV-1 splicing inhibitor, a Rev protein inhibitor, an integrin antagonist, a nucleoprotein inhibitor, a splicing factor modulator, a COMM domain containing protein 1 modulator, a HIV ribonuclease H inhibitor, a retrocyclin modulator, a CDK-9 inhibitor, a dendritic ICAM-3 grabbing nonintegrin 1 inhibitor, a HIV GAG protein inhibitor, a HIV POL protein inhibitor, a Complement Factor H modulator, a ubiquitin ligase inhibitor, a deoxycytidine kinase inhibitor, a cyclin dependent kinase inhibitor, a proprotein convertase PC9 stimulator, a ATP dependent RNA helicase DDX3X inhibitor, a reverse transcriptase priming complex inhibitor, a G6PD and NADH-oxidase inhibitor, a pharmacokinetic enhancer, a HIV gene therapy, a HIV vaccine, and combinations thereof.

In some embodiments, provided herein is a method for treating a Retroviridae viral infection (e.g., an HIV viral infection) in a mammal (e.g., a human), comprising administering a compound of formula I, or a pharmaceutically acceptable salt thereof, to the mammal. Another embodiment provides a method for treating a Retroviridae viral infection (e.g., an HIV viral infection) in a mammal (e.g., a human), comprising administering a compound as detailed herein, including a compound of any one of formulas I, Ia, Ib, Ic, Id, Ie, If, Ig, Ih, Ii, Ij and Ik, or a pharmaceutically acceptable salt thereof, to the mammal. Another embodiment provides a method for treating a HIV infection in a patient in need thereof comprising administering a therapeutically effective amount of a compound as detailed herein, or a pharmaceutically acceptable salt thereof, to the patient.

In some embodiments, provided herein is a method for inhibiting the proliferation of the HIV virus, treating AIDS or delaying the onset of AIDS or ARC symptoms in a mammal (e.g., a human), comprising administering a compound of formula I, or a pharmaceutically acceptable salt thereof, to the mammal. Another embodiment provides a method for inhibiting the proliferation of the HIV virus, treating AIDS or delaying the onset of AIDS or ARC symptoms in a mammal (e.g., a human), comprising administering a compound as detailed herein, including a compound of any one of formulas I, Ia, Ib, Ic, Id, Ie, If, Ig, Ih, Ii, Ij and Ik, or a pharmaceutically acceptable salt thereof, to the mammal.

In some embodiments, provided herein is a method for treating an HIV infection in a mammal (e.g., a human), comprising administering a compound of formula I, or a pharmaceutically acceptable salt thereof, to the mammal. Another embodiment provides a method for treating an HIV infection in a mammal (e.g., a human), comprising administering a compound as detailed herein, including a compound of any one of formulas I, Ia, Ib, Ic, Id, Ie, If, Ig, Ih, Ii, Ij and Ik, or a pharmaceutically acceptable salt thereof, to the mammal.

In some embodiments, provided herein is a method for treating an HIV infection in a mammal (e.g., a human), comprising administering to the mammal in need thereof a therapeutically effective amount of a compound of formula I, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof. Another embodiment provides a method for treating an HIV infection in a mammal (e.g., a human), comprising administering to the mammal in need thereof a therapeutically effective amount of a compound of any one of formulas I, Ia, Ib, Ic, Id, Ie, If, Ig, Ih, Ii, Ij and Ik, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof. Another embodiment provides a method for treating an HIV infection in a patient in need thereof comprising administering to the patient a therapeutically effective amount of a compound as described herein, or a pharmaceutically acceptable salt thereof, in combination with a therapeutically effective amount of an additional therapeutic agent, wherein the additional therapeutic agent is an HIV protease inhibiting compound, an HIV non-nucleoside inhibitor of reverse transcriptase, an HIV nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a capsid polymerization inhibitor, or a non-catalytic site HIV integrase site inhibitor and combinations thereof.

In some embodiments, provided herein is a method for treating an HIV infection in a mammal (e.g., a human), comprising administering to the mammal in need thereof a therapeutically effective amount of a compound of formula I, or a pharmaceutically acceptable salt thereof, in combination with a therapeutically effective amount of an additional therapeutic agent, wherein the additional therapeutic agent is a HIV protease inhibitor, a HIV non-nucleoside or non-nucleotide inhibitor of reverse transcriptase, a HIV nucleoside or nucleotide inhibitor of reverse transcriptase, a HIV integrase inhibitor, a HIV non-catalytic site integrase inhibitor, an HIV entry inhibitor, an HIV maturation inhibitor, a latency reversing agent, a compound that targets the HIV capsid, an immune-based therapy, a phosphatidylinositol 3-kinase (PI3K) inhibitor, a HIV antibody, a bispecific antibody, an antibody-like therapeutic protein, a HIV p17 matrix protein inhibitor, a IL-13 antagonist, a peptidyl-prolyl cis-trans isomerase A modulator, a protein disulfide isomerase inhibitor, a complement C5a receptor antagonist, a DNA methyltransferase inhibitor, a HIV vif gene modulator, a Vif dimerization antagonist, a HIV-1 viral infectivity factor inhibitor, a TAT protein inhibitor, a HIV-1 Nef modulator, a Hck tyrosine kinase modulator, a mixed lineage kinase-3 (MLK-3) inhibitor, a HIV-1 splicing inhibitor, a Rev protein inhibitor, an integrin antagonist, a nucleoprotein inhibitor, a splicing factor modulator, a COMM domain containing protein 1 modulator, a HIV ribonuclease H inhibitor, a retrocyclin modulator, a CDK-9 inhibitor, a dendritic ICAM-3 grabbing nonintegrin 1 inhibitor, a HIV GAG protein inhibitor, a HIV POL protein inhibitor, a Complement Factor H modulator, a ubiquitin ligase inhibitor, a deoxycytidine kinase inhibitor, a cyclin dependent kinase inhibitor, a proprotein convertase PC9 stimulator, a ATP dependent RNA helicase DDX3X inhibitor, a reverse transcriptase priming complex inhibitor, a G6PD and NADH-oxidase inhibitor, a pharmacokinetic enhancer, a HIV gene therapy, or a HIV vaccine. Another embodiment provides a method for treating an HIV infection in a mammal (e.g., a human), comprising administering to the mammal in need thereof a therapeutically effective amount of a compound of any one of formulas I, Ia, Ib, Ic, Id, Ie, If, Ig, Ih, Ii, Ij and Ik, or a pharmaceutically acceptable salt thereof, in combination with a therapeutically effective amount of an additional therapeutic agent, wherein the additional therapeutic agent is a HIV protease inhibitor, a HIV non-nucleoside or non-nucleotide inhibitor of reverse transcriptase, a HIV nucleoside or nucleotide inhibitor of reverse transcriptase, a HIV integrase inhibitor, a HIV non-catalytic site integrase inhibitor, an HIV entry inhibitor, an HIV maturation inhibitor, a latency reversing agent, a compound that targets the HIV capsid, an immune-based therapy, a phosphatidylinositol 3-kinase (PI3K) inhibitor, a HIV antibody, a bispecific antibody, an antibody-like therapeutic protein, a HIV p17 matrix protein inhibitor, a IL-13 antagonist, a peptidyl-prolyl cis-trans isomerase A modulator, a protein disulfide isomerase inhibitor, a complement C5a receptor antagonist, a DNA methyltransferase inhibitor, a HIV vif gene modulator, a Vif dimerization antagonist, a HIV-1 viral infectivity factor inhibitor, a TAT protein inhibitor, a HIV-1 Nef modulator, a Hck tyrosine kinase modulator, a mixed lineage kinase-3 (MLK-3) inhibitor, a HIV-1 splicing inhibitor, a Rev protein inhibitor, an integrin antagonist, a nucleoprotein inhibitor, a splicing factor modulator, a COMM domain containing protein 1 modulator, a HIV ribonuclease H inhibitor, a retrocyclin modulator, a CDK-9 inhibitor, a dendritic ICAM-3 grabbing nonintegrin 1 inhibitor, a HIV GAG protein inhibitor, a HIV POL protein inhibitor, a Complement Factor H modulator, a ubiquitin ligase inhibitor, a deoxycytidine kinase inhibitor, a cyclin dependent kinase inhibitor, a proprotein convertase PC9 stimulator, a ATP dependent RNA helicase DDX3X inhibitor, a reverse transcriptase priming complex inhibitor, a G6PD and NADH-oxidase inhibitor, a pharmacokinetic enhancer, a HIV gene therapy, or a HIV vaccine. Another embodiment provides a method for treating an HIV infection in a patient in need thereof comprising administering to the patient a therapeutically effective amount of a compound as described herein, or a pharmaceutically acceptable salt thereof, in combination with a therapeutically effective amount of an additional therapeutic agent, wherein the additional therapeutic agent is a HIV protease inhibitor, a HIV non-nucleoside or non-nucleotide inhibitor of reverse transcriptase, a HIV nucleoside or nucleotide inhibitor of reverse transcriptase, a HIV integrase inhibitor, a HIV non-catalytic site integrase inhibitor, an HIV entry inhibitor, an HIV maturation inhibitor, a latency reversing agent, a compound that targets the HIV capsid, an immune-based therapy, a phosphatidylinositol 3-kinase (PI3K) inhibitor, a HIV antibody, a bispecific antibody, an antibody-like therapeutic protein, a HIV p17 matrix protein inhibitor, a IL-13 antagonist, a peptidyl-prolyl cis-trans isomerase A modulator, a protein disulfide isomerase inhibitor, a complement C5a receptor antagonist, a DNA methyltransferase inhibitor, a HIV vif gene modulator, a Vif dimerization antagonist, a HIV-1 viral infectivity factor inhibitor, a TAT protein inhibitor, a HIV-1 Nef modulator, a Hck tyrosine kinase modulator, a mixed lineage kinase-3 (MLK-3) inhibitor, a HIV-1 splicing inhibitor, a Rev protein inhibitor, an integrin antagonist, a nucleoprotein inhibitor, a splicing factor modulator, a COMM domain containing protein 1 modulator, a HIV ribonuclease H inhibitor, a retrocyclin modulator, a CDK-9 inhibitor, a dendritic ICAM-3 grabbing nonintegrin 1 inhibitor, a HIV GAG protein inhibitor, a HIV POL protein inhibitor, a Complement Factor H modulator, a ubiquitin ligase inhibitor, a deoxycytidine kinase inhibitor, a cyclin dependent kinase inhibitor, a proprotein convertase PC9 stimulator, a ATP dependent RNA helicase DDX3X inhibitor, a reverse transcriptase priming complex inhibitor, a G6PD and NADH-oxidase inhibitor, a pharmacokinetic enhancer, a HIV gene therapy, or a HIV vaccine.

In some embodiments, provided herein is a method for treating an HIV infection in a mammal (e.g., a human), comprising administering to the mammal in need thereof a therapeutically effective amount of a compound of formula I, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and non-catalytic site HIV integrase inhibitors, and combinations thereof. Another embodiment provides a method for treating an HIV infection in a mammal (e.g., a human), comprising administering to the mammal in need thereof a therapeutically effective amount of a compound as detailed herein, including a compound of any one of formulas I, Ia, Ib, Ic, Id, Ie, If, Ig, Ih, Ii, Ij and Ik, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and non-catalytic site HIV integrase inhibitors, and combinations thereof.

In some embodiments, provided herein is a compound of formula I, or a pharmaceutically acceptable salt thereof, for use in medical therapy (e.g., for use in treating a Retroviridae viral infection (e.g., an HIV viral infection) or the proliferation of the HIV virus or AIDS or delaying the onset of AIDS or ARC symptoms in a mammal (e.g., a human)). Another embodiment provides a compound as detailed herein, including a compound of any one of formulas I, Ia, Ib, Ic, Id, Ie, If, Ig, Ih, Ii, Ij and Ik, or a pharmaceutically acceptable salt thereof, for use in medical therapy (e.g., for use in treating a Retroviridae viral infection (e.g., an HIV viral infection) or the proliferation of the HIV virus or AIDS or delaying the onset of AIDS or ARC symptoms in a mammal (e.g., a human)).

In some embodiments, provided herein is a compound of formula I, or a pharmaceutically acceptable salt thereof for use in the manufacture of a medicament for treating a Retroviridae viral infection (e.g., an HIV viral infection) or the proliferation of the HIV virus or AIDS or delaying the onset of AIDS or ARC symptoms in a mammal (e.g., a human). Another embodiment provides a compound as detailed herein, including a compound of any one of formulas I, Ia, Ib, Ic, Id, Ie, If, Ig, Ih, Ii, Ij and Ik, or a pharmaceutically acceptable salt thereof, for use in the manufacture of a medicament for treating a Retroviridae viral infection (e.g., an HIV viral infection) or the proliferation of the HIV virus or AIDS or delaying the onset of AIDS or ARC symptoms in a mammal (e.g., a human).

In some embodiments, provided herein is a compound of formula I, or a pharmaceutically acceptable salt thereof, for use in the prophylactic (e.g., prevention) or therapeutic treatment of the proliferation of a Retroviridae virus, an HIV virus or AIDS or for use in the therapeutic treatment of delaying the onset of AIDS or ARC symptoms. Another embodiment provides a compound as detailed herein, including a compound of any one of formulas I, Ia, Ib, Ic, Id, Ie, If, Ig, Ih, Ii, Ij and Ik, or a pharmaceutically acceptable salt thereof, for use in the prophylactic (e.g., prevention) or therapeutic treatment of the proliferation of a Retroviridae virus, an HIV virus or AIDS or for use in the therapeutic treatment of delaying the onset of AIDS or ARC symptoms.

In some embodiments, provided herein is a compound of formula I, or a pharmaceutically acceptable salt thereof, for use in the prophylactic (e.g., prevention) or therapeutic treatment of a Retroviridae virus infection (e.g., an HIV virus infection). Another embodiment provides a compound as detailed herein, including a compound of any one of formulas I, Ia, Ib, Ic, Id, Ie, If, Ig, Ih, Ii, Ij and Ik, or a pharmaceutically acceptable salt thereof, for use in the prophylactic (e.g., prevention) or therapeutic treatment of a Retroviridae virus infection (e.g., an HIV virus infection).

In some embodiments, provided herein is a compound of formula I, or a pharmaceutically acceptable salt thereof, for use in the prevention of a Retroviridae virus infection (e.g., an HIV virus infection). Another embodiment provides a compound as detailed herein, including a compound of any one of formulas I, Ia, Ib, Ic, Id, Ie, If, Ig, Ih, Ii, Ij and Ik, or a pharmaceutically acceptable salt thereof, for use in the prevention of a Retroviridae virus infection (e.g., an HIV virus infection).

In some embodiments, provided herein is the use of a compound of formula I, or a pharmaceutically acceptable salt thereof, for the manufacture of a medicament for a Retroviridae virus infection (e.g., an HIV virus infection) in a mammal (e.g., a human). Another embodiment provides a compound as detailed herein, including a compound of any one of formulas I, Ia, Ib, Ic, Id, Ie, If, Ig, Ih, Ii, Ij and Ik, or a pharmaceutically acceptable salt thereof, for the manufacture of a medicament for a Retroviridae virus infection (e.g., an HIV virus infection) in a mammal (e.g., a human).

In some embodiments, provided herein are processes and intermediates that are useful for preparing compounds of formula I or salts thereof. Another embodiment provides processes and intermediates disclosed herein that are useful for preparing compounds of any one of formulas I, Ia, Ib, Ic, Id, Ie, If, Ig, Ih, Ii, Ij and Ik, or salts thereof.

Other embodiments, objects, features and advantages will be set forth in the detailed description of the embodiments that follows, and in part will be apparent from the description, or may be learned by practice, of the claimed invention. These objects and advantages will be realized and attained by the processes and compositions particularly pointed out in the written description and claims hereof. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

DETAILED DESCRIPTION

The description below is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

I. Definitions

Unless defined otherwise, all technical and scientific terms used herein have the same meaning as commonly understood by one of ordinary skill in the art. A dash at the front or end of a chemical group is a matter of convenience; chemical groups may be depicted with or without one or more dashes without losing their ordinary meaning. A wavy line drawn through a line in a structure indicates a point of attachment of a group, e.g.,

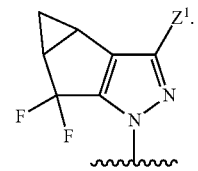

A dashed line indicates an optional bond. A dash at the front or end of a chemical group is a matter of convenience; chemical groups may be depicted with or without one or more dashes without losing their ordinary meaning. When used, a dash indicates the point of attachment, e.g. —S(O)($R^a$)=$NR^b$ indicates the following structure with point of attachment at the S:

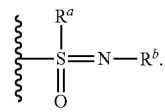

A prefix such as "$C_{u-v}$", "$(C_{u-v})$", or $(C_u$-$C_v)$ indicate that the following group has from u to v carbon atoms. For example, "$C_{1-6}$alkyl", "$(C_{1-6})$alkyl", and "$(C_{1-6})$alkyl" indicate that the alkyl group has from 1 to 6 carbon atoms.

Unless stated otherwise, the following terms and phrases as used herein are intended to have the following meanings:

When trade names are used herein, applicants intend to independently include the tradename product and the active pharmaceutical ingredient(s) of the tradename product.

"Alkyl" is a straight or branched saturated hydrocarbon. For example, an alkyl group can have 1 to 8 carbon atoms (i.e., $(C_1$-$C_8)$alkyl) or 1 to 6 carbon atoms (i.e., $(C_1$-$C_6$ alkyl) or 1 to 4 carbon atoms (i.e., $(C_1$-$C_4)$alkyl). Examples of suitable alkyl groups include, but are not limited to, methyl (Me, —$CH_3$), ethyl (Et, —$CH_2CH_3$), 1-propyl n-propyl, —$CH_2CH_2CH_3$), 2-propyl —$CH(CH_3)_2$), 1-butyl (n-Bu, n-butyl, —CH$_2$CH$_2$CH$_2$CH$_3$), 2-methyl-1-propyl i-butyl, —CH$_2$CH(CH$_3$)$_2$), 2-butyl (s-Bu, s-butyl, —CH(CH$_3$) CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH (CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH (CH$_3$)CH$_2$CH$_2$CH$_2$CH$_3$), 3-hexyl (—CH(CH$_2$CH$_3$) (CH$_2$CH$_2$CH$_3$)), 2-methyl-2-pentyl (—C (CH$_3$)$_2$CH$_2$CH$_2$CH$_3$), 3-methyl-2-pentyl (—CH(CH$_3$)CH (CH$_3$)CH$_2$CH$_3$), 4-methyl-2-pentyl (—CH(CH$_3$)CH$_2$CH (CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, and octyl (—(CH$_2$)$_7$CH$_3$).

"Alkenyl" is a straight or branched hydrocarbon with at least one carbon-carbon, sp$^2$ double bond. For example, an alkenyl group can have 2 to 8 carbon atoms (i.e., C$_2$-C$_8$ alkenyl), or 2 to 6 carbon atoms (i.e., C$_2$-C$_6$ alkenyl). Examples of suitable alkenyl groups include, but are not limited to, ethylene or vinyl (—CH═CH$_2$), allyl (—CH$_2$CH═CH$_2$) and 5-hexenyl (—CH$_2$CH$_2$CH$_2$CH$_2$CH═CH$_2$).

"Alkynyl" is a straight or branched hydrocarbon with at least one carbon-carbon, sp triple bond. For example, an alkynyl group can have 2 to 8 carbon atoms (i.e., C$_2$-C$_8$ alkyne) or 2 to 6 carbon atoms (i.e., C$_2$-C$_6$ alkynyl). Examples of suitable alkynyl groups include, but are not limited to, acetylenic (—C≡CH), propargyl (—CH$_2$C≡CH), and the like.

The term "halo" or "halogen" as used herein refers to fluoro, chloro, bromo and iodo.

The term "haloalkyl" as used herein refers to an alkyl as defined herein, wherein one or more hydrogen atoms of the alkyl are each independently replaced by a halo substituent. For example, (C$_1$-C$_6$)haloalkyl is a (C$_1$-C$_6$)alkyl wherein one or more of the hydrogen atoms of the (C$_1$-C$_6$)alkyl have been replaced by a halo substituent. Examples of haloalkyls include but are not limited to fluoromethyl, fluorochloromethyl, difluoromethyl, difluorochloromethyl, trifluoromethyl, 1,1,1, trifluoroethyl and pentafluoroethyl.

The term "heteroalkyl" as used herein refers to an alkyl as defined herein, wherein one or more of the carbon atoms of the alkyl are replaced by an O, S, or NR, (or if the carbon atom being replaced is a terminal carbon with an OH, SH or N(R)$_2$) wherein each R is independently H or (C$_1$-C$_6$)alkyl. For example, (C$_1$-C$_8$)heteroalkyl includes a heteroalkyl of one to eight carbons and one or more heteroatoms (e.g., O, S, NR, OH, SH or N(R)$_2$). Thus, for example, a C$_1$ heteroalkyl encompasses, e.g., —CH$_2$—NH$_2$. Examples of heteroalkyls include but are not limited to methoxymethyl, ethoxymethyl, methoxy, 2-hydroxyethyl and N,N'-dimethylpropylamine.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. It is also to be understood that when reference is made to a certain atom-range membered aryl (e.g., 6-12 membered aryl), the atom range is for the total ring atoms of the aryl. For example, a 6-membered aryl would include phenyl and a 10-membered aryl would include naphthyl and 1, 2, 3, 4-tetrahydronaphthyl. Non-limiting examples of aryl groups include, but are not limited to, phenyl, indenyl, naphthyl, 1, 2, 3, 4-tetrahydronaphthyl, anthracenyl, and the like.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl), heterocycles, (to form for example 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system. It is also to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5-14 membered heteroaryl), the atom range is for the total ring atoms of the heteroaryl and includes carbon atoms and heteroatoms. For example, a 5-membered heteroaryl would include a thiazolyl and a 10-membered heteroaryl would include a quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclopenta[1,2-c]pyrazole.

The term "C-linked-heteroaryl" (carbon-linked heteroaryl) as used herein refers to a heteroaryl that is linked at a carbon atom of the heteroaryl to the remainder of the compound of formula I (e.g., a C-linked-heteroaryl of $Z^2$ bonded to the A ring of formula I through a carbon atom of the C-linked-heteroaryl).

The term "heterocyclyl" or "heterocycle" as used herein refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from heterocycles (to form for example a 1,8-decahydronapthyridinyl), carbocycles (to form for example a decahydroquinolyl) and aryls to form the multiple condensed ring system. Thus, a heterocycle (a single saturated or single partially unsaturated ring or multiple condensed ring system) has about 2-20 carbon atoms and 1-6 heteroatoms within the heterocycle ring. Such multiple condensed ring systems may be optionally substituted with one or more (e.g., 1, 2, 3 or 4) oxo groups on the carbocycle or heterocycle portions of the multiple condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g., a nitrogen). It is also to be understood that when reference is made to a certain atom-range membered heterocycle (e.g., a 3-14 membered heterocycle), the atom range is for the total ring atoms of the heterocycle and includes carbon atoms and heteroatoms. For example, a 3-membered heterocycle would include an aziridinyl and a 10-membered heterocycle would include a 1,2,3,4-tetrahydroquinolyl. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one and pyrrolidin-2-one.

The term "C-linked-heterocycle" (carbon-linked heterocycle) as used herein refers to a "heterocycle that is linked at a carbon atom of the heterocycle to the remainder of the compound of formula I.

The term "carbocycle" refers to a cyclic alkyl and alkenyl groups. A carbocycle group can have one or more cyclic rings and includes fused and bridged groups that are fully saturated or partially unsaturated. Examples include, but are not limited to, cyclopropyl, cyclobutyl, cyclopentyl, cyclohexyl, adamantyl, methylcyclproyl (cyclopropylmethyl), ethylcyclopropyl, cyclohexenyl and the like.

The term "fused" refers to a ring which is bound to an adjacent ring.

"Bridged" refers to a ring fusion wherein non-adjacent atoms on a ring are joined by a divalent substituent, such as an alkylenyl or heteroalkylenyl group or a single heteroatom. Quinuclidinyl and admantanyl are examples of bridged ring systems.

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents.

The phrase "meta (3) position with respect to the point of attachment of the A ring", refers to the position on the ring where the substituent (e.g. —CN) is adjoined and is shown below with an arrow, wherein z represents a carbon atom or nitrogen:

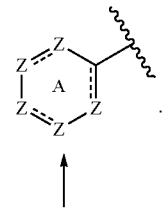

Similarly, para (4) position substitution refers to attachment of a substituent at the position indicated below, with respect to the point of attachment (e.g. of the B ring):

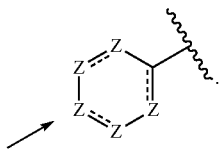

Similarly, ortho or 2-position refers to attachment of a substituent at the position indicated below, with respect to the point of attachment:

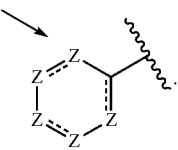

The term "halophenyl" as used herein refers to phenyl, wherein one or more (e.g., 1, 2, 3, 4 or 5) hydrogen atoms of the phenyl are each replaced independently by a halo substituent. Examples of halophenyl include but are not limited to fluorophenyl, 2,3-dichlorophenyl, 3-bromo-4-fluorophenyl and pentafluorophenyl.

The term "haloheteroaryl" as used herein refers to a heteroaryl, wherein one or more (e.g., 1, 2, 3, 4 or 5) hydrogen atoms of the heteroaryl are each replaced independently by a halo substituent. Examples of haloheteroaryl include but are not limited to 2-fluorofuryl, 2,3-dichloropyridinyl and 8-chloro-3-fluoroquinolinyl.

The term "haloheterocycle" as used herein refers to a heterocycle, wherein one or more (e.g., 1, 2, 3, 4 or 5) hydrogen atoms of the heterocycle are each replaced independently by a halo substituent. Examples of haloheteroaryl include but are not limited to 2-fluoropiperidinyl, 2-chloro-3-fluoropiperazinyl and 3-bromopyrrolidinyl.

One skilled in the art will recognize that substituents and other moieties of the compounds of formula I should be selected in order to provide a compound which is sufficiently stable to provide a pharmaceutically useful compound which can be formulated into an acceptably stable pharmaceutical composition. Compounds of formula I which have such stability are contemplated as falling within the scope of the present invention. Similarly, one skilled in the art will recognize that substituents and other moieties of the compounds detailed herein, including a compound of any one of formulas I, Ia, Ib, Ic, Id, Ie, If, Ig, Ih, Ii, Ij and Ik, or a pharmaceutically acceptable salt thereof, should be selected in order to provide a compound which is sufficiently stable to provide a pharmaceutically useful compound which can be formulated into an acceptably stable pharmaceutical composition. Compounds as detailed herein which have such stability are contemplated as falling within the scope of the present invention.

The modifier "about" used in connection with a quantity is inclusive of the stated value and has the meaning dictated by the context (e.g., includes the degree of error associated with measurement of the particular quantity). The word "about" may also be represented symbolically by "~" in the context of a chemical measurement (e.g., ~50 mg or pH~7).

As used herein, "treatment" or "treating" is an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In some embodiments, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and/or c) relieving the disease or condition, e.g., causing the regression of clinical symptoms, ameliorating the disease state, delaying the progression of the disease, increasing the quality of life, and/or prolonging survival.

As used herein, "delaying" development of a disease or condition means to defer, hinder, slow, retard, stabilize and/or postpone development of the disease or condition. This delay can be of varying lengths of time, depending on the history of the disease and/or subject being treated. As is evident to one skilled in the art, a sufficient or significant delay can, in effect, encompass prevention, in that the subject does not develop the disease or condition. For example, a method that "delays" development of AIDS is a method that reduces the probability of disease development in a given time frame and/or reduces extent of the disease in a given time frame, when compared to not using the method. Such comparisons may be based on clinical studies, using a statistically significant number of subjects. For example, the development of AIDS can be detected using known methods, such as confirming a subject's $HIV^+$ status and assessing the subject's T-cell count or other indication of AIDS development, such as extreme fatigue, weight loss, persistent diarrhea, high fever, swollen lymph nodes in the neck, armpits or groin, or presence of an opportunistic condition that is known to be associated with AIDS (e.g., a condition that is generally not present in subjects with functioning immune systems but does occur in AIDS patients). Development may also refer to disease progression that may be initially undetectable and includes occurrence, recurrence and onset.

As used herein, "prevention" or "preventing" refers to a regimen that protects against the onset of the disease or disorder such that the clinical symptoms of the disease do not develop. Thus, "prevention" relates to administration of a therapy (e.g., administration of a therapeutic substance) to a subject before signs of the disease are detectable in the subject (e.g., administration of a therapeutic substance to a subject in the absence of detectable infectious agent (e.g., virus) in the subject). The subject may be an individual at risk of developing the disease or disorder, such as an individual who has one or more risk factors known to be associated with development or onset of the disease or disorder. Thus, the term "preventing HIV infection" refers to administering to a subject who does not have a detectable HIV infection an anti-HIV therapeutic substance. It is understood that the subject for anti-HIV preventative therapy may be an individual at risk of contracting the HIV virus. Further, it is understood that prevention may not result in complete protection against onset of the disease or disorder. In some instances, prevention includes reducing the risk of developing the disease or disorder. The reduction of the risk may not result in complete elimination of the risk of developing the disease or disorder.

As used herein, an "at risk" individual is an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). For example, individuals at risk for AIDS are those having HIV.

As used herein, the term "therapeutically effective amount" or "effective amount" refers to an amount that is effective to elicit the desired biological or medical response, including the amount of a compound that, when administered to a subject for treating a disease, is sufficient to effect such treatment for the disease or to an amount that is effective to protect against the contracting or onset of a disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment outcome. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

Stereoisomers

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York.

The term "chiral" refers to molecules which have the property of non-superimposability of the minor image partner, while the term "achiral" refers to molecules which are superimposable on their minor image partner.

The term "stereoisomers" refers to compounds which have identical chemical constitution, but differ with regard to the arrangement of the atoms or groups in space.

"Diastereomer" refers to a stereoisomer with two or more centers or axes of chirality and whose molecules are not mirror images of one another. Diastereomers typically have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another. A mixture of enantiomers at a ratio other than 1:1 is a "scalemic" mixture.

The compounds disclosed herein may have chiral centers, e.g., chiral carbon atoms. Such compounds thus include racemic mixtures of all stereoisomers, including enantiomers, diastereomers, and atropisomers. In addition, the compounds disclosed herein include enriched or resolved optical isomers at any or all asymmetric, chiral atoms. Similarly, compositions disclosed herein also include racemic mixtures of all stereoisomers, including enantiomers, diastereomers, and atropisomers of compounds disclosed herein. In addition, the compounds and compositions disclosed herein include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures can be separated into their individual, substantially optically pure isomers through well-known techniques such as, for example, the separation of diastereomeric salts formed with optically active adjuncts, e.g., acids or bases followed by conversion back to the optically active substances. The desired optical isomer can also be synthesized by means of stereospecific reactions, beginning with the appropriate stereoisomer of the desired starting material.

The invention includes any or all of the stereochemical forms, including any enantiomeric or diastereomeric forms and geometric isomers of the compounds described, or mixtures thereof. Unless stereochemistry is explicitly indicated in a chemical structure or name, the structure or name is intended to embrace all possible stereoisomers, including geometric isomers, of a compound depicted. Compositions comprising a compound of the invention are also intended, such as a composition of substantially pure compound, including a specific stereochemical form, including a specific geometric isomer, thereof. Compositions comprising a mixture of compounds of the invention in any ratio are also embraced by the invention, including mixtures of two or more stereochemical forms of a compound of the invention in any ratio, such that racemic, non-racemic, enantio-enriched and scalemic mixtures of a compound are embraced, or mixtures thereof.

It is to be understood that for compounds disclosed herein when a bond is drawn in a non-stereochemical manner (e.g., flat) the atom to which the bond is attached includes all stereochemical possibilities. It is also to be understood that when a bond is drawn in a stereochemical manner (e.g., bold, bold-wedge, dashed or dashed-wedge) the atom to which the stereochemical bond is attached has the stereochemistry as shown unless otherwise noted. Accordingly, in some embodiments, a compound disclosed herein is greater than 50% a single enantiomer. In some embodiments, a compound disclosed herein is at least 80% a single enantiomer. In some embodiments, a compound disclosed herein is at least 90% a single enantiomer. In some embodiments, a compound disclosed herein is at least 98% a single enantiomer. In some embodiments, a compound disclosed herein is at least 99% a single enantiomer. In some embodiments, a compound disclosed herein is greater than 50% a single diastereomer. In some embodiments, a compound disclosed herein is at least 80% a single diastereomer. In some embodiments, a compound disclosed herein is at least 90% a single diastereomer. In some embodiments, a compound disclosed herein is at least 98% a single diastereomer. In some embodiments, a compound disclosed herein is at least 99% a single diastereomer.

Accordingly, in some embodiments, a composition disclosed herein is greater than 50% a single enantiomer. In some embodiments, a composition disclosed herein is at least 80% a single enantiomer. In some embodiments, a composition disclosed herein is at least 90% a single enantiomer. In some embodiments, a composition disclosed herein is at least 98% a single enantiomer. In some embodiments, a composition disclosed herein is at least 99% a single enantiomer. In some embodiments, a composition disclosed herein is greater than 50% a single diastereomer. In some embodiments, a composition disclosed herein is at least 80% a single diastereomer. In some embodiments, a composition disclosed herein is at least 90% a single diastereomer. In some embodiments, a composition disclosed herein is at least 98% a single diastereomer. In some embodiments, a composition disclosed herein is at least 99% a single diastereomer.

In some embodiments, the compounds disclosed herein display atropisomerism resulting from steric hindrance affecting the axial rotation rate around a single bond. In certain circumstances, the resultant conformational isomers are observed as distinct entities by characterization techniques such as NMR and HPLC. In certain embodiments, the compounds disclosed herein exist as a mixture of atropisomers. The synthetic examples provided herein note where such mixtures of atropisomers have been observed. However, the detection of atropisomers is dependent on factors such as temperature, solvent, conditions of purification, and timescale of spectroscopic technique. Characterization data presented herein may not represent the equilibrium state depending on the conditions of purification, isolation, handling, solvents used, and temperature.

Tautomers

The compounds disclosed herein can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention. Another non-limiting example includes keto-enol tautomers of heteroaryls. Such tautomers are exemplified by T1/T1', T2/T2' and T3/T3'. All such tautomeric forms are also within the scope of the invention.

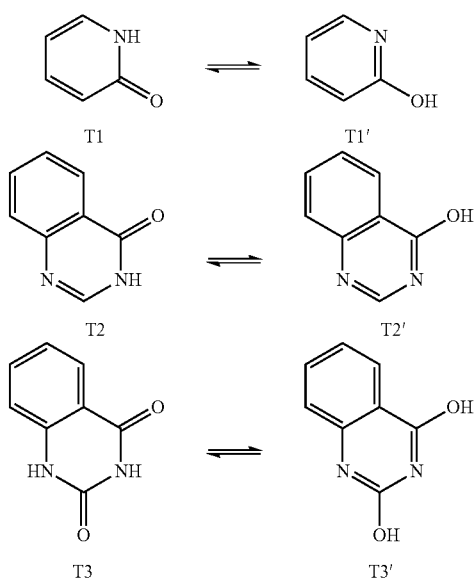

Protecting Groups

"Protecting group" refers to a moiety of a compound that masks or alters the properties of a functional group or the properties of the compound as a whole. Chemical protecting groups and strategies for protection/de-protection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Salts and Hydrates

"Pharmaceutically acceptable salt" refers to a salt of a compound that is pharmaceutically acceptable and that possesses (or can be converted to a form that possesses) the desired pharmacological activity of the parent compound. Pharmaceutically acceptable salts are generally regarded as safe and suitable for use without undue toxicity, irritation, allergic response, and the like, commensurate with a reasonable benefit/risk ratio. Examples of "pharmaceutically acceptable salts" of the compounds disclosed herein include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a nitrogen atom or an amino group include for example salts of organic carboxylic acids such as acetic, benzoic, camphorsulfonic, citric, glucoheptonic, gluconic, lactic, fumaric, tartaric, maleic, malonic, malic, mandelic, isethionic, lactobionic, succinic, 2-napththalenesulfonic, oleic, palmitic, propionic, stearic, and trimethylacetic acids; organic sulfonic acids, such as methanesulfonic, ethanesulfonic, benzenesulfonic and p-toluenesulfonic acids; and inorganic acids, such as hydrochloric, hydrobromic, sulfuric, nitric, phosphoric and sulfamic acids. Pharmaceutically acceptable salts of a compound of a hydroxy group include the anion of said compound in combination with a suitable cation such as $Na^+$ and $NX_4^+$ (wherein X is independently selected from H or a $C_1$-$C_4$ alkyl group). Pharmaceutically acceptable salts also include salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, Pa., (2005), at p. 732, Table 38-5, both of which are hereby incorporated by reference herein.

For therapeutic use, salts of active ingredients of the compounds disclosed herein will typically be pharmaceutically acceptable, i.e., they will be salts derived from a physiologically acceptable acid or base. However, salts of acids or bases which are not pharmaceutically acceptable may also find use, for example, in the preparation or purification of a compound of formula I or another compound disclosed herein. All salts, whether or not derived from a physiologically acceptable acid or base, are within the scope of the present invention.

Metal salts typically are prepared by reacting the metal hydroxide with a compound disclosed herein. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, such as amines. Finally, it is to be understood that the compositions herein comprise compounds disclosed herein in their un-ionized, as well as zwitterionic form, and combinations with stoichiometric amounts of water as in hydrates.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

Isotopes

Any formula or structure given herein, including Formula I, or any Formula disclosed herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium) $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes compounds of Formula I, or any Formula disclosed herein, in which from 1 to "n" hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal. See, for example, Foster, "Deuterium Isotope Effects in Studies of Drug Metabolism", *Trends Pharmacol. Sci.* 5(12): 524-527 (1984). Such compounds are synthesized by means well known in the art, for example by employing starting materials in which one or more hydrogen atoms have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the Formula I, or any Formula disclosed herein.

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, in certain embodiments, a —CH$_3$ group is replaced with —CD$_3$.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

Specific values listed below for radicals, substituents, and ranges in the embodiments of the invention are for illustration only; they do not exclude other defined values or other values within defined ranges for the radicals and substituents.

II. Compounds

In some embodiments, disclosed herein is a compound of formula I:

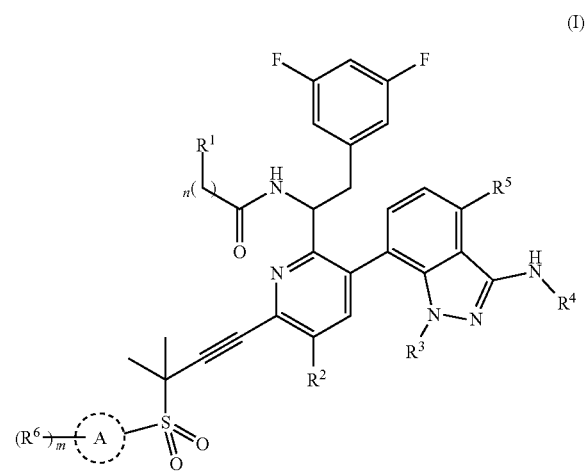

wherein
A is 3-6 membered carbocycle;
n is 0, 1, or 2;
m is 0, 1, or 2;
$R^1$ is 5-12 membered heteroaryl or 5-12 membered heterocycle, wherein any 5-12 membered heteroaryl or 5-12 membered heterocycle of $R^1$ is unsubstituted or substituted with 1, 2, 3, 4 or 5 $Z^1$ groups, wherein the $Z^1$ groups are the same or different;
each $Z^1$ is independently (C$_1$-C$_6$)alkyl, (C$_3$-C$_7$)carbocycle, halogen, or —CN, wherein any (C$_1$-C$_6$)alkyl or (C$_3$-C$_7$) carbocycle of $Z^1$ is unsubstituted or substituted with 1, 2, 3, 4 or 5 $Z^{1a}$ groups, wherein the $Z^{1a}$ groups are the same or different;
each $Z^{1a}$ is independently halogen, (C$_3$-C$_7$)carbocycle, —OH, or —CN;
$R^2$ is hydrogen, halogen, —OH, or —CN;
$R^3$ is (C$_1$-C$_6$)alkyl or 3-5 membered heterocycle, wherein the (C$_1$-C$_6$)alkyl is unsubstituted or substituted with 1, 2, or 3 halogen atoms;
$R^4$ is hydrogen, —S(O)$_2$—(C$_1$-C$_6$)alkyl, —S(O)$_2$—(C$_3$-C$_6$) carbocycle, or 5-6 membered heteroaryl, wherein any —S(O)$_2$—(C$_1$-C$_6$) alkyl, —S(O)$_2$—(C$_3$-C$_6$)carbocycle, or 5-6 membered heteroaryl of $R^4$ is unsubstituted or substituted with 1, 2, or 3 $Z^2$ groups, wherein the $Z^2$ groups are the same or different;
$Z^2$ is (C$_1$-C$_6$)alkyl or (C$_3$-C$_6$)carbocycle, wherein any (C$_1$-C$_6$)alkyl or (C$_3$-C$_6$)carbocycle is unsubstituted or substituted with 1, 2, or 3 $Z^{2a}$ groups, wherein the $Z^{2a}$ groups are the same or different;

$Z^2a$ is hydroxyl or halogen;
$R^5$ is hydrogen or halogen; and
$R^6$ is $(C_1-C_3)$alkyl;
or a pharmaceutically acceptable salt thereof.

In some embodiments, disclosed herein is a compound of formula Ia:

(Ia)

wherein:
n is 0, 1, or 2;
m is 0 or 1;
$R^1$ is 5-9 membered heteroaryl or 5-9 membered heterocycle, wherein any 5-9 membered heteroaryl or 5-9 membered heterocycle of $R^1$ is unsubstituted or substituted with 1, 2, 3, 4 or 5 $Z^1$ groups, wherein the $Z^1$ groups are the same or different;
each $Z^1$ is independently $(C_1-C_6)$alkyl, $(C_3-C_7)$carbocycle, or halogen, wherein any $(C_1-C_6)$alkyl or $(C_3-C_7)$carbocycle of $Z^1$ is unsubstituted or substituted with 1, 2, 3, 4 or 5 $Z^{1a}$ groups, wherein the $Z^{1a}$ groups are the same or different;
each $Z^{1a}$ is independently halogen or $(C_3-C_7)$carbocycle;
$R^2$ is hydrogen or iodide;
$R^3$ is $(C_1-C_2)$alkyl or 3-5 membered heterocycle, wherein the $(C_1-C_2)$alkyl is unsubstituted or substituted with 2 or 3 halogen atoms;
$R^4$ is hydrogen, $-S(O)_2-(C_1-C_2)$alkyl, $-S(O)_2$-cyclopropyl, or 5-membered heteroaryl, wherein any $-S(O)_2-(C_1-C_2)$alkyl, $-S(O)_2$-cyclopropyl, or 5-membered heteroaryl of $R^4$ is unsubstituted or substituted with 1, 2, or 3 $Z^2$ groups, wherein the $Z^2$ groups are the same or different;
$Z^2$ is $(C_1-C_3)$alkyl or cyclopropyl, wherein any $(C_1-C_3)$alkyl or cyclopropyl is unsubstituted or substituted with 1, 2, or 3 $Z^{2a}$ groups, wherein the $Z^{2a}$ groups are the same or different;
$Z^{2a}$ is hydroxyl or fluorine;
$R^5$ is hydrogen, chorine, or fluorine; and
$R^6$ is $(C_1-C_3)$alkyl.

In some embodiments, disclosed herein is a compound of Formula (Ia), or a pharmaceutically acceptable salt thereof, wherein:
n is 0, 1, or 2;
m is 0 or 1;
$R^1$ is 5-9 membered heteroaryl that is unsubstituted or substituted with 1, 2, 3, 4 or 5 $Z^1$ groups, wherein the $Z^1$ groups are the same or different;
each $Z^1$ is independently $(C_1-C_6)$alkyl, $(C_3-C_7)$carbocycle, or halogen, wherein any $(C_1-C_6)$alkyl or $(C_3-C_7)$carbocycle of $Z^1$ is unsubstituted or substituted with 1, 2, 3, 4 or 5 $Z^{1a}$ groups, wherein the $Z^{1a}$ groups are the same or different;
each $Z^{1a}$ is independently halogen or $(C_3-C_7)$carbocycle;
$R^2$ is hydrogen or iodide;
$R^3$ is $(C_1-C_2)$alkyl or 3-5 membered heterocycle, wherein the $(C_1-C_2)$alkyl is unsubstituted or substituted with 2 or 3 fluorine atoms;
$R^4$ is hydrogen, $-S(O)_2-(C_1-C_2)$alkyl, $-S(O)_2$-cyclopropyl, or 5-membered heteroaryl, wherein any $-S(O)_2-(C_1-C_2)$alkyl, $-S(O)_2$-cyclopropyl, or 5-membered heteroaryl of $R^4$ is unsubstituted or substituted with 1, 2, or 3 $Z^2$ groups, wherein the $Z^2$ groups are the same or different;
$Z^2$ is $(C_1-C_3)$alkyl or cyclopropyl, wherein any $(C_1-C_3)$alkyl or cyclopropyl is unsubstituted or substituted with 1, 2, or 3 $Z^{2a}$ groups, wherein the $Z^{2a}$ groups are the same or different;
$Z^{2a}$ is hydroxyl or fluorine;
$R^5$ is hydrogen, chorine, or fluorine; and
$R^6$ is methyl.

In some embodiments, disclosed herein is a compound of Formula (Ia), or a pharmaceutically acceptable salt thereof, wherein:
n is 0, 1, or 2;
m is 0 or 1;
$R^1$ is 5-9 membered heteroaryl that is unsubstituted or substituted with 1, 2, 3, 4 or 5 $Z^1$ groups, wherein the $Z^1$ groups are the same or different;
each $Z^1$ is independently $(C_1-C_6)$alkyl, $(C_3-C_7)$carbocycle, or halogen, wherein any $(C_1-C_6)$alkyl or $(C_3-C_7)$carbocycle of $Z^1$ is unsubstituted or substituted with 1, 2, 3, 4 or 5 $Z^{1a}$ groups, wherein the $Z^{1a}$ groups are the same or different;
each $Z^{1a}$ is independently halogen or $(C_3-C_7)$carbocycle;
$R^2$ is hydrogen or iodide;
$R^3$ is $(C_1-C_2)$alkyl or 4-membered heterocycle, wherein the $(C_1-C_2)$alkyl is unsubstituted or substituted with 2 or 3 fluorine atoms;
$R^4$ is $-S(O)_2-(C_1-C_2)$alkyl, $-S(O)_2$-cyclopropyl, or 5-membered heteroaryl, wherein any $-S(O)_2-(C_1-C_2)$alkyl, $-S(O)_2$-cyclopropyl, or 5-membered heteroaryl of $R^4$ is unsubstituted or substituted with 1, 2, or 3 $Z^2$ groups, wherein the $Z^2$ groups are the same or different;
$Z^2$ is $(C_1-C_3)$alkyl or cyclopropyl, wherein any $(C_1-C_3)$alkyl or cyclopropyl is unsubstituted or substituted with 1, 2, or 3 $Z^{2a}$ groups, wherein the $Z^{2a}$ groups are the same or different;
$Z^{2a}$ is hydroxyl or fluorine;
$R^5$ is hydrogen, chorine, or fluorine; and
$R^6$ is methyl.

In some embodiments, disclosed herein is a compound of Formula (Ia), or a pharmaceutically acceptable salt thereof, wherein:
n is 0, 1, or 2;
m is 0 or 1;
$R^1$ is 5-9 membered heteroaryl that is unsubstituted or substituted with 1, 2, 3, 4 or 5 $Z^1$ groups, wherein the $Z^1$ groups are the same or different;
each $Z^1$ is independently $(C_1-C_6)$alkyl, $(C_3-C_7)$carbocycle, or halogen, wherein any $(C_1-C_6)$alkyl or $(C_3-C_7)$carbocycle of $Z^1$ is unsubstituted or substituted with 1, 2, 3, 4 or 5 $Z^{1a}$ groups, wherein the $Z^{1a}$ groups are the same or different;

each $Z^{1a}$ is independently halogen or $(C_3$-$C_7)$carbocycle;
$R^2$ is hydrogen;
$R^3$ is $(C_1$-$C_2)$alkyl or 4 membered heterocycle, wherein the $(C_1$-$C_2)$alkyl is unsubstituted or substituted with 2 or 3 fluorine atoms;
$R^4$ is $—S(O)_2—(C_1$-$C_2)$alkyl, $—S(O)_2$-cyclopropyl, or 5-membered heteroaryl, wherein any $—S(O)_2—(C_1$-$C_2)$ alkyl, $—S(O)_2$-cyclopropyl, or 5-membered heteroaryl of $R^4$ is unsubstituted or substituted with 1, 2, or 3 $Z^2$ groups, wherein the $Z^2$ groups are the same or different;
$Z^2$ is $(C_1$-$C_3)$alkyl or cyclopropyl, wherein any $(C_1$-$C_3)$alkyl or cyclopropyl is unsubstituted or substituted with 1, 2, or 3 $Z^{2a}$ groups, wherein the $Z^{2a}$ groups are the same or different;
$Z^2$a is hydroxyl or fluorine;
$R^5$ is hydrogen, chorine, or fluorine; and
$R^6$ is methyl.

In some embodiments, a specific group of compounds of formula I are compounds of formula (Ib):

(Ib)

or a pharmaceutically acceptable salt thereof.

In some embodiments, a specific group of compounds of formula I are compounds of formula (Ic):

(Ic)

or a pharmaceutically acceptable salt thereof.

In some embodiments, a specific group of compounds of formula I are compounds of formula (Id):

(Id)

or a pharmaceutically acceptable salt thereof.

In some embodiments, a specific group of compounds of formula I are compounds of formula (Ie):

(Ie)

wherein
each $X^1$ and $X^2$ are independently N or CH;
or a pharmaceutically acceptable salt thereof.

In some embodiments, a specific group of compounds of formula I are compounds of formula (If):

(If)

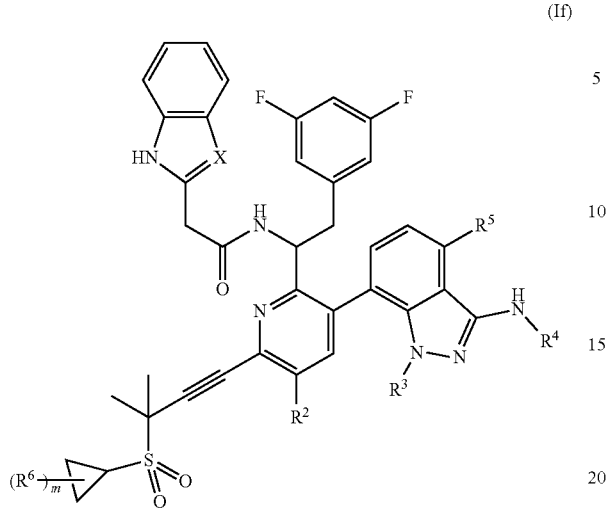

wherein
X¹ is N or CH;
or a pharmaceutically acceptable salt thereof.

(Ih)

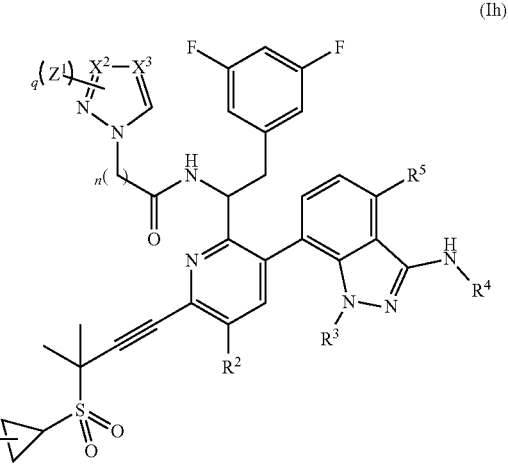

wherein
q is 0, 1, 2, or 3;
each X² and X³ are independently N or CH;
or a pharmaceutically acceptable salt thereof.

In some embodiments, a specific group of compounds of formula I are compounds of formula (Ig):

(Ig)

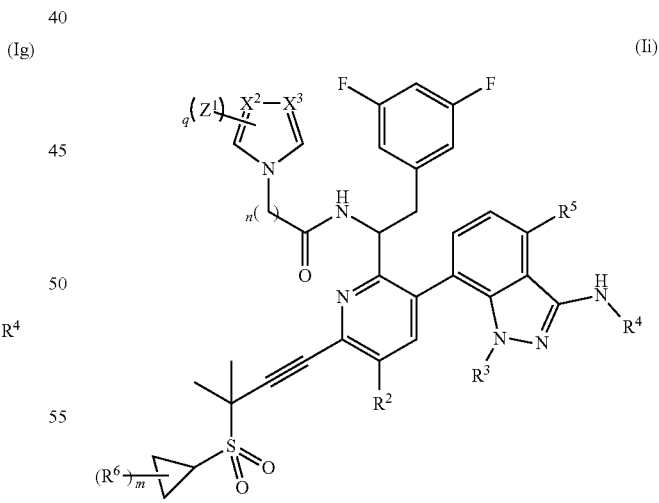

wherein
q is 0, 1, 2, or 3;
each X¹, X², and X³ are independently N or CH;
or a pharmaceutically acceptable salt thereof.

In some embodiments, a specific group of compounds of formula I are compounds of formula (Ih):

In some embodiments, a specific group of compounds of formula I are compounds of formula (Ii):

(Ii)

wherein
q is 0, 1, 2, or 3;
each X² and X³ are independently N or CH;
or a pharmaceutically acceptable salt thereof.

In some embodiments, a specific group of compounds of formula I are compounds of formula (Ij):

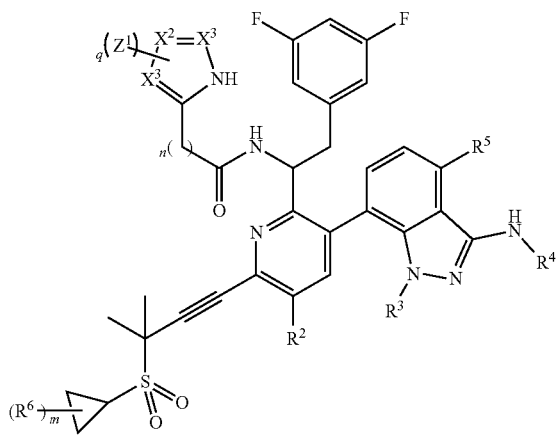

(Ij)

wherein
q is 0, 1, 2, or 3;
each $X^1$, $X^2$, and $X^3$ are independently N or CH;
or a pharmaceutically acceptable salt thereof.

In some embodiments, a specific group of compounds of formula I are compounds of formula (Ik):

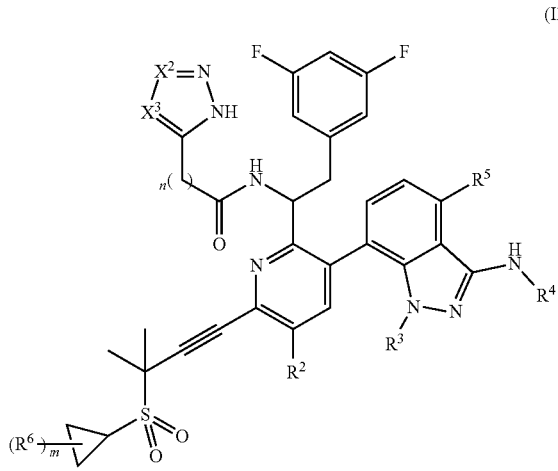

(Ik)

wherein
each $X^2$ and $X^3$ are independently N or CH;
or a pharmaceutically acceptable salt thereof.

Specific values listed below are values for compounds of formula I as well as all related formulas (e.g., formulas I, Ia, Ib, Ic, Id, Ie, If, Ig, Ih, Ii, Ij and Ik). It is to be understood that two or more values may combined. Thus, it is to be understood that any variable for compounds of formula I may be combined with any other variable for compounds of formula I the same as if each and every combination of variables were specifically and individually listed. For example, it is understood that any specific value of $R^1$ detailed herein for compounds of formula I may be combined with any other specific value for one or more of the variables, e.g., $Z^1$, $Z^2$, $R^2$, $R^3$, $R^4$, $R^5$, $R^6$ the same as if each and every combination were specifically and individually listed.

In some embodiments, a specific group of compounds of formula I, or a pharmaceutically acceptable salt thereof, are compounds wherein A is a cyclopropyl group that is unsubstituted or substituted with 1 or 2 $R^6$ groups In some embodiments, a specific group of compounds of formula I, or a pharmaceutically acceptable salt thereof, are compounds wherein n is 0.

In some embodiments, a specific group of compounds of formula I, or a pharmaceutically acceptable salt thereof, are compounds wherein n is 1.

In some embodiments, a specific group of compounds of formula I, or a pharmaceutically acceptable salt thereof, are compounds wherein n is 2.

In some embodiments, a specific group of compounds of formula I, or a pharmaceutically acceptable salt thereof, are compounds wherein n is 3.

In some embodiments, a specific group of compounds of formula I, or a pharmaceutically acceptable salt thereof, are compounds wherein m is 0.

In some embodiments, a specific group of compounds of formula I, or a pharmaceutically acceptable salt thereof, are compounds wherein m is 1.

In some embodiments, a specific group of compounds of formula I, or a pharmaceutically acceptable salt thereof, are compounds wherein $1Z^1$ is:

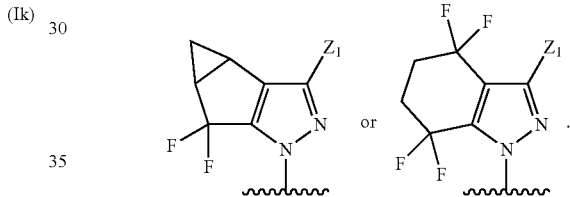

In some embodiments, a specific group of compounds of formula I, or a pharmaceutically acceptable salt thereof, are compounds wherein $1Z^1$ is:

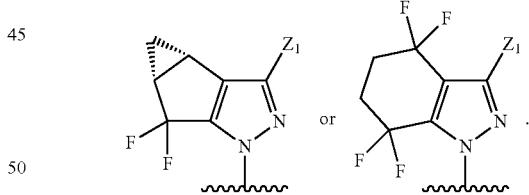

In some embodiments, a specific group of compounds of formula I, or a pharmaceutically acceptable salt thereof, are compounds wherein $1Z^1$ is:

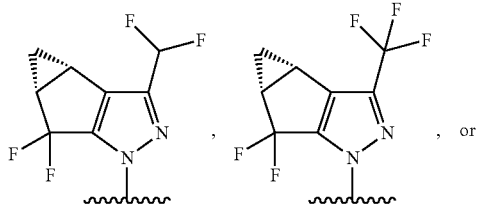

-continued

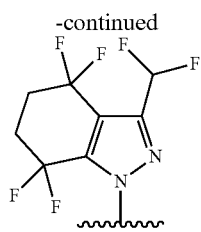

In some embodiments, a specific group of compounds of formula I, or a pharmaceutically acceptable salt thereof, are compounds wherein $1Z^1$ is:

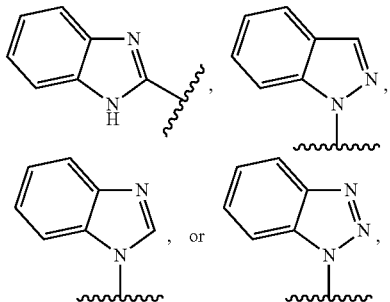

In some embodiments, a specific group of compounds of formula I, or a pharmaceutically acceptable salt thereof, are compounds wherein $R^1$ is:

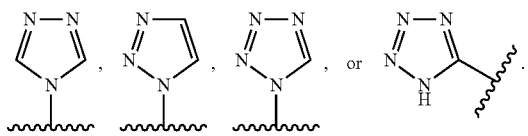

In some embodiments, a specific group of compounds of formula I, or a pharmaceutically acceptable salt thereof, are compounds wherein $R^1$ is:

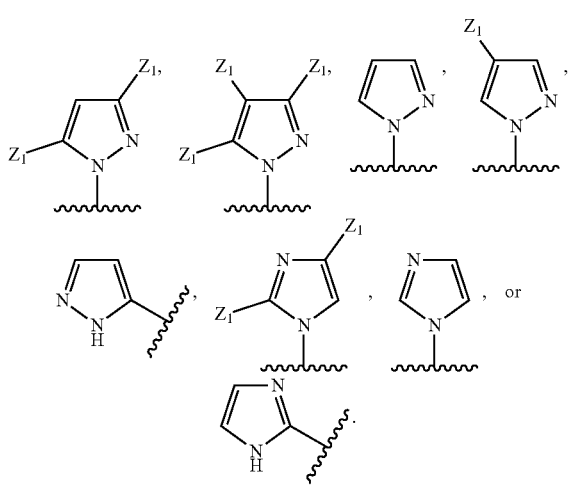

In some embodiments, a specific group of compounds of formula I, or a pharmaceutically acceptable salt thereof, are compounds wherein $R^1$ is:

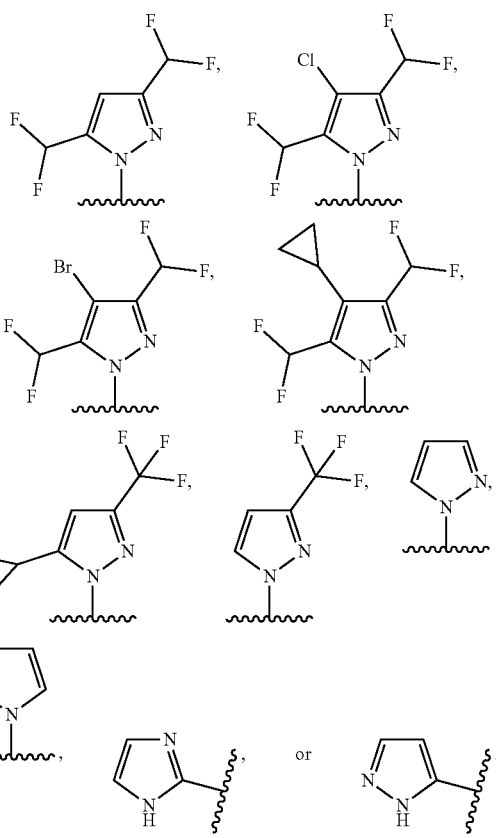

In some embodiments, a specific group of compounds of formula I, or a pharmaceutically acceptable salt thereof, are compounds wherein $Z^1$ is $(C_1-C_6)$alkyl substituted with 2 or 3 halogen atoms, a cyclopropyl group, or halogen.

In some embodiments, a specific group of compounds of formula I, or a pharmaceutically acceptable salt thereof, are compounds wherein $Z^1$ is —$CHF_2$, —$CF_3$, or halogen.

In some embodiments, a specific group of compounds of formula I, or a pharmaceutically acceptable salt thereof, are compounds wherein $Z^1$ is —$CHF_2$ or —$CF_3$.

In some embodiments, a specific group of compounds of formula I, or a pharmaceutically acceptable salt thereof, are compounds wherein $R^2$ is hydrogen or iodide.

In some embodiments, a specific group of compounds of formula I, or a pharmaceutically acceptable salt thereof, are compounds wherein $R^2$ is hydrogen.

In some embodiments, a specific group of compounds of formula I, or a pharmaceutically acceptable salt thereof, are compounds wherein $R^2$ is iodide.

In some embodiments, a specific group of compounds of formula I, or a pharmaceutically acceptable salt thereof, are compounds wherein $R^3$ is $(C_{1-3})$alkyl or a 4 membered heterocycle, wherein the $(C_{1-3})$alkyl is unsubstituted or substituted with 1, 2, or 3 halogen atoms.

In some embodiments, a specific group of compounds of formula I, or a pharmaceutically acceptable salt thereof, are compounds wherein $R^3$ is methyl, —$CH_2CHF_2$, —$CH_2CF_3$, or

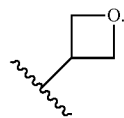

In some embodiments, a specific group of compounds of formula I, or a pharmaceutically acceptable salt thereof, are compounds wherein $R^3$ is methyl, —$CH_2CHF_2$, or —$CH_2CF_3$.

In some embodiments, a specific group of compounds of formula I, or a pharmaceutically acceptable salt thereof, are compounds wherein $R^4$ is hydrogen, —$S(O)_2$—$(C_{1-6})$alkyl, —$S(O)_2$—$(C_{3-6})$carbocycle, or 5-6 membered heteroaryl, wherein any —$S(O)_2$—$(C_{1-6})$alkyl, —$S(O)_2$—$(C_{3-6})$carbocycle, or 5-6 membered heteroaryl of $R^4$ is unsubstituted or substituted with 1, 2, or 3 $Z^2$ groups, wherein the $Z^2$ groups are the same or different.

In some embodiments, a specific group of compounds of formula I, or a pharmaceutically acceptable salt thereof, are compounds wherein $R^4$ is hydrogen.

In some embodiments, a specific group of compounds of formula I, or a pharmaceutically acceptable salt thereof, are compounds wherein $R^4$ is —$S(O)_2$—$(C_{1-2})$alkyl, —$S(O)_2$-cyclopropyl, or 5-membered heteroaryl, wherein any —$S(O)_2$—$(C_{1-2})$alkyl, —$S(O)_2$-cyclopropyl, or 5-membered heteroaryl of $R^4$ is unsubstituted or substituted with 1, 2, or 3 $Z^2$ groups, wherein the $Z^2$ groups are the same or different.

In some embodiments, a specific group of compounds of formula I, or a pharmaceutically acceptable salt thereof, are compounds wherein $R^4$ is —$S(O)_2$—$(C_{1-2})$alkyl, —$S(O)_2$-cyclopropyl, or an oxadiazole, wherein any —$S(O)_2$—$(C_{1-2})$alkyl, —$S(O)_2$-cyclopropyl, or oxadiazole of $R^4$ is unsubstituted or substituted with 1, 2, or 3 $Z^2$ groups, wherein the $Z^2$ groups are the same or different.

In some embodiments, a specific group of compounds of formula I, or a pharmaceutically acceptable salt thereof, are compounds wherein $R^4$ is

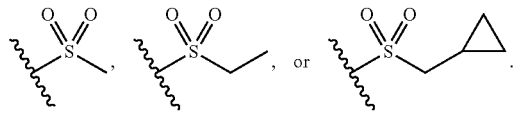

In some embodiments, a specific group of compounds of formula I, or a pharmaceutically acceptable salt thereof, are compounds wherein $R^4$ is

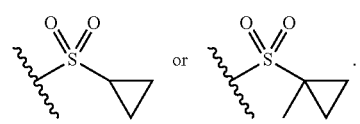

In some embodiments, a specific group of compounds of formula I, or a pharmaceutically acceptable salt thereof, are compounds wherein $R^4$ is

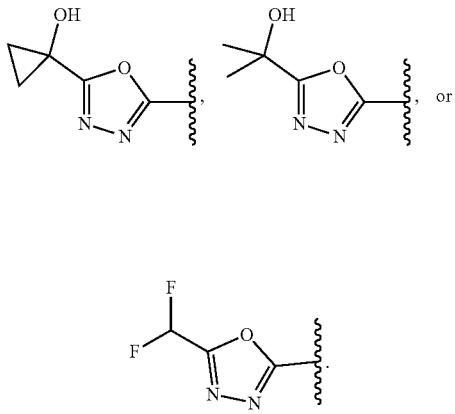

In some embodiments, a specific group of compounds of formula I, or a pharmaceutically acceptable salt thereof, are compounds wherein $R^5$ is hydrogen or halogen.

In some embodiments, a specific group of compounds of formula I, or a pharmaceutically acceptable salt thereof, are compounds wherein $R^5$ is hydrogen, chloride, or fluoride.

In some embodiments, a specific group of compounds of formula I, or a pharmaceutically acceptable salt thereof, are compounds wherein $R^5$ is chloride.

In some embodiments, a specific group of compounds of formula I, or a pharmaceutically acceptable salt thereof, are compounds wherein $R^6$ is hydrogen or methyl.

In some embodiments, a specific group of compounds of formula I, or a pharmaceutically acceptable salt thereof, are compounds wherein m is 1 and $R^6$ is $(C_1$-$C_3)$alkyl.

In some embodiments, a specific group of compounds of formula I, or a pharmaceutically acceptable salt thereof, are compounds wherein m is 1 and $R^6$ is methyl.

In some embodiments, the compound of formula I is selected from:

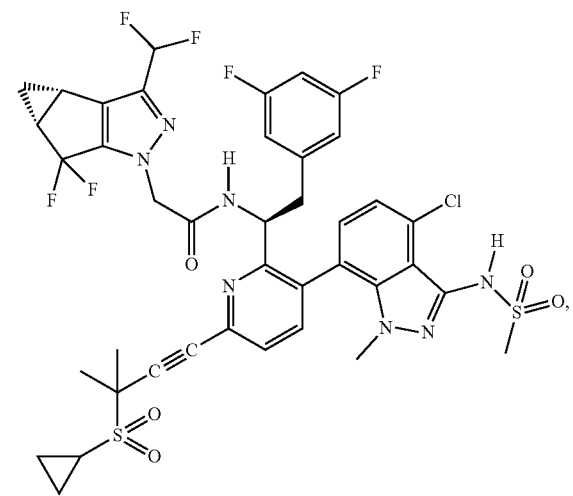

39
-continued
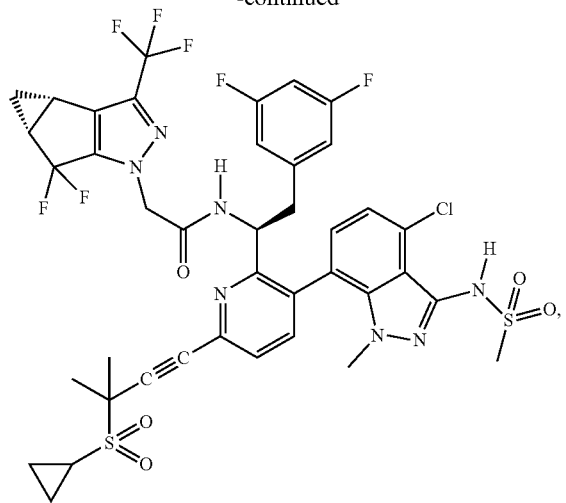
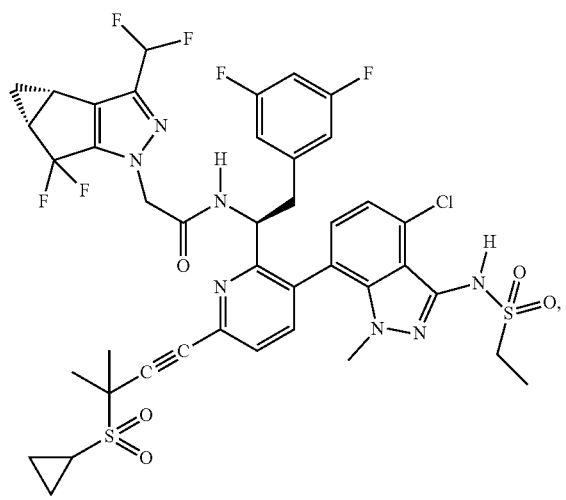
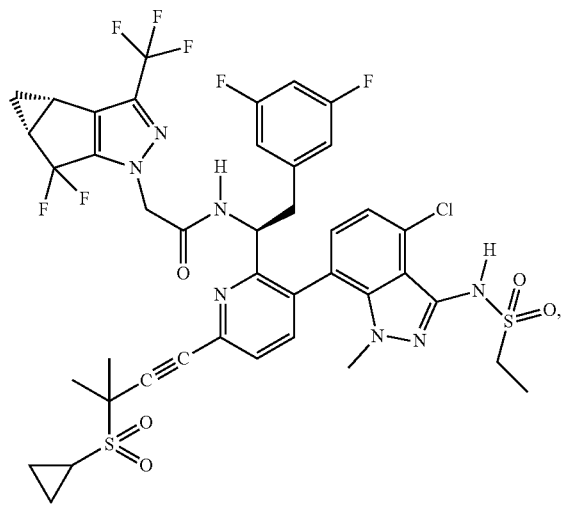
40
-continued
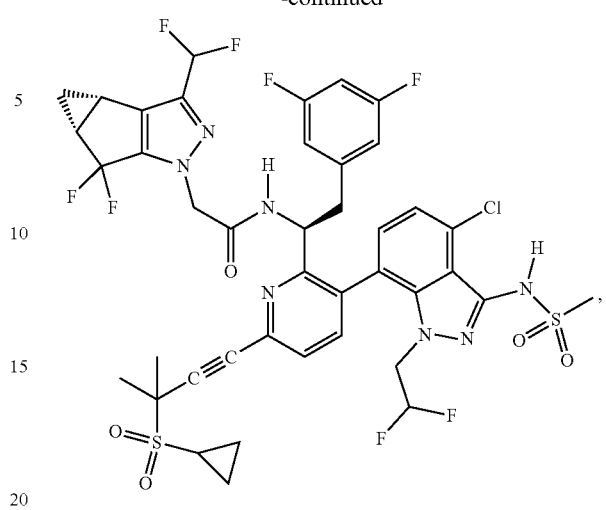
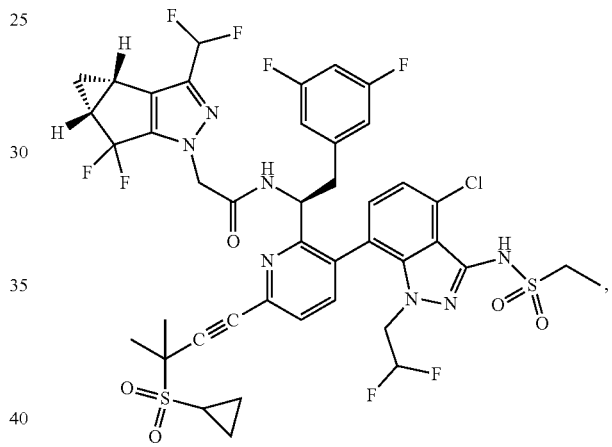
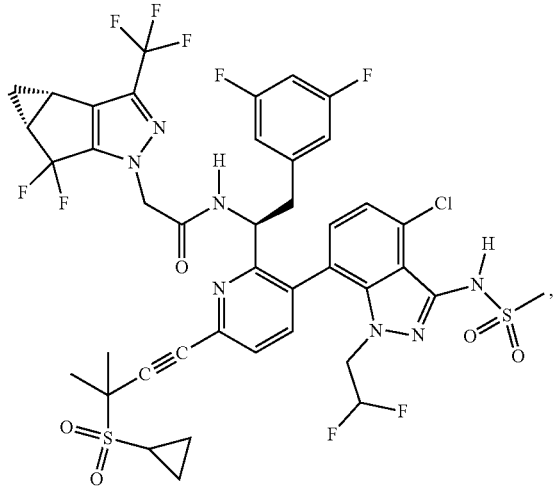

41
-continued
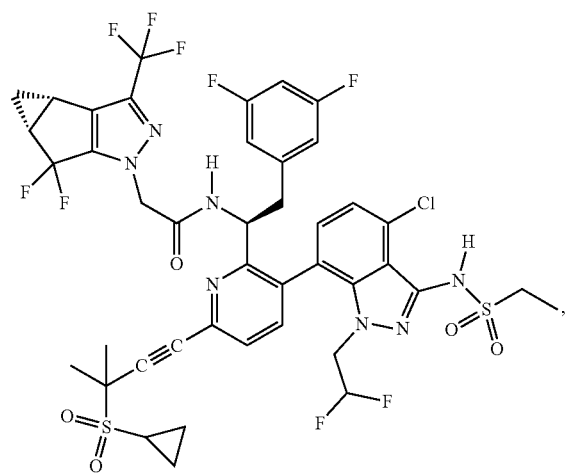
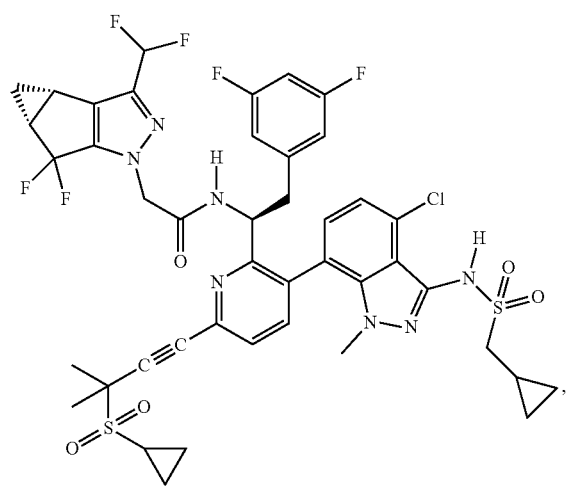
42
-continued
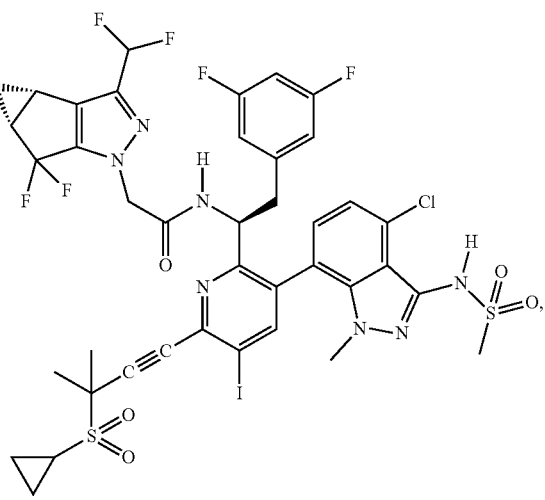
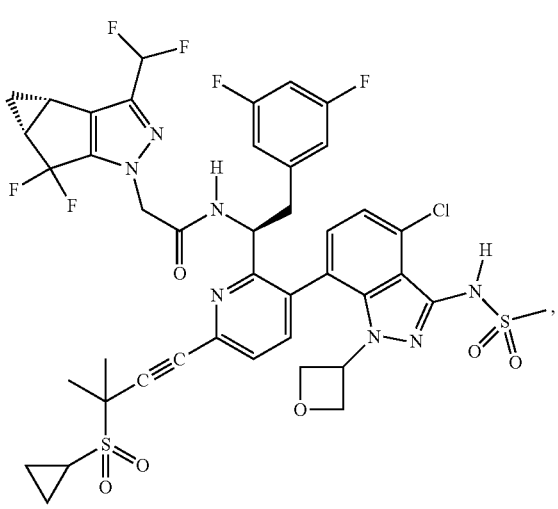

43
-continued
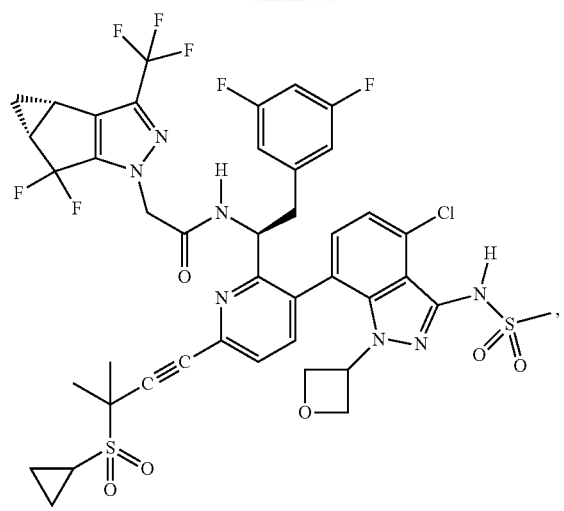
44
-continued
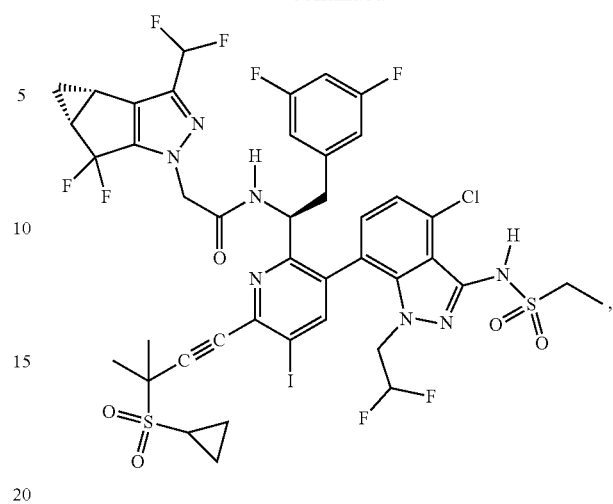
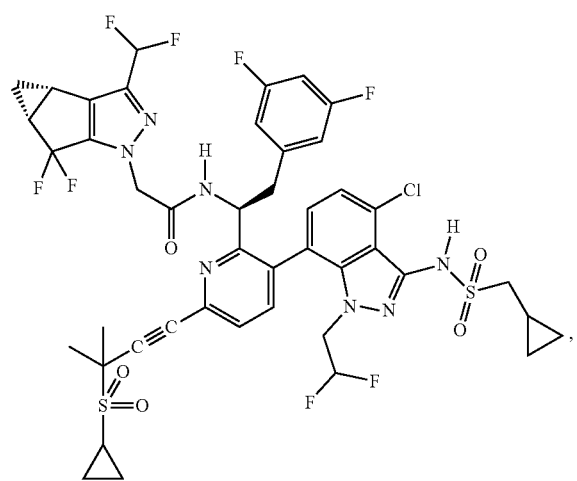
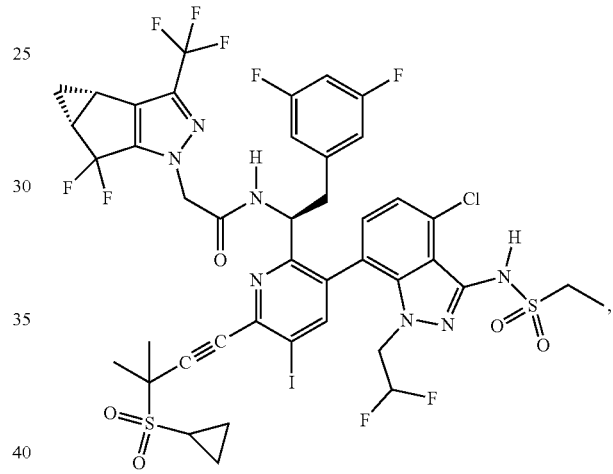
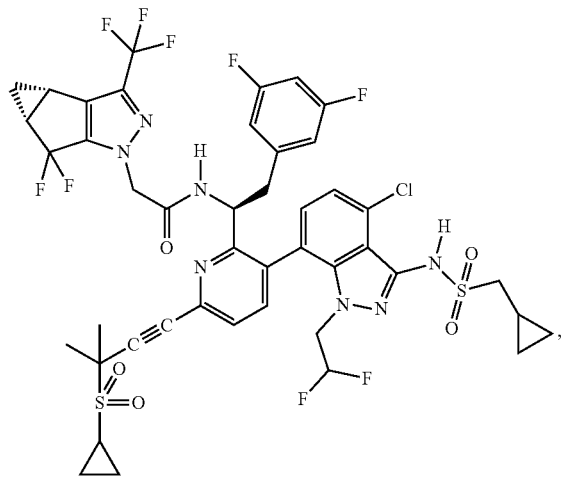
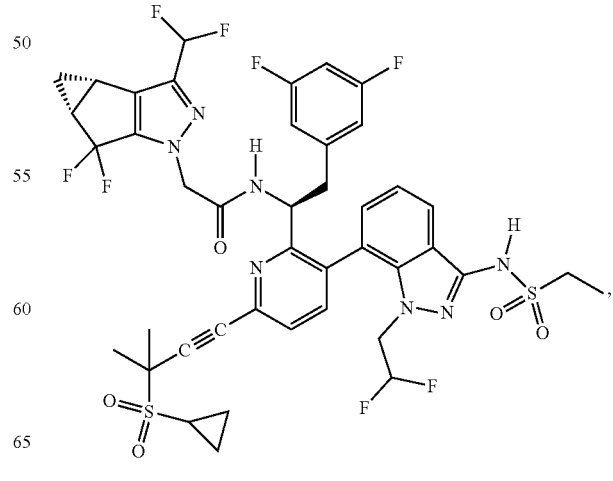

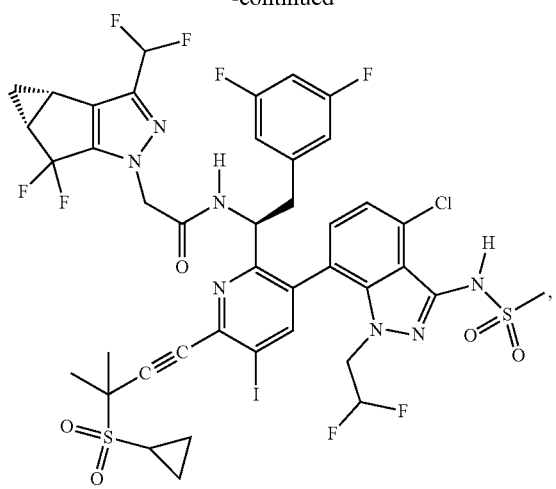
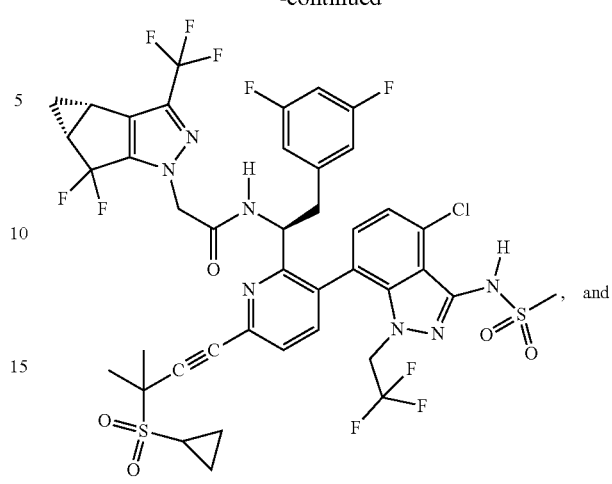
, and
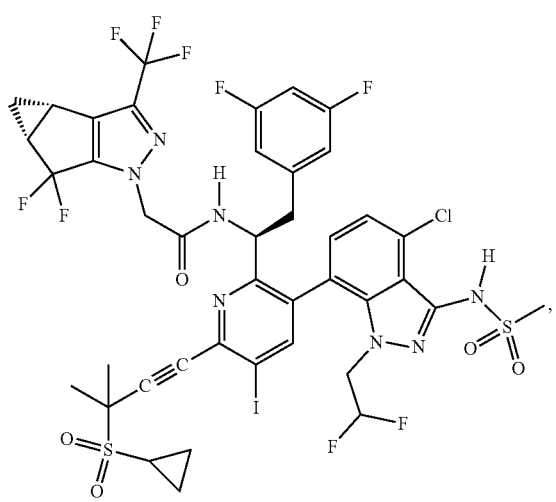
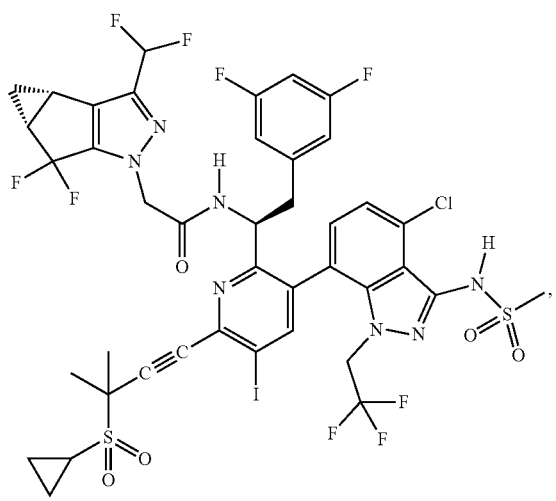
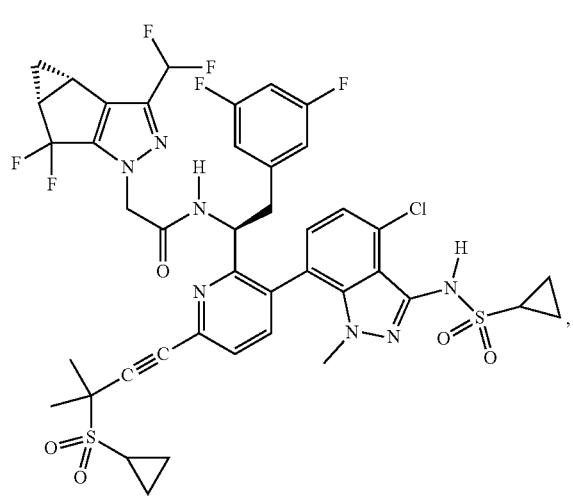
or a pharmaceutically acceptable salt thereof.
In some embodiments, the compound of formula I is selected from:

47
-continued
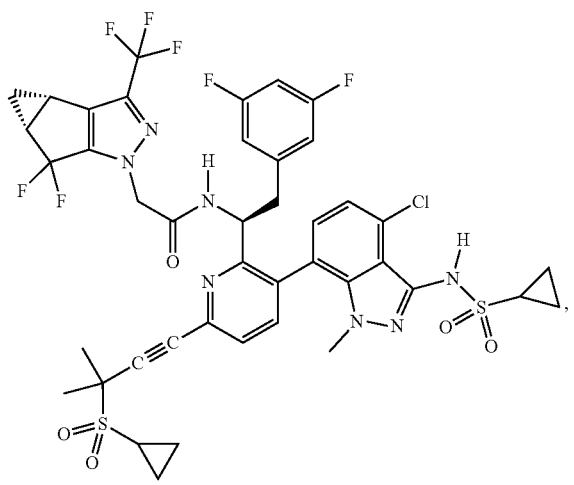
48
-continued
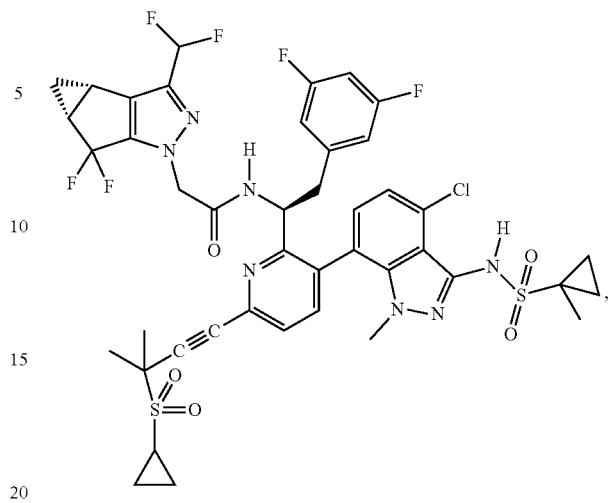
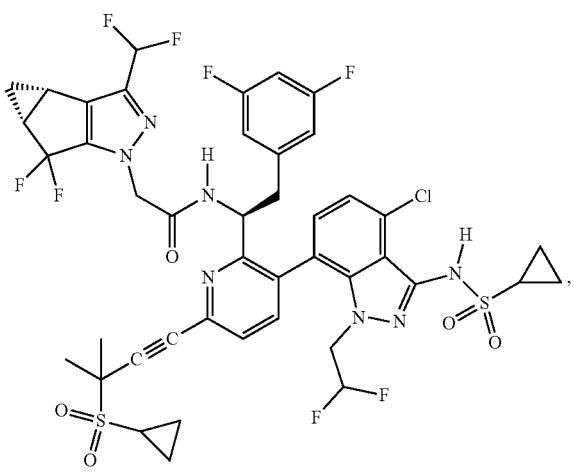
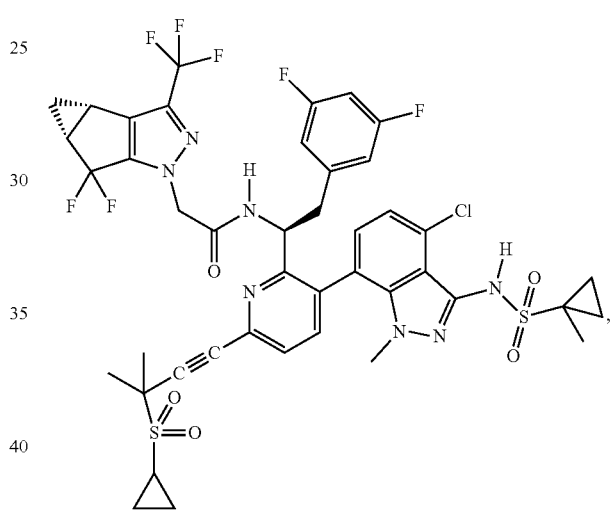
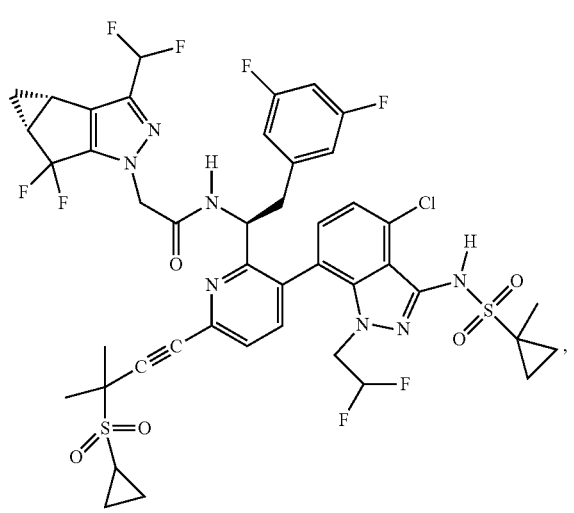
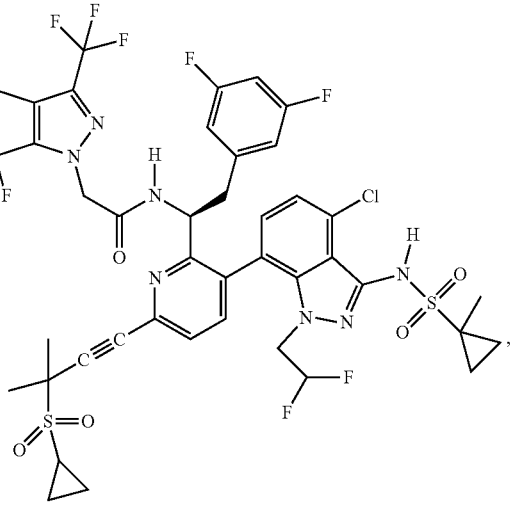

49
-continued
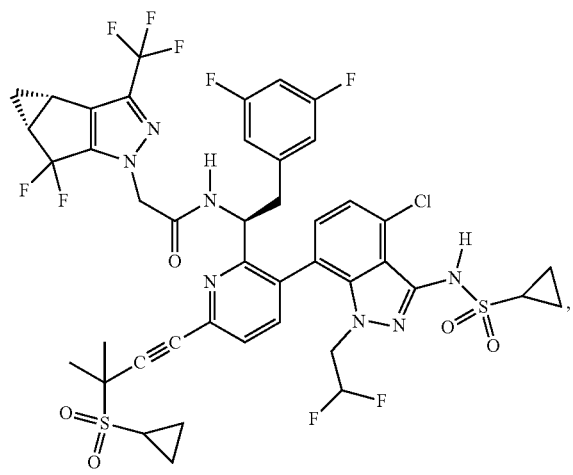
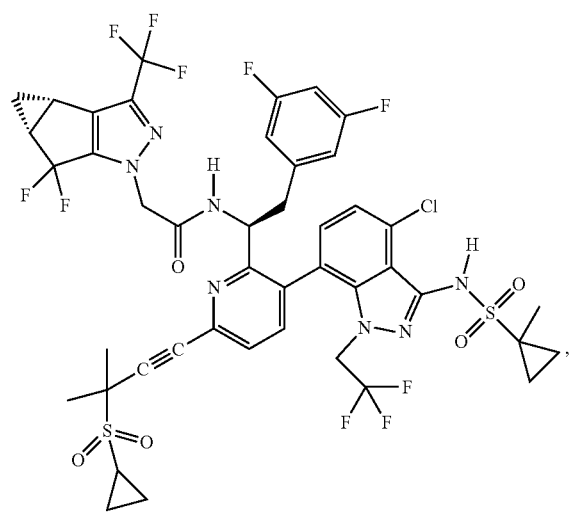
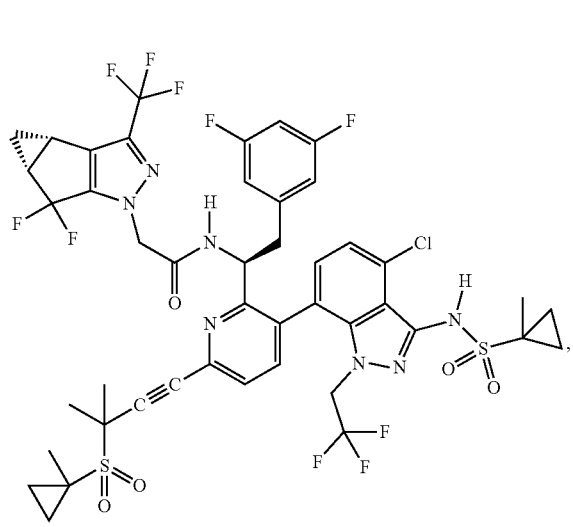
50
-continued
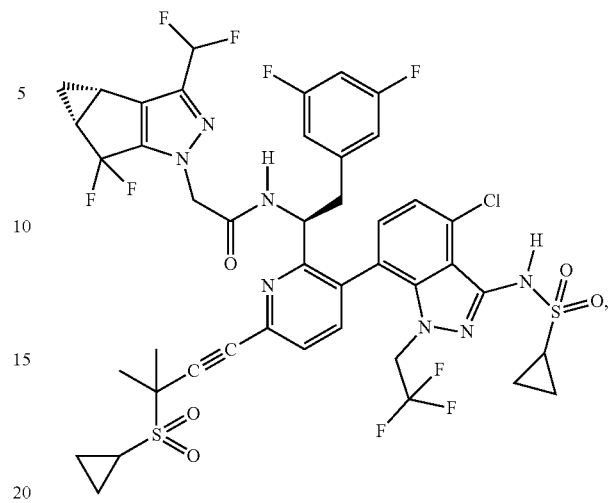
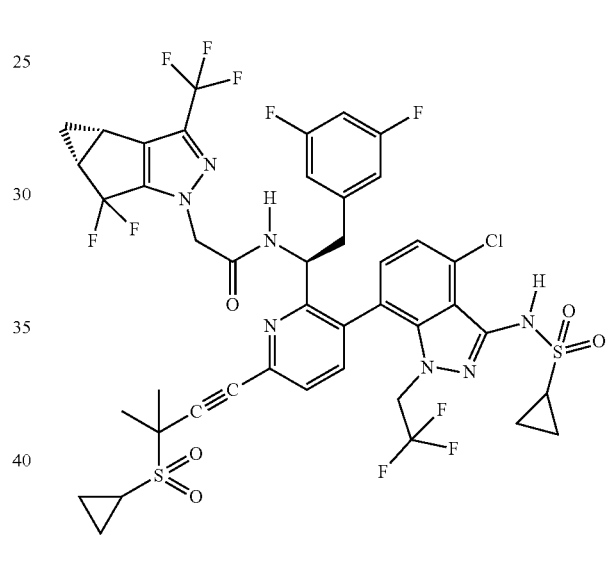
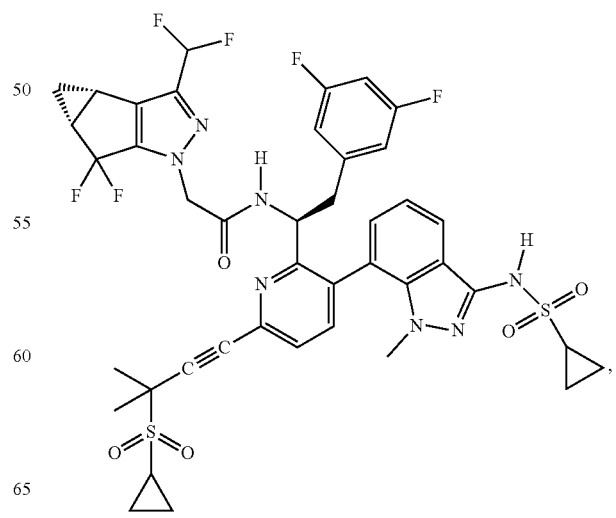

51
-continued
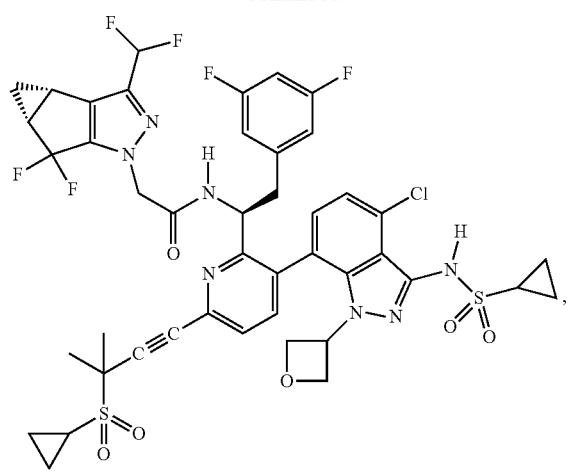
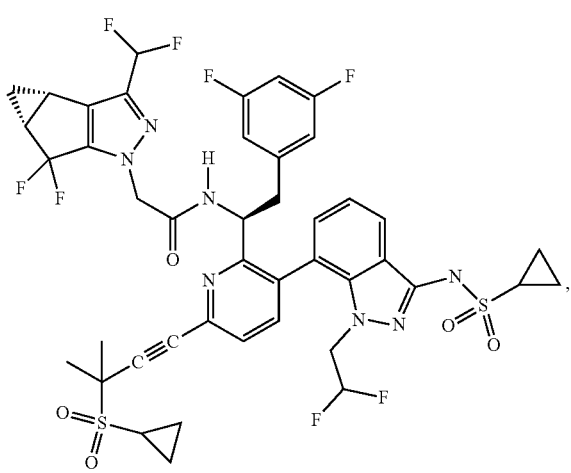
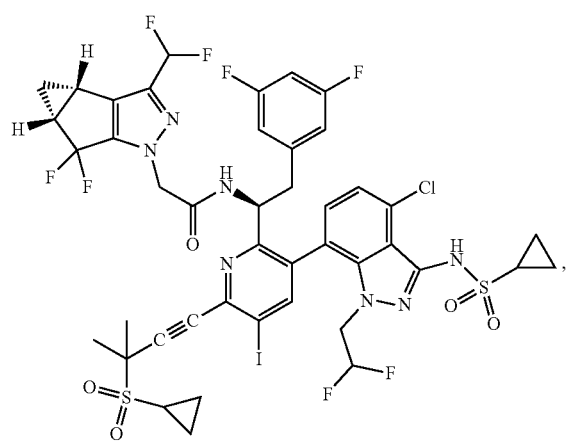
52
-continued
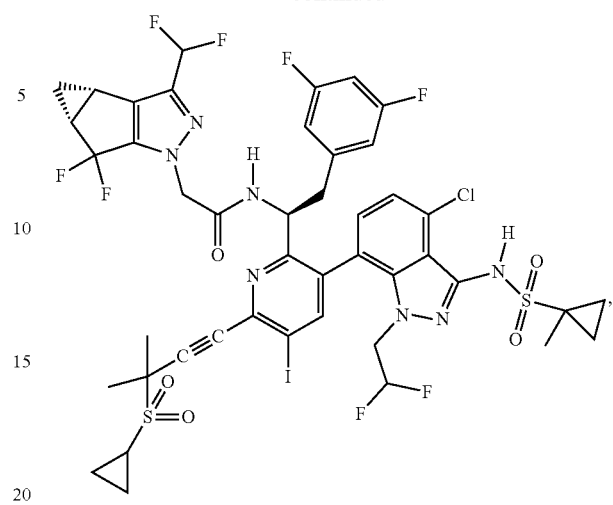
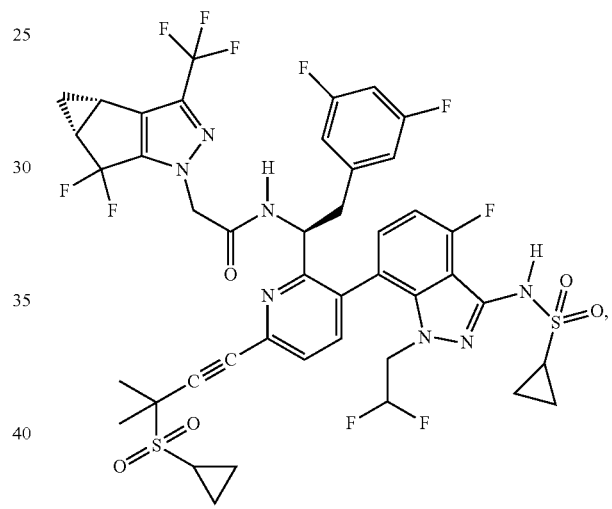
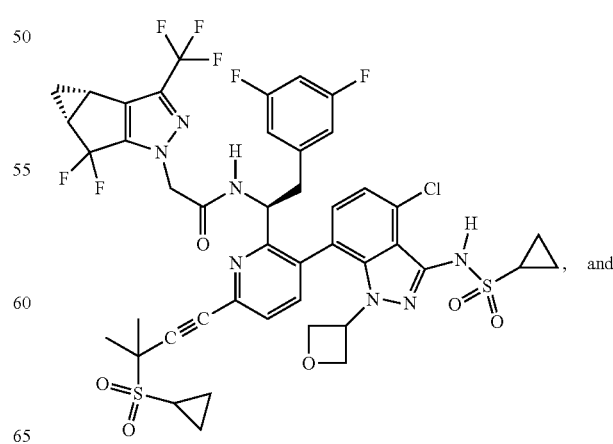
, and

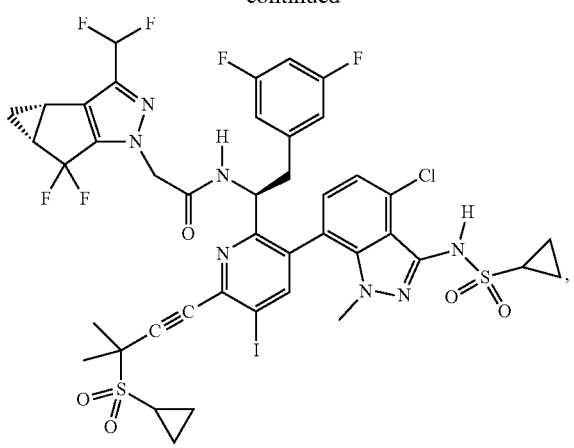
or a pharmaceutically acceptable salt thereof.
In some embodiments, the compound of formula I is selected from:
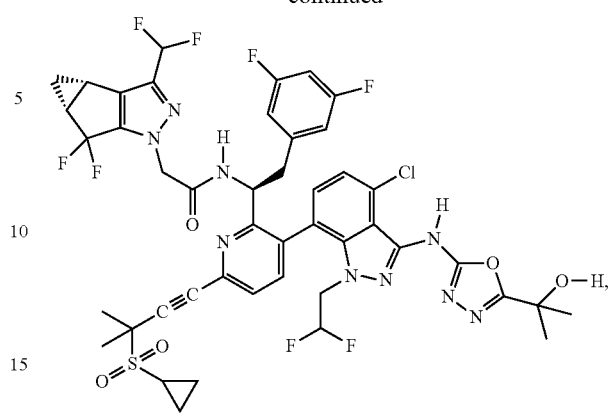
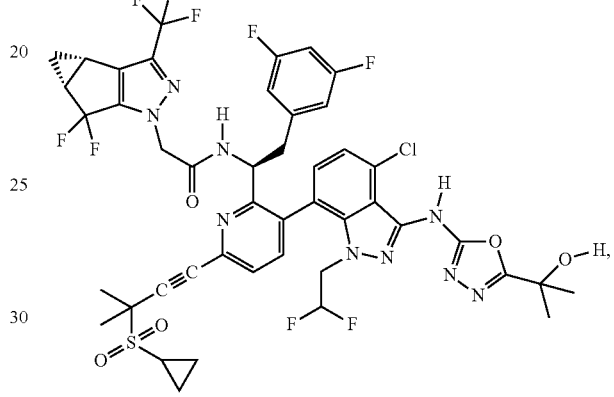
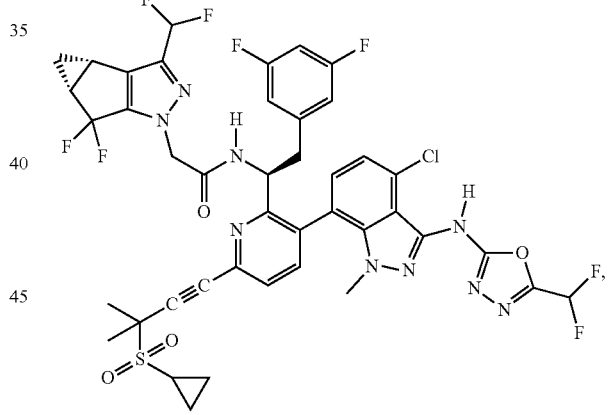
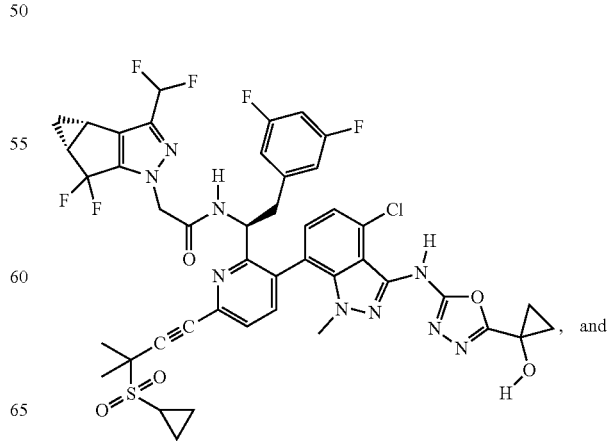

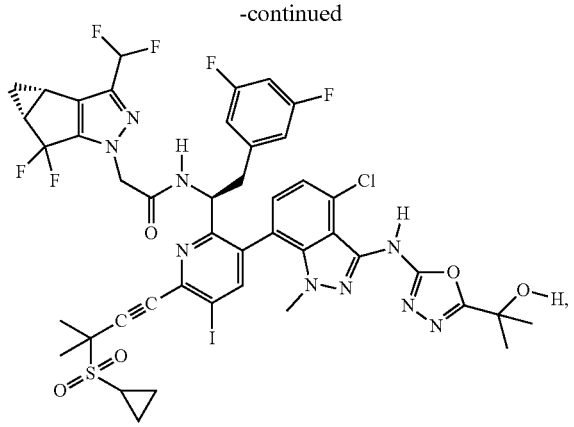
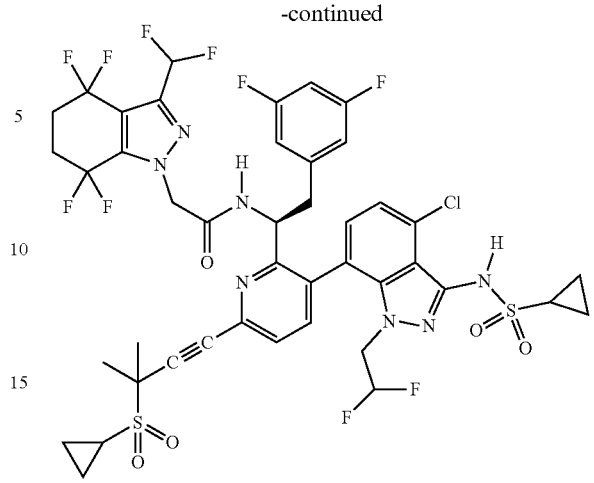
or a pharmaceutically acceptable salt thereof.
In some embodiments, the compound of formula I is:
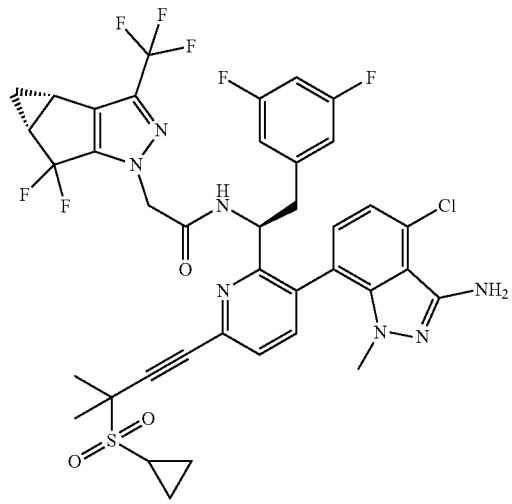 [SMILES: Cn1nc(N)c2c(Cl)ccc(-c3ccc(C#CC(C)(C)S(=O)(=O)C4CC4)nc3[C@H](Cc3cc(F)cc(F)c3)NC(=O)Cn3nc(C(F)(F)F)c4c3C(F)(F)[C@@H]3C[C@H]43)c21]
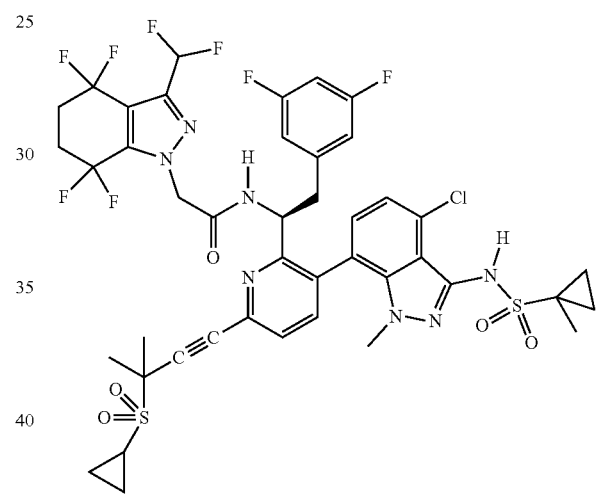
or a pharmaceutically acceptable salt thereof.
In some embodiments, the compound of formula I is selected from:
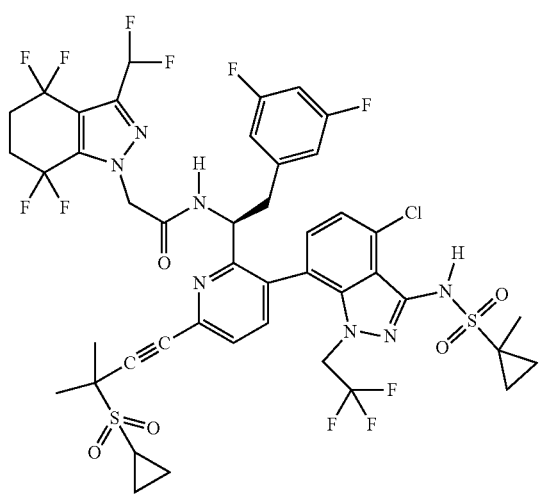
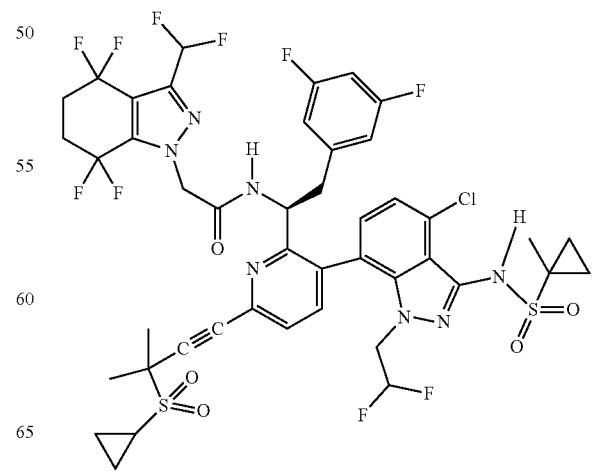

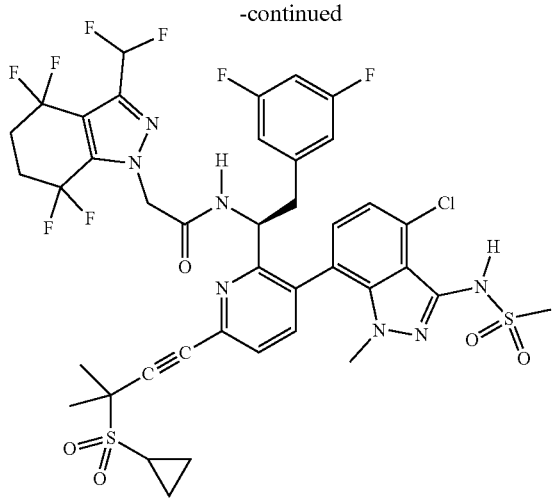
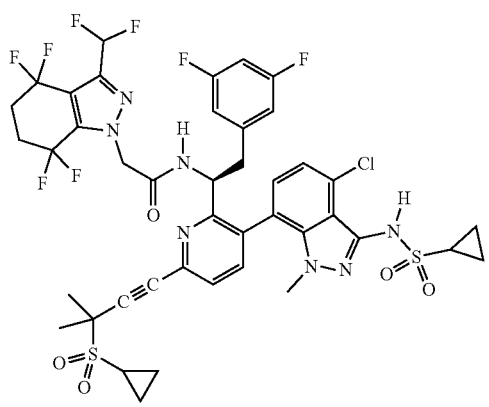
, and
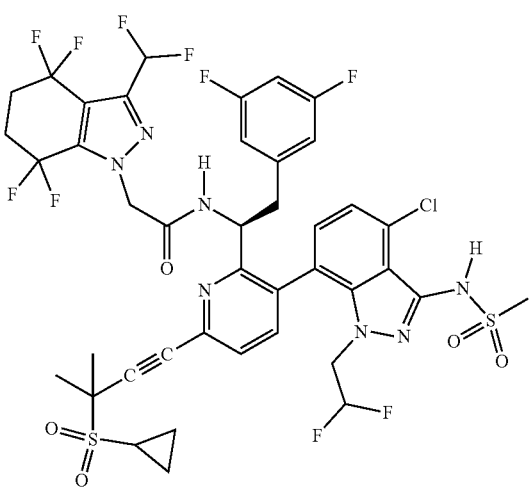
or a pharmaceutically acceptable salt thereof.
In some embodiments, the compound of formula I is selected from:
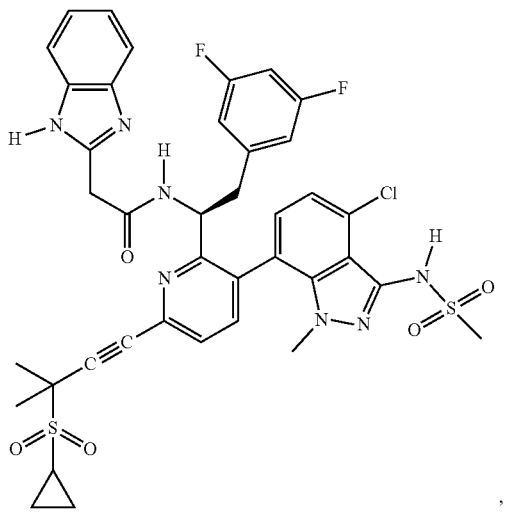
,
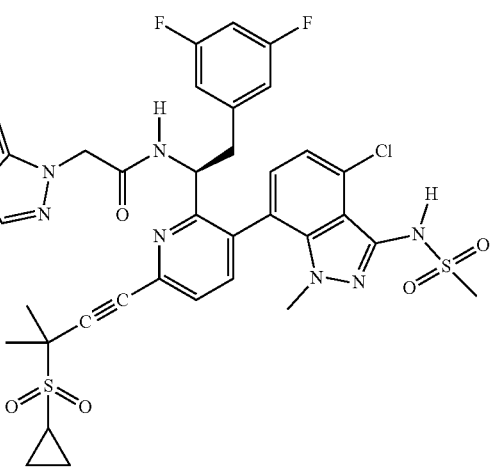
,
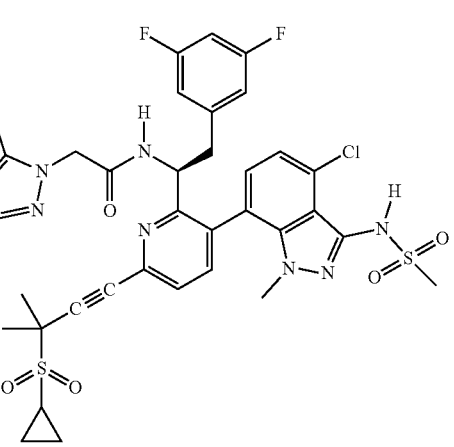
, and -continued
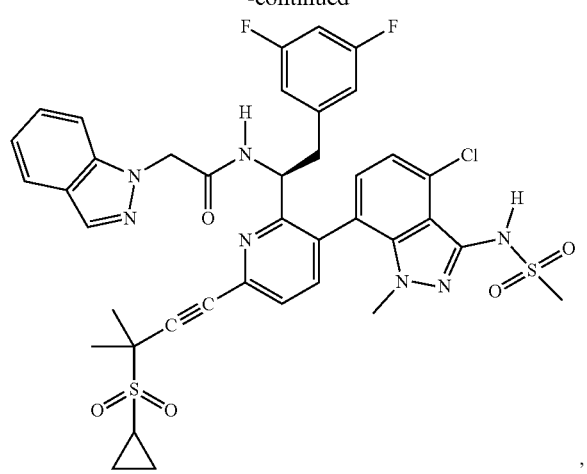
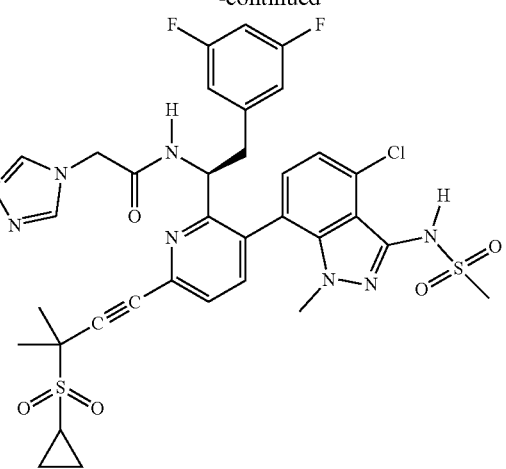
, and
or a pharmaceutically acceptable salt thereof.
In some embodiments, the compound of formula I is selected from:
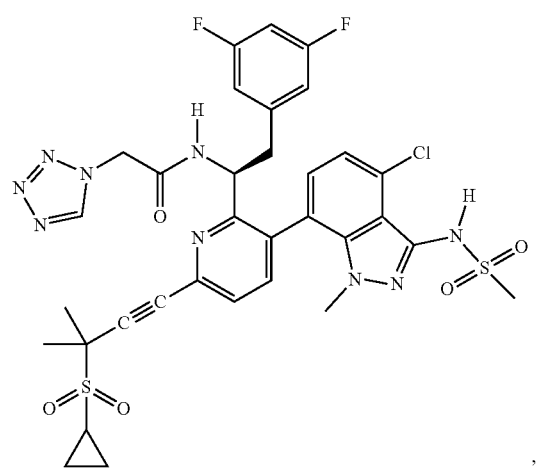
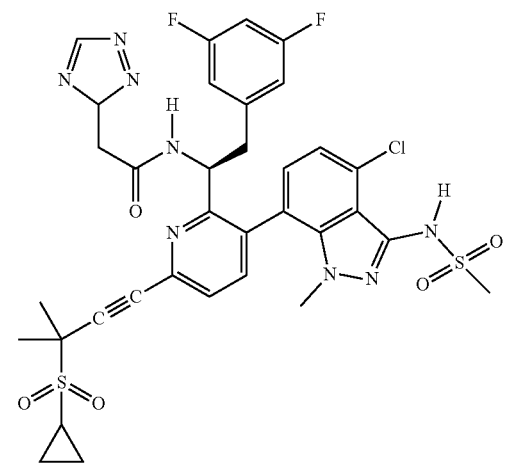
,
or a pharmaceutically acceptable salt thereof.
In some embodiments, the compound of formula I is selected from:
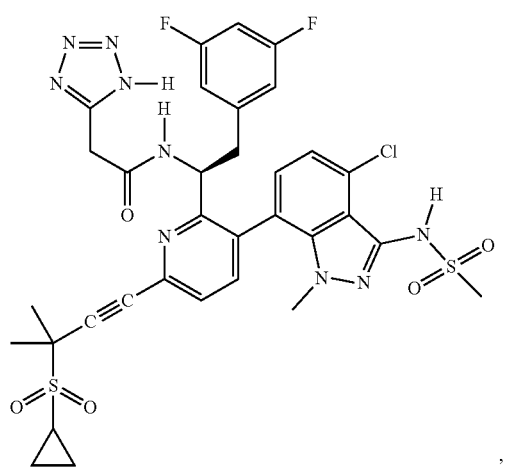 [SMILES: Cn1nc(NS(C)(=O)=O)c2c(Cl)ccc(-c3ccc(C#CC(C)(C)S(=O)(=O)C4CC4)nc3[C@H](Cc3cc(F)cc(F)c3)NC(=O)CC3N=CN=N3)c21]
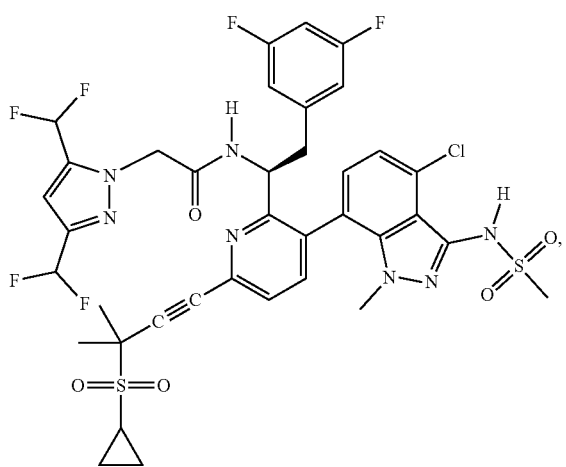
, 61
-continued
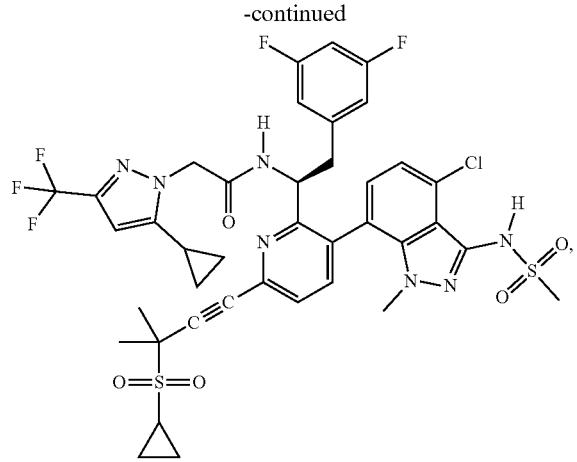
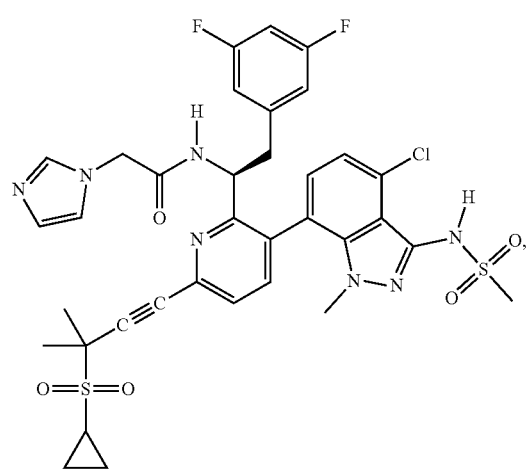
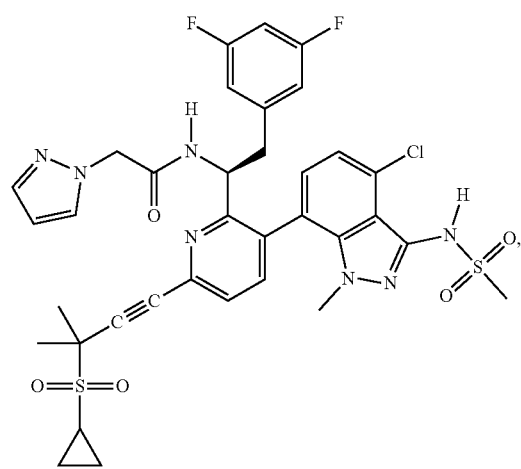
62
-continued
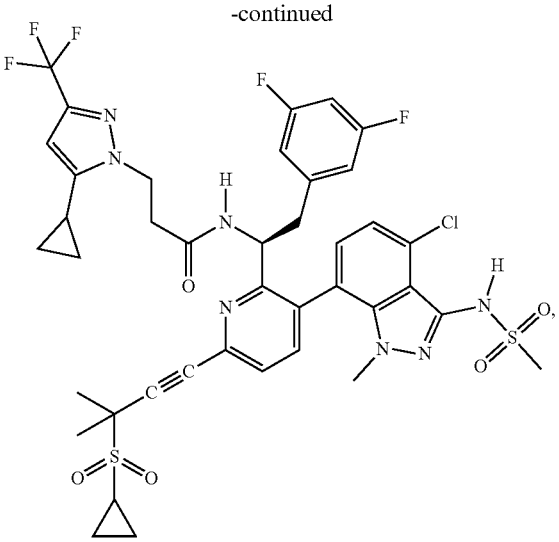
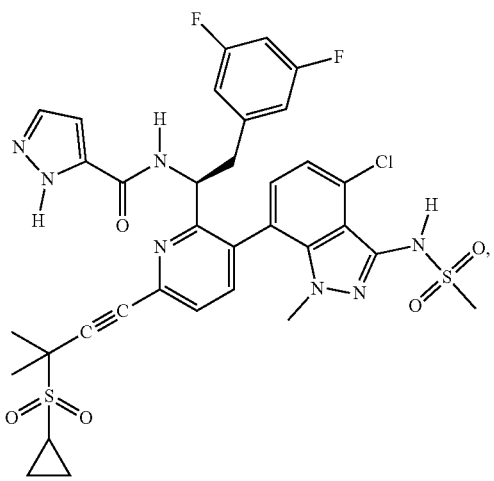
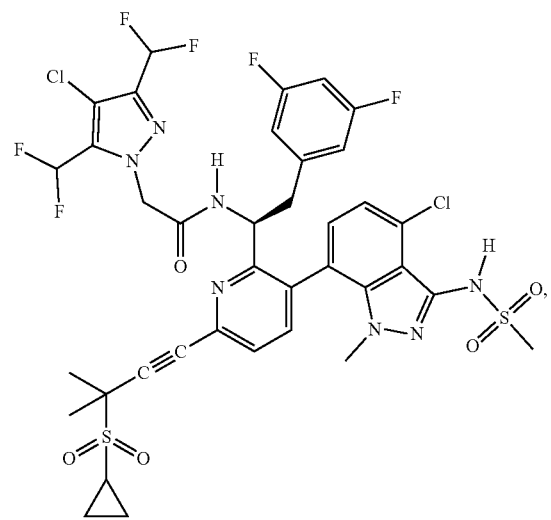

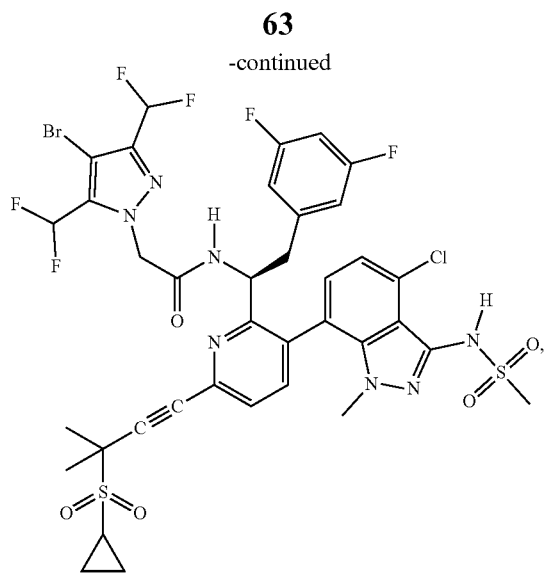

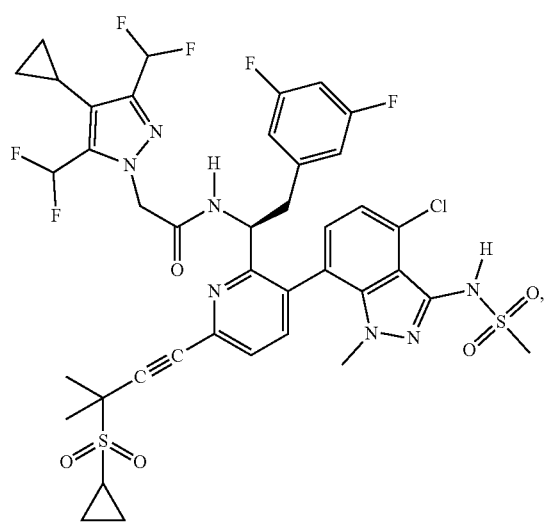

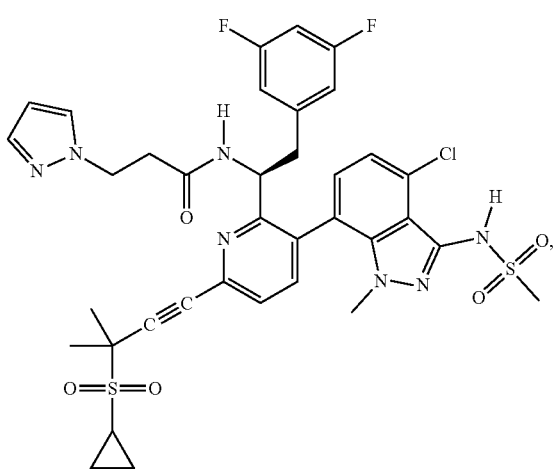

or a pharmaceutically acceptable salt thereof.

III. Combination Therapy

In some embodiments, the invention provides a method for preventing or treating an HIV infection, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating an HIV infection.

A compound as disclosed herein (e.g., a compound of any of formulas I, Ia, Ib, Ic, Id, Ie, If, Ig, Ih, Ii, Ij and Ik, or a pharmaceutically acceptable salt thereof) may be combined with one or more additional therapeutic agents in any dosage amount of the compound (e.g., from 1 mg to 5 mg, 5 mg to 10 mg, 10 mg to 50 mg, 50 mg to 100 mg, 100 mg to 300 mg).

In some embodiments, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more additional therapeutic agents.

In some embodiments, the invention provides pharmaceutical compositions comprising a compound disclosed herein, or a pharmaceutically acceptable salt thereof, in combination with at least one additional therapeutic agent, and a pharmaceutically acceptable carrier. For example, the therapeutic agent used in combination with the compound disclosed herein can be any anti-HIV agent.

In some embodiments, combination pharmaceutical agents comprising a compound disclosed herein, or a pharmaceutically acceptable salt thereof, in combination with one or more additional therapeutic agents are provided.

In some embodiments, provided herein are pharmaceutical compositions comprising a compound disclosed herein, or a pharmaceutically acceptable salt thereof, in combination with at least one additional therapeutic agent, and a pharmaceutically acceptable carrier.

In some embodiments, the additional therapeutic agent may be an anti-HIV agent. For example, in some embodiments, the additional therapeutic agent is selected from the group consisting of HIV protease inhibiting compounds (HIV protease inhibitors), HIV non-nucleoside inhibitors of reverse transcriptase, HIV nucleoside inhibitors of reverse transcriptase, HIV nucleotide inhibitors of reverse transcriptase, HIV integrase inhibitors, HIV non-catalytic site (or allosteric) integrase inhibitors, HIV entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, additional capsid polymerization inhibitors or capsid disrupting compounds such as those disclosed in US 2013/0165489 (University of Pennsylvania), and WO 2013/006792 (Pharma Resources), pharmacokinetic enhancers, HIV maturation inhibitors, latency reversing agents, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, HIV gene therapy, HIV vaccines, and combinations thereof.

In some embodiments, the additional therapeutic agent is selected from immunomodulators, immunotherapeutic agents, antibody-drug conjugates, gene modifiers, gene editors (such as CRISPR/Cas9, zinc finger nucleases, homing nucleases, synthetic nucleases, TALENs), and cell therapies such as chimeric antigen receptor T-cell, CAR-T (e.g., YESCARTA® (axicabtagene ciloleucel)), and engineered T cell receptors, TCR-T.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, additional capsid inhibitors, immune-based therapies, PI3K inhibitors, HIV antibodies, and bispecific antibodies, and "antibody-like" therapeutic proteins, and combinations thereof.

HIV Combination Drugs

Examples of combination drugs include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALTJVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine; Vacc-4x and romidepsin; and APH-0812.

Other HIV Drugs

Examples of other drugs for treating HIV include acemannan, alisporivir, BanLec, deferiprone, Gamimune, metenkefalin, naltrexone, Prolastin, REP 9, RPI-MN, VSSP, Hlviral, SB-728-T, 1,5-dicaffeoylquinic acid, rHIV7-shl-TAR-CCR5RZ, AAV-eCD4-Ig gene therapy, MazF gene therapy, BlockAide, ABX-464, AG-1105, APH-0812, BIT-225, CYT-107, HGTV-43, HPH-116, HS-10234, IMO-3100, IND-02, MK-1376, MK-8507, MK-8591, NOV-205, PA-1050040 (PA-040), PGN-007, SCY-635, SB-9200, SCB- 719, TR-452, TEV-90110, TEV-90112, TEV-90111, TEV-90113, RN-18, Immuglo, and VIR-576.

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, AIC-292, KM-023, PC-1005, and VM-1500.

Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, GS-9131, GS-9148, and KP-1461.

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169 and cabotegravir.

Examples of HIV non-catalytic site, or allosteric, integrase inhibitors (NCINI) include CX-05045, CX-05168, and CX-14442.

HIV Entry Inhibitors

Examples of HIV entry (fusion) inhibitors include cenicriviroc, CCR5 inhibitors, gp41 inhibitors, CD4 attachment inhibitors, gp120 inhibitors, and CXCR4 inhibitors.

Examples of CCR5 inhibitors include aplaviroc, vicriviroc, maraviroc, cenicriviroc, PRO-140, adaptavir (RAP-101), nifeviroc (TD-0232), anti-GP120/CD4 or CCR5 bispecific antibodies, B-07, MB-66, polypeptide C25P, TD-0680, and vMIP (Haimipu).

Examples of gp41 inhibitors include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

Examples of CD4 attachment inhibitors include ibalizumab and CADA analogs

Examples of gp120 inhibitors include Radha-108 (receptol) 3B3-PE38, BanLec, bentonite-based nanomedicine, fostemsavir tromethamine, IQP-0831, and BMS-663068

Examples of CXCR4 inhibitors include plerixafor, ALT-1188, N15 peptide, and vMIP (Haimipu).

HIV Maturation Inhibitors

Examples of HIV maturation inhibitors include BMS-955176 and GSK-2838232.

Latency Reversing Agents

Examples of latency reversing agents include histone deacetylase (HDAC) inhibitors, proteasome inhibitors such as velcade, protein kinase C (PKC) activators, BET-bromodomain 4 (BRD4) inhibitors, ionomycin, PMA, SAHA (suberanilohydroxamic acid, or suberoyl, anilide, and hydroxamic acid), IL-15, JQ1, disulfram, amphotericin B, and ubiquitin inhibitors such as largazole analogs, and GSK-343.

Examples of HDAC inhibitors include romidepsin, vorinostat, and panobinostat.

Examples of PKC activators include indolactam, prostratin, ingenol B, and DAG-lactones.

HIV Capsid Inhibitors

Examples of additional capsid inhibitors include capsid polymerization inhibitors or capsid disrupting compounds, HIV nucleocapsid p7 (NCp7) inhibitors such as azodicarbonamide, HIV p24 capsid protein inhibitors, AVI-621, AVI-101, AVI-201, AVI-301, and AVI-CAN1-15 series.

In some embodiments, examples of additional capsid inhibitors include:

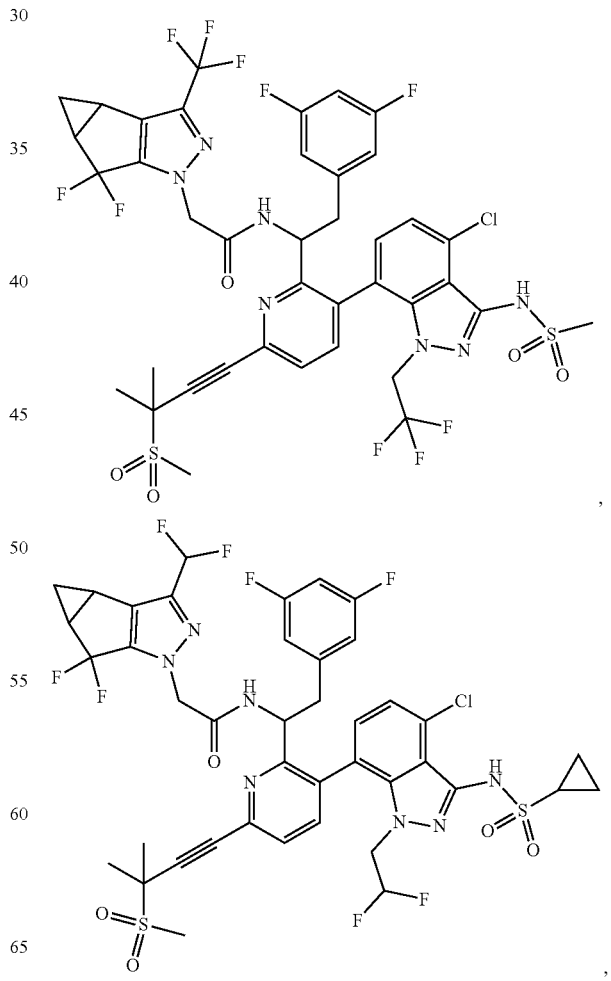

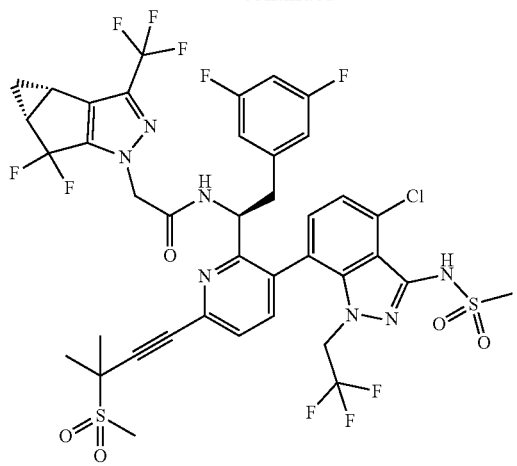
, and
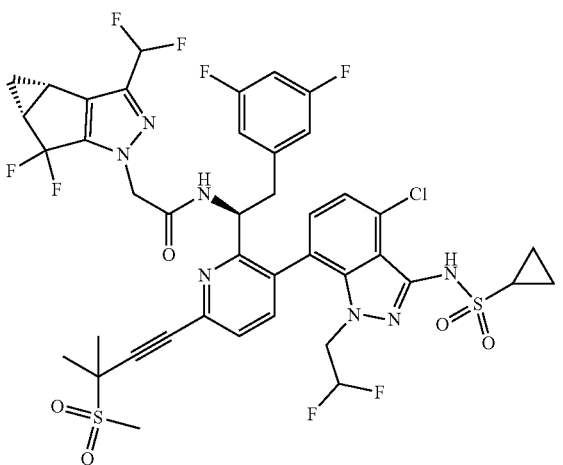
or a pharmaceutically acceptable salt thereof.
In some embodiments, the additional capsid inhibitor is selected from:
, and
or a pharmaceutically acceptable salt thereof.
In some embodiments, the additional capsid inhibitor is:
,
or a pharmaceutically acceptable salt thereof.

In some embodiments, the additional capsid inhibitor is:

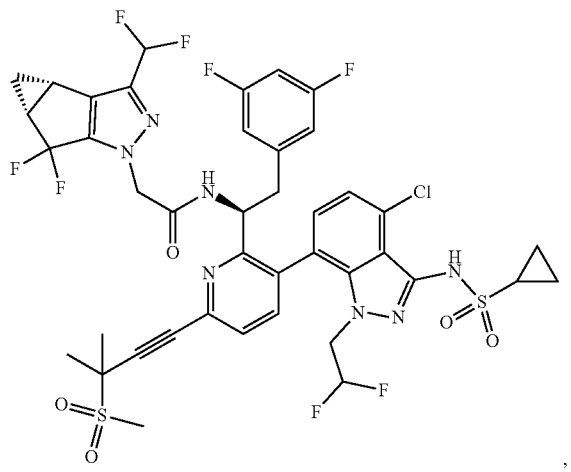 [SMILES: CC(C)(C#Cc1ccc(-c2ccc(Cl)c3c(NS(=O)(=O)C4CC4)nn(CC(F)F)c23)c([C@H](Cc2cc(F)cc(F)c2)NC(=O)Cn2nc(C(F)F)c3c2C(F)(F)[C@@H]2C[C@H]32)n1)S(C)(=O)=O]

or a pharmaceutically acceptable salt thereof.

Immune-Based Therapies

Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 agonists; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; rintatolimod, polymer polyethyleneimine (PEI); gepon; rintatolimod; IL-12; WF-10; VGV-1; MOR-22; BMS-936559; CYT-107, interleukin-15/Fc fusion protein, normferon, peginterferon alfa-2a, peginterferon alfa-2b, recombinant interleukin-15, RPI-MN, GS-9620, STING modulators, RIG-I modulators, NOD2 modulators, and IR-103.

Phosphatidylinositol 3-Kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

Alpha-4/Beta-7 Antagonists

Examples of Integrin alpha-4/beta-7 antagonists include PTG-100, TRK-170, abrilumab, etrolizumab, carotegrast methyl, and vedolizumab.

HIV Antibodies, Bispecific Antibodies, and "Antibody-Like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, bnABs (broadly neutralizing HIV-1 antibodies), BMS-936559, TMB-360, and those targeting HIV gp120 or gp41, antibody-Recruiting Molecules targeting HIV, anti-CD63 monoclonal antibodies, anti-GB virus C antibodies, anti-GP120/CD4, CCR5 bispecific antibodies, anti-nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, MB-66.

In some embodiments, examples of those targeting HIV in such a manner include bavituximab, UB-421, C2F5, 2G12, C4E10, C2F5+C2G12+C4E10, 8ANC195, 3BNC117, 3BNC60, 10-1074, PGT145, PGT121, PGT-151, PGT-133, MDX010 (ipilimumab), DH511, N6, VRC01 PGDM1400, A32, 7B2, 10E8, 10E8v4, CAP256-VRC26.25, DRVIA7, VRC-07-523, VRC-HIVMAB080-00-AB, VRC-HIVMAB060-00-AB, MGD-014 and VRC07. Example of HIV bispecific antibodies include MGD014.

Pharmacokinetic Enhancers

Examples of pharmacokinetic enhancers include cobicistat and ritonavir.

Additional Therapeutic Agents

Examples of additional therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

HIV Vaccines

Examples of HIV vaccines include peptide vaccines, recombinant subunit protein vaccines, live vector vaccines, DNA vaccines, CD4-derived peptide vaccines, vaccine combinations, rgp120 (AIDSVAX), ALVAC HIV (vCP1521)/AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-05, VAC-3S, multiclade DNA recombinant adenovirus-5 (rAd5), Pennvax-G, Pennvax-GP, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multi-HIV (FIT-06), gp140[delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TVI-HIV-1, Ad-4 (Ad4-env Clade C+Ad4-mGag), EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVlCH-vac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc- 4x+romidepsin, variant gp120 polypeptide vaccine, rAd5 gag-pol env A/B/C vaccine, DNA.HTI and MVA.HTI.

HIV Combination Therapy

In a particular embodiment, a compound disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

It will be appreciated by one of skill in the art that the additional therapeutic agents listed above may be included in more than one of the classes listed above. The particular classes are not intended to limit the functionality of those compounds listed in those classes.

In some embodiments, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase.

In a particular embodiment, a compound disclosed herein, or a pharmaceutically acceptable salt thereof, is combined with GS-9131, MK-8591, abacavir sulfate, bictegravir, tenofovir, tenofovir disoproxil, tenofovir disoproxil fumarate, tenofovir disoproxil hemifumarate, tenofovir alafenamide, or tenofovir alafenamide hemifumarate, or a combination thereof.

In a particular embodiment, a compound disclosed herein, or a pharmaceutically acceptable salt thereof, is combined with bictegravir, GS-9131, tenofovir, tenofovir disoproxil, tenofovir disoproxil fumarate, tenofovir alafenamide, or tenofovir alafenamide hemifumarate, or a combination thereof.

In a particular embodiment, a compound disclosed herein, or a pharmaceutically acceptable salt thereof, is combined with a first additional therapeutic agent selected from the group consisting of abacavir sulfate, bictegravir, GS-9131, tenofovir, tenofovir disoproxil, tenofovir disoproxil fumarate, tenofovir alafenamide, and tenofovir alafenamide hemifumarate, or a combination thereof, and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of bictegravir, GS-9131, tenofovir, tenofovir disoproxil, tenofovir disoproxil fumarate, tenofovir alafenamide, and tenofovir alafenamide hemifumarate, or a combination thereof, and a second additional therapeutic agent, wherein the second additional therapeutic agent is emtricitabine.

In some embodiments, a compound disclosed herein, or a pharmaceutically acceptable salt thereof, is combined with 40-60 mg of bictegravir, 20-70 mg GS-9131, 5-30 mg tenofovir alafenamide fumarate, tenofovir alafenamide hemifumarate, or tenofovir alafenamide and 200 mg emtricitabine. In some embodiments, a compound disclosed herein, or a pharmaceutically acceptable salt thereof, is combined with 1-3, 3-5, 5-10; 5-15; 5-20; 5-25; 25-30; 20-30; 15-30; or 10-30 mg tenofovir alafenamide fumarate, tenofovir alafenamide hemifumarate, or tenofovir alafenamide and/or 200 mg emtricitabine. In some embodiments, a compound disclosed herein, or a pharmaceutically acceptable salt thereof, is combined with 30-50, 50-75, 75-100; 100-150; 150-200; 250-300; 350-400; 400-450; 450-500; or 500-550 mg tenofovir alafenamide fumarate, tenofovir alafenamide hemifumarate, or tenofovir alafenamide and/or 200 mg emtricitabine. In some embodiments, a compound disclosed herein, or a pharmaceutically acceptable salt thereof, is combined with 500-750, 750-1000, 1000-1500, 1500-2000, 2000-2500 mg tenofovir alafenamide fumarate, tenofovir alafenamide hemifumarate, or tenofovir alafenamide and/or 200 mg emtricitabine. In some embodiments, a compound disclosed herein, or a pharmaceutically acceptable salt thereof, is combined with 10 mg tenofovir alafenamide fumarate, tenofovir alafenamide hemifumarate, or tenofovir alafenamide and 200 mg emtricitabine. In some embodiments, a compound disclosed herein, or a pharmaceutically acceptable salt thereof, is combined with 25 mg tenofovir alafenamide fumarate, tenofovir alafenamide hemifumarate, or tenofovir alafenamide and 200 mg emtricitabine. In some embodiments, a compound disclosed herein, or a pharmaceutically acceptable salt thereof, is combined with 50 mg of bictegravir. A compound as disclosed herein (e.g., a compound of any of formulas I, Ia, Ib, Ic, Id, Ie, If, Ig, Ih, Ii, Ij and Ik, or a pharmaceutically acceptable salt thereof) may be combined with the agents provided herein in any dosage amount of the compound (e.g., from 50 mg to 300 mg of compound) the same as if each combination of dosages were specifically and individually listed.

In some embodiments, a compound disclosed herein, or a pharmaceutically acceptable salt thereof, is combined with 200-400 mg tenofovir disoproxil fumarate, tenofovir disoproxil hemifumarate, or tenofovir disoproxil and 200 mg emtricitabine. In some embodiments, a compound disclosed herein, or a pharmaceutically acceptable salt thereof, is combined with 200-250; 200-300; 200-350; 250-350; 250-400; 350-400; 300-400; or 250-400 mg tenofovir disoproxil fumarate, tenofovir disoproxil hemifumarate, or tenofovir disoproxil and and 200 mg emtricitabine. In some embodiments, a compound disclosed herein, or a pharmaceutically acceptable salt thereof, is combined with 300 mg tenofovir disoproxil fumarate, tenofovir disoproxil hemifumarate, or tenofovir disoproxil and and 200 mg emtricitabine. A compound as disclosed herein (e.g., a compound of any of formulas I, Ia, Ib, Ic, Id, Ie, If, Ig, Ih, Ii, Ij and Ik, or a pharmaceutically acceptable salt thereof) may be combined with the agents provided herein in any dosage amount of the compound (e.g., from 50 mg to 300 mg of compound) the same as if each combination of dosages were specifically and individually listed.

In some embodiments, kits comprising a compound disclosed herein, or a pharmaceutically acceptable salt thereof, in combination with one or more (e.g., one, two, three, one or two, or one to three) additional therapeutic agents are provided. Birth control (contraceptive) combination therapy Therapeutic agents used for birth control (contraceptive) include cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

Gene Therapy and Cell Therapy

Gene Therapy and Cell Therapy including the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection.

Examples of dendritic cell therapy include AGS-004.

Gene Editors

The genome editing system is selected from the group consisting of: a CRISPR/Cas9 system, a zinc finger nuclease system, a TALEN system, a homing endonucleases system, and a meganuclease system.

Examples of HIV targeting CRISPR/Cas9 systems include EBT101.

CAR-T Cell Therapy

A population of immune effector cells engineered to express a chimeric antigen receptor (CAR), wherein the CAR comprises an HIV antigen-binding domain. The HIV antigen include an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T cell or an NK cell. In some embodiments, the T cell is a CD4+ T cell, a CD8+ T cell, or a combination thereof.

Examples of HIV CAR-T include VC-CAR-T.

TCR-T Cell Therapy

TCR-T cells are engineered to target HIV derived peptides present on the surface of virus-infected cells.

In some embodiments, one or more of the compounds disclosed herein are combined with one or more other active therapeutic agents in a unitary dosage form for simultaneous or sequential administration to a patient. In certain embodiments, a pharmaceutical composition including one or more of the compounds disclosed herein combined with one or more other active therapeutic agents is provided. In certain embodiments, the compounds disclosed herein are combined with one or more other active therapeutic agents in a solid dosage form. The combination therapy may be administered as a simultaneous or sequential regimen. When administered sequentially, the combination may be administered in two or more administrations.

In some embodiments, one or more of the compounds disclosed herein are co-administered with one or more other active therapeutic agents. Co-administration of a compound disclosed herein with one or more other active therapeutic agents generally refers to simultaneous or sequential administration of a compound disclosed herein and one or more other active therapeutic agents, such that therapeutically effective amounts of disclosed herein and one or more other active therapeutic agents are both present in the body of the patient.

In yet another embodiment, the present application provides a method for treating an HIV infection comprising administering to a patient in need thereof a therapeutically effective amount of a compound disclosed herein, or a pharmaceutically acceptable salt thereof, in combination with a therapeutically effective amount of one or more additional therapeutic agents such as those disclosed above.

In some embodiments, the methods disclosed herein involve administration prior to and/or after an event that would expose the individual to HIV or that would otherwise increase the individual's risk of acquiring HIV, e.g., as pre-exposure prophylaxis (PrEP) and/or as post-exposure prophylaxis (PEP). Examples of events that could increase an individual's risk of acquiring HIV include, without limitation, no condom use during anal intercourse with an HIV positive partner or a partner of unknown HIV status; anal intercourse with more than 3 sex partners; exchange of money, gifts, shelter or drugs for anal sex; sex with male partner and diagnosis of sexually transmitted infection; and no consistent use of condoms with sex partner known to be HIV positive.

IV. Pharmaceutical Formulations

The compounds disclosed herein are formulated with conventional carriers (e.g., inactive ingredient or excipient material) which will be selected in accord with ordinary practice. Tablets will contain excipients including glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. One embodiment provides the formulation as a solid dosage form including a solid oral dosage form. The pH of the formulations ranges from about 3 to about 11, but is ordinarily about 7 to 10.

While it is possible for the active ingredients to be administered alone it may be preferable to present them as pharmaceutical formulations (compositions). The formulations, both for veterinary and for human use, of the invention comprise at least one active ingredient, as above defined, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with inactive ingredients (e.g., a carrier, pharmaceutical excipients, etc.) which constitutes one or more accessory ingredients. In general the formulations are prepared by uniformly and intimately bringing into association the active ingredient with liquid carriers or finely divided solid carriers or both, and then, if necessary, shaping the product.

Formulations described herein that are suitable for oral administration may be presented as discrete units including but not limited to capsules, cachets or tablets each containing a predetermined amount of the active ingredient.

Pharmaceutical formulations disclosed herein comprise one or more compounds disclosed herein together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that is combined with the inactive ingredients to produce a dosage form will vary depending upon the host treated and the particular mode of administration. For example, in some embodiments, a dosage form for oral administration to humans contains approximately 1 to 1000 mg of active material formulated with an appropriate and convenient amount of carrier material (e.g., inactive ingredient or excipient material). In some embodiments, a dosage form (e.g., for oral administration to humans) contains: from 1 mg to 1000 mg or from 3 mg to 1000 mg or 5 mg to 1000 mg or 10 mg to 1000 mg or from 50 mg to 1000 mg or from 100 mg to 1000 mg or from 200 mg to 1000 mg or from 300 mg to 1000 mg or from 10 mg to 800 mg or from 10 mg to 600 mg or from 10 mg to 500 mg or from 10 mg to 400 mg or from 10 mg to 300 mg or from 50 mg to 800 mg or from 100 mg to 600 mg or from 150 mg to 500 mg or from 200 mg to 400 mg or from 50 mg to 500 mg or from 10 mg to 300 mg or from 50 mg to 300 mg or from 10 mg to 200 mg or from 50 mg to 200 mg or from 100 mg to 300 mg or from 100 mg to 200 mg or from 200 mg to 300 mg of active material (e.g., a compound of any of formulae I, Ia, Ib, Ic, Id, Ie, If, Ig, Ih, Ii, Ij and Ik, or a pharmaceutically acceptable salt thereof). In some embodiments, a dosage form for oral administration to humans contains at least any of 1, 3, 5, 10, 25, 50, 100, 150, 200, 250 or 300 mg and no more than 500 or 800 or 1000 mg of active material (e.g., from at least 50 mg to no more than 500 mg). In some embodiments, a dosage form for oral administration to humans contains at least any of 1, 3, 5, 10, 25, 50, 100, 150, 200, 250 or 300 mg or no more than 500 or 800 or 1000 mg of active material. In some embodiments, a dosage form for oral administration to humans contains any of 1, 3, 5, 10, 25, 50, 100, 150, 200, 250, 300, 350, 400, 450, 500, 550, 600, 650, 700, 750, 800, 850, 900, 950, or 1000 mg of active material. It is understood that a dosage form in an amount provided herein may be administered to a patient (e.g., a human in need thereof) in accordance with a dosing regimen provided herein, such as once, twice or thrice daily dosing. In one aspect, a dosing regimen provides for administration of at least 10 mg and no more than 1,000 mg of active material (e.g., a compound of any of formulas I, Ia, Ib, Ic, Id, Ie, If, Ig, Ih, Ii, Ij and Ik, or a pharmaceutically acceptable salt thereof) daily, and it is understood that the amount may be provided in any suitable dosage form and amount (e.g., 500 mg twice daily or 1,000 mg once daily would provide the same amount of 1,000 mg/day dosing). The invention embraces once daily dosing to an individual (e.g., a human in need thereof) of a dosage form of compound (e.g., a compound of any of formulas I, Ia, Ib, Ic, Id, Ie, If, Ig, Ih, Ii, Ij and Ik, or a pharmaceutically acceptable salt thereof) containing at least 50 mg and not more than 300 mg of compound. In certain embodiments, the carrier material varies from about 5 to about 95% of the total compositions (weight: weight).

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

V. Routes of Administration

One or more compounds disclosed herein (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. In some embodiments, one or more compounds disclosed herein are administered parenterally (e.g., subcutaneous, intramuscular). It will be appreciated that the preferred route may vary with for example the condition of the recipient.

VI. Dosing Regimen

The compound, such as a compound of any of Formulas I, Ia, Ib, Ic, Id, Ie, If, Ig, Ih, Ii, Ij and Ik, may be administered to an individual in accordance with an effective dosing regimen for a desired period of time or duration, such as daily (QD, BID, TID, etc.), at least about one month, at least about 2 months, at least about 3 months, at least about 6 months, or at least about 12 months or longer. In one variation, the compound is administered on a daily or intermittent schedule for the duration of the individual's life.

The dosage or dosing frequency of a compound of any of Formulas I, Ia, Ib, Ic, Id, Ie, If, Ig, Ih, Ii, Ij and Ik, may be adjusted over the course of the treatment, e.g., based on the judgment of the administering physician.

The compound may be administered to an individual (e.g., a human) in an effective amount. In one aspect, the compound is administered once daily. In one aspect, the compound is administered twice a day. In one aspect, the compound is administered three times daily. It is understood that the compound may be administered in any dosage amount provided herein, such as a dosage amount that would provide at least 10 mg/day dosing and no more than 1,000 mg/day dosing. Once daily oral dosing is embraced, such as by administering a dosage form containing from 50 mg to 300 mg of compound.

VII. Methods and Examples

Synthesis of certain compounds and intermediates used to prepare compounds, are detailed in the following sections.

Abbreviations

The following is a list of abbreviations and acronyms used throughout the application:

| Abbreviation | Meaning |
| --- | --- |
| ° C. | Degree Celsius |
| $CH_3CN$ | Acetonitrile |
| d | Doublet |
| dd | Doublet of doublets |
| DCE | 1,2-dichloroethane |
| DCM | Dichloromethane |
| DEAD | Diethyl azodicarboxylate |
| DIAD | Diisopropyl azodicarboxylate |
| DIPEA/DIEA | N,N-diisopropylethylamine |
| DMAP | 4-dimethylaminopyridine |
| DME | 1,2-dimethoxyethane |

-continued

| Abbreviation | Meaning |
| --- | --- |
| DMF | Dimethylformamide |
| DMSO | Dimethylsulfoxide |
| equiv/eq | Equivalents |
| ESI | Electrospray ionization |
| Ac | Acetate |
| Et | Ethyl |
| g | Grams |
| HATU | 2-(7-Aza-1H-Benzotriazole-1-yl)-1,1,3,3-tetramethyluronium hexafluorophosphate |
| HPLC | High-performance liquid chromatography |
| h/hr | Hours |
| Hz | Hertz |
| J | Coupling constant |
| Kg | Kilogram |
| L | Liter |
| M | Molar |
| m | multiplet |
| m/z | mass-to-charge ratio |
| M+ | Mass peak |
| M + H | Mass peak plus hydrogen |
| mg | Milligram |
| MHz | Megahertz |
| min/m | Minute |
| ml/mL | Milliliter |
| mM | Millimolar |
| mmol | Millimole |
| MS | Mass spectroscopy |
| mol | Mole |
| NMR | Nuclear magnetic resonance |
| Ph | Phenyl |
| ppm | Parts per million |
| RP | Reverse phase |
| RT/rt | Room temperature |
| s | Singlet |
| t | Triplet |
| $NEt_3$ | Triethylamine |
| TFA | Trifluoroacetic acid |
| TH | Tetrahydrofuran |
| TLC | Thin layer chromatography |
| TMS | trimethylsilyl |
| δ | Chemical shift |
| μg | Microgram |
| μL/μl | Microliter |
| μM | Micromolar |
| μm | Micrometer |
| μmol | Micromole |

Example numbers for reactions or compounds are listed for convenience.

When production of starting materials is not particularly described, the compounds are known or may be prepared analogously to methods known in the art or as disclosed in the Examples. One of skill in the art will appreciate that synthetic methodologies described herein are only representative of methods for preparation of the compounds described herein, and that other known methods and variants of methods described herein may be used. The methods or features described in various Examples may be combined or adapted in various ways to provide additional ways of making the compounds described herein.

General Synthetic Procedures

The following schemes describe methods that are useful for preparing compounds of formula I (e.g., compounds of formula Ia). For example, as detailed below, compounds of formula I may be prepared using General Scheme 1, General Scheme 2, General Scheme 3, and/or General Scheme 4.

General Scheme 1

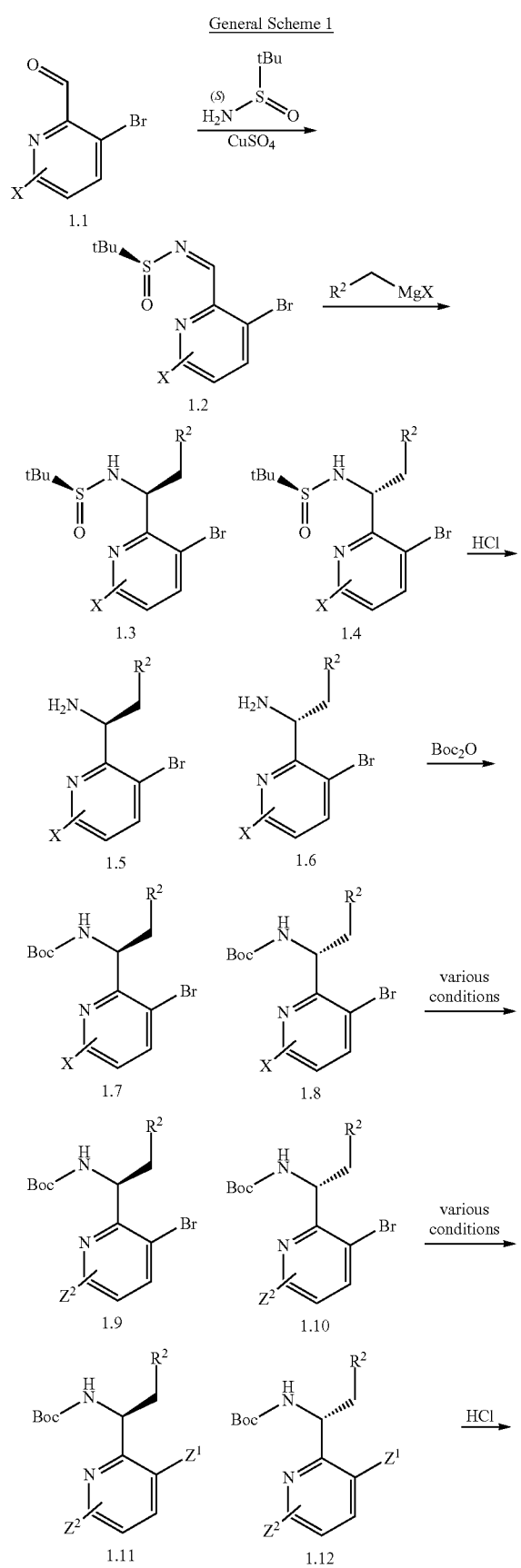

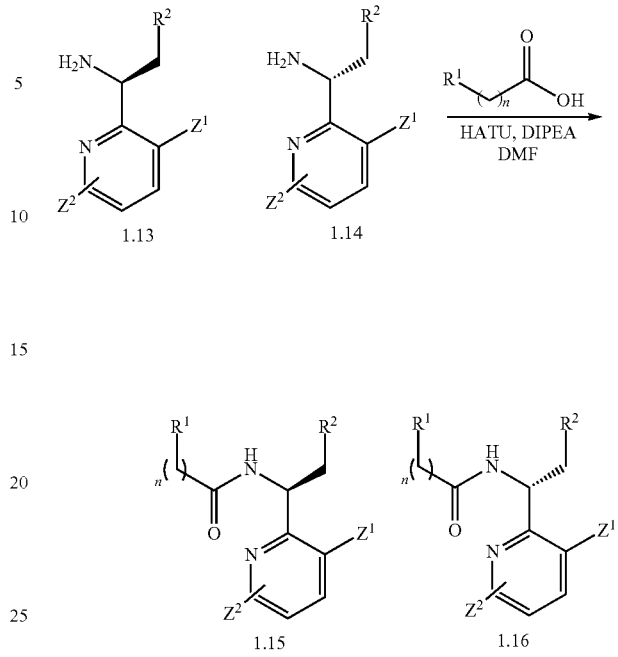

Scheme 1 describes a general stereoselective route that is used to prepare compounds of Formula I (e.g., compounds 1.15 and 1.16). Heteroaryl aldehydes of formula 1.1 (where X represents diversifiable chemical group such as $NH_2$, SH, or halogen that are suitably protected) are condensed with chiral auxiliary (S)-tert-butane sulfinamide followed by stereoselective addition of a nucleophilic Grignard reagent to provide a mixture of 1.3 and 1.4 enriched in 1.3. This mixture is separated by column chromatography on silica gel to provide pure diastereomers. Removal of the auxiliary provides amines 1.5 and 1.6 which are protected. Sequential diversification of 1.7 and 1.8 is accomplished by a variety of methods including alkylation, acylation, cyanation, nucleophilic aromatic displacement, and metal catalyzed cross coupling reactions such as Suzuki couplings, Buchwald-Hartwig type couplings, and Sonogashira couplings. Lastly, the BOC protecting group is removed and the resultant amines are coupled to a variety of carboxylic acids to provide heteroaryl compounds of formula 1.15 and 1.16.

General Scheme 2

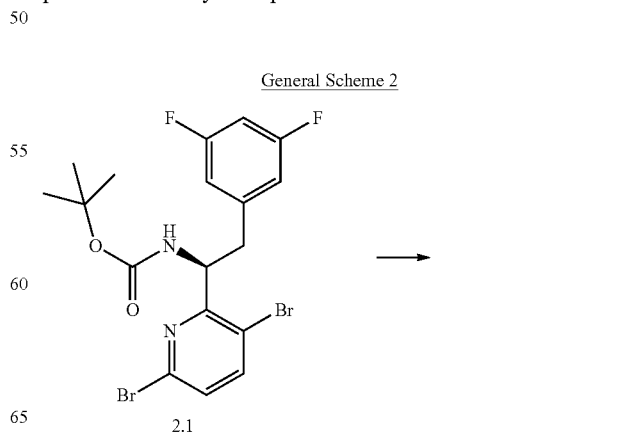

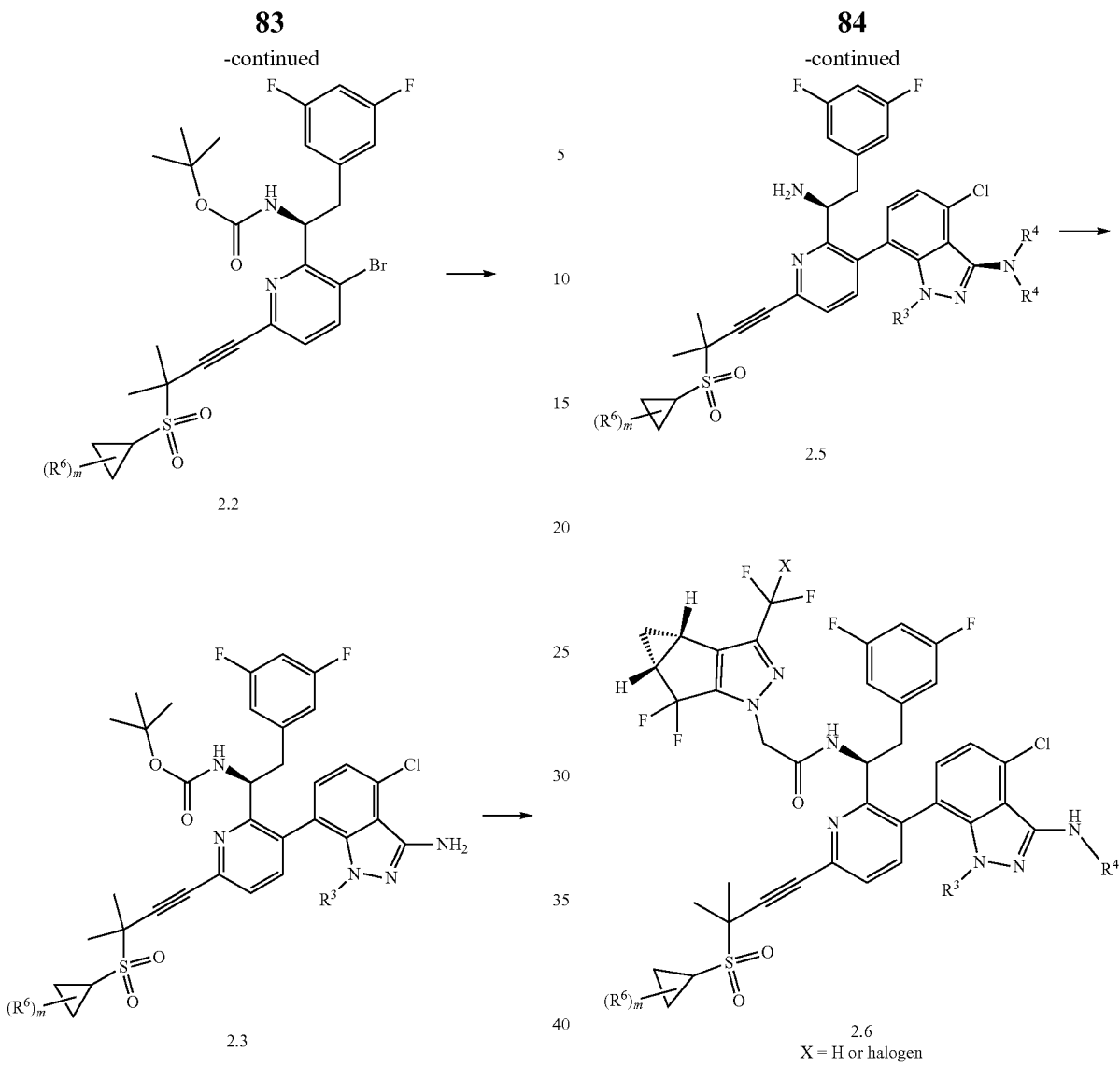

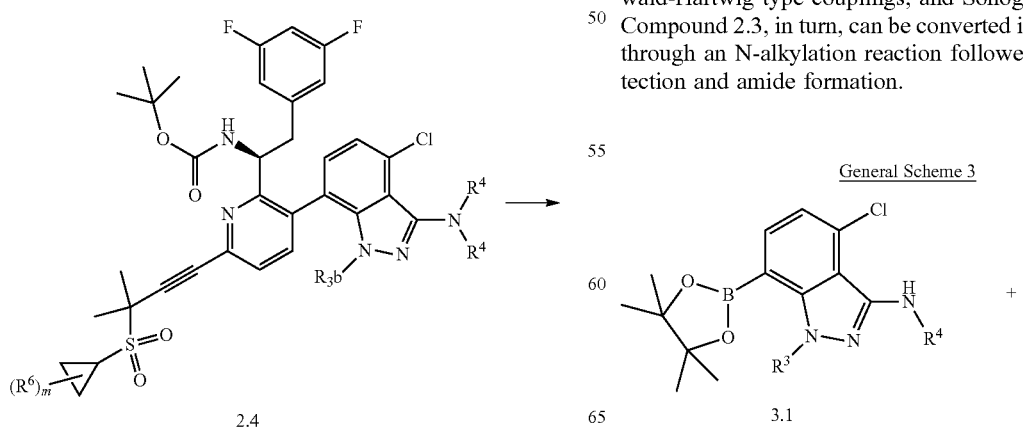

Scheme 2 describes a general stereoselective route that is used to prepare compounds of Formula 2.6 from intermediate 2.1. For example, compound 2.1 can be converted into compound 2.3 through a variety of methods such as metal catalyzed coupling reactions (e.g., Suzuki couplings, Buchwald-Hartwig type couplings, and Sonogashira couplings). Compound 2.3, in turn, can be converted into compound 2.6 through an N-alkylation reaction followed by BOC-deprotection and amide formation.

General Scheme 3

85
-continued

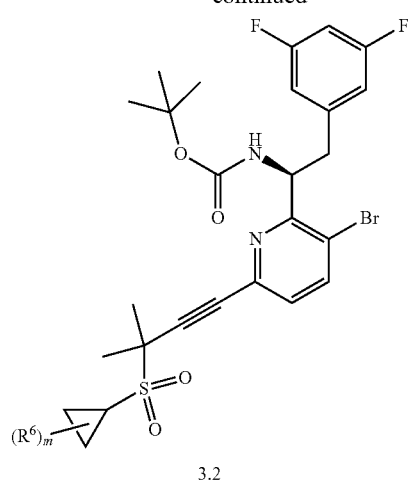

3.2

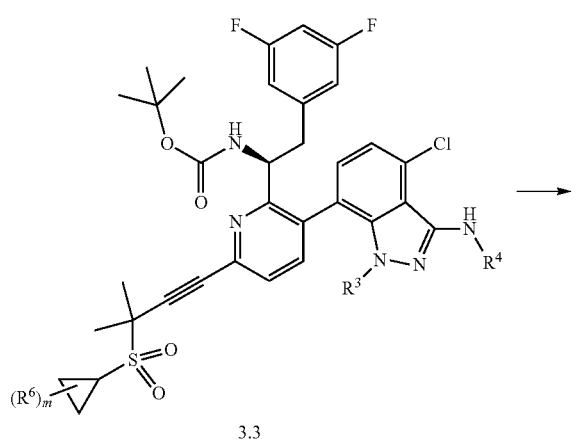

3.3

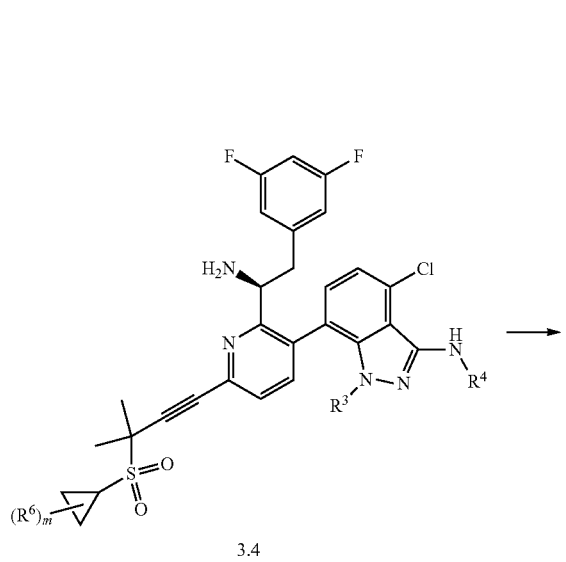

3.4

86
-continued

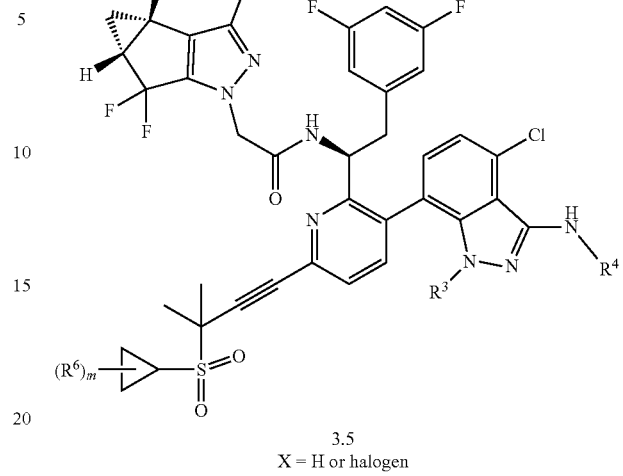

3.5
X = H or halogen

Scheme 3 describes a general stereoselective route that is used to prepare compounds of Formula 3.5 from intermediate 3.1. For example, compounds 3.1 (where R⁴ is not H) and 3.2 are reacted to give compounds of formula 3.3 via a metal catalyzed coupling reaction (e.g., Suzuki couplings). Deprotection of 3.3 is followed by amide formation to give compounds of formula 3.5.

General Scheme 4

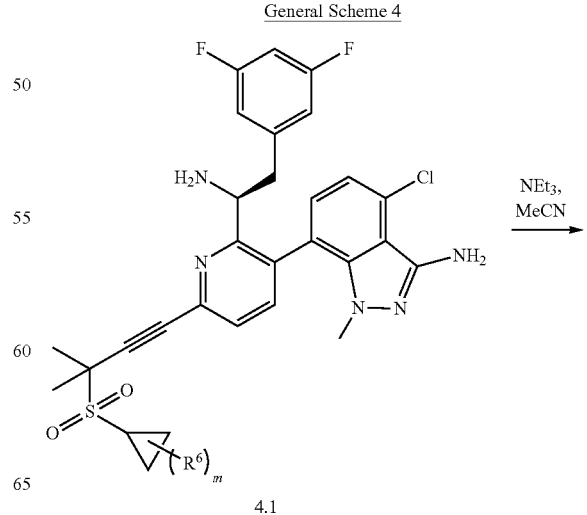

4.1

NEt₃,
MeCN

87
-continued
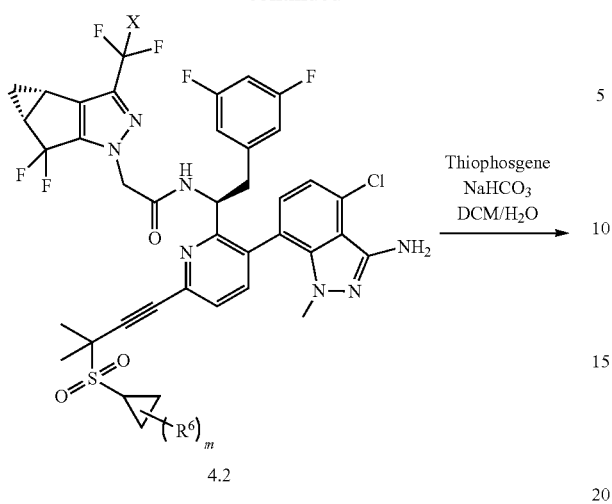
4.2
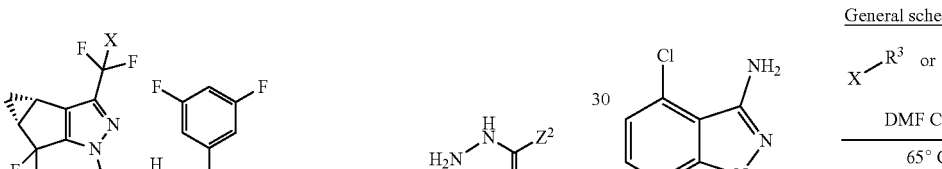
4.3
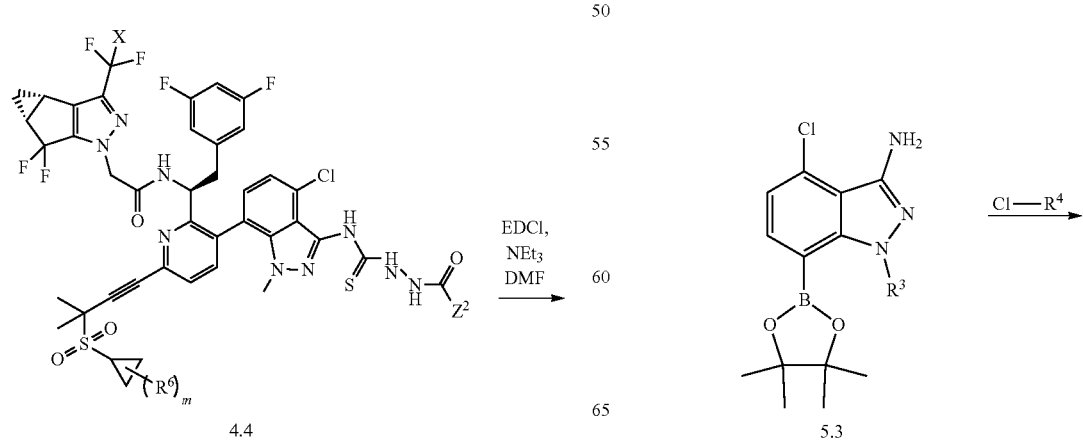
4.4
88
-continued
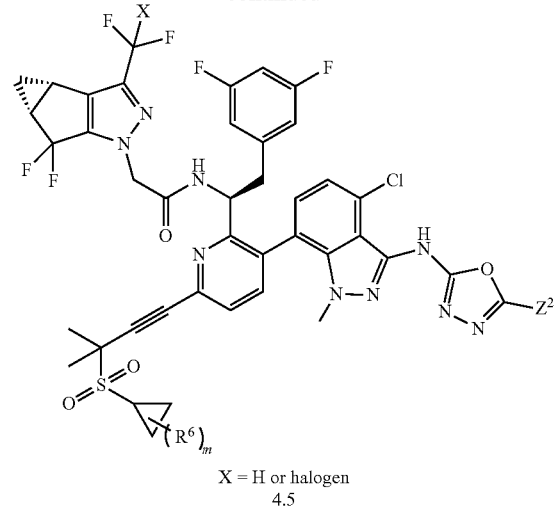
X = H or halogen
4.5
Scheme 4 describes a general stereoselective route that is used to prepare compounds of Formula 4.5.
General scheme 5
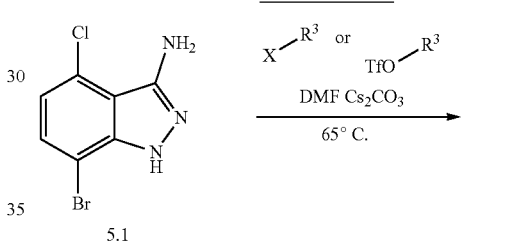
5.1
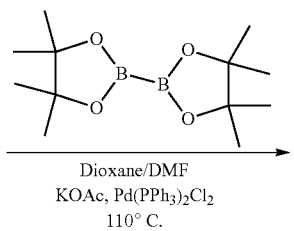
5.2
5.3

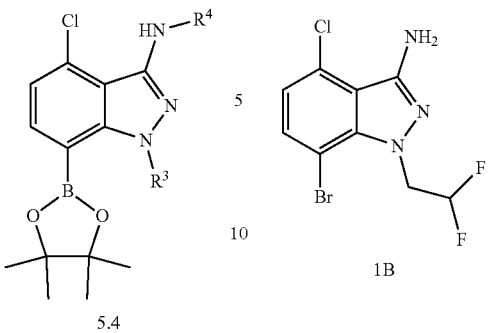

5.4

Scheme 5 describes a general route that is used to prepare compounds of Formula 5.4.

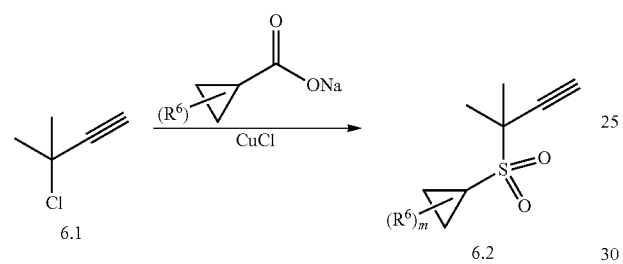

Scheme 6 describes a general route that is used to prepare compounds of Formula 6.2.

Example Procedures of Intermediates and Compound Examples

Methods for obtaining the novel compounds described herein will be apparent to those of ordinary skill in the art, with suitable procedures being described, for example, in the reaction schemes and examples below, and in the references cited herein.

While the foregoing description describes specific embodiments and aspects, those with ordinary skill in the art will appreciate that various modifications and alternatives can be developed. Accordingly, the particular embodiments and aspects described above are meant to be illustrative only, and not to limit the scope of the present disclosure, which is to be given the full breadth of the appended claims, and any and all equivalents thereof. Each of the foregoing references are hereby incorporated by reference.

The following Examples are illustrative of syntheses carried out within the context of the General Schemes above.

Example 1

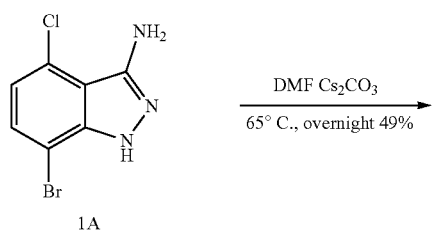

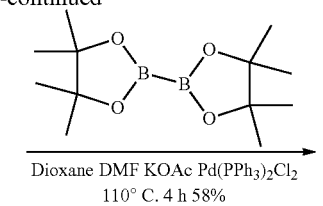

Synthesis of 7-bromo-4-chloro-1-(2,2-difluoro-ethyl)-1H-indazol-3-amine (1B)

To a 2000-mL 4-necked round-bottom flask was placed 7-bromo-4-chloro-1H-indazol-3-amine (130 g, 527.40 mmol, 1.00 equiv), N,N-dimethylformamide (1300 mL), $Cs_2CO_3$ (260 g, 797.99 mmol, 1.50 equiv) with stirring for 20 min, followed by the addition of 1,1-difluoro-2-iodoethane (122 g, 635.59 mmol, 1.20 equiv). The resulting mixture was stirred overnight at 65° C., then cooled to room temperature, quenched by the addition of 3 L of water/ice, extracted with 3×1.5 L of ethyl acetate. The combined organic layer was washed with 1×1.5 L of $H_2O$, 1×1.5 L of brine, dried over anhydrous sodium sulfate and concentrated under vacuum, and recrystallized from ethanol to afford 7-bromo-4-chloro-1-(2,2-difluoroethyl)-1H-indazol-3-amine.

Synthesis of 4-chloro-1-(2,2-difluoroethyl)-7-(4,4,5,5-tetramethyl-1,3,2-dioxaborolan-2-yl)-1H-indazol-3-amine (1C)

To a 3000-mL 4-necked round-bottom flask purged and maintained with an inert atmosphere of nitrogen was placed 7-bromo-4-chloro-1-(2,2-difluoroethyl)-1H-indazol-3-amine (80 g, 257.63 mmol, 1.00 equiv), 1,4-dioxane (800 mL), N,N-dimethylformamide (800 mL), KOAc (76 g, 774.40 mmol, 3.00 equiv), 4,4,5,5-tetramethyl-2-(tetramethyl-1,3,2-dioxaborolan-2-yl)-1,3,2-dioxaborolane (197 g, 775.78 mmol, 3.00 equiv) and $Pd(PPh_3)_2Cl_2$ (8 g, 11.40 mmol, 0.04 equiv). The mixture was stirred for 4 h at 110° C., then cooled to room temperature, quenched by the addition of 5 L of water/ice, extracted with 2×2 L of ethyl acetate. The combined organic layer was washed with 1×1 L of $H_2O$, 1×1 L of brine, dried over anhydrous sodium sulfate and concentrated under vacuum. The residue was applied onto a silica gel column eluted with ethyl acetate/petroleum ether (1:10) to afford 4-chloro-1-(2,2-difluoro-ethyl)-7-(tetramethyl-1,3,2-dioxaborolan-2-yl)-1H-indazol-3-amine. MS (m/z): 358 $[M+H]^+$. (DMSO-d6, 300 MHz, ppm): δ7.63-7.66 (1H, d), 7.00-7.03 (1H, d), 6.06-6.43 (1H, t), 5.46 (2H, s), 4.90-5.01 (2H, t), 1.34 (12H, s).
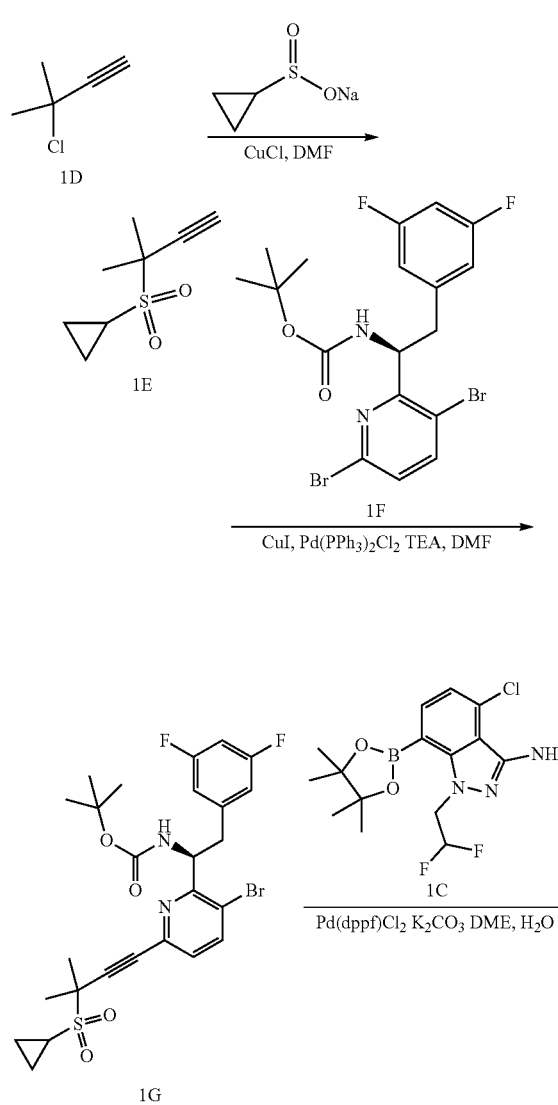
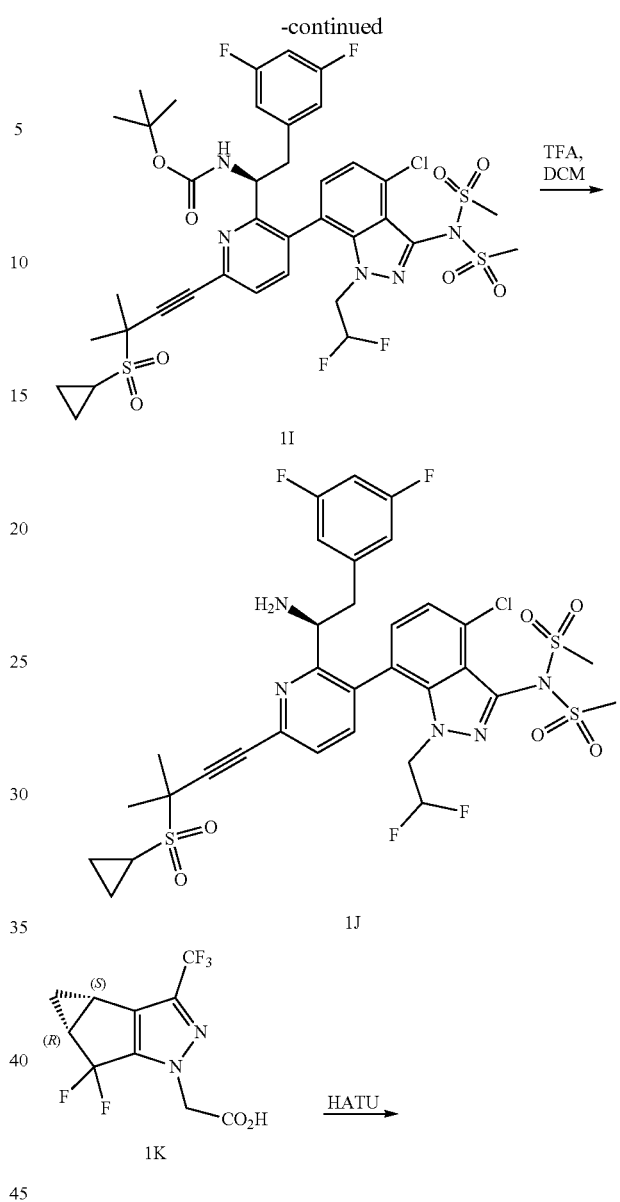
-continued
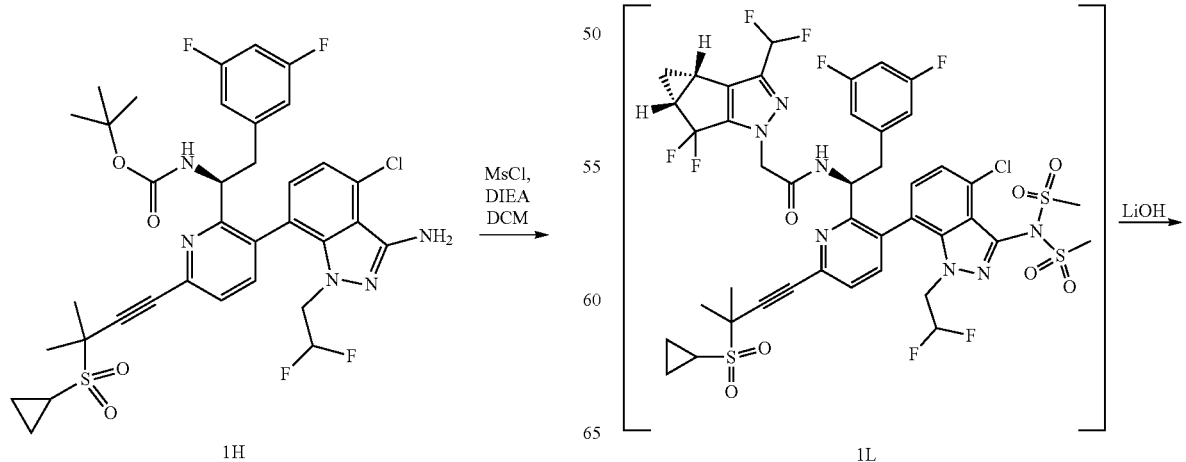

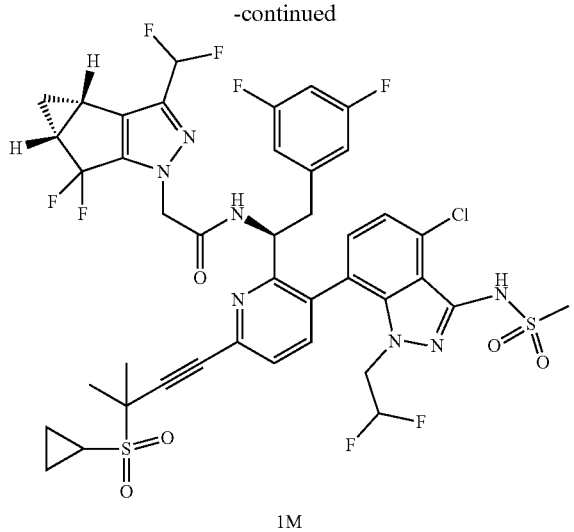

1M

Synthesis of ((2-methylbut-3-yn-2-yl)sulfonyl)cyclopropane (1E)

To a suspension of sodium cyclopropanesulfinate and copper chloride in DMF, 3-chloro-3-methylbut-1-yne was added to the suspension slowly. It was stirred at 40° C. overnight. The mixture was diluted with ethyl acetate and washed with 5% LiCl and brine. The organic layer was dried and concentrated and purified by silica gel chromatography. $^1$H NMR (400 MHz, Chloroform-d) δ 2.71 (tt, 1H), 1.68 (s, 6H), 1.36-1.26 (m, 2H), 1.21-1.01 (m, 2H).

Synthesis of tert-butyl (S)-(1-(3-bromo-6-(3-(cyclopropylsulfonyl)-3-methylbut-1-yn-1-yl)pyridin-2-yl)-2-(3,5-difluorophenyl)ethyl)carbamate (1G)

A round bottom flask was charged with tert-butyl (S)-(1-(3,6-dibromopyridin-2-yl)-2-(3,5-difluorophenyl)ethyl)carbamate (5 g, 10.16 mmol) synthesized as described in WO2014/134566, ((2-methylbut-3-yn-2-yl)sulfonyl)cyclopropane (2.54 g, 14.73 mmol), Bis(triphenylphosphine)palladium(II) dichloride (214 mg, 0.31 mmol) and copper(I) iodide (58 mg, 0.31 mmol). DMF (dimethylformamide) (6 mL) and Et$_3$N (trimethylamine) (5.7 mL, 40.64 mmol) were added. The reaction mixture was degassed and purged with argon then heated to 50° C. for 40 minutes. It was partitioned between EtOAc and 5% LiCl aqueous solution. The organic layer was separated and washed with NH4Cl (sat'd) and brine, dried over MgSO$_4$, filtered and concentrated to afford crude product. It was purified by silica gel chromatography eluting with EtOAc/hexanes to afford the title compound. MS (m/z):584.79 [M+H]$^+$.

Synthesis of tert-butyl (S)-(1-(3-(3-amino-4-chloro-1-(2,2-difluoroethyl)-1H-indazol-7-yl)-6-(3-(cyclopropylsulfonyl)-3-methylbut-1-yn-1-yl)pyridin-2-yl)-2-(3,5-difluorophenyl)ethyl)carbamate (1H)

tert-butyl (S)-(1-(3-bromo-6-(3-(cyclopropylsulfonyl)-3-methylbut-1-yn-1-yl)pyridin-2-yl)-2-(3,5-difluorophenyl)ethyl)carbamate (1000.0 mg, 1.71 mmol), 4-chloro-1-(2,2-difluoroethyl)-7-(4,4,5,5-tetramethyl-1,3,2-dioxaborolan-2-yl)-1H-indazol-3-amine (796.7 mg, 2.23 mmol), [1,1'-bis(diphenylphosphino)ferrocene]dichloropalladium(II) (43.33 mg, 0.051 mmol), and potassium carbonate (592 mg, 4.29 mmol) were charged in a microwave tube and placed under argon. Dimethoxyethane (12 mL) and water (2 mL) were added, and the suspension was degassed by bubbling argon for 60 seconds. After degassing the reaction mixture was heated to 125° C. in a microwave reactor (Biotage® Initiator+) for 20 minutes, and the reaction mixture was cooled to room temperature. It was partitioned between EtOAc and 0.1 N HCl. the aqueous layer was removed. The organic layer was concentrated under vacuum, and the resulting residue was purified by silica gel column chromatography to provide the title compound. MS (m/z) 734.49 [M+H]$^+$).

Synthesis of tert-butyl (S)-(1-(3-(4-chloro-1-(2,2-difluoroethyl)-3-(N-(methylsulfonyl)methylsulfonamido)-1H-indazol-7-yl)-6-(3-(cyclopropylsulfonyl)-3-methylbut-1-yn-1-yl)pyridin-2-yl)-2-(3,5-difluorophenyl)ethyl)carbamate (H)

tert-butyl (S)-(1-(3-(3-amino-4-chloro-1-(2,2-difluoroethyl)-1H-indazol-7-yl)-6-(3-(cyclopropylsulfonyl)-3-methylbut-1-yn-1-yl)pyridin-2-yl)-2-(3,5-difluorophenyl)ethyl)carbamate (300 mg, 0.41 mmol) was dissolved in methylene chloride (6 mL) with stirring at ambient temperature. To it was added N,N-Diisopropylethylamine (0.21 mL, 1.23 mmol) followed by slow addition of methanesulfonyl chloride (0.063 mL, 0.82 mmol). When the reaction was complete, water was added and stirred for 0.5 hours. The organic layer was separated and the aqueous layer was extracted with methylene chloride once. The combined organic layers were washed with water and brine, dried over MgSO$_4$, filtered and concentrated. The residue was purified by silica gel column chromatography to provide the title compound. MS (m/z) 890.01 [M+H]$^+$).

Synthesis of (S)—N-(7-(2-(1-amino-2-(3,5-difluorophenyl)ethyl)-6-(3-(cyclopropylsulfonyl)-3-methylbut-1-yn-1-yl)pyridin-3-yl)-4-chloro-1-(2,2-difluoroethyl)-1H-indazol-3-yl)-N-(methylsulfonyl)methanesulfonamide (1J)

To tert-butyl (S)-(1-(3-(4-chloro-1-(2,2-difluoroethyl)-3-(N-(methylsulfonyl)methylsulfonamido)-1H-indazol-7-yl)-6-(3-(cyclopropylsulfonyl)-3-methylbut-1-yn-1-yl)pyridin-2-yl)-2-(3, 5-difluorophenyl)ethyl)carbamate (288 mg, 0.32 mmol) dissolved in methylene chloride (3 mL) was added trifluoroacetic acid (1 mL). The reaction mixture was stirred at ambient temperature for 30 minutes. The solvent was removed to afford the title compound as TFA salt. MS (m/z): 790.28 [M+H]+).

Synthesis of N—((S)-1-(3-(4-chloro-1-(2,2-difluoroethyl)-3-(methylsulfonamido)-1H-indazol-7-yl)-6-(3-(cyclopropylsulfonyl)-3-methylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (1M)

(S)—N-(7-(2-(1-amino-2-(3,5-difluorophenyl)ethyl)-6-(3-(cyclopropylsulfonyl)-3-methylbut-1-yn-1-yl)pyridin-3-yl)-4-chloro-1-(2,2-difluoroethyl)-1H-indazol-3-yl)-N-(methylsulfonyl)methanesulfonamide (115 mg, 0.13 mmol), 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (36.57 mg, 0.13 mmol), and HATU (1-[bis(dimethylamino)methylene]-1H-1,2,3-triazolo[4,5-b]

pyridinium 3-oxid hexafluorophosphate) (59.13 mg, 0.16 mmol) were charged in a round bottom flask and dissolved in DMF (dimethylformamide) (3 mL). To the solution was added N,N-diisopropylethylamine (0.11 mL, 0.65 mmol). After addition was complete, the reaction mixture was stirred at room temperature for 15 minutes to provide the intermediate 1 L which was not isolated (MS (m/z) 1054.75 [M+H]$^+$). To the solution was added 1 mL ethanol and 2 drops of 15% of sodium hydroxide solution. The mixture was stirred at room temperature for 30 minutes. The reaction mixture was partitioned between water and ethyl acetate. The organic layer was collected and washed with two portions of 5% lithium chloride solution followed by brine. The organic layer was isolated, dried over sodium sulfate, filtered, and concentrated under vacuum. The resulting residue was purified by RP-HPLC to yield the title compound. MS (m/z) 976.22 [M+H]$^+$. $^1$H NMR (400 MHz, Methanol-d$_4$) δ 8.86 (d), 8.73 (d), 7.79 (d), 7.72 (d), 7.65 (dd), 7.20 (q), 7.13 (d), 6.83-6.72 (m), 6.72-6.61 (m), 6.52 (d), 6.43 (dd), 6.36-6.25 (m), 6.21-5.51 (m), 5.05 (q), 4.93-4.62 (m), 4.35-4.11 (m), 3.91-3.38 (m), 3.24 (s), 3.07 (ddd), 3.02-2.89 (m), 2.85 (d), 2.68-2.36 (m), 1.84 (s), 1.47-1.35 (m), 1.36-1.18 (m), 1.17-0.98 (m), 2.35 (m), 1.82 (s), 1.48-1.24 (m), 1.21-0.79 (m).

Example 2

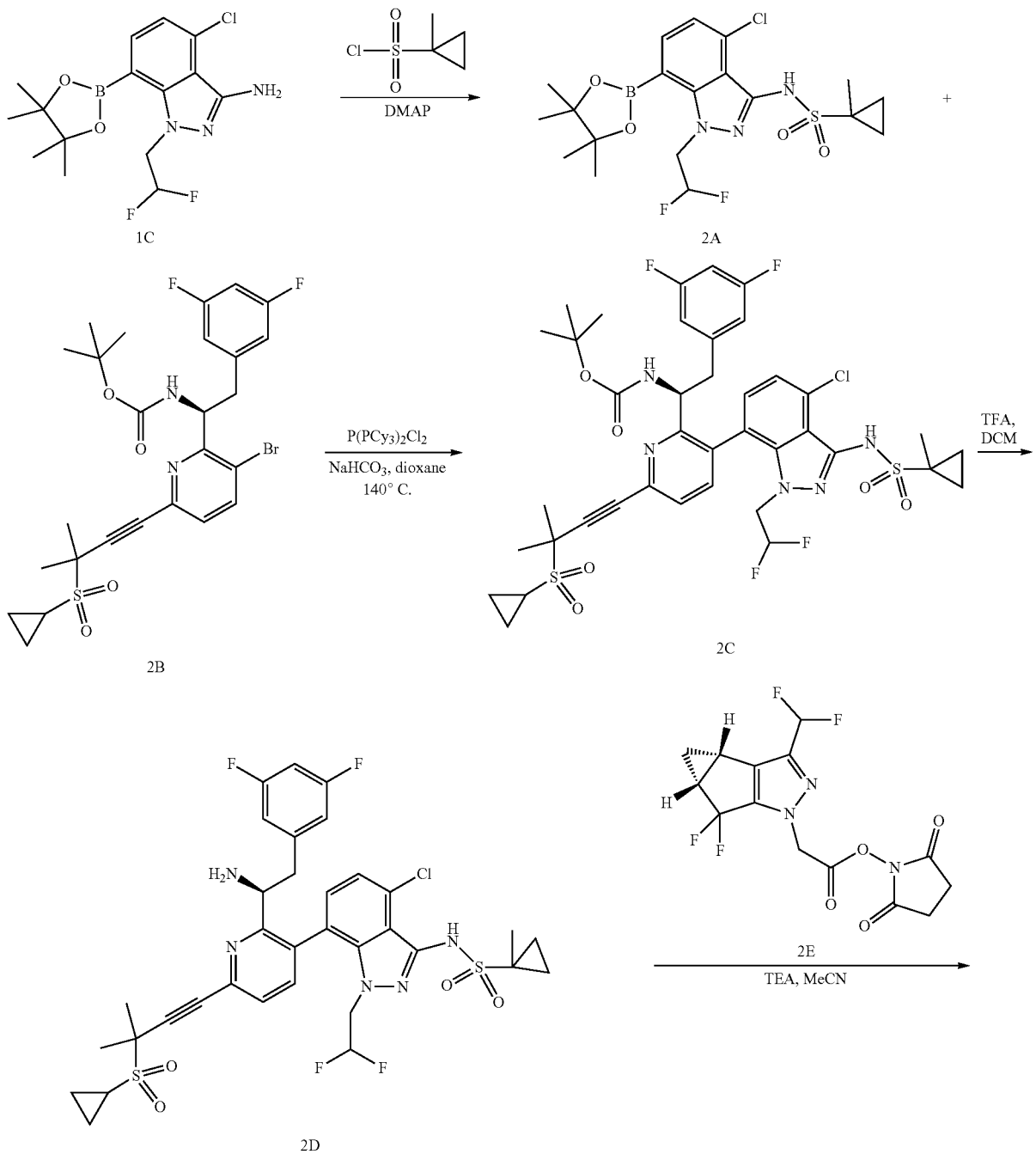

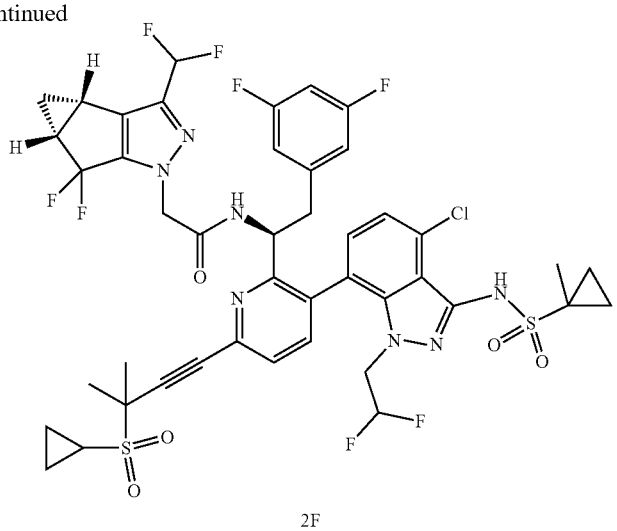

2F

Synthesis of N-(4-chloro-1-(2,2-difluoroethyl)-7-(4,4,5,5-tetramethyl-1,3,2-dioxaborolan-2-yl)-1H-indazol-3-yl)-1-methylcyclopropane-1-sulfonamide (2A)

At 0° C., to mixture of 4-chloro-1-methyl-7-(4,4,5,5-tetramethyl-1,3,2-dioxaborolan-2-yl)-1H-indazol-3-amine (1.5 g, 0.005 mol) in pyridine (10 mL) was added DMAP (0.119 g, 0.001 mol) and followed by the addition of 1-methylcyclopropane-1-sulfonyl chloride (2.262 g, 0.015 mol) in DCM (10 mL). The mixture was stirred at 120° C. for 12 hr. The solvent was removed under vacuum and residue was diluted with EtOAc (20 mL) and acidified with HCl(2N). The organic phase was washed with H$_2$O and brine and dried with MgSO$_4$. Solvent was removed under vacuum. 2 ml EtOAc was added and the solid was filtered to obtain the title product.

Synthesis of tert-butyl (S)-(1-(3-(4-chloro-1-(2,2-difluoroethyl)-3-((1-methylcyclopropane)-1-sulfonamido)-1H-indazol-7-yl)-6-(3-(cyclopropylsulfonyl)-3-methylbut-1-yn-1-yl)pyridin-2-yl)-2-(3,5-difluorophenyl)ethyl)carbamate (2C)

A round bottom flask was charged with N-(4-chloro-1-(2,2-difluoroethyl)-7-(4,4,5,5-tetramethyl-1,3,2-dioxaborolan-2-yl)-1H-indazol-3-yl)-1-methylcyclopropane-1-sulfonamide (98 mg, 0.206 mmol), tert-butyl (S)-(1-(3-bromo-6-(3-(cyclopropylsulfonyl)-3-methylbut-1-yn-1-yl)pyridin-2-yl)-2-(3,5-difluorophenyl)ethyl)carbamate (100 mg, 0.17 mmol), dichlorobis(tricyclohexlphosphine)palladium(II) (5.7 mg) and dioxane (1.5 mL), 1N solution of sodium bicarbonate in water (0.4 mL) were added. The reaction mixture was degased and purged with argon then heated to 140° C. for 15 minutes. It was partitioned between EtOAc and aqueous solution. The organic layer was separated and washed with brine, dried over MgSO$_4$, filtered and concentrated to afford crude product. It was purified by silica gel chromatography eluting with EtOAc/hexanes to afford the title compound. MS (m/z):853.8 [M+H]$^+$.

Synthesis of (S)—N-(7-(2-(1-amino-2-(3,5-difluorophenyl)ethyl)-6-(3-(cyclopropylsulfonyl)-3-methylbut-1-yn-1-yl)pyridin-3-yl)-4-chloro-1-(2,2-difluoroethyl)-1H-indazol-3-yl)-1-methylcyclopropane-1-sulfonamide (2D)

Into the solution of tert-butyl (S)-(1-(3-(4-chloro-1-(2,2-difluoroethyl)-3-((1-methylcyclopropane)-1-sulfonamido)-1H-indazol-7-yl)-6-(3-(cyclopropylsulfonyl)-3-methylbut-1-yn-1-yl)pyridin-2-yl)-2-(3,5-difluorophenyl)ethyl)carbamate (135 mg, 0.16 mmol) in methylene chloride (3 mL) was added trifluoroacetic acid (1 mL). The reaction mixture was stirred at ambient temperature for 60 minutes. The solvent was removed, then it was partitioned between EtOAc and sodium bicarbonate aqueous solution. The organic layer was separated and washed with brine, dried over MgSO$_4$, filtered and concentrated to afford crude product. MS (m/z): 754.11 [M+H]$^+$.

Synthesis of N—((S)-1-(3-(4-chloro-1-(2,2-difluoroethyl)-3-((1-methylcyclopropane)-1-sulfonamido)-1H-indazol-7-yl)-6-(3-(cyclopropylsulfonyl)-3-methylbut-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (2F)

Into the solution of (S)—N-(7-(2-(1-amino-2-(3,5-difluorophenyl)ethyl)-6-(3-(cyclopropylsulfonyl)-3-methylbut-1-yn-1-yl)pyridin-3-yl)-4-chloro-1-(2,2-difluoroethyl)-1H-indazol-3-yl)-1-methylcyclopropane-1-sulfonamide (80 mg, 0.106 mmol) and 2,5-dioxopyrrolidin-1-yl 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetate (46 mg, 0.128 mmol) in MeCN (5 ml), was added TEA (22 mg, 0.213 mmol) at room temperature. After 2h, the reaction mixture was partitioned between water and ethyl acetate. The organic layer was collected and washed with brine. The organic layer was isolated, dried over sodium sulfate, filtered, and concentrated under vacuum. The resulting residue was purified by RP-HPLC to yield 100 mg of title compound. MS (m/z) 1000.12 [M+H]$^+$. $^1$H NMR (400 MHz, Methanol-d$_4$) δ 8.86 (d), 7.86-7.61 (m), 7.31-7.07 (m), 6.89-6.65 (m), 6.50-6.27 (m), 6.09-5.67 (m), 4.90 (s), 4.83-

4.67 (m), 4.29-4.02 (m), 3.68 (s), 3.09 (dd), 3.02-2.90 (m), 2.54-2.41 (m), 1.84 (s), 1.72 (d), 1.63 (s), 1.40 (d), 1.33-1.27 (m), 1.27-1.18 (m), 1.06 (d), 0.76 (d).

Example 3

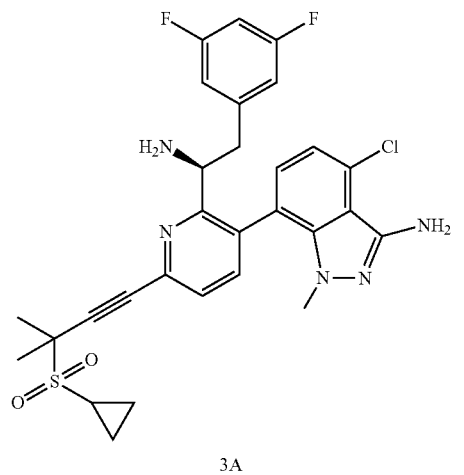

3A

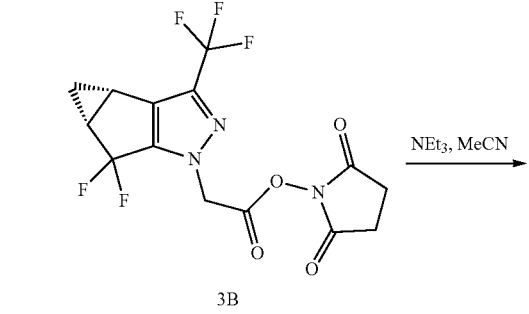

3B

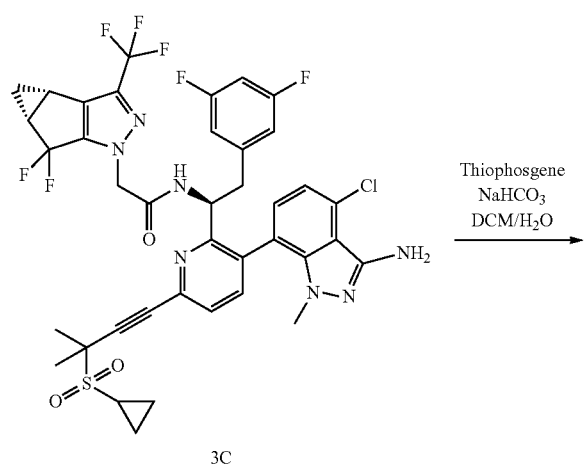

3C

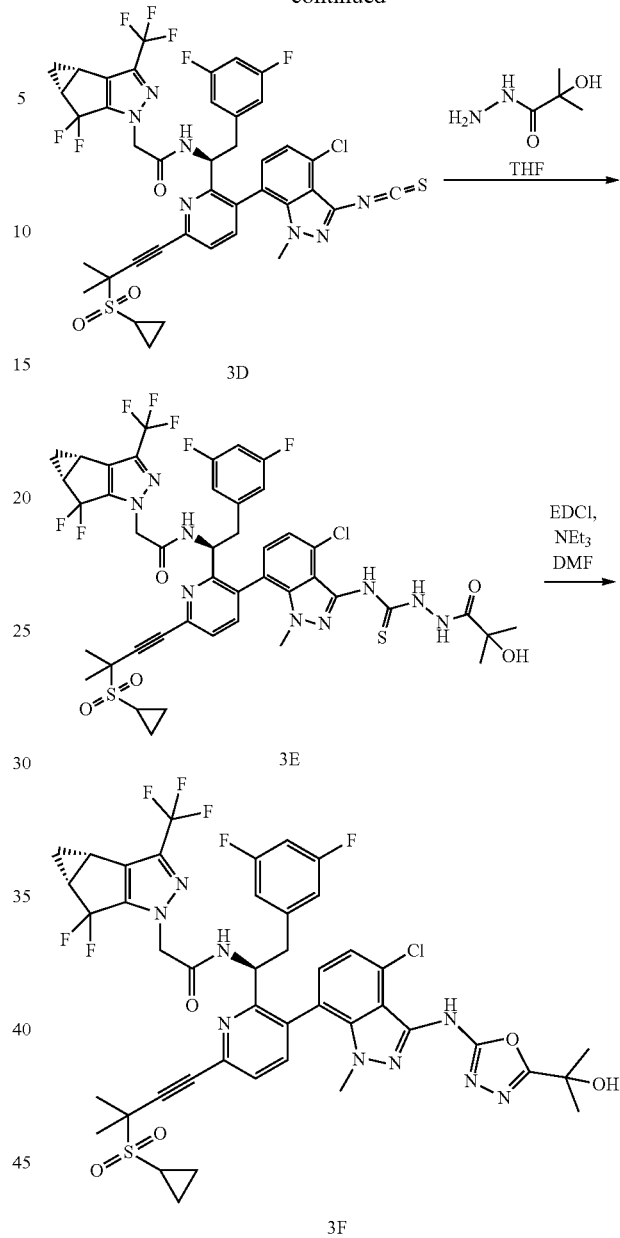

Synthesis of N—((S)-1-(3-(3-amino-4-chloro-1-methyl-1H-indazol-7-yl)-6-(3-(cyclopropyl sulfonyl)-3-methylbut-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl) acetamide (3C)

To a solution of (S)-7-(2-(1-amino-2-(3,5-difluorophenyl) ethyl)-6-(3-(cyclopropylsulfonyl)-3-methylbut-1-yn-1-yl) pyridin-3-yl)-4-chloro-1-methyl-1H-indazol-3-amine (3A, synthesized according to procedures described in Example 1, 26.0 mg, 0.045 mmol) in MeCN (3 mL) was added trimethylamine (31 μL, 0.22 mmol) followed by 2,5-dioxopyrrolidin-1-yl 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetate (3B, 23.6 mg, 0.062 mmol). The reaction mixture was stirred at room temperature for 30 minutes, then concentrated to provide crude 3C which was used without additional purification. MS (m/z) 848.16 [M+H]⁺.

Synthesis of N—((S)-1-(3-(4-chloro-3-isothiocyanato-1-methyl-1H-indazol-7-yl)-6-(3-(cyclopropylsulfonyl)-3-methylbut-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (3D)

To a solution of crude 3C (37.8 mg, 0.045 mmol) in DCM (1.0 mL) and saturated aqueous sodium bicarbonate (1.0 mL) was added thiophosgene (6.8 µL, 0.089 mmol). The reaction mixture was stirred at room temperature for 30 minutes. The organic layer was isolated, and the aqueous layer was extracted with an additional portion of DCM (1.0 mL). The combined organic layers were dried over sodium sulfate, filtered, and concentrated in vacuo. The resulting residue was purified by silica gel column chromatography to provide the title compound. MS (m/z) 890.09 [M+H]⁺.

Synthesis of N—((S)-1-(3-(4-chloro-3-(2-(2-hydroxy-2-methylpropanoyl)hydrazine-1-carbothioamido)-1-methyl-1H-indazol-7-yl)-6-(3-(cyclopropylsulfonyl)-3-methylbut-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (3E)

To a solution of N—((S)-1-(3-(4-chloro-3-isothiocyanato-1-methyl-1H-indazol-7-yl)-6-(3-(cyclopropylsulfonyl)-3-methylbut-1-yn-1-yl)pyridin-2-yl)-2-(3,5-difluorophenyl)ethyl)-2-43bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (3D, 23.6 mg, 0.027 mmol) in THF (1.5 mL) was added 2-hydroxy-2-methylpropanohydrazide (4.7 mg, 0.040 mmol). The reaction mixture was stirred at room temperature for 2 hours. The reaction mixture was concentrated in vacuo to provide crude title compound which was used without additional purification. MS (m/z) 1008.20 [M+H]⁺.

Synthesis of N—((S)-1-(3-(4-chloro-3-((5-(2-hydroxypropan-2-yl)-1,3,4-oxadiazol-2-yl)amino)-1-methyl-1H-indazol-7-yl)-6-(3-(cyclopropylsulfonyl)-3-methylbut-1-yn-1-yl)pyridin-2-yl)-2-(3,5-difluorophenyl)ethyl)-2-((3bS,4 aR)-5,5-difluoro-3-(trifluoromethyl)-3b,4,4a,5-tetrahydro-1H-cyclopropa[3,4]cyclopenta[1,2-c]pyrazol-1-yl)acetamide (3F)

To a solution of crude N—((S)-1-(3-(4-chloro-3-(2-(2-hydroxy-2-methylpropanoyl)hydrazine-1-carbothioamido)-1-methyl-1H-indazol-7-yl)-6-(3-(cyclopropylsulfonyl)-3-methylbut-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (3E, 26.7 mg, 0.027 mmol) in DMF was added triethylamine (0.030 mL, 0.21 mmol) followed by 1-ethyl-3-(3-dimethylaminopropyl)carbodiimide (16.5 mg, 0.11 mmol). The reaction mixture was stirred at room temperature overnight then filtered and directly purified by reverse phase HPLC to provide the title compound. MS (m/z) 974.23 [M+H]⁺. ¹H NMR (400 MHz, Methanol-d₄) δ 8.90-8.82 (m), 7.80-7.72 (m), 7.68-7.58 (m), 7.22 (d), 7.16 (d), 7.11 (s), 7.09 (s), 6.83-6.73 (m), 6.70-6.61 (m), 6.52 (s), 6.50 (s), 6.47-6.38 (m), 5.40-5.23 (m), 5.10-4.98 (m), 4.78 (s), 4.77 (s), 3.35 (s), 3.23-3.15 (m), 3.07-2.91 (m), 2.59-2.39 (m), 1.84 (s), 1.84 (s), 1.64-1.56 (m), 1.50-1.36 (m), 1.35-1.21 (m), 1.20-1.01 (m).

| | Compound Table | |
|---|---|---|
| Structure | Compound Example Number | General Procedure used for Compound Synthesis |
| | 1M | 2 |

-continued

Compound Table

| Structure | Compound Example Number | General Procedure used for Compound Synthesis |
|---|---|---|
| 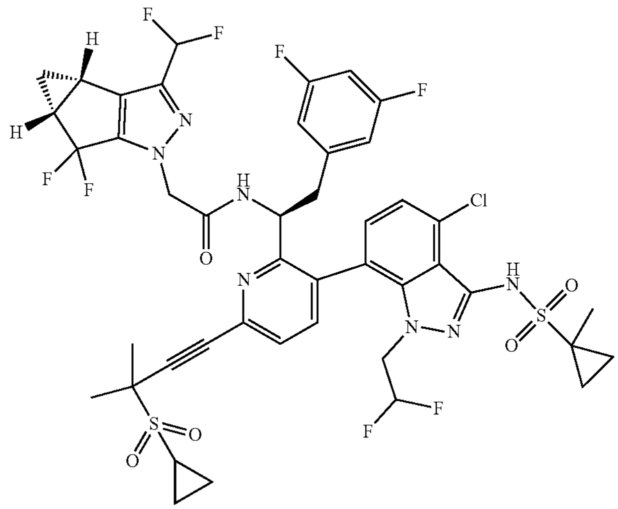 [SMILES: CC1(S(=O)(=O)Nc2nn(CC(F)F)c3c(-c4ccc(C#CC(C)(C)S(=O)(=O)C5CC5)nc4[C@H](Cc4cc(F)cc(F)c4)NC(=O)Cn4nc(C(F)F)c5c4C(F)(F)[C@@H]4C[C@H]54)ccc(Cl)c23)CC1] | 2F | 3 |
| 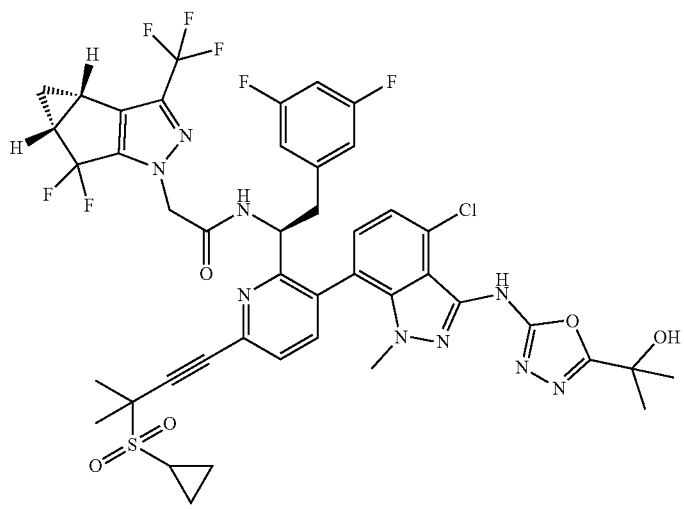 [SMILES: Cn1nc(Nc2nnc(C(C)(C)O)o2)c2c(Cl)ccc(-c3ccc(C#CC(C)(C)S(=O)(=O)C4CC4)nc3[C@H](Cc3cc(F)cc(F)c3)NC(=O)Cn3nc(C(F)(F)F)c4c3C(F)(F)[C@@H]3C[C@H]43)c21] | 3F | 4 |
| 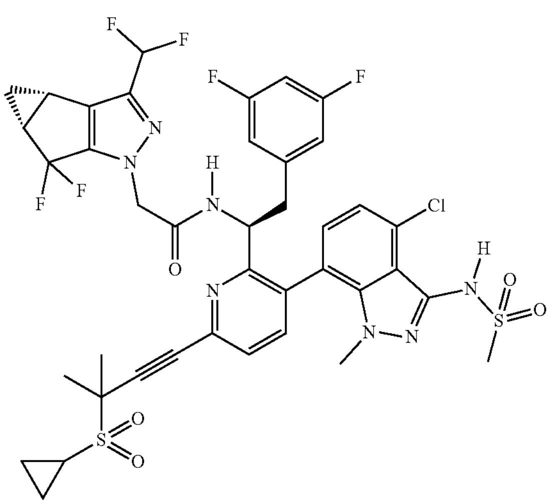 [SMILES: Cn1nc(NS(C)(=O)=O)c2c(Cl)ccc(-c3ccc(C#CC(C)(C)S(=O)(=O)C4CC4)nc3[C@H](Cc3cc(F)cc(F)c3)NC(=O)Cn3nc(C(F)F)c4c3C(F)(F)[C@@H]3C[C@H]43)c21] | 4 | 2 |

-continued

Compound Table

| Structure | Compound Example Number | General Procedure used for Compound Synthesis |
|---|---|---|
| 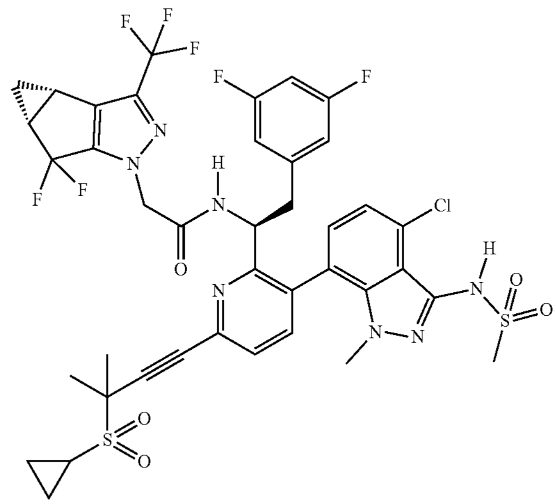 [SMILES: Cn1nc(NS(C)(=O)=O)c2c(Cl)ccc(-c3ccc(C#CC(C)(C)S(=O)(=O)C4CC4)nc3[C@H](Cc3cc(F)cc(F)c3)NC(=O)Cn3nc(C(F)(F)F)c4c3C(F)(F)[C@@H]3C[C@H]43)c21] | 5 | 2 |
| 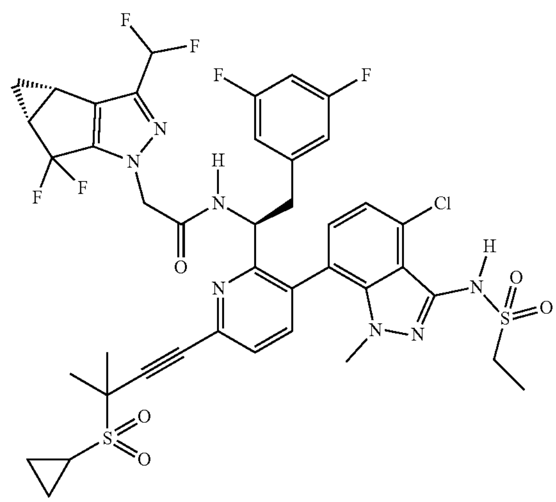 [SMILES: CCS(=O)(=O)Nc1nn(C)c2c(-c3ccc(C#CC(C)(C)S(=O)(=O)C4CC4)nc3[C@H](Cc3cc(F)cc(F)c3)NC(=O)Cn3nc(C(F)F)c4c3C(F)(F)[C@@H]3C[C@H]43)ccc(Cl)c12] | 6 | 2 |
| 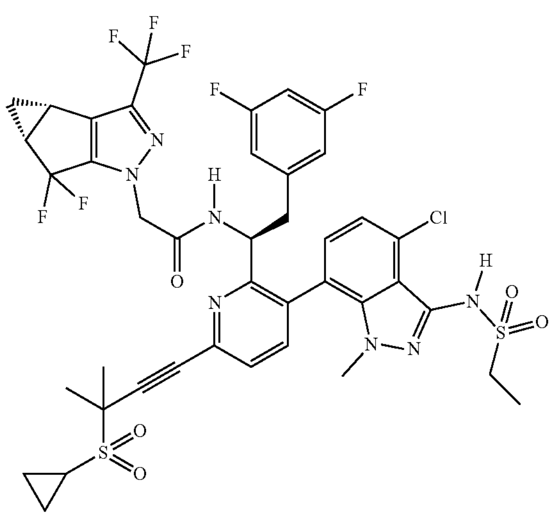 [SMILES: CCS(=O)(=O)Nc1nn(C)c2c(-c3ccc(C#CC(C)(C)S(=O)(=O)C4CC4)nc3[C@H](Cc3cc(F)cc(F)c3)NC(=O)Cn3nc(C(F)(F)F)c4c3C(F)(F)[C@@H]3C[C@H]43)ccc(Cl)c12] | 7 | 2 |

-continued

Compound Table

| Structure | Compound Example Number | General Procedure used for Compound Synthesis |
|---|---|---|
| 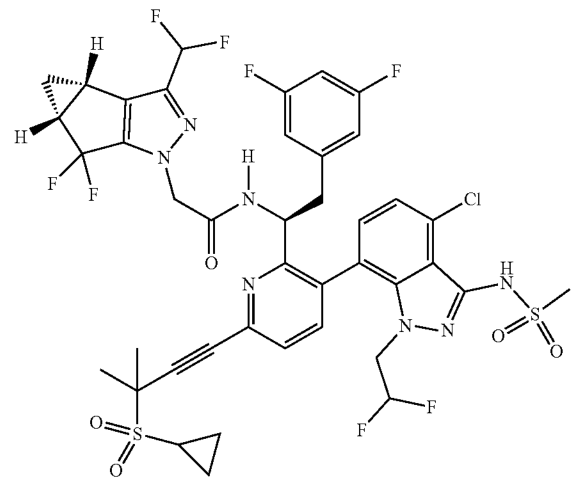 [SMILES: CC(C)(C#Cc1ccc(-c2ccc(Cl)c3c(NS(C)(=O)=O)nn(CC(F)F)c23)c([C@H](Cc2cc(F)cc(F)c2)NC(=O)Cn2nc(C(F)F)c3c2C(F)(F)[C@@H]2C[C@H]32)n1)S(=O)(=O)C1CC1] | 8 | 2 |
| 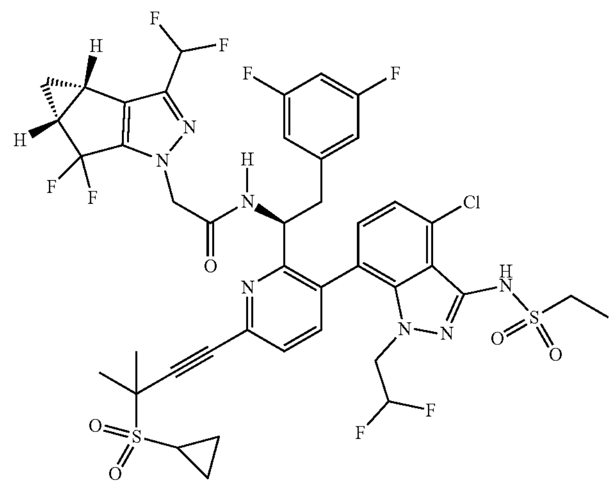 [SMILES: CCS(=O)(=O)Nc1nn(CC(F)F)c2c(-c3ccc(C#CC(C)(C)S(=O)(=O)C4CC4)nc3[C@H](Cc3cc(F)cc(F)c3)NC(=O)Cn3nc(C(F)F)c4c3C(F)(F)[C@@H]3C[C@H]43)ccc(Cl)c12] | 9 | 3 |
| 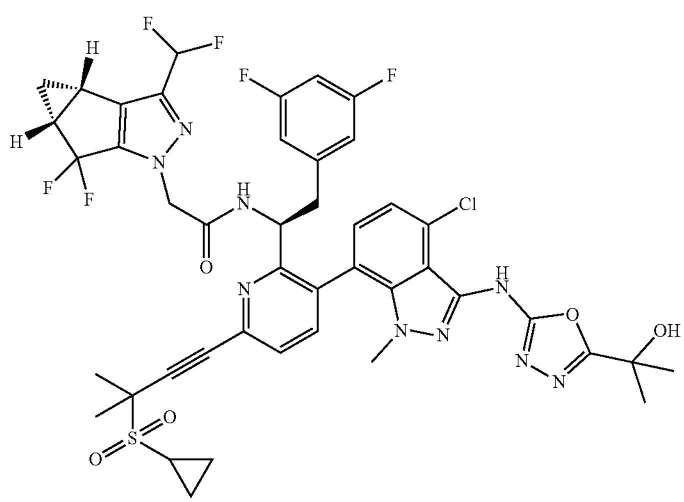 [SMILES: Cn1nc(Nc2nnc(C(C)(C)O)o2)c2c(Cl)ccc(-c3ccc(C#CC(C)(C)S(=O)(=O)C4CC4)nc3[C@H](Cc3cc(F)cc(F)c3)NC(=O)Cn3nc(C(F)F)c4c3C(F)(F)[C@@H]3C[C@H]43)c21] | 10 | 4 |

Compound Table

| Structure | Compound Example Number | General Procedure used for Compound Synthesis |
|---|---|---|
| 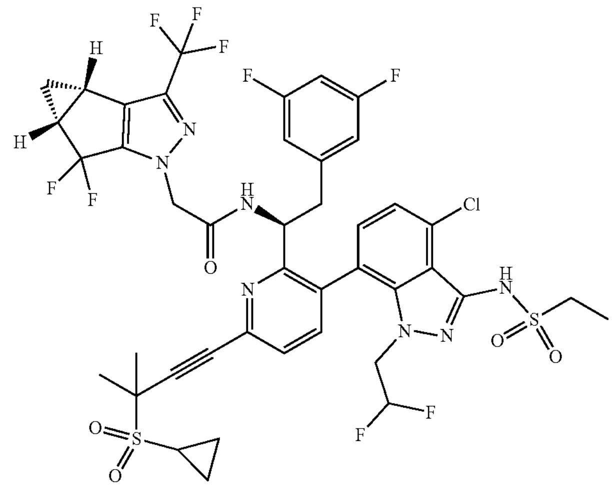 [SMILES: CCS(=O)(=O)Nc1nn(CC(F)F)c2c(-c3ccc(C#CC(C)(C)S(=O)(=O)C4CC4)nc3[C@H](Cc3cc(F)cc(F)c3)NC(=O)Cn3nc(C(F)(F)F)c4c3C(F)(F)[C@@H]3C[C@H]43)ccc(Cl)c12] | 11 | 3 |
| 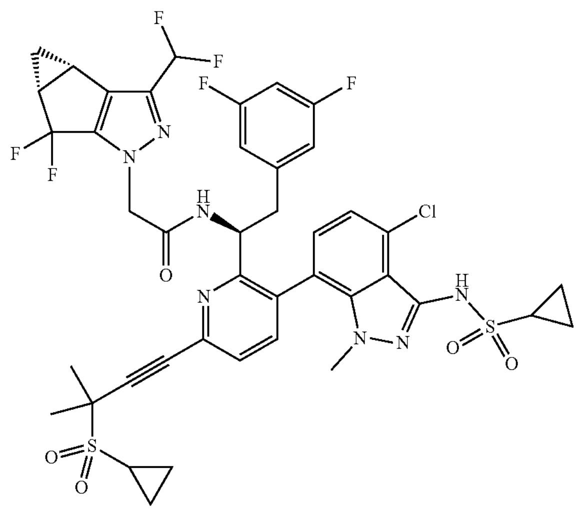 [SMILES: Cn1nc(NS(=O)(=O)C2CC2)c2c(Cl)ccc(-c3ccc(C#CC(C)(C)S(=O)(=O)C4CC4)nc3[C@H](Cc3cc(F)cc(F)c3)NC(=O)Cn3nc(C(F)F)c4c3C(F)(F)[C@@H]3C[C@H]43)c21] | 12 | 3 |
| 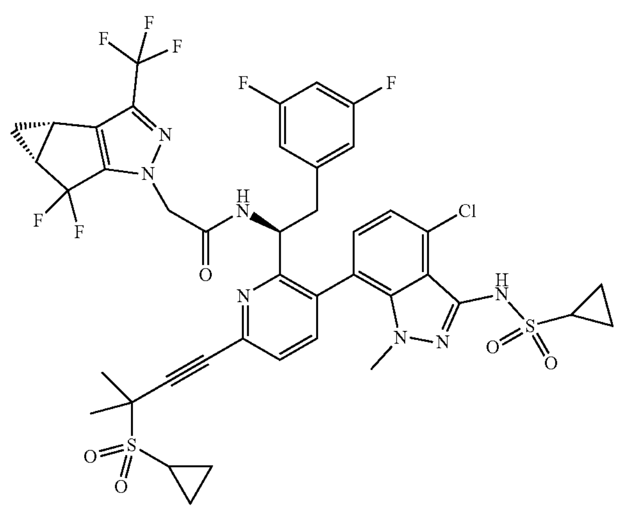 [SMILES: Cn1nc(NS(=O)(=O)C2CC2)c2c(Cl)ccc(-c3ccc(C#CC(C)(C)S(=O)(=O)C4CC4)nc3[C@H](Cc3cc(F)cc(F)c3)NC(=O)Cn3nc(C(F)(F)F)c4c3C(F)(F)[C@@H]3C[C@H]43)c21] | 13 | 3 |

-continued

Compound Table

| Structure | Compound Example Number | General Procedure used for Compound Synthesis |
|---|---|---|
| 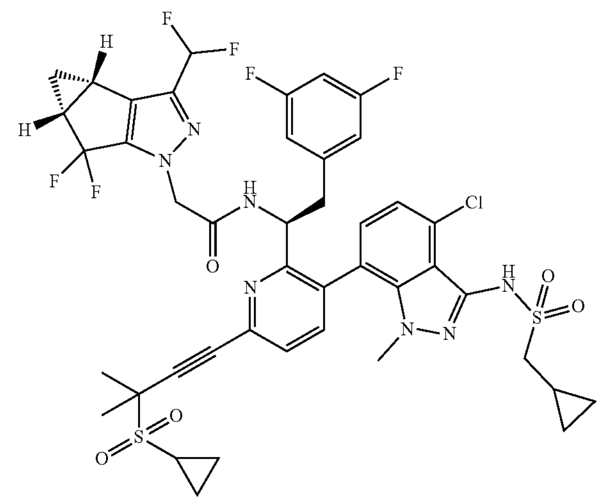 [SMILES: Cn1nc(NS(=O)(=O)CC2CC2)c2c(Cl)ccc(-c3ccc(C#CC(C)(C)S(=O)(=O)C4CC4)nc3[C@H](Cc3cc(F)cc(F)c3)NC(=O)Cn3nc(C(F)F)c4c3C(F)(F)[C@@H]3C[C@H]43)c21] | 14 | 3 |
| 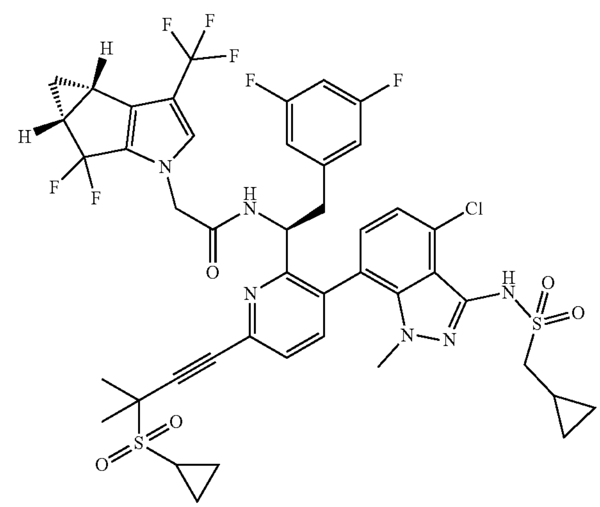 [SMILES: Cn1nc(NS(=O)(=O)CC2CC2)c2c(Cl)ccc(-c3ccc(C#CC(C)(C)S(=O)(=O)C4CC4)nc3[C@H](Cc3cc(F)cc(F)c3)NC(=O)Cn3cc(C(F)(F)F)c4c3C(F)(F)[C@@H]3C[C@H]43)c21] | 15 | 3 |
| 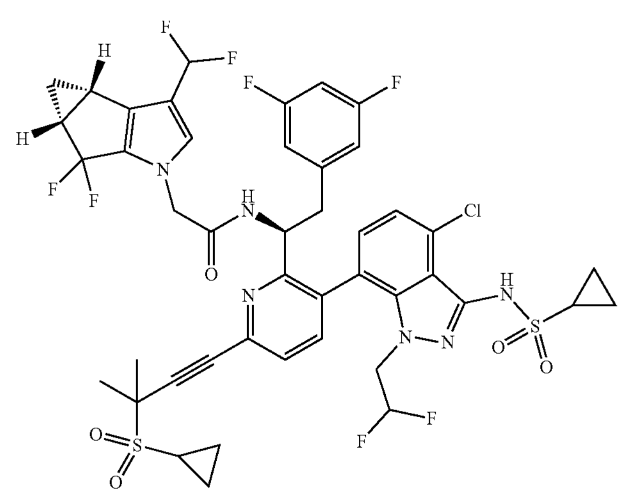 [SMILES: CC(C)(C#Cc1ccc(-c2ccc(Cl)c3c(NS(=O)(=O)C4CC4)nn(CC(F)F)c23)c([C@H](Cc2cc(F)cc(F)c2)NC(=O)Cn2cc(C(F)F)c3c2C(F)(F)[C@@H]2C[C@H]32)n1)S(=O)(=O)C1CC1] | 16 | 2 |

-continued

Compound Table

| Structure | Compound Example Number | General Procedure used for Compound Synthesis |
|---|---|---|
| 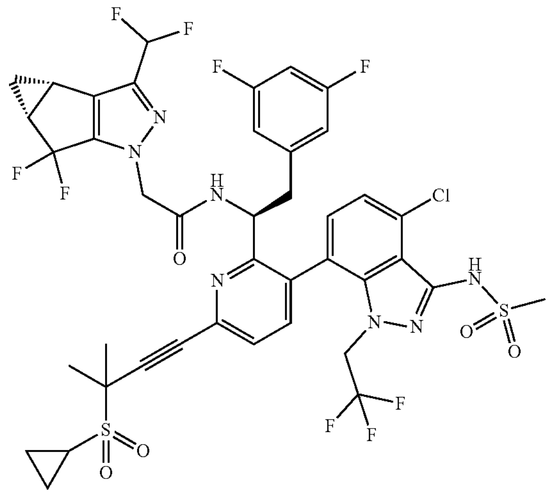 [SMILES: CC(C)(C#Cc1ccc(-c2ccc(Cl)c3c(NS(C)(=O)=O)nn(CC(F)(F)F)c23)c([C@H](Cc2cc(F)cc(F)c2)NC(=O)Cn2nc(C(F)F)c3c2C(F)(F)[C@@H]2C[C@H]32)n1)S(=O)(=O)C1CC1] | 17 | 2 |
| 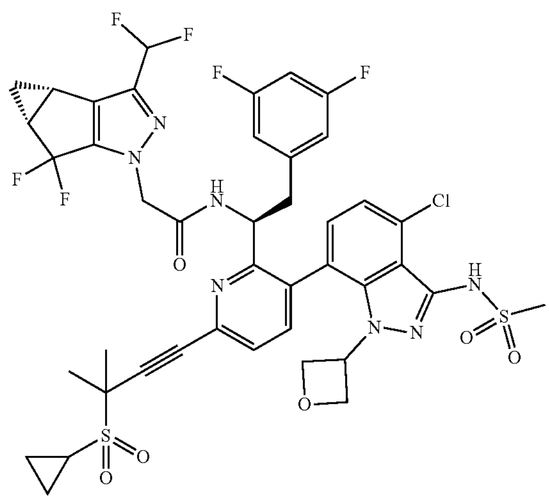 [SMILES: CC(C)(C#Cc1ccc(-c2ccc(Cl)c3c(NS(C)(=O)=O)nn(C4COC4)c23)c([C@H](Cc2cc(F)cc(F)c2)NC(=O)Cn2nc(C(F)F)c3c2C(F)(F)[C@@H]2C[C@H]32)n1)S(=O)(=O)C1CC1] | 18 | 2 |
| 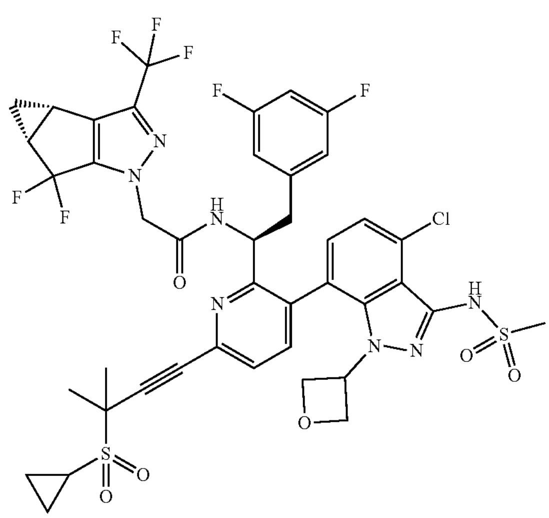 [SMILES: CC(C)(C#Cc1ccc(-c2ccc(Cl)c3c(NS(C)(=O)=O)nn(C4COC4)c23)c([C@H](Cc2cc(F)cc(F)c2)NC(=O)Cn2nc(C(F)(F)F)c3c2C(F)(F)[C@@H]2C[C@H]32)n1)S(=O)(=O)C1CC1] | 19 | 2 |

-continued
Compound Table
| Structure | Compound Example Number | General Procedure used for Compound Synthesis |
| --- | --- | --- |
| 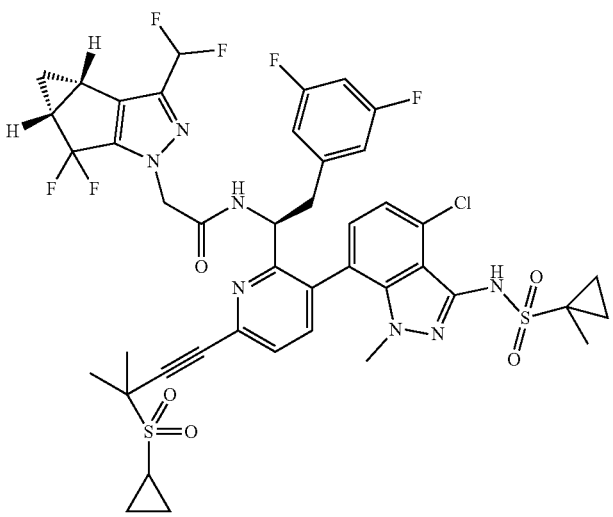 [SMILES: Cn1nc(NS(=O)(=O)C2(C)CC2)c2c(Cl)ccc(-c3ccc(C#CC(C)(C)S(=O)(=O)C4CC4)nc3[C@H](Cc3cc(F)cc(F)c3)NC(=O)Cn3nc(C(F)F)c4c3C(F)(F)[C@@H]3C[C@H]43)c21] | 20 | 3 |
| 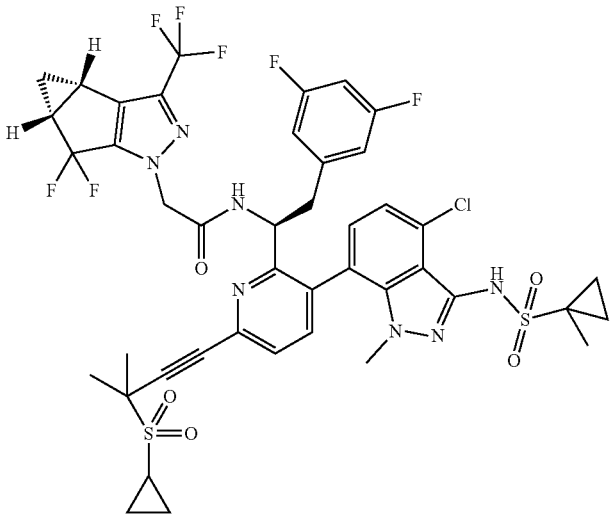 [SMILES: Cn1nc(NS(=O)(=O)C2(C)CC2)c2c(Cl)ccc(-c3ccc(C#CC(C)(C)S(=O)(=O)C4CC4)nc3[C@H](Cc3cc(F)cc(F)c3)NC(=O)Cn3nc(C(F)(F)F)c4c3C(F)(F)[C@@H]3C[C@H]43)c21] | 21 | 3 |

-continued

Compound Table

| Structure | Compound Example Number | General Procedure used for Compound Synthesis |
|---|---|---|
| 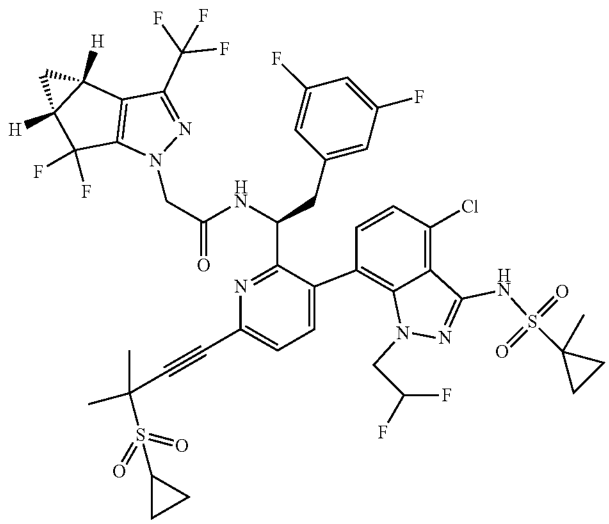 [SMILES: CC1(S(=O)(=O)Nc2nn(CC(F)F)c3c(-c4ccc(C#CC(C)(C)S(=O)(=O)C5CC5)nc4[C@H](Cc4cc(F)cc(F)c4)NC(=O)Cn4nc(C(F)(F)F)c5c4C(F)(F)[C@@H]4C[C@H]54)ccc(Cl)c23)CC1] | 22 | 3 |
| 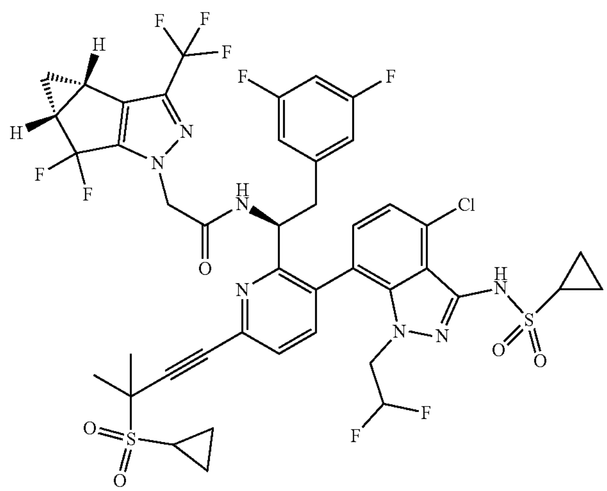 [SMILES: CC(C)(C#Cc1ccc(-c2ccc(Cl)c3c(NS(=O)(=O)C4CC4)nn(CC(F)F)c23)c([C@H](Cc2cc(F)cc(F)c2)NC(=O)Cn2nc(C(F)(F)F)c3c2C(F)(F)[C@@H]2C[C@H]32)n1)S(=O)(=O)C1CC1] | 23 | 2 |
| 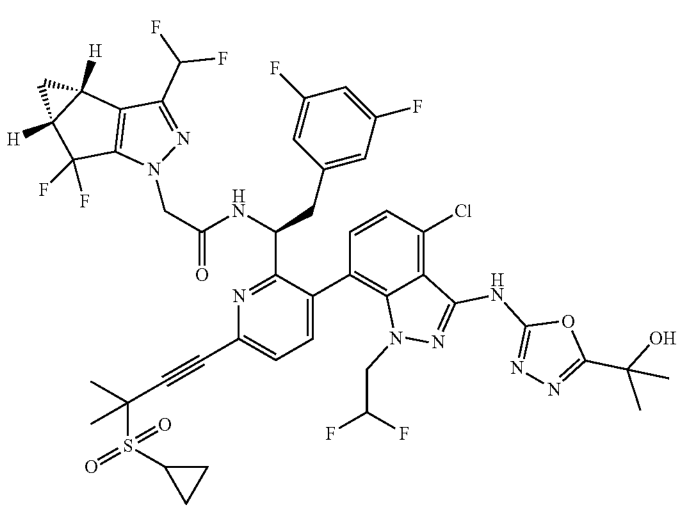 [SMILES: CC(C)(O)c1nnc(Nc2nn(CC(F)F)c3c(-c4ccc(C#CC(C)(C)S(=O)(=O)C5CC5)nc4[C@H](Cc4cc(F)cc(F)c4)NC(=O)Cn4nc(C(F)F)c5c4C(F)(F)[C@@H]4C[C@H]54)ccc(Cl)c23)o1] | 24 | 4 |

-continued

Compound Table

| Structure | Compound Example Number | General Procedure used for Compound Synthesis |
|---|---|---|
| 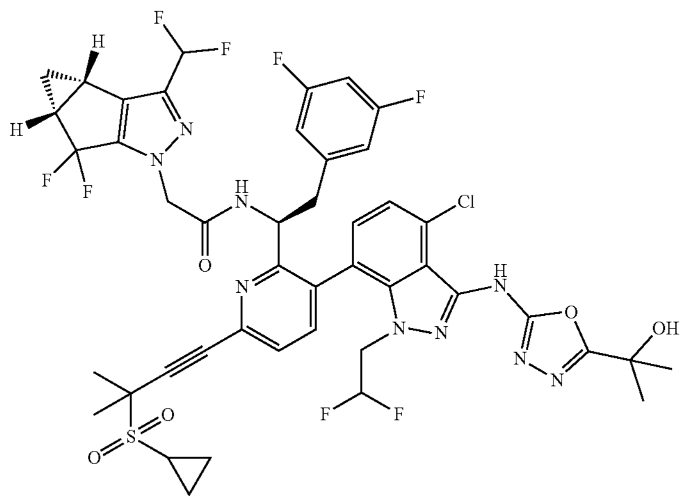 [SMILES: CC(C)(O)c1nnc(Nc2nn(CC(F)F)c3c(-c4ccc(C#CC(C)(C)S(=O)(=O)C5CC5)nc4[C@H](Cc4cc(F)cc(F)c4)NC(=O)Cn4nc(C(F)F)c5c4C(F)(F)[C@@H]4C[C@H]54)ccc(Cl)c23)o1] | 25 | 4 |
| 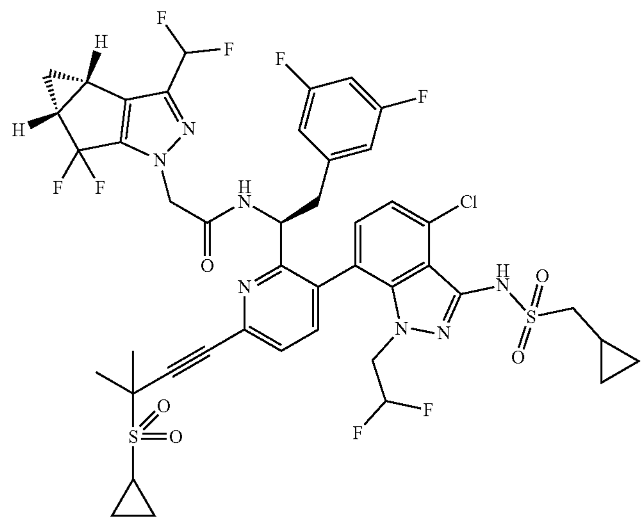 [SMILES: CC(C)(C#Cc1ccc(-c2ccc(Cl)c3c(NS(=O)(=O)CC4CC4)nn(CC(F)F)c23)c([C@H](Cc2cc(F)cc(F)c2)NC(=O)Cn2nc(C(F)F)c3c2C(F)(F)[C@@H]2C[C@H]32)n1)S(=O)(=O)C1CC1] | 26 | 3 |
| 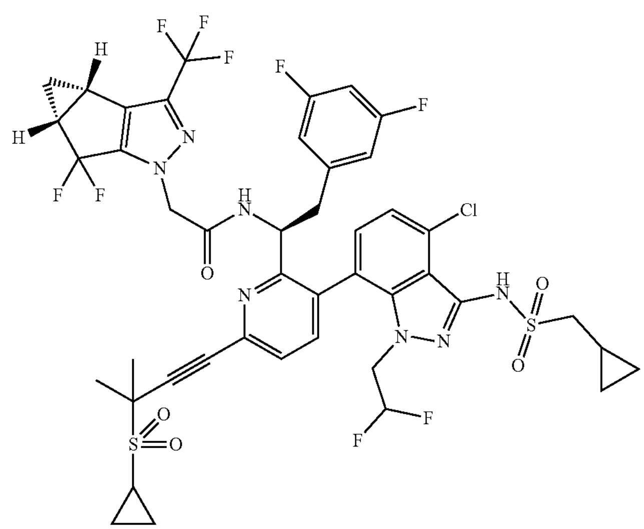 [SMILES: CC(C)(C#Cc1ccc(-c2ccc(Cl)c3c(NS(=O)(=O)CC4CC4)nn(CC(F)F)c23)c([C@H](Cc2cc(F)cc(F)c2)NC(=O)Cn2nc(C(F)(F)F)c3c2C(F)(F)[C@@H]2C[C@H]32)n1)S(=O)(=O)C1CC1] | 27 | 3 |

-continued

Compound Table

| Structure | Compound Example Number | General Procedure used for Compound Synthesis |
|---|---|---|
| 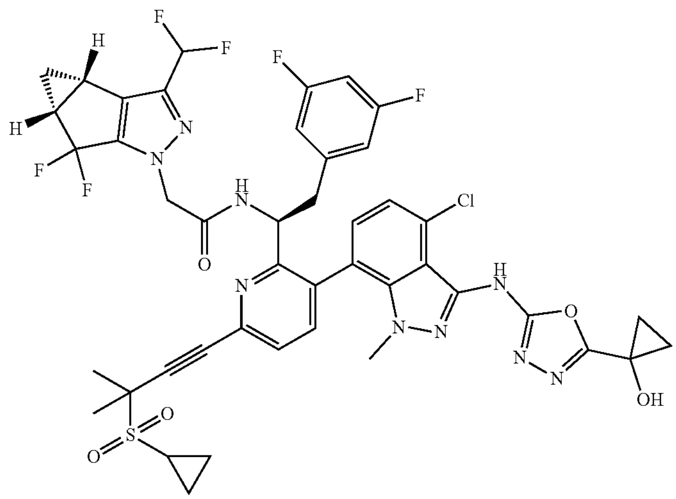 [SMILES: Cn1nc(Nc2nnc(C3(O)CC3)o2)c2c(Cl)ccc(-c3ccc(C#CC(C)(C)S(=O)(=O)C4CC4)nc3[C@H](Cc3cc(F)cc(F)c3)NC(=O)Cn3nc(C(F)F)c4c3C(F)(F)[C@@H]3C[C@H]43)c21] | 28 | 4 |
| 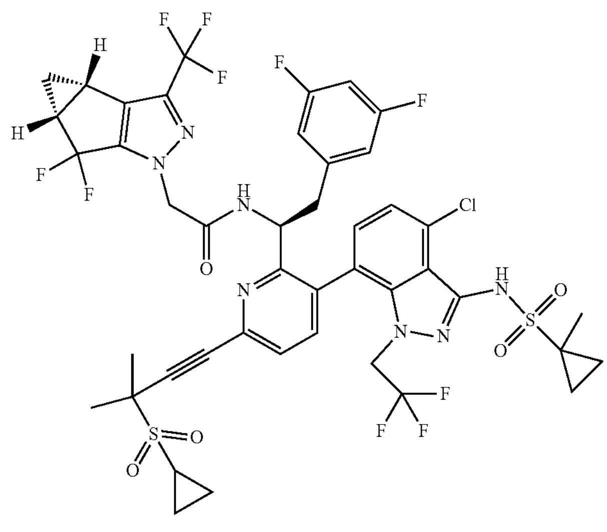 [SMILES: CC1(S(=O)(=O)Nc2nn(CC(F)(F)F)c3c(-c4ccc(C#CC(C)(C)S(=O)(=O)C5CC5)nc4[C@H](Cc4cc(F)cc(F)c4)NC(=O)Cn4nc(C(F)(F)F)c5c4C(F)(F)[C@@H]4C[C@H]54)ccc(Cl)c23)CC1] | 29 | 3 |
| 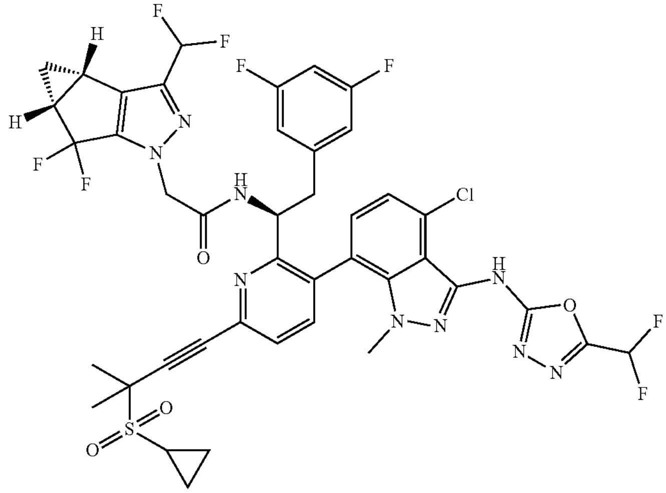 [SMILES: Cn1nc(Nc2nnc(C(F)F)o2)c2c(Cl)ccc(-c3ccc(C#CC(C)(C)S(=O)(=O)C4CC4)nc3[C@H](Cc3cc(F)cc(F)c3)NC(=O)Cn3nc(C(F)F)c4c3C(F)(F)[C@@H]3C[C@H]43)c21] | 30 | 4 |

-continued

Compound Table

| Structure | Compound Example Number | General Procedure used for Compound Synthesis |
|---|---|---|
| 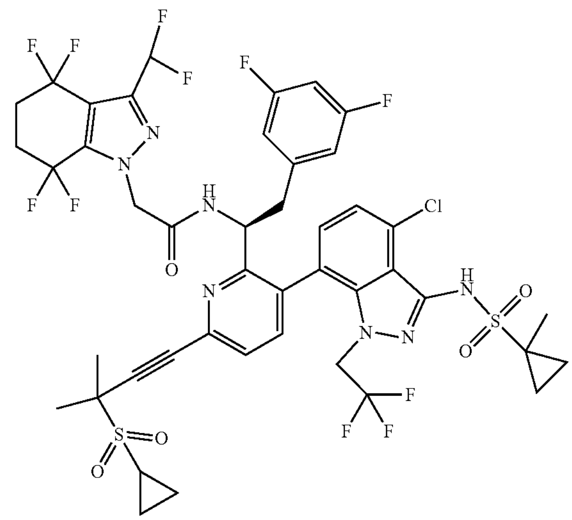 [SMILES: CC1(S(=O)(=O)Nc2nn(CC(F)(F)F)c3c(-c4ccc(C#CC(C)(C)S(=O)(=O)C5CC5)nc4[C@H](Cc4cc(F)cc(F)c4)NC(=O)Cn4nc(C(F)F)c5c4C(F)(F)CCC5(F)F)ccc(Cl)c23)CC1] | 31 | 3 |
| 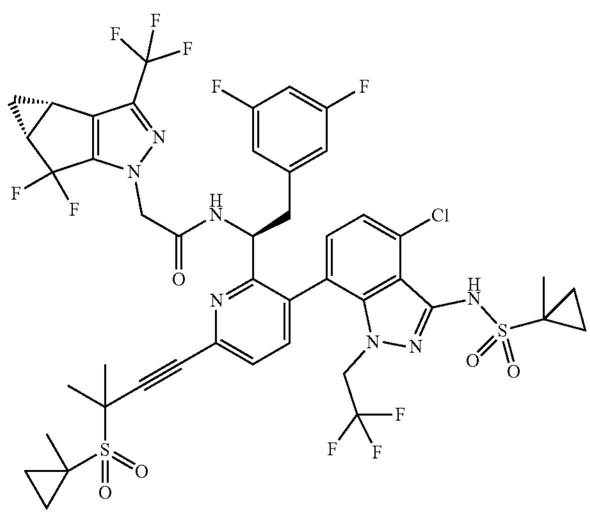 [SMILES: CC1(S(=O)(=O)Nc2nn(CC(F)(F)F)c3c(-c4ccc(C#CC(C)(C)S(=O)(=O)C5(C)CC5)nc4[C@H](Cc4cc(F)cc(F)c4)NC(=O)Cn4nc(C(F)(F)F)c5c4C(F)(F)[C@@H]4C[C@H]54)ccc(Cl)c23)CC1] | 32 | 2 |
| 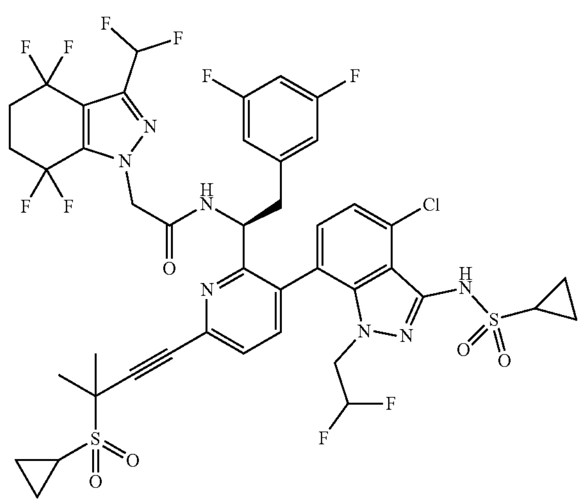 [SMILES: CC(C)(C#Cc1ccc(-c2ccc(Cl)c3c(NS(=O)(=O)C4CC4)nn(CC(F)F)c23)c([C@H](Cc2cc(F)cc(F)c2)NC(=O)Cn2nc(C(F)F)c3c2C(F)(F)CCC3(F)F)n1)S(=O)(=O)C1CC1] | 33 | 2 |

-continued

Compound Table

| Structure | Compound Example Number | General Procedure used for Compound Synthesis |
|---|---|---|
| 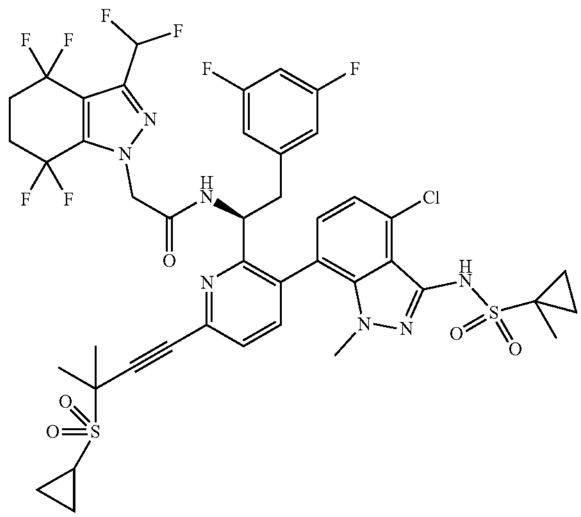 [SMILES: Cn1nc(NS(=O)(=O)C2(C)CC2)c2c(Cl)ccc(-c3ccc(C#CC(C)(C)S(=O)(=O)C4CC4)nc3[C@H](Cc3cc(F)cc(F)c3)NC(=O)Cn3nc(C(F)F)c4c3C(F)(F)CCC4(F)F)c21] | 34 | 3 |
| 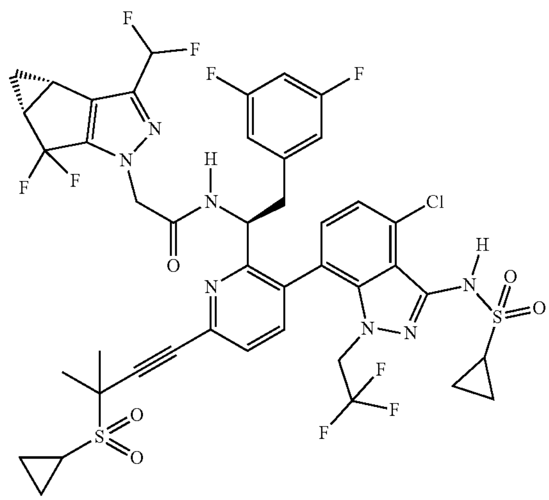 [SMILES: CC(C)(C#Cc1ccc(-c2ccc(Cl)c3c(NS(=O)(=O)C4CC4)nn(CC(F)(F)F)c23)c([C@H](Cc2cc(F)cc(F)c2)NC(=O)Cn2nc(C(F)F)c3c2C(F)(F)[C@@H]2C[C@H]32)n1)S(=O)(=O)C1CC1] | 35 | 2 |
| 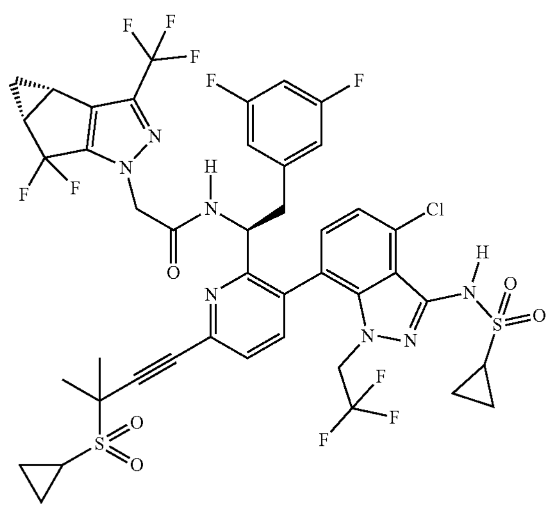 [SMILES: CC(C)(C#Cc1ccc(-c2ccc(Cl)c3c(NS(=O)(=O)C4CC4)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(=O)(=O)C1CC1] | 36 | 2 |

-continued

Compound Table

| Structure | Compound Example Number | General Procedure used for Compound Synthesis |
|---|---|---|
| 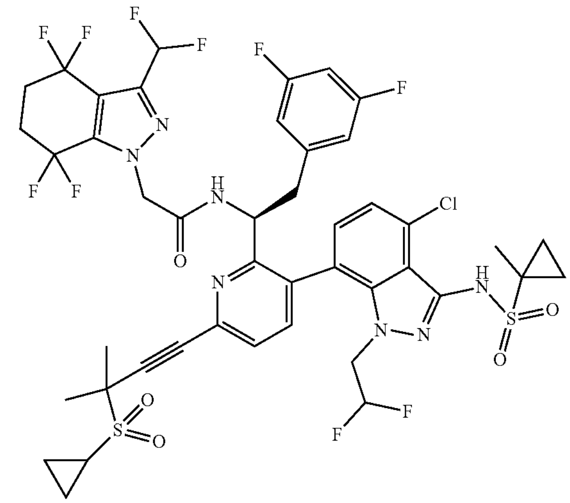 [SMILES: CC1(S(=O)(=O)Nc2nn(CC(F)F)c3c(-c4ccc(C#CC(C)(C)S(=O)(=O)C5CC5)nc4[C@H](Cc4cc(F)cc(F)c4)NC(=O)Cn4nc(C(F)F)c5c4C(F)(F)CCC5(F)F)ccc(Cl)c23)CC1] | 37 | 3 |
| 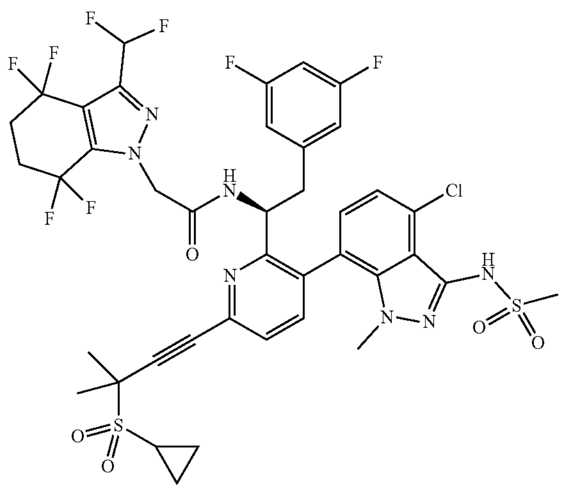 [SMILES: Cn1nc(NS(C)(=O)=O)c2c(Cl)ccc(-c3ccc(C#CC(C)(C)S(=O)(=O)C4CC4)nc3[C@H](Cc3cc(F)cc(F)c3)NC(=O)Cn3nc(C(F)F)c4c3C(F)(F)CCC4(F)F)c21] | 38 | 3 |
| 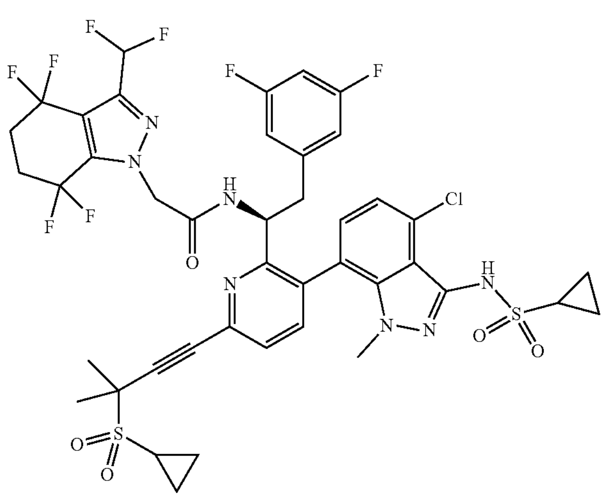 [SMILES: Cn1nc(NS(=O)(=O)C2CC2)c2c(Cl)ccc(-c3ccc(C#CC(C)(C)S(=O)(=O)C4CC4)nc3[C@H](Cc3cc(F)cc(F)c3)NC(=O)Cn3nc(C(F)F)c4c3C(F)(F)CCC4(F)F)c21] | 39 | 3 |

-continued
Compound Table
| Structure | Compound Example Number | General Procedure used for Compound Synthesis |
|---|---|---|
| 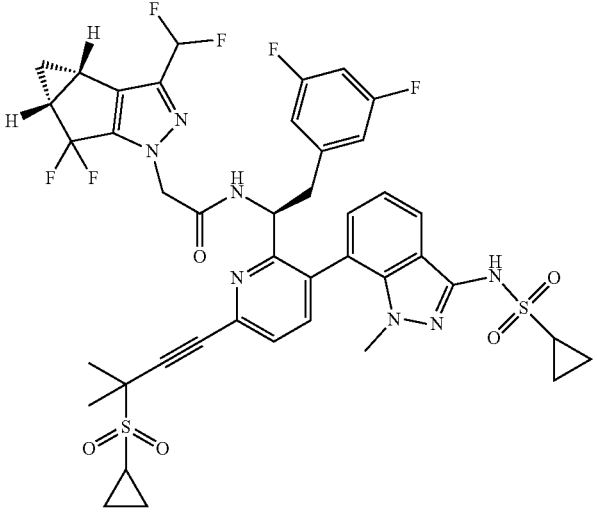 [SMILES: Cn1nc(NS(=O)(=O)C2CC2)c2cccc(-c3ccc(C#CC(C)(C)S(=O)(=O)C4CC4)nc3[C@H](Cc3cc(F)cc(F)c3)NC(=O)Cn3nc(C(F)F)c4c3C(F)(F)[C@@H]3C[C@H]43)c21] | 40 | 3 |
| 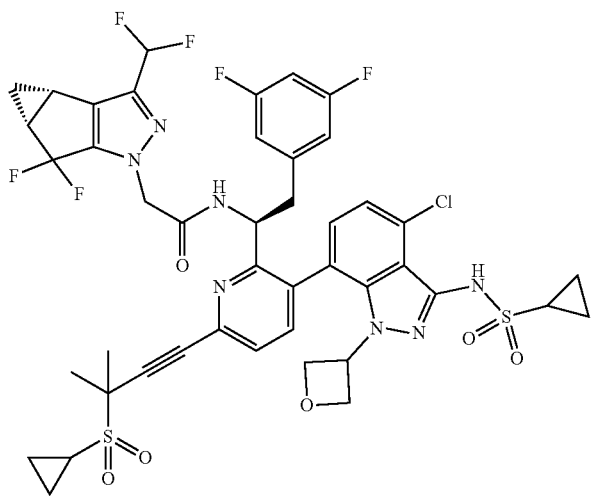 [SMILES: CC(C)(C#Cc1ccc(-c2ccc(Cl)c3c(NS(=O)(=O)C4CC4)nn(C4COC4)c23)c([C@H](Cc2cc(F)cc(F)c2)NC(=O)Cn2nc(C(F)F)c3c2C(F)(F)[C@@H]2C[C@H]32)n1)S(=O)(=O)C1CC1] | 41 | — |
| 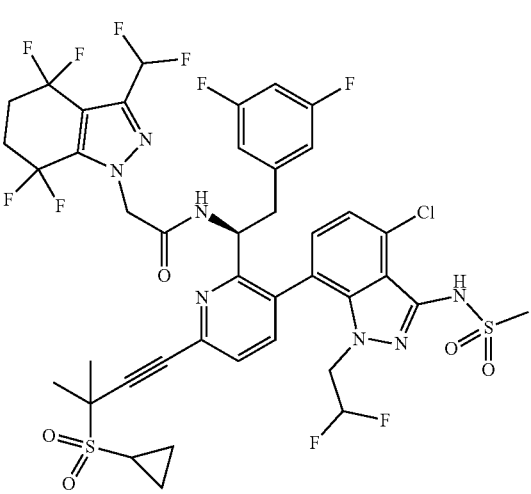 [SMILES: CC(C)(C#Cc1ccc(-c2ccc(Cl)c3c(NS(C)(=O)=O)nn(CC(F)F)c23)c([C@H](Cc2cc(F)cc(F)c2)NC(=O)Cn2nc(C(F)F)c3c2C(F)(F)CCC3(F)F)n1)S(=O)(=O)C1CC1] | 42 | 2 |

| Compound Table | | |
|---|---|---|
| Structure | Compound Example Number | General Procedure used for Compound Synthesis |
| | 43 | 3 |
| | 44 | 3 |
| | 45 | 3 |

Compound Table

| Structure | Compound Example Number | General Procedure used for Compound Synthesis |
|---|---|---|
| 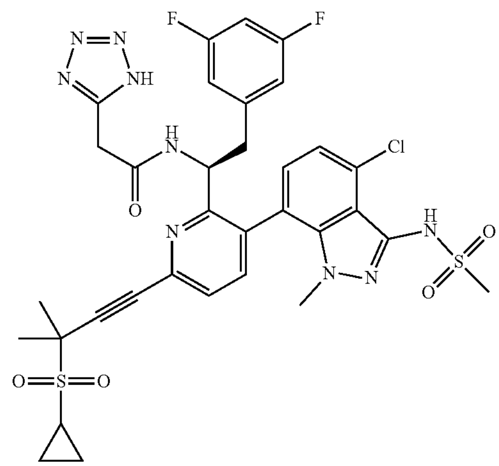 [SMILES: Cn1nc(NS(C)(=O)=O)c2c(Cl)ccc(-c3ccc(C#CC(C)(C)S(=O)(=O)C4CC4)nc3[C@H](Cc3cc(F)cc(F)c3)NC(=O)Cc3nnn[nH]3)c21] | 46 | 3 |
| 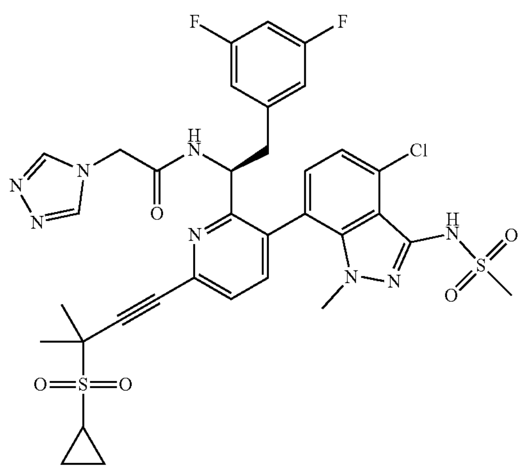 [SMILES: Cn1nc(NS(C)(=O)=O)c2c(Cl)ccc(-c3ccc(C#CC(C)(C)S(=O)(=O)C4CC4)nc3[C@H](Cc3cc(F)cc(F)c3)NC(=O)Cn3cnnc3)c21] | 47 | 3 |
| 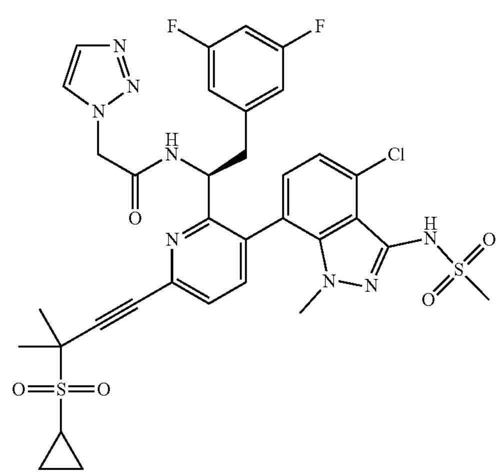 [SMILES: Cn1nc(NS(C)(=O)=O)c2c(Cl)ccc(-c3ccc(C#CC(C)(C)S(=O)(=O)C4CC4)nc3[C@H](Cc3cc(F)cc(F)c3)NC(=O)Cn3ccnn3)c21] | 48 | 3 |

-continued

Compound Table

| Structure | Compound Example Number | General Procedure used for Compound Synthesis |
|---|---|---|
| 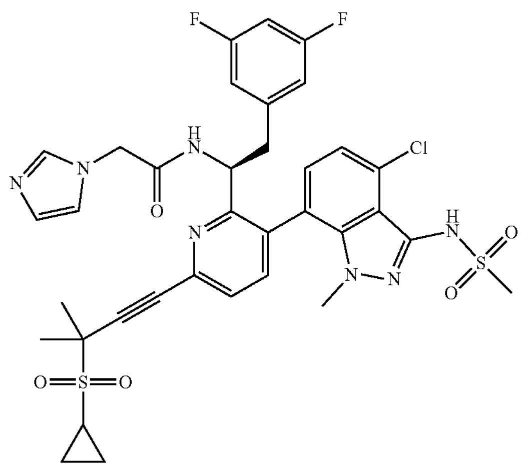 [SMILES: Cn1nc(NS(C)(=O)=O)c2c(Cl)ccc(-c3ccc(C#CC(C)(C)S(=O)(=O)C4CC4)nc3[C@H](Cc3cc(F)cc(F)c3)NC(=O)Cn3ccnc3)c21] | 49 | 3 |
| 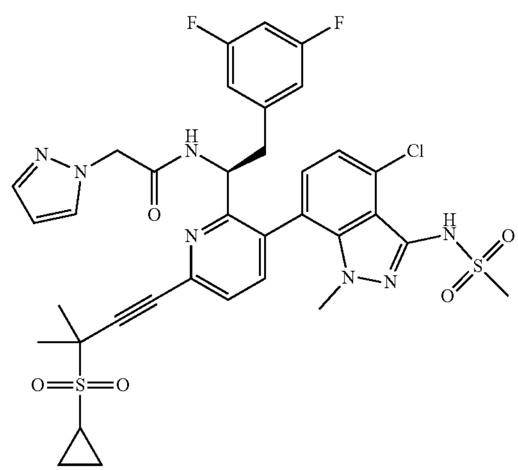 [SMILES: Cn1nc(NS(C)(=O)=O)c2c(Cl)ccc(-c3ccc(C#CC(C)(C)S(=O)(=O)C4CC4)nc3[C@H](Cc3cc(F)cc(F)c3)NC(=O)Cn3cccn3)c21] | 50 | 3 |
| 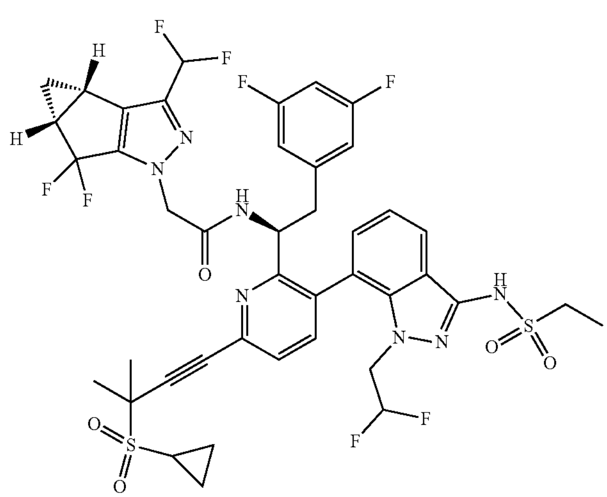 [SMILES: CCS(=O)(=O)Nc1nn(CC(F)F)c2c(-c3ccc(C#CC(C)(C)S(=O)(=O)C4CC4)nc3[C@H](Cc3cc(F)cc(F)c3)NC(=O)Cn3nc(C(F)F)c4c3C(F)(F)[C@@H]3C[C@H]43)cccc12] | 51 | 2 |

-continued

Compound Table

| Structure | Compound Example Number | General Procedure used for Compound Synthesis |
|---|---|---|
| 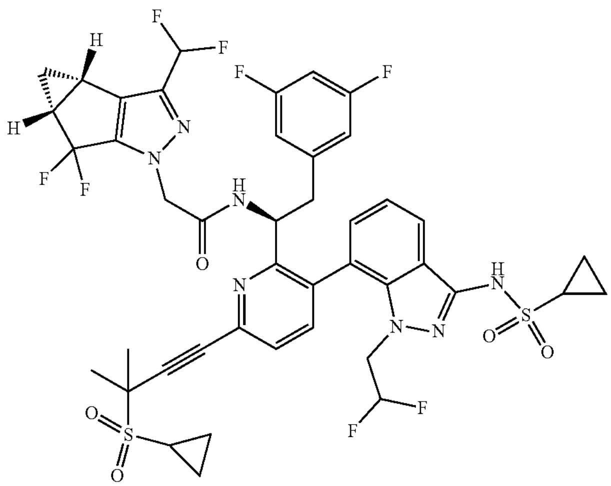 [SMILES: CC(C)(C#Cc1ccc(-c2cccc3c(NS(=O)(=O)C4CC4)nn(CC(F)F)c23)c([C@H](Cc2cc(F)cc(F)c2)NC(=O)Cn2nc(C(F)F)c3c2C(F)(F)[C@@H]2C[C@H]32)n1)S(=O)(=O)C1CC1] | 52 | 2 |
| 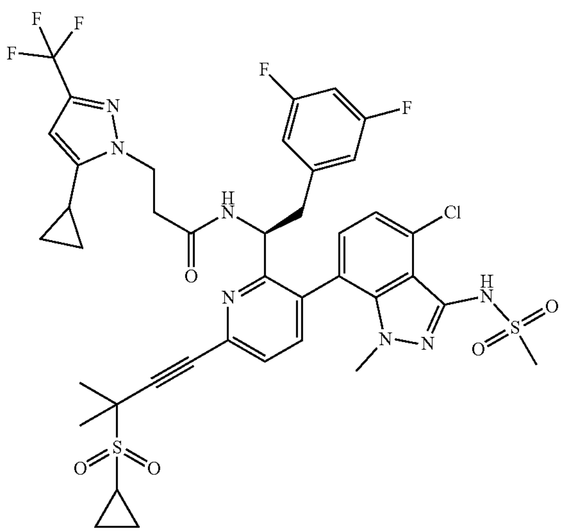 [SMILES: Cn1nc(NS(C)(=O)=O)c2c(Cl)ccc(-c3ccc(C#CC(C)(C)S(=O)(=O)C4CC4)nc3[C@H](Cc3cc(F)cc(F)c3)NC(=O)CCn3nc(C(F)(F)F)cc3C3CC3)c21] | 53 | 3 |
| 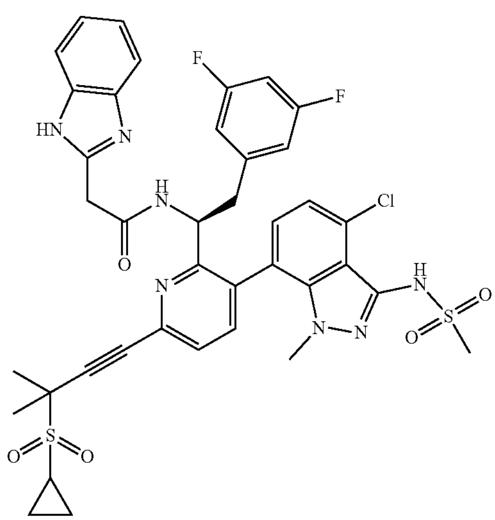 [SMILES: Cn1nc(NS(C)(=O)=O)c2c(Cl)ccc(-c3ccc(C#CC(C)(C)S(=O)(=O)C4CC4)nc3[C@H](Cc3cc(F)cc(F)c3)NC(=O)Cc3nc4ccccc4[nH]3)c21] | 54 | 3 |

-continued

Compound Table

| Structure | Compound Example Number | General Procedure used for Compound Synthesis |
|---|---|---|
| 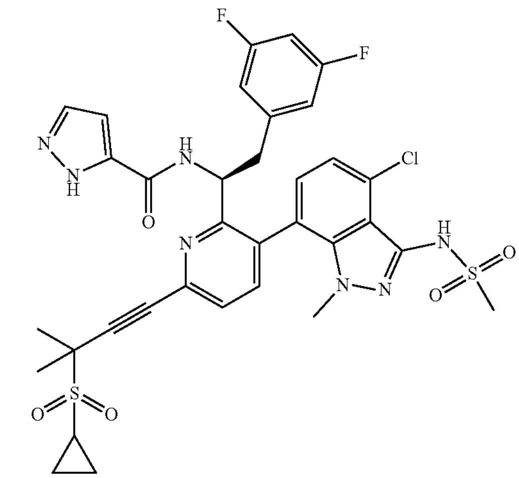 [SMILES: Cn1nc(NS(C)(=O)=O)c2c(Cl)ccc(-c3ccc(C#CC(C)(C)S(=O)(=O)C4CC4)nc3[C@H](Cc3cc(F)cc(F)c3)NC(=O)c3ccn[nH]3)c21] | 55 | 3 |
| 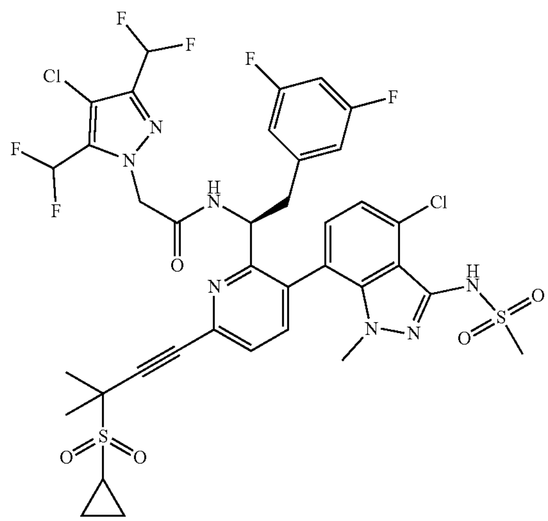 | 56 | 3 |
| 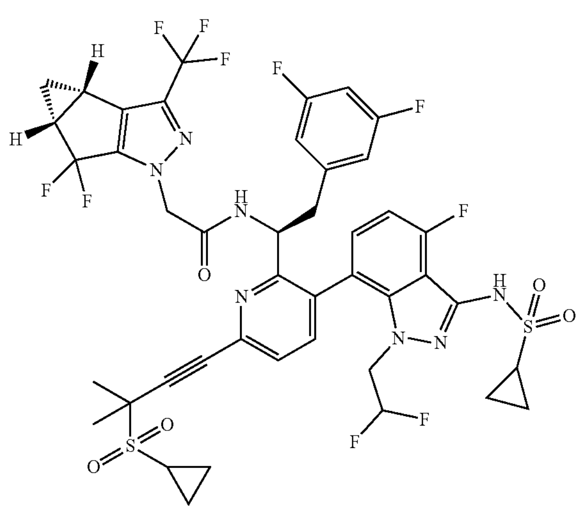 | 57 | 2 |

-continued

Compound Table

| Structure | Compound Example Number | General Procedure used for Compound Synthesis |
|---|---|---|
| 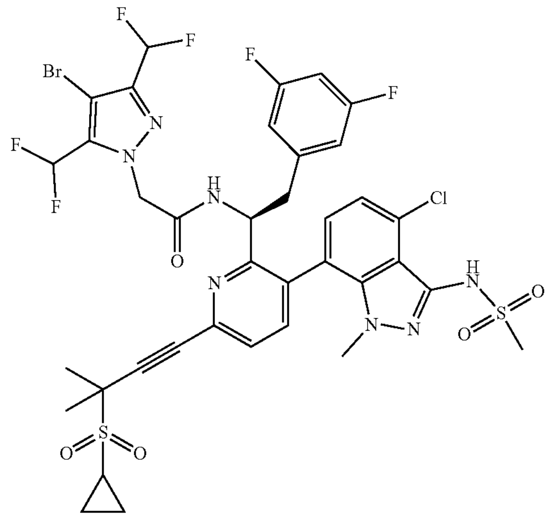 [SMILES: Cn1nc(NS(C)(=O)=O)c2c(Cl)ccc(-c3ccc(C#CC(C)(C)S(=O)(=O)C4CC4)nc3[C@H](Cc3cc(F)cc(F)c3)NC(=O)Cn3nc(C(F)F)c(Cl)c3C(F)F)c21] | 58 | 3 |
| 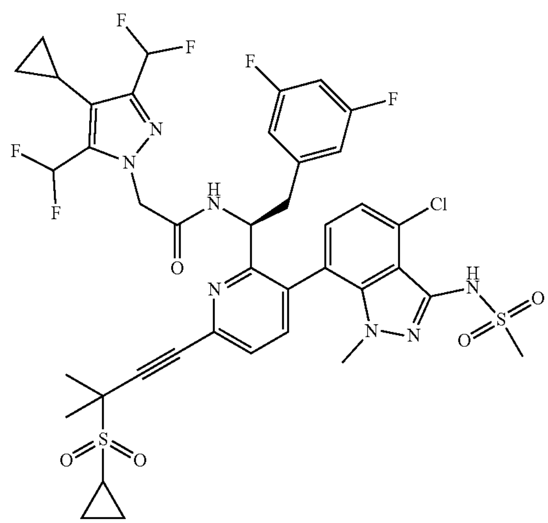 [SMILES: Cn1nc(NS(C)(=O)=O)c2c(Cl)ccc(-c3ccc(C#CC(C)(C)S(=O)(=O)C4CC4)nc3[C@H](Cc3cc(F)cc(F)c3)NC(=O)Cn3nc(C(F)F)c(C4CC4)c3C(F)F)c21] | 59 | 3 |
| 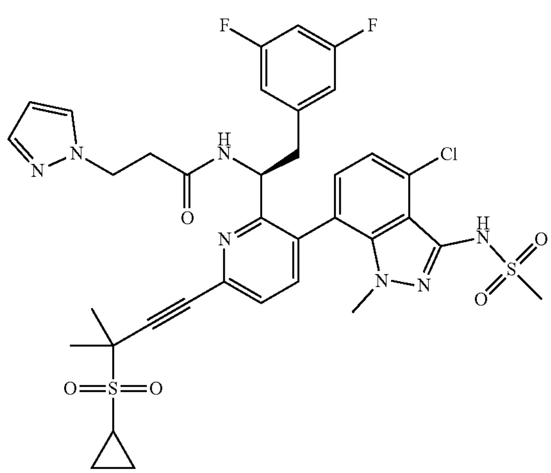 [SMILES: Cn1nc(NS(C)(=O)=O)c2c(Cl)ccc(-c3ccc(C#CC(C)(C)S(=O)(=O)C4CC4)nc3[C@H](Cc3cc(F)cc(F)c3)NC(=O)CCn3cccn3)c21] | 60 | 3 |

-continued

| Structure | Compound Example Number | General Procedure used for Compound Synthesis |
|---|---|---|
| 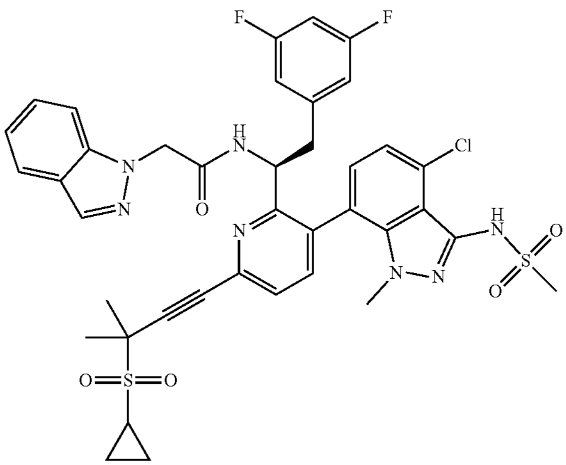 [SMILES: Cn1nc(NS(C)(=O)=O)c2c(Cl)ccc(-c3ccc(C#CC(C)(C)S(=O)(=O)C4CC4)nc3[C@H](Cc3cc(F)cc(F)c3)NC(=O)Cn3ncc4ccccc43)c21] | 61 | 3 |
| 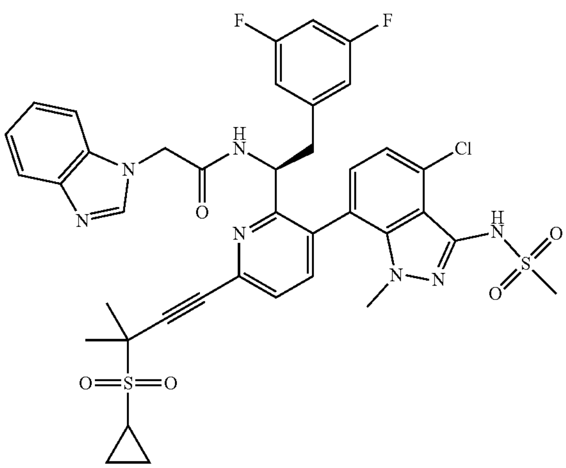 [SMILES: Cn1nc(NS(C)(=O)=O)c2c(Cl)ccc(-c3ccc(C#CC(C)(C)S(=O)(=O)C4CC4)nc3[C@H](Cc3cc(F)cc(F)c3)NC(=O)Cn3cnc4ccccc43)c21] | 62 | 3 |
| 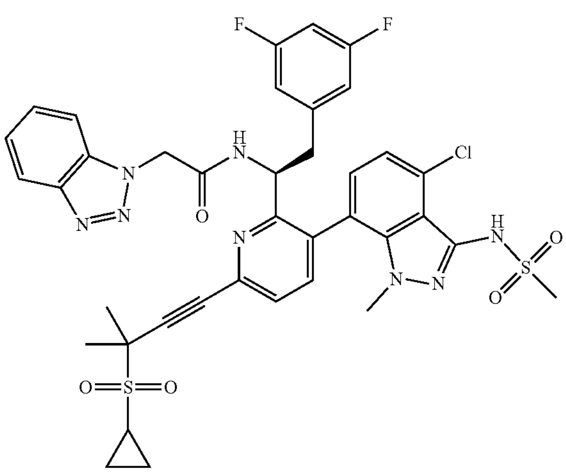 [SMILES: Cn1nc(NS(C)(=O)=O)c2c(Cl)ccc(-c3ccc(C#CC(C)(C)S(=O)(=O)C4CC4)nc3[C@H](Cc3cc(F)cc(F)c3)NC(=O)Cn3nnc4ccccc43)c21] | 63 | 3 |

Compound Table

| Structure | Compound Example Number | General Procedure used for Compound Synthesis |
|---|---|---|
| 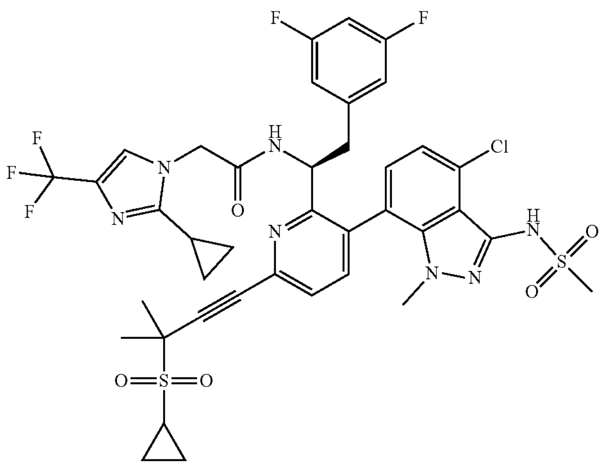 [SMILES: Cn1nc(NS(C)(=O)=O)c2c(Cl)ccc(-c3ccc(C#CC(C)(C)S(=O)(=O)C4CC4)nc3[C@H](Cc3cc(F)cc(F)c3)NC(=O)Cn3cc(C(F)(F)F)nc3C3CC3)c21] | 64 | 3 |
| 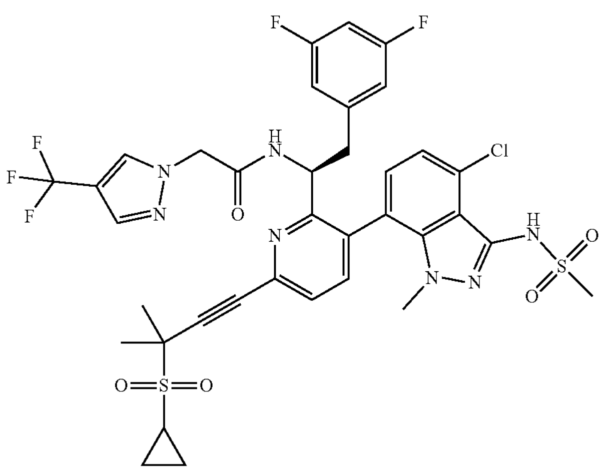 [SMILES: Cn1nc(NS(C)(=O)=O)c2c(Cl)ccc(-c3ccc(C#CC(C)(C)S(=O)(=O)C4CC4)nc3[C@H](Cc3cc(F)cc(F)c3)NC(=O)Cn3cc(C(F)(F)F)cn3)c21] | 65 | 3 |
| 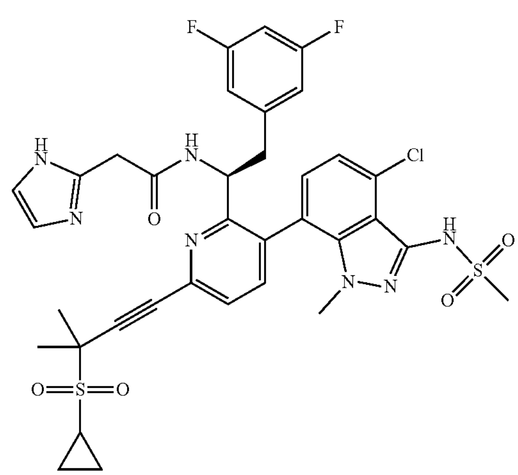 [SMILES: Cn1nc(NS(C)(=O)=O)c2c(Cl)ccc(-c3ccc(C#CC(C)(C)S(=O)(=O)C4CC4)nc3[C@H](Cc3cc(F)cc(F)c3)NC(=O)Cc3ncc[nH]3)c21] | 66 | 3 |

-continued
Compound Table
| Structure | Compound Example Number | General Procedure used for Compound Synthesis |
|---|---|---|
| 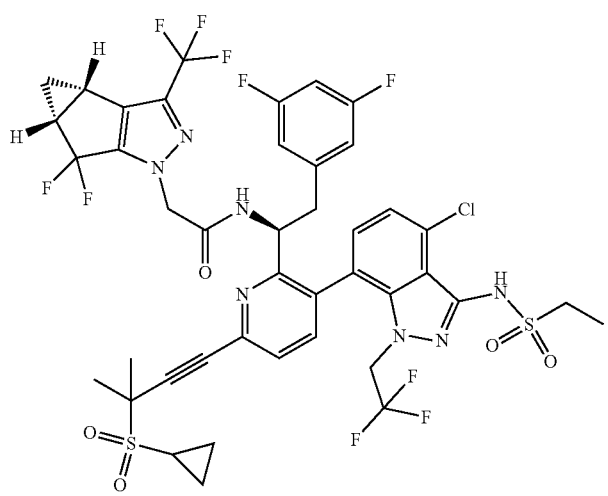 [SMILES: CCS(=O)(=O)Nc1nn(CC(F)(F)F)c2c(-c3ccc(C#CC(C)(C)S(=O)(=O)C4CC4)nc3[C@H](Cc3cc(F)cc(F)c3)NC(=O)Cn3nc(C(F)(F)F)c4c3C(F)(F)[C@@H]3C[C@H]43)ccc(Cl)c12] | 67 | 2 |
| 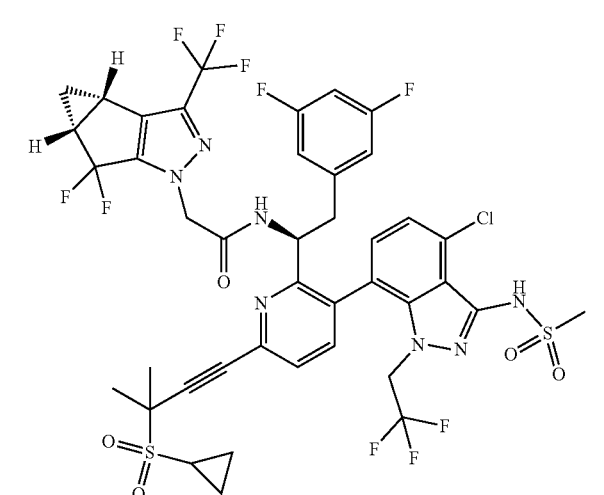 [SMILES: CC(C)(C#Cc1ccc(-c2ccc(Cl)c3c(NS(C)(=O)=O)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(=O)(=O)C1CC1] | 68 | 2 |
| 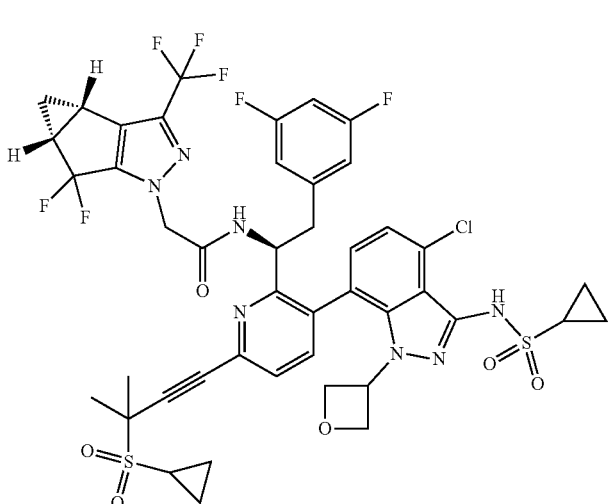 [SMILES: CC(C)(C#Cc1ccc(-c2ccc(Cl)c3c(NS(=O)(=O)C4CC4)nn(C4COC4)c23)c([C@H](Cc2cc(F)cc(F)c2)NC(=O)Cn2nc(C(F)(F)F)c3c2C(F)(F)[C@@H]2C[C@H]32)n1)S(=O)(=O)C1CC1] | 69 | 2 |

Characterization Table

| Example | ES/MS (m/z) | ¹H NMR |
|---|---|---|
| 1M | 976.2 | 1H NMR (400 MHz, Methanol-d4) δ 8.86 (d), 8.73 (d), 7.79 (d), 7.72 (d), 7.65 (dd), 7.20 (q), 7.13 (d), 6.83-6.72 (m), 6.72-6.61 (m), 6.52 (d), 6.43 (dd), 6.36-6.25 (m), 6.21-5.51 (m), 5.05 (q), 4.93-4.62 (m), 4.35-4.11 (m), 3.91-3.38 (m), 3.24 (s), 3.07 (ddd), 3.02-2.89 (m), 2.85 (d), 2.68-2.36 (m), 1.84 (s), 1.47-1.35 (m), 1.36-1.18 (m), 1.17-0.98 (m), 2.35 (m), 1.82 (s), 1.48-1.24 (m), 1.21-0.79 (m). |
| 2F | 998.2 | 1H NMR (400 MHz, Methanol-d4) δ 8.86 (d), 7.86-7.61 (m), 7.31-7.07 (m), 6.89-6.65 (m), 6.50-6.27 (m), 6.09-5.67 (m), 4.90 (s), 4.83-4.67 (m), 4.29-4.02 (m), 3.68 (s), 3.09 (dd), 3.02-2.90 (m), 2.54-2.41 (m), 1.84 (s), 1.72 (d), 1.63 (s), 1.40 (d), 1.33-1.27 (m), 1.27-1.18 (m), 1.06 (d), 0.76 (d). |
| 3F | 974.2 | 1H N MR (400 MHz, Methanol-d4) δ 8.90-8.82 (m), 7.80-7.72 (m), 7.68-7.58 (m), 7.22 (d), 7.16 (d), 7.11 (s), 7.09 (s), 6.83-6.73 (m), 6.70-6.61 (m), 6.52 (s), 6.50 (s), 6.47-6.38 (m), 5.40-5.23 (m), 5.10-4.98 (m), 4.78 (s), 4.77 (s), 3.35 (s), 3.23-3.15 (m), 3.07-2.91 (m), 2.59-2.39 (m), 1.84 (s), 1.84 (s), 1.64-1.56 (m), 1.50-1.36 (m), 1.35-1.21 (m), 1.20-1.01 (m). |
| 4 | 908.7 | 1H NMR (400 MHz, Methanol-d4) δ 8.72 (dd), 7.74 (t), 7.61 (dd), 7.25-7.14 (m), 7.08 (d), 6.88-6.49 (m), 6.50-6.25 (m), 5.36-4.93 (m), 3.24 (d), 3.18-3.06 (m), 3.04-2.89 (m), 2.44 (ddd), 1.83 (d), 1.50-1.19 (m), 1.04 (d). |
| 5 | 962.2 | 1H NMR (400 MHz, Methanol-d4) δ 7.76-7.67 (m), 7.60 (dd), 7.17 (q), 7.07 (d), 6.84-6.55 (m), 6.49-6.32 (m), 5.34-4.92 (m), 4.78-4.69 (m), 4.09 (q), 3.41-3.28 (m), 3.22-2.87 (m), 2.48 (dtt), 2.00 (s), 1.83 (d), 1.53-1.35 (m), 1.35-1.19 (m), 1.17-1.00 (m). |
| 6 | 922.4 | 1H NMR (400 MHz, Methanol-d4) δ 7.73 (t), 7.61 (dd), 7.24-7.02 (m), 6.89-6.50 (m), 6.48-6.31 (m), 5.36-4.95 (m), 4.77-4.66 (m), 3.52-3.35 (m), 3.25-3.06 (m), 3.06-2.90 (m), 2.46 (dddd), 1.83 (d), 1.50-1.19 (m), 1.14-0.97 (m). |
| 7 | 940.2 | 1H NMR (400 MHz, Methanol-d4) δ 7.73 (dd), 7.61 (dd), 7.24-7.11 (m), 7.08 (d), 6.87-6.59 (m), 6.40 (ddd), 5.34-4.95 (m), 4.81-4.68 (m), 3.41 (ddt), 3.23-2.88 (m), 2.49 (ddd), 1.83 (d), 1.44 (q), 1.35-1.18 (m), 1.17-0.95 (m). |
| 8 | 958.2 | 1H NMR (400 MHz, Methanol-d4) δ 8.76 (d), 8.64 (d), 7.78 (d), 7.72 (d), 7.68-7.62 (m), 7.30-7.06 (m), 6.94-6.54 (m), 6.54-6.47 (m), 6.45 (dd), 6.37-6.27 (m), 5.87 (tdd), 5.05 (q), 4.83-4.56 (m), 4.44-4.08 (m), 3.96-3.55 (m), 3.56-3.32 (m), 3.27-2.83 (m), 2.45 (td), 1.84 (s), 1.54-1.34 (m), 1.35-1.16 (m), 1.03 (q). |
| 9 | 972.5 | — |
| 10 | 956.2 | 1H NMR (400 MHz, Methanol-d4) δ 8.77 (d), 7.77 (d), 7.75 (d), 7.65 (d), 7.62 (d), 7.22 (d), 7.17 (d), 7.11 (d), 6.85 (s), 6.81 (s), 6.77 (tt), 6.72 (s), 6.70-6.60 (m), 6.58-6.50 (m), 6.49-6.35 (m), 5.37-5.28 (m), 5.08-4.97 (m), 4.77 (s), 4.76 (s), 4.71 (d), 4.66 (s), 3.35 (s), 3.19 (d), 3.15 (d), 3.06-2.91 (m), 2.86 (s), 2.53-2.36 (m), 1.84 (s), 1.84 (s), 1.61 (s), 1.60 (s), 1.60 (s), 1.45-1.20 (m), 1.13-1.06 (m), 1.04-0.96 (m). |
| 11 | 990.4 | 1H NMR (400 MHz, Methanol-d4) δ 8.86 (d), 8.72 (d), 7.78 (d), 7.72 (d), 7.65 (dd), 7.25-7.10 (m), 6.87-6.64 (m), 6.52 (d), 6.43 (dd), 6.38-6.24 (m), 6.19-5.68 (m), 5.05 (q), 4.96-4.53 (m), 4.32-4.10 (m), 3.90-3.60 (m), 3.43 (ddq), 3.30-2.80 (m), 2.68-2.29 (m), 1.84 (s), 1.52-1.37 (m), 1.37-1.17 (m), 1.17-0.88 (m). |
| 12 | 934.2 | — |
| 13 | 952.2 | — |
| 14 | 948.0 | 1H NMR (400 MHz, Methanol-d4) δ 8.80-8.67 (m), 7.78-7.70 (m), 7.63 (d), 7.60 (d), 7.21-7.15 (m), 7.10 (s), 7.08 (s), 6.86 (s), 6.82 (s), 6.78 (tt), 6.72 (s), 6.68 (s), 6.67-6.60 (m), 6.58 (s), 6.55 (s), 6.46 (s), 6.44 (s), 6.44-6.34 (m), 5.33-5.22 (m), 5.03-4.94 (m), 4.76 (s), 4.76 (s), 4.72 (s), 4.70 (s), 4.66 (s), 3.36 (s), 3.34 (s), 3.25-3.18 (m), 3.16 (d), 3.13 (d), 3.06-2.92 (m), 2.57-2.35 (m), 1.84 (s), 1.44-1.34 (m), 1.34-1.20 (m), 1.12-1.06 (m), 1.06-0.98 (m), 0.73-0.63 (m), 0.57-0.38 (m). |
| 15 | 966.2 | — |
| 16 | 984.4 | 1H NMR (400 MHz, Methanol-d4) δ 8.75 (d), 8.66 (d), 7.86-7.57 (m), 7.34-7.05 (m), 6.94-6.54 (m), 6.52 (d), 6.45 (dd), 6.38-6.20 (m), 6.18-5.57 (m), 5.19-4.97 (m), 4.95-4.46 (m), 4.35-4.09 (m), 3.92-3.39 (m), 3.27-2.76 (m), 2.62-2.29 (m), 1.84 (s), 1.51-0.71 (m) |

-continued

Characterization Table

| Example | ES/MS (m/z) | ¹H NMR |
|---|---|---|
| 17 | 976.4 | — |
| 18 | 950.7 | 1H NMR (Chloroform-d) δ: 7.57 (s), 7.55 (s), 7.49 (s), 7.47 (s), 7.42 (s), 7.21 (s), 7.19 (s), 7.01 (s), 6.99 (s), 6.81 (s), 6.69-6.67 (m), 6.67-6.65 (m), 6.65-6.62 (m), 6.54 (s), 6.25-6.18 (m), 5.16 (t), 4.94-4.83 (m), 4.76-4.68 (m), 4.65 (d), 4.43 (t), 4.35 (t), 3.54-3.48 (m), 3.01-2.90 (m), 2.86-2.79 (m), 2.54-2.43 (m), 1.87 (s), 1.45-1.39 (m), 1.33 (s), 1.28-1.19 (m), 1.18-1.10 (m) |
| 19 | 968.8 | 1H NMR (Chloroform-d) δ: 7.55 (d), 7.46 (d), 7.41 (s), 7.18-7.14 (m), 6.99 (d), 6.69-6.62 (m), 6.24-6.22 (m), 6.21-6.20 (m), 6.19 (s), 5.15 (t), 4.95-4.88 (m), 4.83 (t), 4.76-4.70 (m), 4.68 (d), 4.41 (t), 4.34 (t), 3.50 (s), 3.03-2.95 (m), 2.93-2.87 (m), 2.85-2.78 (m), 2.52-2.39 (m), 1.87 (s), 1.48-1.36 (m), 1.29-1.18 (m), 1.18-1.10 (m) |
| 20 | 948.2 | 1H NMR (400 MHz, Methanol-d4) δ 7.73 (m), 7.61 (m), 7.16 (s), 7.07 (m), 6.69 (m), 6.39(m), 5.27 (m,), 4.99 (m), 4.73(m), 3.30 (m), 3.13 (m), 2.97 (m), 2.44 (m), 1.83 (d), 1.64(d), 1.50-1.19 (m), 1.14-0.8 (m). |
| 21 | 966.2 | 1H NMR (400 MHz, Methanol-d4) δ 7.64 (m), 7.52 (m), 7.16 (s), 7.07 (m), 6.97 (m), 6.65 (m), 6.29(m), 5.17 (m,), 4.90 (m), 4.75(m), 3.21 (m), 3.05 (m), 2.89 (m), 2.38 (m), 1.54 (m), 1.31(m), 1.19 (m), 0.97 (m), 0.71 (m). |
| 22 | 1016.3 | 1H NMR (400 MHz, Methanol-d4) δ 8.94 (d), 7.74-7.64 (m), 7.28-7.12 (m), 6.80-6.73 (m), 6.57-6.52 (m), 6.42 (dd), 6.34-6.23 (m), 4.84 (d), 4.77 (s), 4.73 (s), 4.67 (d), 4.56 (dd), 3.93 (dd), 3.07 (dd), 2.95 (qd), 2.56-2.44 (m), 1.84 (s, 18H), 1.64 (s), 1.41 (d), 1.29 (dd), 1.27-1.18 (m), 1.10-0.98 (m), 0.84 (t), 0.80-0.67 (m). |
| 23 | 1002.2 | 1H NMR (400 MHz, Methanol-d4) δ 8.84 (d), 8.73 (d), 7.79 (d), 7.72 (d), 7.66 (d), 7.26-7.07 (m), 6.86-6.59 (m), 6.59-6.24 (m), 6.18-5.53 (m), 5.05 (q), 4.93-4.54 (m), 4.32-3.96 (m), 4.01-3.42 (m), 3.34-2.72 (m), 2.68-2.23 (m), 1.84 (s), 1.56-0.72 (m). |
| 24 | 1006.1 | 1H NMR (400 MHz, Methanol-d4) δ 8.82 (d), 8.72 (d), 7.84-7.77 (m), 7.77-7.71 (m), 7.70-7.65 (m), 7.22-7.19 (m), 7.18-7.12 (m), 6.83 (d), 6.82 (s), 6.77 (tt), 6.71-6.67 (m), 6.58-6.48 (m), 6.39-6.31 (m), 6.16-6.11 (m), 6.08-5.94 (m), 5.89-5.80 (m), 5.14-5.06 (m), 4.96-4.89 (m), 4.74 (s), 4.72 (s), 4.69-4.63 (m), 4.30-4.11 (m), 3.83-3.53 (m), 3.16-3.07 (m), 3.02-2.92 (m), 2.51-2.39 (m), 1.85 (s), 1.62 (s), 1.61 (s), 1.60 (s), 1.45-1.43 (m), 1.40-1.35 (m), 1.34-1.29 (m), 1.28-1.23 (m), 1.10-0.99 (m). |
| 25 | 1024.2 | 1H NMR (400 MHz, Methanol-d4) δ 8.89 (d), 8.77 (d), 7.98 (s), 7.83-7.77 (m), 7.77-7.71 (m), 7.70-7.64 (m), 7.23-7.11 (m), 6.80-6.72 (m), 6.73-6.64 (m), 6.58-6.48 (m), 6.39-6.31 (m), 6.22-6.18 (m), 6.14-6.09 (m), 6.07-6.03 (m), 5.97 (s), 5.87-5.78 (m), 5.13-5.04 (m), 4.98-4.87 (m), 4.80 (s), 4.78 (s), 4.76-4.65 (m), 4.25-4.08 (m), 3.82-3.62 (m), 3.59-3.46 (m), 3.28-3.20 (m), 3.18-3.06 (m), 3.02-2.92 (m), 2.86 (s), 2.58-2.40 (m), 1.85 (s), 1.65-1.57 (m), 1.46-1.41 (m), 1.42-1.36 (m), 1.34-1.21 (m), 1.07 (s). |
| 26 | 998.0 | 1H NMR (400 MHz, Methanol-d4) δ 8.34(m), 7.58-7.29 (m), 7.69-6.70 (m), 7.16 (s), 7.07 (m), 6.48-6.25(m), 6.15-6.09(m), 5.92 (m), 5.75-5.28 (m), 4.65(m), 4.40-4.30 (m,), 3.79 (m), 3.40-3.00(m), 2.81-2.50 (m), 2.06 (m), 1.05-0.80 (m), 0.64 (m), 0.25 (m), 0.03 (m). |
| 27 | 1016.3 | 1H NMR (400 MHz, Methanol-d4) δ 8.79(m), 7.88-7.67 (m), 7.07 (m), 6.67 (m), 6.43 (m), 6.34(m), 6.22 (m), 5.90-5.60(m), 4.71 (m), 4.06 (m), 3.56 (m), 3.26-2.80 (m,), 2.40 (m), 1.74 (s), 1.40-0.95(m), 0.55 (m), 0.34 (m). |
| 28 | 954.1 | 1H NMR (400 MHz, Methanol-d4) δ 8.90-8.67 (m), 7.80-7.69 (m), 7.68-7.56 (m), 7.24-7.14 (m), 7.14-7.04 (m), 6.89-6.70 (m), 6.67 (s), 6.63-6.47 (m), 6.46-6.34 (m), 5.09-4.95 (m), 4.70 (s), 4.69 (s), 3.39-3.34 (m), 3.21-3.14 (m), 3.06-2.92 (m), 2.53-2.36 (m), 1.87-1.75 (m), 1.44-1.16 (m), 1.11-0.96 (m). |
| 29 | 1034.3 | 1H NMR (400 MHz, Methanol-d4) δ 8.94 (d), 7.82-7.62 (m), 7.27-7.07 (m), 6.84-6.67 (m), 6.61-6.51 (m), 6.42 (dd), 6.35-6.23 (m), 4.84 (d), 4.75 (d), 4.67 (d), 4.56 (dd), 3.93 |

Characterization Table

| Example | ES/MS (m/z) | ¹H NMR |
|---|---|---|
| | | (dd), 3.07 (dd), 2.95 (qd), 2.58-2.38 (m), 1.84 (s), 1.64 (d), 1.41 (q), 1.35-1.27 (m), 1.27-1.20 (m), 1.12-1.02 (m), 0.84 (t), 0.80-0.69 (m). |
| 30 | 948.0 | 1H NMR (400 MHz, Methanol-d4) δ 8.89-8.68 (m), 7.80-7.75 (m), 7.65 (d), 7.62 (d), 7.25 (d), 7.20 (d), 7.14-7.07 (m), 6.99 (s), 6.98 (s), 6.85 (s), 6.81 (s), 6.78 (tt), 6.72 (s), 6.68 (s), 6.67-6.60 (m), 6.58 (s), 6.56-6.49 (m), 6.48-6.38 (m), 5.40-5.26 (m), 5.09-4.97 (m), 4.79 (s), 4.77-4.75 (m), 4.71 (s), 4.70 (s), 3.37 (s), 3.22-3.14 (m), 3.08-2.92 (m), 2.56-2.38 (m), 1.84 (s), 1.84 (s), 1.84 (s), 1.49-1.18 (m), 1.12-0.96 (m). |
| 31 | 1054.3 | 1H NMR (400 MHz, Methanol-d4) δ 8.86 (dd), 7.82-7.61 (m), 7.31-7.13 (m), 6.84-6.65 (m), 6.48 (d), 6.38-6.24 (m), 5.10-4.93 (m), 4.56 (dd), 3.95 (dd), 3.07 (dd), 3.00-2.91 (m), 2.51 (d), 1.84 (s), 1.62 (s), 1.36-1.27 (m), 1.25 (dd), 1.20 (s), 0.72 (d). |
| 32 | 1048.4 | 1H NMR (Chloroform-d) δ: 7.60-7.55 (m), 7.55-7.50 (m), 7.28 (s), 7.19-7.13 (m), 7.04 (d), 6.69-6.61 (m), 6.21-6.13 (m), 4.84 (q), 4.73 (d), 4.48-4.32 (m), 3.92-3.73 (m), 3.02-2.86 (m), 1.84 (s), 1.71-1.64 (m), 1.64-1.57 (m), 1.48-1.40 (m), 1.19-1.12 (m), 0.96-0.90 (m), 0.89-0.80 (m) |
| 33 | 1022.1 | 1H NMR (Chloroform-d) δ: 7.72-7.65 (m), 7.59-7.53 (m), 7.24 (s), 7.02-6.95 (m), 6.91 (s), 6.79-6.74 (m), 6.64 (s), 6.57-6.50 (m), 6.25 (d), 6.21-6.15 (m), 6.00-5.95 (m), 5.86-5.79 (m), 5.36-5.26 (m), 4.95-4.91 (m), 3.86-3.72 (m), 3.70-3.54 (m), 3.03-2.88 (m), 2.87-2.76 (m), 2.58-2.40 (m), 1.44-1.33 (m), 1.23-1.15 (m), 1.12-1.02 (m) |
| 34 | 986.2 | 1H NMR (400 MHz, Methanol-d4) δ 8.85 (t), 7.75 (dd), 7.62 (dd), 7.19 (d), 7.08 (d), 6.85-6.72 (m), 6.40 (m), 5.07-4.89 (m), 3.34 (s), 3.30-3.12 (m), 3.06-2.90 (m), 2.51 (s), 2.47 (d), 1.83 (d), 1.62 (d), 1.36-1.16 (m), 1.22 (s), 0.87-0.66 (m). |
| 35 | 1003.2 | 1H NMR (400 MHz, Methanol-d4) δ 7.85-7.56 (m), 7.32-7.10 (m), 6.92-6.56 (m), 6.52 (ddd), 6.40-6.21 (m), 4.76-4.49 (m), 4.01-3.60 (m), 3.06 (dd), 3.02-2.79 (m), 2.46 (ddd), 1.84 (s), 1.44-1.19 (m), 1.18-0.92 (m). |
| 36 | 1020.9 | 1H NMR (400 MHz, Methanol-d4) δ 7.72 (d), 7.66 (d), 7.30-7.13 (m), 6.76 (t), 6.46 (d), 6.29 (d), 4.69-4.46 (m), 3.06 (dd), 3.02-2.80 (m), 2.49 (s), 1.84 (s), 1.49-1.17 (m), 1.11-0.92 (m). |
| 37 | 1036.3 | 1H NMR (400 MHz, Methanol-d4) δ 8.85 (dd), 7.84-7.62 (m), 7.28-7.05 (m), 6.93-6.64 (m), 6.44 (dd), 6.39-6.30 (m), 6.15-5.68 (m), 5.05-4.96 (m), 4.94-4.87 (m), 4.26-4.05 (m), 3.86-3.61 (m), 3.09 (dt), 3.00-2.91 (m), 2.49 (qd), 1.84 (s), 1.63 (d), 1.36-1.27 (m), 1.27-1.22 (m), 1.23-1.16 (m), 0.80-0.66 (m). |
| 38 | 946.2 | — |
| 39 | 972.2 | — |
| 40 | 900.2 | 1H NMR (400 MHz, Methanol-d4) δ 7.91-7.85 (m), 7.77-7.72 (m), 7.66-7.58 (m), 7.29-7.24 (m), 7.23-7.15 (m), 7.11 (dd), 6.85-6.51 (m), 6.40-6.27 (m), 5.36-5.27 (m), 5.06-4.97 (m), 4.81-4.65 (m), 3.33 (s), 3.24-3.16 (m), 3.15-3.06 (m), 3.03 (s), 3.02-2.88 (m), 2.80-2.73 (m), 2.73-2.65 (m), 2.54-2.37 (m), 1.83 (d), 1.44-1.22 (m), 1.12-0.88 (m). |
| 41 | 976.2 | 1H NMR (Chloroform-d) δ: 7.60-7.56 (m), 7.55-7.47 (m), 7.42 (s), 7.41-7.36 (m), 7.33-7.29 (m), 7.25-7.24 (m), 7.24-7.22 (m), 7.21-7.17 (m), 7.12-7.06 (m), 7.03-6.98 (m), 6.83-6.80 (m), 6.70-6.68 (m), 6.68-6.66 (m), 6.66-6.62 (m), 6.56-6.53 (m), 6.52-6.46 (m), 6.24 (dd), 5.31 (t), 5.18 (t), 4.95-4.85 (m), 4.83-4.76 (m), 4.75-4.68 (m), 4.65 (d), 4.59 (t), 4.51-4.44 (m), 4.43-4.34 (m), 3.16-3.05 (m), 3.03-2.88 (m), 2.87-2.78 (m), 2.53-2.41 (m), 1.89-1.85 (m), 1.59-1.48 (m), 1.47-1.33 (m), 1.29-1.13 (m) |
| 42 | — | 1H NMR (400 MHz, Methanol-d4) δ 8.90-8.70(m), 7.80-7.66 (m), 7.23-7.05 (m), 6.94-6.70 (m), 6.50 (m), 6.34(m), 6.25-5.80 (m), 5.10-4.90(m), 4.18 (m), 3.80-3.60 (m), 3.35-2.90 (m,), 2.51 (m), 1.84 (s), 1.28 (m) |
| 43 | 870.0 | 1H NMR (400 MHz, Methanol-d4) δ 7.74 (dd), 7.65-7.57 (m), 7.24-7.14 (m), 7.09 (d), 7.00-6.56 (m), 6.50-6.34 (m), 5.27 (dd), 5.04-4.88 (m), 3.25 (s), 3.21 (s), 3.15 (dd), 3.07-2.91 (m), 1.83 (s), 1.39-1.16 (m). |
| 44 | 878.1 | 1H NMR (400 MHz, Methanol-d4) δ 7.79-7.70 (m), 7.66-7.57 (m), 7.27 (d), 7.17 (d), 7.11 (d), 6.80-6.71 (m), 6.68-6.59 (m), 6.55 (d), 6.46-6.35 (m), 6.25 (s), |

-continued

| | | Characterization Table |
|---|---|---|
| Example | ES/MS (m/z) | ¹H NMR |
| | | 6.20 (s), 5.31 (dd), 5.01 (t), 4.94-4.86 (m), 3.35-3.32 (m), 3.25 (s), 3.22 (s), 3.19-3.12 (m), 3.05-2.90 (m), 1.83 (d), 1.70-1.58 (m), 1.58-1.51 (m), 1.36-1.18 (m), 0.97-0.83 (m), 0.72-0.55 (m). |
| 45 | 771.9 | 1H NMR (400 MHz, Methanol-d4) δ 9.11 (s), 9.10-8.99 (m), 7.76 (d), 7.69-7.58 (m), 7.28-7.14 (m), 7.11 (d), 6.79-6.70 (m), 6.68-6.56 (m), 6.56-6.47 (m), 6.42 (t), 5.34-5.25 (m), 5.21 (d), 5.14 (s), 4.98 (q), 3.33 (s), 3.27-3.17 (m), 3.06-2.92 (m), 1.83 (d), 1.34-1.22 (m). |
| 46 | 772.0 | 1H NMR (400 MHz, Methanol-d4) δ 7.76-7.71 (m), 7.61 (dd), 7.23 (d), 7.14-7.06 (m), 6.74 (t), 6.67-6.59 (m), 6.51 (d), 6.42 (dd), 5.31-5.23 (m), 4.99 (t), 3.95-3.78 (m), 3.25 (s), 3.23 (s), 3.21-3.13 (m), 3.07-2.88 (m), 1.83 (s), 1.35-1.17 (m). |
| 47 | 771.1 | 1H NMR (400 MHz, Methanol-d4) δ 9.02 (d), 8.93 (d), 8.80 (s), 8.73 (s), 7.78 (d), 7.77 (d), 7.64 (d), 7.60 (d), 7.30-7.19 (m), 7.13 (d), 6.80-6.72 (m), 6.68-6.60 (m), 6.57-6.54 (m), 6.42 (d), 5.34 (t), 5.01-4.94 (m), 4.93-4.86 (m), 3.34 (s), 3.27-3.18 (m), 3.04 (s), 3.03-2.89 (m), 1.83 (d), 1.36-1.18 (m). |
| 48 | 771.0 | 1H NMR (400 MHz, Methanol-d4) δ 9.01-8.89 (m), 7.94 (s), 7.83 (s), 7.77-7.73 (m), 7.70 (d), 7.63 (d), 7.60 (d), 5.32-5.26 (m), 5.12 (s), 5.06 (s), 5.03-4.95 (m), 3.28-3.17 (m), 3.06-2.92 (m), 1.83 (s), 1.35-1.21 (m). |
| 49 | 770.1 | 1H NMR (400 MHz, Methanol-d4) δ 9.04 (d), 8.97 (d), 8.86 (s), 8.73 (t), 7.78 (dd), 7.65 (d), 7.61 (d), 7.59-7.56 (m), 7.53-7.48 (m), 7.40-7.35 (m), 7.29 (d), 7.20 (d), 7.15 (d), 6.80-6.72 (m), 6.69-6.58 (m), 6.43 (d), 5.39-5.29 (m), 5.02-4.90 (m), 4.88 (d), 3.35 (s), 3.29-3.18 (m), 3.07-2.85 (m), 1.83 (s), 1.38-1.18 (m). |
| 50 | 770.0 | 1H NMR (400 MHz, Methanol-d4) δ 7.74 (dd), 7.64-7.50 (m), 7.20 (dd), 7.11 (d), 6.79-6.69 (m), 6.68-6.58 (m), 6.53 (d), 6.44-6.33 (m), 6.30 (t), 5.31 (dd), 4.99 (t), 4.80 (s), 4.75 (s), 3.28-3.09 (m), 3.02 (s), 3.01-2.91 (m), 1.84 (d), 1.35-1.18 (m). |
| 51 | 938.9 | — |
| 52 | 950.0 | — |
| 53 | 896.1 | 1H NMR (400 MHz, Chloroform-d) δ 7.57-7.47 (m), 7.32 (d), 7.13 (d), 7.02 (d), 6.95 (d), 6.69-6.58 (m), 6.51-6.42 (m), 6.20 (t), 6.15 (d), 6.06 (s), 5.54-5.44 (m), 4.99 (q), 4.49 (t), 4.45-4.37 (m), 3.40 (s), 3.39 (s), 3.17 (s), 2.99 (s), 2.96-2.75 (m), 1.88 (d), 1.83-1.67 (m), 1.45-1.36 (m), 1.29-1.17 (m), 1.09-0.97 (m), 0.73-0.58 (m). |
| 54 | 820.2 | 1H NMR (400 MHz, Chloroform-d) δ 8.09 (s), 7.86-7.76 (m), 7.66-7.49 (m), 7.08 (d), 6.59-6.44 (m), 6.32 (d), 6.30-6.18 (m), 4.84-4.69 (m), 4.36-4.08 (m), 3.42 (s), 3.36 (s), 3.24-3.12 (m), 3.02 (s), 2.99-2.84 (m), 1.87 (d), 1.43-1.20 (m). |
| 55 | 756.1 | — |
| 56 | 904.1 | 1H NMR (400 MHz, Chloroform-d) δ 7.67-7.50 (m), 7.38 (s), 7.31-7.27 (m), 7.23-7.15 (m), 6.97 (d), 6.92-6.57 (m), 6.55-6.45 (m), 6.25 (d), 6.20 (t), 5.60-5.52 (m), 5.06-4.96 (m), 4.93 (s), 3.40 (s), 3.39 (s), 3.30 (s), 3.09 (s), 3.04-2.88 (m), 2.85-2.72 (m), 1.87 (s), 1.46-1.37 (m), 1.28-1.15 (m). |
| 57 | 986.0 | 1H NMR (400 MHz, Methanol-d4) δ 8.88 (d), 8.79 (s), 7.79 (d), 7.72 (d), 7.66 (d), 7.21 (dd), 6.90 (d), 6.88 (d), 6.84 (d), 6.81 (d), 6.80-6.73 (m), 6.73-6.64 (m), 6.56-6.51 (m), 6.49 (d), 6.47 (d), 6.37-6.29 (m), 6.14-5.74 (m), 4.83-4.80 (m), 4.80-4.76 (m), 4.76-4.70 (m), 4.27-4.07 (m), 3.83-3.59 (m), 3.28-3.21 (m), 3.12-3.02 (m), 3.01-2.91 (m), 2.90-2.81 (m), 2.56-2.41 (m), 1.84 (s), 1.40 (q), 1.35-1.22 (m), 1.16-1.01 (m), 1.01-0.92 (m). |
| 58 | 950.0 | 1H NMR (400 MHz, Chloroform-d) δ 7.61-7.48 (m), 7.37 (s), 7.21-7.08 (m), 7.01-6.46 (m), 6.22 (dd), 5.02 (dd), 4.95 (s), 3.40 (s), 3.39 (s), 3.29 (s), 3.09 (s), 3.05-2.88 (m), 2.87-2.69 (m), 1.87 (s), 1.44-1.36 (m), 1.29-1.14 (m). |
| 59 | 910.1 | 1H NMR (400 MHz, Chloroform-d) δ 7.61-7.48 (m), 7.37 (s), 7.21-7.08 (m), 7.01-6.46 (m), 6.22 (dd), 5.02 (dd), 4.95 (s), 3.40 (s), 3.39 (s), 3.29 (s), 3.09 (s), 3.05-2.88 (m), 2.87-2.69 (m), 1.87 (s), 1.44-1.36 (m), 1.29-1.14 (m). |

Characterization Table

| Example | ES/MS (m/z) | ¹H NMR |
|---|---|---|
| 60 | 784.2 | 1H NMR (400 MHz, Chloroform-d) δ 7.71 (s), 7.68 (s), 7.57-7.48 (m), 7.40-7.29 (m), 7.20-7.13 (m), 6.98 (d), 6.67-6.59 (m), 6.55-6.42 (m), 6.36 (s), 6.31-6.27 (m), 6.22 (d), 5.45 (q), 4.99-4.89 (m), 4.54 (d), 3.40 (d), 3.20 (s), 2.94-2.73 (m), 1.87 (s), 1.44-1.37 (m), 1.28-1.14 (m). |
| 61 | 821.1 | 1H NMR (400 MHz, Chloroform-d) δ 8.22 (d), 8.19 (d), 7.85-7.73 (m), 7.59-7.37 (m), 7.37-7.27 (m), 7.25-7.15 (m), 7.13 (s), 6.98 (d), 6.62-6.50 (m), 6.49-6.39 (m), 6.33 (d), 6.17-6.04 (m), 5.45 (q), 5.08-4.99 (m), 4.95 (q), 3.39 (d), 3.22 (s), 3.08 (s), 2.88-2.72 (m), 1.88 (d), 1.45-1.38 (m), 1.26-1.17 (m). |
| 62 | 820.3 | 1H NMR (400 MHz, Chloroform-d) δ 9.59 (s), 9.40 (s), 8.30-8.11 (m), 8.07 (s), 7.90-7.73 (m), 7.64-7.37 (m), 7.10 (d), 7.02 (d), 6.56 (t), 6.45 (d), 6.26 (dd), 5.51-5.37 (m), 5.34-4.90 (m), 3.39 (s), 3.30 (s), 3.28 (s), 3.16-2.82 (m), 1.87 (s), 1.32 (d). |
| 63 | 821.2 | 1H NMR (400 MHz, Chloroform-d) δ 9.59 (s), 9.40 (s), 8.30-8.11 (m), 8.07 (s), 7.90-7.73 (m), 7.64-7.37 (m), 7.10 (d), 7.02 (d), 6.56 (t), 6.45 (d), 6.26 (dd), 5.51-5.37 (m), 5.34-4.90 (m), 3.39 (s), 3.30 (s), 3.28 (s), 3.16-2.82 (m), 1.87 (s), 1.32 (d). |
| 64 | 878.3 | 1H NMR (400 MHz, Chloroform-d) δ 7.88-7.73 (m), 7.66 (t), 7.60-7.52 (m), 7.44 (s), 7.40-7.32 (m), 7.34-7.18 (m), 7.06 (d), 6.71-6.62 (m), 6.57-6.49 (m), 6.48 (d), 6.32-6.27 (m), 6.24-6.18 (m), 5.54 (q), 5.04-4.96 (m), 4.91-4.69 (m), 3.40 (s), 3.36 (s), 3.32 (s), 3.17 (s), 3.12-3.01 (m), 2.99-2.88 (m), 2.75 (s), 1.85 (s), 1.73 (dt), 1.42-1.35 (m), 1.27-1.16 (m), 1.07 (t). |
| 65 | 838.2 | 1H NMR (400 MHz, Chloroform-d) δ 7.85 (s), 7.75 (s), 7.62-7.50 (m), 7.50-7.44 (m), 7.43-7.36 (m), 7.30 (s), 7.19 (d), 7.02 (d), 6.66-6.59 (m), 6.55-6.46 (m), 6.38 (d), 6.21 (td), 5.51 (q), 4.97 (q), 4.78 (s), 4.74 (d), 3.41 (s), 3.39 (s), 3.25 (s), 3.13 (s), 3.04-2.86 (m), 2.85-2.76 (m), 1.87 (s), 1.45-1.39 (m), 1.29-1.15 (m). |
| 66 | 770.3 | 1H NMR (400 MHz, Chloroform-d) δ 8.06 (s), 7.79 (s), 7.63 (d), 7.60-7.49 (m), 7.26 (s), 7.13-7.02 (m), 6.61 (t), 6.51 (s), 6.42 (d), 6.27 (dd), 5.44-5.22 (m), 4.77 (d), 4.00 (s), 3.41 (s), 3.39 (s), 3.36 (s), 3.21-3.13 (m), 3.03-2.97 (m), 2.97-2.87 (m), 1.86 (s), 1.40-1.19 (m). |
| 67 | 1008.8 | 1H NMR (400 MHz, Methanol-d4) δ 8.90 (d), 8.69 (d), 7.90-7.56 (m), 7.30-7.05 (m), 6.91-6.62 (m), 6.55 (d), 6.45 (dd), 6.38-6.15 (m), 5.48 (s), 5.06-4.91 (m), 4.70-4.48 (m), 4.43-4.05 (m), 3.93 (dq), 3.73 (dd), 3.57-3.34 (m), 3.27-3.01 (m), 3.03-2.82 (m), 2.62-2.30 (m), 1.84 (s), 1.52-1.35 (m), 1.39-1.17 (m), 1.19-0.81 (m). |
| 68 | 994.4 | 1H NMR (400 MHz, Methanol-d4) δ 7.81-7.62 (m), 7.28-7.14 (m), 6.81-6.69 (m), 6.55 (d, J = 6.9 Hz), 6.46 (d, J = 7.7 Hz), 6.32-6.25 (m), 4.98 (s), 4.88 (s), 4.75 (d, J = 16.3 Hz), 4.68-4.62 (m), 4.58 (dd, J = 15.7, 7.5 Hz), 4.21 (d, J = 8.0 Hz), 3.93 (dd, J = 16.1, 8.1 Hz), 3.74 (d, J = 7.9 Hz), 3.66 (d, J = 5.0 Hz), 3.56 (d, J = 5.0 Hz), 3.22 (s), 3.08 (dd, J = 13.4, 7.4 Hz), 3.01-2.88 (m), 2.51 (t, J = 4.5 Hz), 2.48 (s), 1.83 (s), 1.41 (q, J = 7.0 Hz), 1.32-1.19 (m). |
| 69 | 994.2 | 1H NMR (400 MHz, Methanol-d4) δ 8.85 (dd), 7.97 (s), 7.75-7.53 (m), 7.23 (s), 7.14 (d), 6.84-6.56 (m), 6.54-6.38 (m), 5.42-4.96 (m), 4.94-4.50 (m), 4.38 (dt), 3.16 (dd), 3.11-2.92 (m), 2.86 (d), 2.67-2.30 (m), 1.84 (s), 1.51-0.93 (m). |

VIII. Results

Biological Assay Description

The antiviral properties of a compound disclosed herein may be determined using Test A described below.

Test A: Antiviral Assay in MT4 Cells

For the antiviral assay, 40 μL of a concentration required to achieve a final effective 1X test concentration of 3-fold serially diluted compound in culture medium with 10% Fetal Bovine Serum (FBS) was added to each well of a 384-well plate (10 concentrations) in quadruplicate. MT-4 cells were next mixed with HIV-IIIb at a multiplicity of infection (m.o.i) of 0.003 for 1 hour, after which time 35 μL of virus/cell mixture (2000 cells) was immediately added to each well containing 40 μL of diluted compound. The plates were then incubated at 37° C. for 5 days.

After 5 days of incubation, 25 μl of 2× concentrated CellTiter-Glo™ Reagent (catalog #G7571, Promega Biosciences, Inc., Madison, Wis.) was added to each well containing MT-4 cells. Cell lysis was carried out by incubating at room temperature for 10 min and then chemiluminescence was read. EC50 values were calculated as the compound concentration that caused a 50% decrease in luminescence signal, a measure of HIV-1 replication. Percent inhibition of virus-induced cell killing calculated from the dose response curve at 200 nM and 10 nM drug concentrations are shown in the table below.

Test B: Cytotoxicity Assay

Compound cytotoxicity and the corresponding CC50 values was determined using the same protocol as described in the antiviral assay (Test A) except that uninfected cells were used.

Compounds of the present invention demonstrate antiviral activity (Test A) as depicted in the table below. Shown below are the corresponding values for CC50 and percent inhibition of virus-induced cell killing in the presence of 0.20 µM and 0.01 µM drug concentration.

| Example | % inhibition at 0.20 µM | % inhibition at 0.01 µM | $CC_{50}$ (nM) |
|---|---|---|---|
| 1M | 96 | 96 | >57143 |
| 2F | 100 | 100 | >57143 |
| 3F | 100 | 100 | 21812 |
| 4 | 92 | 92 | >44108 |
| 5 | 93 | 93 | >57143 |
| 6 | 100 | 100 | >57143 |
| 7 | 94 | 94 | >57143 |
| 8 | 94 | 94 | >57143 |
| 9 | 96 | 96 | >57143 |
| 10 | 100 | 100 | 18453 |
| 11 | 92 | 92 | >57143 |
| 12 | 94 | 94 | >57143 |
| 13 | 100 | 100 | >57143 |
| 14 | 100 | 100 | >57143 |
| 15 | 98 | 98 | >57143 |
| 16 | 98 | 98 | >57143 |
| 17 | 98 | 98 | >23951 |
| 18 | 100 | 100 | 41578 |
| 19 | 97 | 97 | >57143 |
| 20 | 89 | 89 | >57143 |
| 21 | 100 | 100 | >57143 |
| 22 | 94 | 94 | >57143 |
| 23 | 100 | 100 | >57143 |
| 24 | 100 | 100 | 9074 |
| 25 | 100 | 100 | >57143 |
| 26 | 100 | 100 | >57143 |
| 27 | 100 | 100 | >57143 |
| 28 | 99 | 99 | 16538 |
| 29 | 100 | 100 | >57143 |
| 30 | 99 | 99 | >57143 |
| 31 | 98 | 97 | >57143 |
| 32 | 100 | 100 | >57143 |
| 33 | 97 | 97 | >57143 |
| 34 | 90 | 89 | >57143 |
| 35 | 97 | 97 | >57143 |
| 36 | 93 | 93 | >57143 |
| 37 | 92 | 92 | >57143 |
| 38 | 93 | 93 | >57143 |
| 39 | 99 | 99 | >57143 |
| 40 | 84 | 84 | >57143 |
| 41 | 100 | 100 | >57143 |
| 42 | 89 | 89 | >57143 |
| 43 | 87 | 87 | >57143 |
| 44 | 92 | 87 | >54761 |
| 45 | 97 | 96 | 20075 |
| 46 | 10 | 0 | >54612 |
| 47 | 0 | 0 | >57143 |
| 48 | 0 | 0 | >57143 |
| 49 | 90 | 0 | >57143 |
| 50 | 36 | 0 | >53589 |
| 51 | 91 | 67 | 51193 |
| 52 | 93 | 93 | >57143 |
| 53 | 93 | 93 | >57143 |
| 54 | 99 | 18 | 29815 |
| 55 | 96 | 86 | 22158 |
| 56 | 91 | 0 | 23516 |
| 57 | 91 | 59 | >57143 |
| 58 | 95 | 95 | >57143 |
| 59 | 93 | 81 | >57143 |
| 60 | 100 | 100 | 19225 |
| 61 | 98 | 3 | 28377 |
| 62 | 93 | 56 | 30666 |
| 63 | 100 | 1 | 21835 |
| 64 | 94 | 45 | >50000 |
| 65 | 100 | 27 | >50000 |
| 66 | 97 | 61 | 11699 |
| 67 | 0 | 13 | >50000 |
| 68 | 100 | 100 | >50000 |
| 69 | 92 | 92 | >50000 |
| 70 | 85 | 85 | >50000 |

The data above represent an average over time of each assay for each compound. For certain compounds, multiple assays have been conducted over the life of the project. Thus, the data reported in the tables include the data reported in the priority document, as well as data from assays run in the intervening period. In the above table, percent inhibition values have been normalized to 100% where the calculation of percent inhibition would have resulted in a value greater than 100

In some embodiments, the compounds demonstrate>10% inhibition at 0.20 µM. In one embodiment, the compounds demonstrate>30% inhibition at 0.20 µM. In some embodiments, the compounds demonstrate>50% inhibition at 0.20 µM. In some embodiments, the compounds demonstrate>70% inhibition at 0.20 µM. In some embodiments, the compounds demonstrate>75% inhibition at 0.20 µM. In some embodiments, the compounds demonstrate>80% inhibition at 0.20 µM. In some embodiments, the compounds demonstrate>85% inhibition at 0.20 µM. In some embodiments, the compounds demonstrate>90% inhibition at 0.20 µM. In some embodiments, the compounds demonstrate>95% inhibition at 0.20 µM. It is to be understood that the compounds disclosed herein can be grouped according to their % inhibition as described above.

In some embodiments, the compounds demonstrate>10% inhibition at 0.20 µM. In one embodiment, the compounds demonstrate>30% inhibition at 0.20 µM. In some embodiments, the compounds demonstrate>50% inhibition at 0.20 µM. In some embodiments, the compounds demonstrate>70% inhibition at 0.20 µM. In some embodiments, the compounds demonstrate>75% inhibition at 0.20 µM. In some embodiments, the compounds demonstrate>80% inhibition at 0.20 µM. In some embodiments, the compounds demonstrate>85% inhibition at 0.20 µM. In some embodiments, the compounds demonstrate>90% inhibition at 0.20 µM. In some embodiments, the compounds demonstrate>95% inhibition at 0.20 µM. It is to be understood that the compounds disclosed herein can be grouped according to their % inhibition as described above.

In some embodiments, a compound is of any formulae provided herein, wherein the compound exhibits from 85%-110% inhibition of virus-induced cell killing at 0.20 µM. In some embodiments, a compound is of any formulae provided herein, wherein the compound exhibits from 85%-110% inhibition of virus-induced cell killing at 0.20 µM. In some embodiments, a compound is of any formulae provided herein wherein the compound exhibits from 50-100, 60-100, 70-100, 80-100, or 90-100% inhibition of virus-induced cell killing at 0.20 µM or at 0.01 µM.

It is understood that % inhibition may be evaluated by techniques known in the art. In a particular variation, a compound is of any formulae provided herein wherein the compound exhibits from 85%-100% inhibition of virus-induced cell killing at 0.20 μM or at 0.01 μM as measured by the method provided in the Test A and Test B sections discussed above.

The percent inhibition of virus-induced cell killing at 0.20 μM and 0.01 μM was measured by the method provided in the Test A and Test B sections discussed above.

The specific pharmacological responses observed may vary according to and depending on the particular active compound selected and whether there are present pharmaceutical carriers and/or pharmaceutically active compounds, as well as the type of formulation and mode of administration employed, and such expected variations or differences in the results are contemplated in accordance with practice of the present invention.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

All references, including publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The use of the terms "a" and "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

Alternative embodiments of the claimed disclosure are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein. Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values is stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein. In one aspect, about a value includes and intends that value per se. For example, about x includes and intends x per se.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

What is claimed is:
1. A compound of formula I:

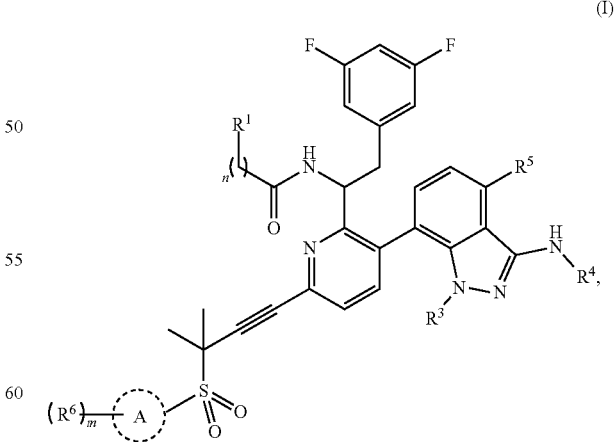

wherein
A is 3-6 membered carbocycle;
n is 0, 1, or 2;
m is 0, 1, or 2;

$R^1$ is

[structures shown: 4,4,7,7-tetrafluoro-4,5,6,7-tetrahydroindazolyl with $Z_1$; benzimidazolyl; indazolyl; benzimidazolyl (N-linked); benzotriazolyl; 1,2,4-triazolyl (two isomers); tetrazolyl; tetrazolyl (C-linked, NH); pyrazolyl (N-linked); pyrazolyl with $Z_1$ substituents (three isomers); pyrazolyl with $Z_1$; pyrazolyl (NH, C-linked); imidazolyl with $Z_1$; imidazolyl (N-linked); or imidazolyl (NH, C-linked)]

each $Z^1$ is independently $(C_1-C_6)$alkyl, $(C_3-C_7)$carbocycle, halogen, or —CN, wherein any $(C_1-C_6)$alkyl or $(C_3-C_7)$carbocycle of $Z^1$ is unsubstituted or substituted with 1, 2, 3, 4 or 5 $Z^{1a}$ groups, wherein the $Z^{1a}$ groups are the same or different;
each $Z^{1a}$ is independently halogen, $(C_3-C_7)$carbocycle, —OH, or —CN;
$R^2$ is hydrogen, halogen, —OH, or —CN;
$R^3$ is $(C_1-C_6)$alkyl or 3-5 membered heterocycle, wherein the $(C_1-C_6)$alkyl is unsubstituted or substituted with 1, 2, or 3 halogen atoms;
$R^4$ is hydrogen, —S(O)$_2$-(C$_1$-C$_6$)alkyk, —S(O)$_2$-(C$_3$-C$_6$) carbocycle, or 5-6 membered heteroaryl, wherein any —S(O)$_2$—(C$_1$-C$_6$) alkyl, —S(O)$_2$—(C$_3$-C$_6$)carbocycle, or 5-6 membered heteroaryl of $R^4$ is unsubstituted or substituted with 1, 2, or 3 $Z^2$ groups, wherein the $Z^2$ groups are the same or different;
$Z^2$ is $(C_1-C_6)$alkyl or $(C_3-C_6)$carbocycle, wherein any $(C_1-C_6)$alkyl or $(C_3-C_6)$carbocycle is unsubstituted or substituted with 1, 2, or 3 $Z^2$a groups, wherein the $Z^2$a groups are the same or different;
$Z^{2a}$ is hydroxyl or halogen;
$R^5$ is hydrogen or halogen; and
$R^6$ is $(C_1-C_3)$alkyl;
or a pharmaceutically acceptable salt thereof.

2. The compound of claim 1, or a pharmaceutically acceptable salt thereof, which is a compound of formula Ia:

(Ia)

[structure of formula Ia shown]

wherein:
n is 0, 1, or 2;
m is 0 or 1;
each $Z^1$ is independently $(C_1-C_6)$alkyl, $(C_3-C_7)$carbocycle, or halogen, wherein any $(C_1-C_6)$alkyl or $(C_3-C_7)$ carbocycle of $Z^1$ is unsubstituted or substituted with 1, 2, 3, 4 or 5 $Z^{1a}$ groups, wherein the $Z^{1a}$ groups are the same or different;
each $Z^{1a}$ is independently halogen or $(C_3-C_7)$carbocycle;
$R^2$ is hydrogen or iodide;
$R^3$ is $(C_1-C_2)$alkyl or 3-5 membered heterocycle, wherein the $(C_1-C_2)$alkyl is unsubstituted or substituted with 2 or 3 halogen atoms;
$R^4$ is hydrogen, —S(O)$_2$—(C$_1$-C$_2$)alkyl, —S(O)$_2$-cyclopropyl, or 5-membered heteroaryl, wherein any —S(O)$_2$—(C$_1$-C$_2$)alkyl, —S(O)$_2$-cyclopropyl, or 5-membered heteroaryl of $R^4$ is unsubstituted or substituted with 1, 2, or 3 $Z^2$ groups, wherein the $Z^2$ groups are the same or different;
$Z^2$ is $(C_1-C_3)$alkyl or cyclopropyl, wherein any $(C_1-C_3)$alkyl or cyclopropyl is unsubstituted or substituted with 1, 2, or 3 $Z^{2a}$ groups, wherein the $Z^{2a}$ groups are the same or different;
$Z^{2a}$ is hydroxyl or fluorine;
$R^5$ is hydrogen, chorine, or fluorine; and
$R^6$ is $(C_1-C_3)$alkyl.

3. The compound of claim 1, or a pharmaceutically acceptable salt thereof, wherein:
n is 0, 1, or 2;
m is 0 or 1;
each $Z^1$ is independently $(C_1-C_6)$alkyl, $(C_3-C_7)$carbocycle, or halogen, wherein any $(C_1-C_6)$alkyl or $(C_3-C_7)$carbocycle of $Z^1$ is unsubstituted or substituted with 1, 2, 3, 4 or 5 $Z^{1a}$ groups, wherein the $Z^{1a}$ groups are the same or different;

each $Z^i$a is independently halogen or $(C_3-C_7)$carbocycle;

$R^2$ is hydrogen or iodide;

$R^3$ is $(C_1-C_2)$alkyl or 3-5 membered heterocycle, wherein the $(C_1-C_2)$alkyl is unsubstituted or substituted with 2 or 3 fluorine atoms;

$R^4$ is hydrogen, —$S(O)_2$—$(C_1-C_2)$alkyl, —$S(O)_2$-cyclopropyl, or 5-membered heteroaryl, wherein any —$S(O)_2$—$(C_1-C_2)$alkyl, —$S(O)_2$-cyclopropyl, or 5-membered heteroaryl of $R^4$ is unsubstituted or substituted with 1, 2, or 3 $Z^2$ groups, wherein the $Z^2$ groups are the same or different;

$Z^2$ is $(C_1-C_3)$alkyl or cyclopropyl, wherein any $(C_1-C_3)$alkyl or cyclopropyl is unsubstituted or substituted with 1, 2, or 3 $Z^{2a}$ groups, wherein the $Z^{2a}$ groups are the same or different;

$Z^{2a}$ is hydroxyl or fluorine;

$R^5$ is hydrogen, chorine, or fluorine; and $R^6$ is methyl.

4. The compound of claim 1, or a pharmaceutically acceptable salt thereof, wherein:

n is 0, 1, or 2;

m is 0 or 1;

each $Z^1$ is independently $(C_1-C_6)$alkyl, $(C_3-C_7)$carbocycle, or halogen, wherein any $(C_1-C_6)$alkyl or $(C_3-C_7)$carbocycle of $Z^1$ is unsubstituted or substituted with 1, 2, 3, 4 or 5 $Z^{1a}$ groups, wherein the $Z^{1a}$ groups are the same or different;

each $Z^{1a}$ is independently halogen or $(C_3-C_7)$carbocycle;

$R^2$ is hydrogen;

$R^3$ is $(C_1-C_2)$alkyl or 4-membered heterocycle, wherein the $(C_1-C_2)$alkyl is unsubstituted or substituted with 2 or 3 fluorine atoms;

$R^4$ is —$S(O)_2$—$(C_1-C_2)$alkyl, —$S(O)_2$-cyclopropyl, or 5-membered heteroaryl, wherein any —$S(O)_2$-$(C_1-C_2)$alkyl, —$S(O)_2$-cyclopropyl, or 5-membered heteroaryl of $R^4$ is unsubstituted or substituted with 1, 2, or 3 $Z^2$ groups, wherein the $Z^2$ groups are the same or different;

$Z^2$ is (C1-C3)alkyl or cyclopropyl, wherein any (C1-C3)alkyl or cyclopropyl is unsubstituted or substituted with 1, 2, or 3 $Z^{2a}$ groups, wherein the $Z^{2a}$ groups are the same or different;

$Z^{2a}$ is hydroxyl or fluorine;

$R^5$ is hydrogen, chorine, or fluorine; and $R^6$ is methyl.

5. The compound of claim 1, or a pharmaceutically acceptable salt thereof, wherein n is 1.

6. The compound of claim 1, or a pharmaceutically acceptable salt thereof, wherein m is 0.

7. The compound of claim 1, or a pharmaceutically acceptable salt thereof, wherein $R^1$ is

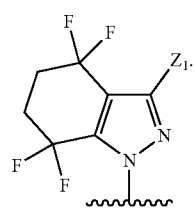

8. The compound of claim 1, or a pharmaceutically acceptable salt thereof, wherein $R^1$ is

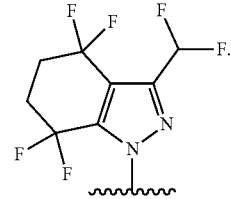

9. The compound of claim 1, or a pharmaceutically acceptable salt thereof, wherein $R^1$ is

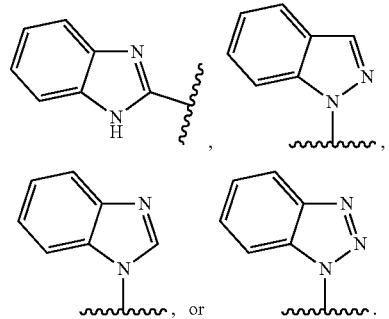

10. The compound of claim 1, or a pharmaceutically acceptable salt thereof, wherein $R^1$ is

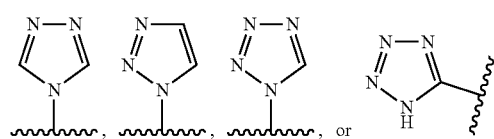

11. The compound of claim 1, or a pharmaceutically acceptable salt thereof, wherein $R^1$ is

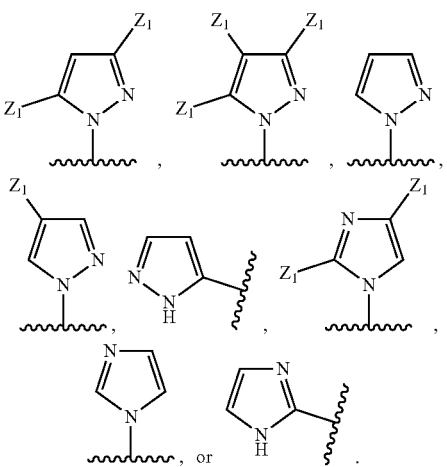

12. The compound of claim 1, or a pharmaceutically acceptable salt thereof, wherein $R^1$ is

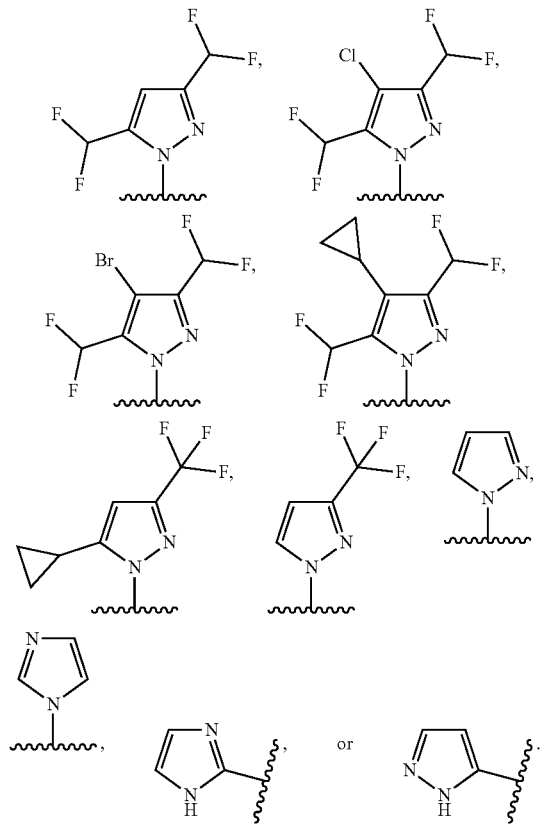

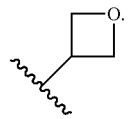

13. The compound of claim 1, or a pharmaceutically acceptable salt thereof, wherein $Z^1$ is $(C_1-C_6)$alkyl substituted with 2 or 3 halogen atoms, a cyclopropyl group, or halogen.

14. The compound of any one of claim 1, or a pharmaceutically acceptable salt thereof, wherein $R^2$ is hydrogen or iodide.

15. The compound of any one of claims 1, or a pharmaceutically acceptable salt thereof, wherein $R^3$ is $(C_1-C_3)$alkyl or a 4-membered heterocycle, wherein the $(C_1-C_3)$alkyl is unsubstituted or substituted with 1, 2, or 3 halogen atoms.

16. The compound of claim 1, or a pharmaceutically acceptable salt thereof, wherein $R^3$ is methyl, —$CH_2CHF_2$, —$CH_2CF_3$, or 17. The compound of claim 1, or a pharmaceutically acceptable salt thereof, wherein $R^4$ is hydrogen, —$S(O)_2$-$(C_{1-2})$alkyl, —$S(O)_2$-cyclopropyl, or an oxadiazole, wherein any —$S(O)_2$-$(C_{1-2})$alkyl, —$S(O)_2$-cyclopropyl, or oxadiazole of $R^4$ is unsubstituted or substituted with 1, 2, or 3 $Z^2$ groups, wherein the $Z^2$ groups are the same or different.

18. The compound of claim 1, or a pharmaceutically acceptable salt thereof, wherein $R^4$ is

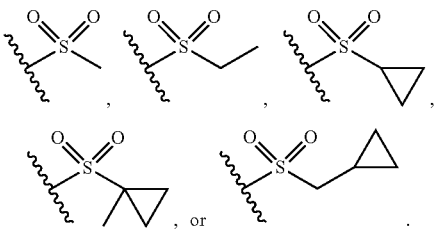

19. The compound of any one of claim 1, or a pharmaceutically acceptable salt thereof, wherein $R^5$ is hydrogen, chloride, or fluoride.

20. The compound of any one of claim 1, or a pharmaceutically acceptable salt thereof, which is

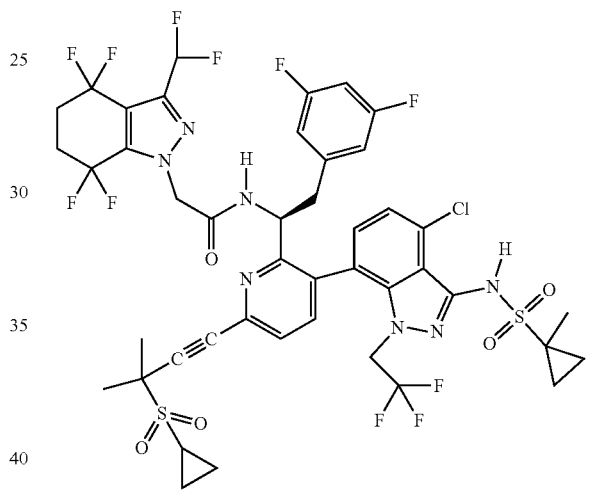

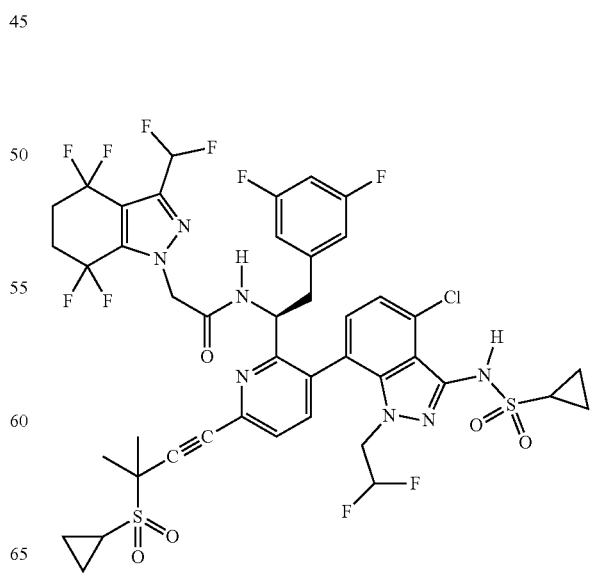

169
-continued
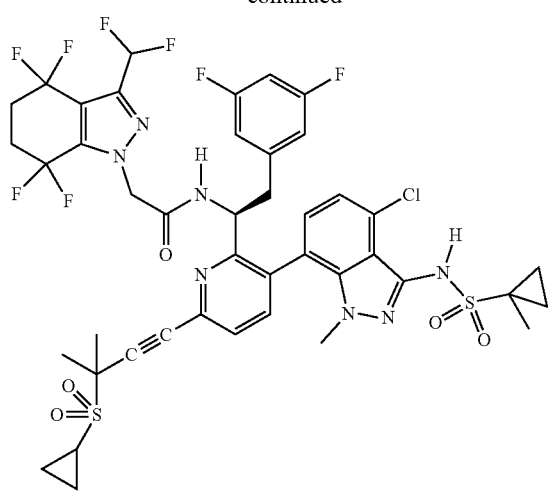
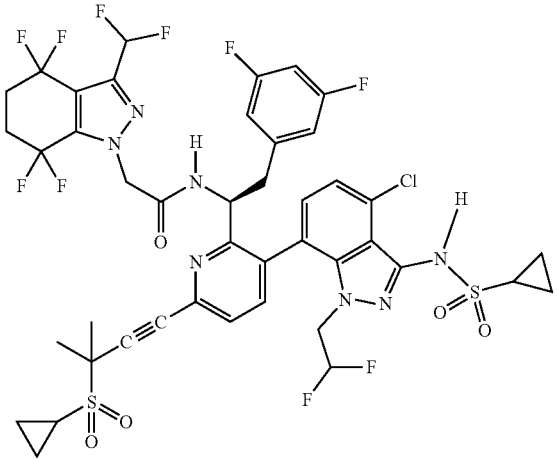
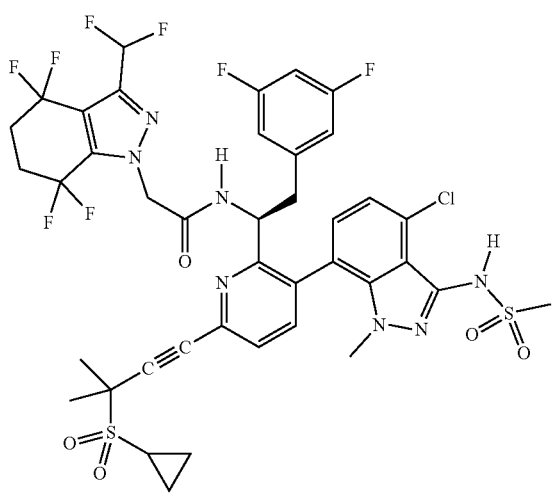
,
170
-continued
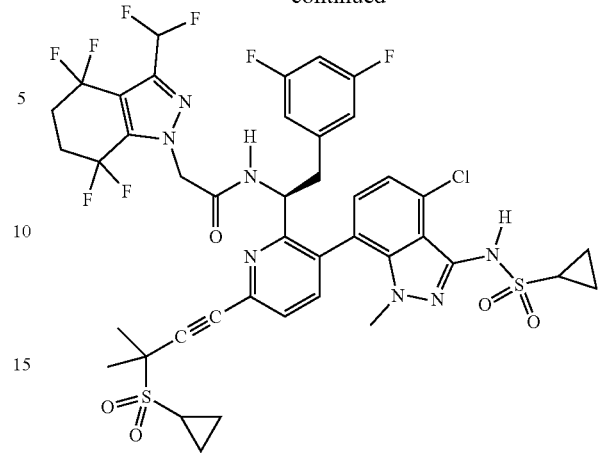
,
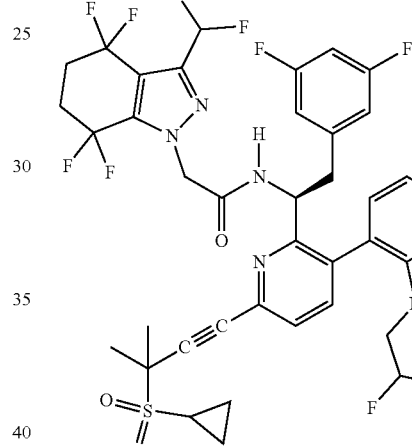
,
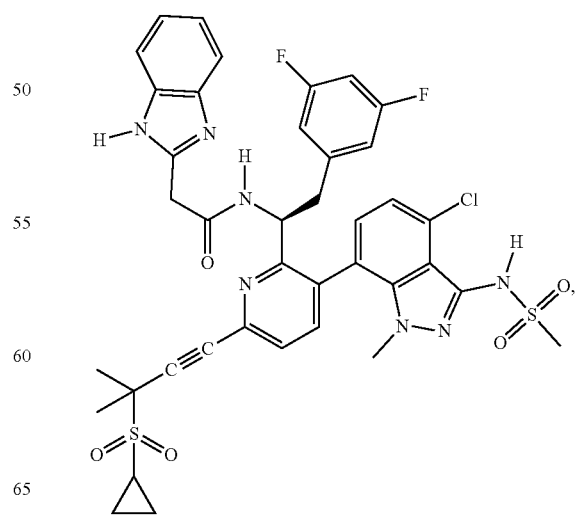
,

171
-continued
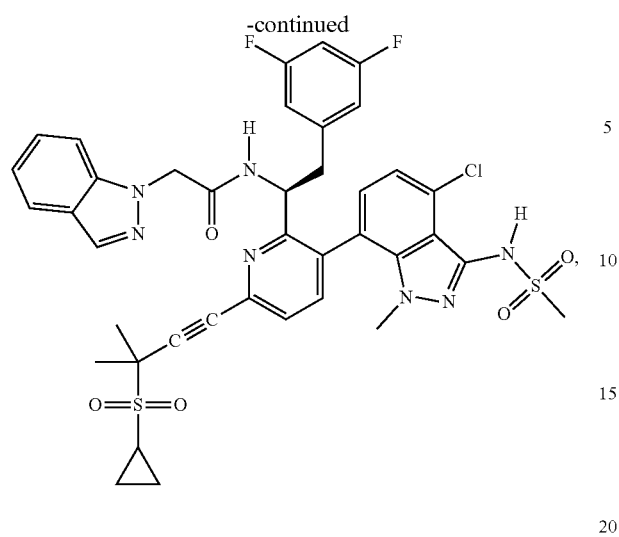
172
-continued
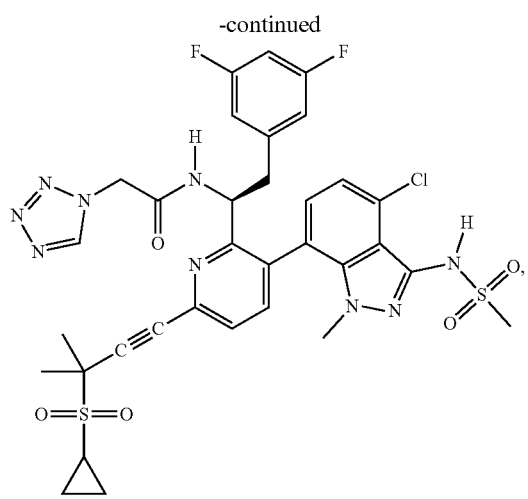
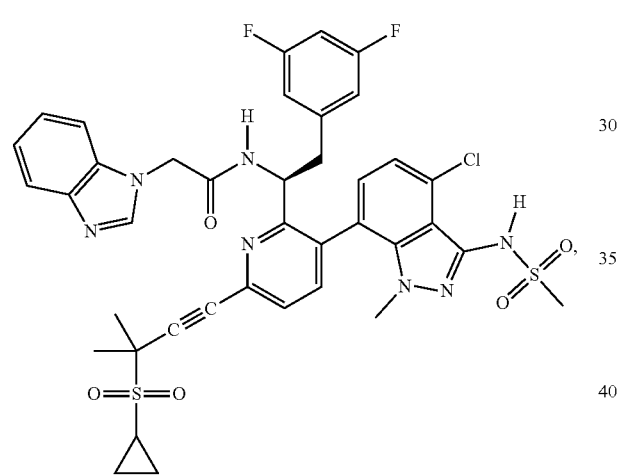
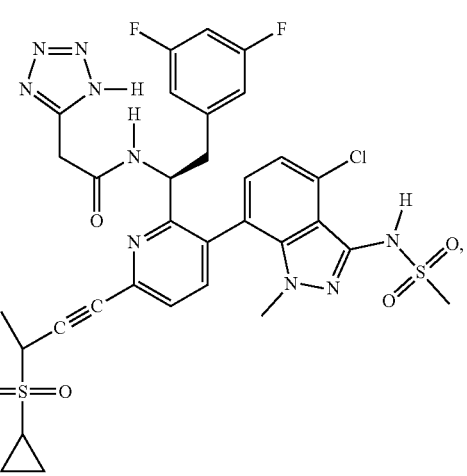
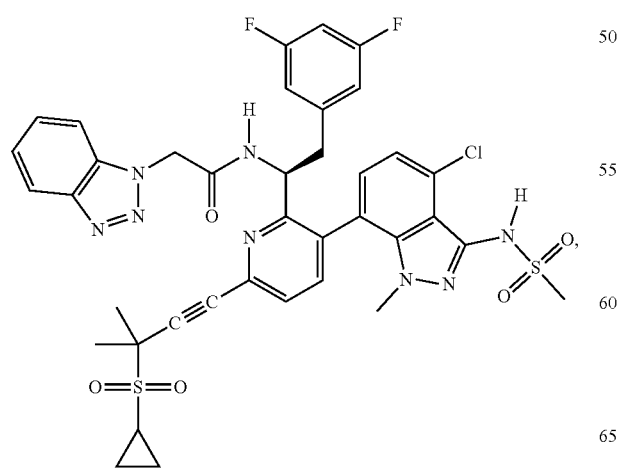
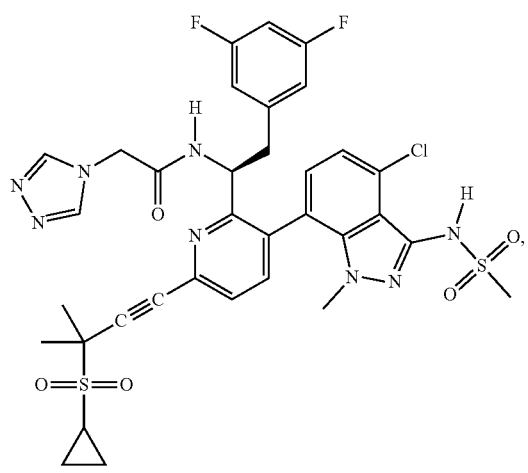

173
-continued
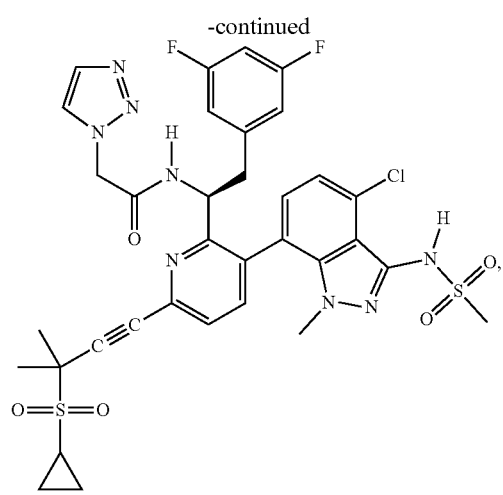
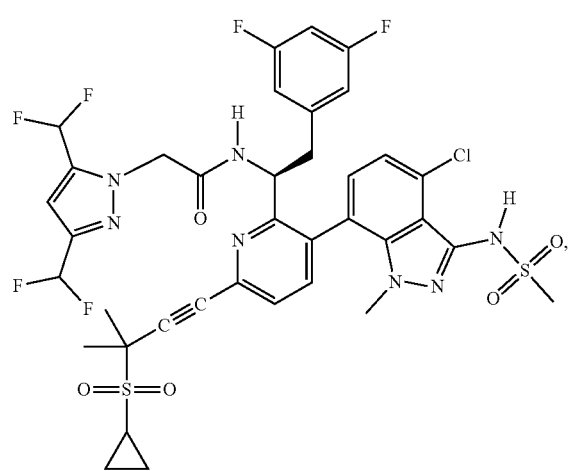
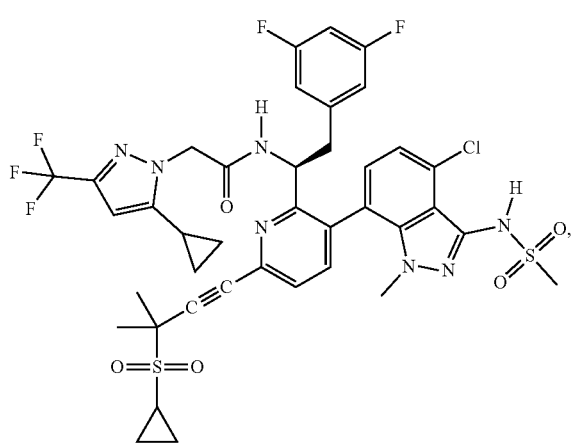
174
-continued
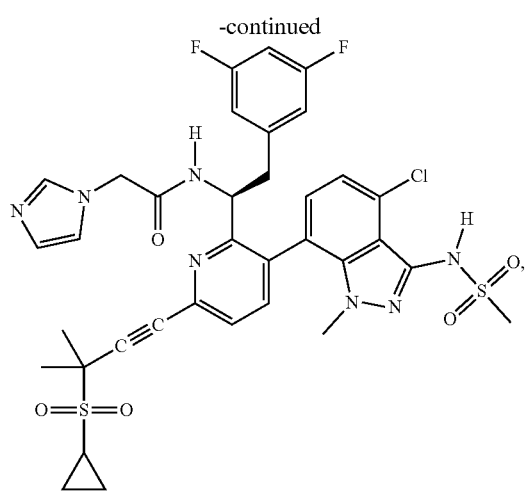
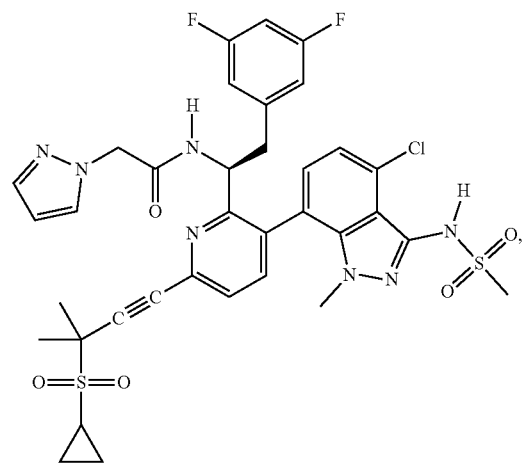
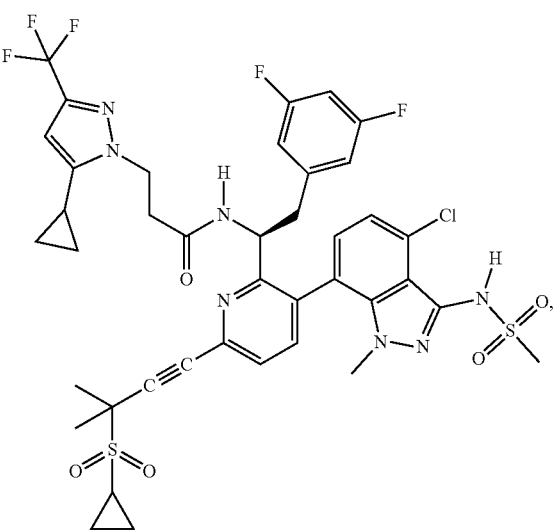

175
-continued
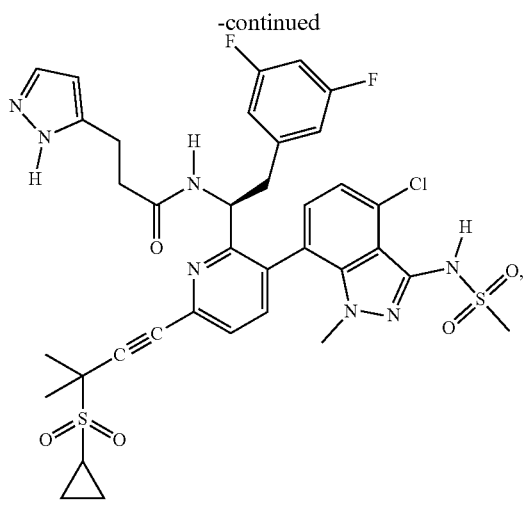
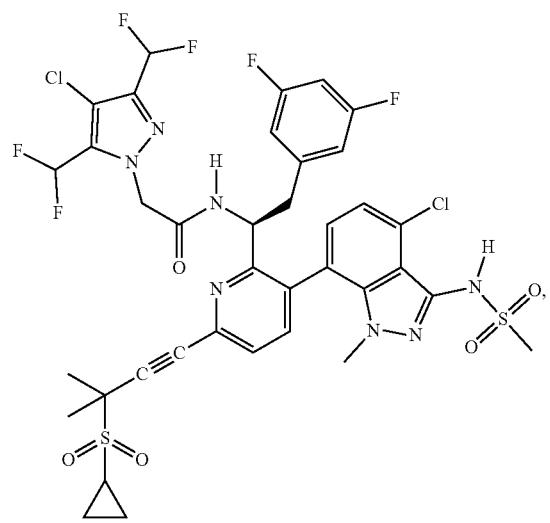
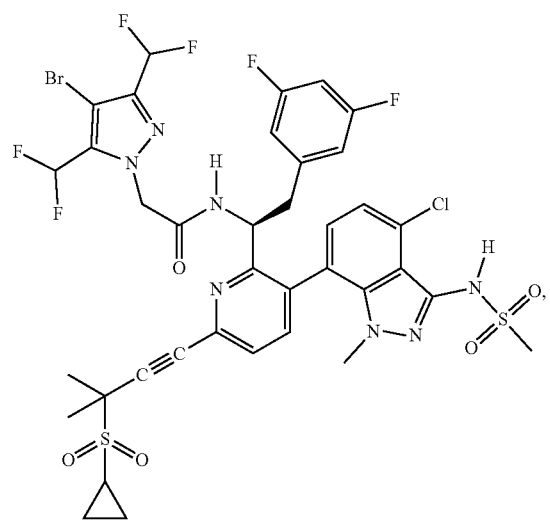
176
-continued
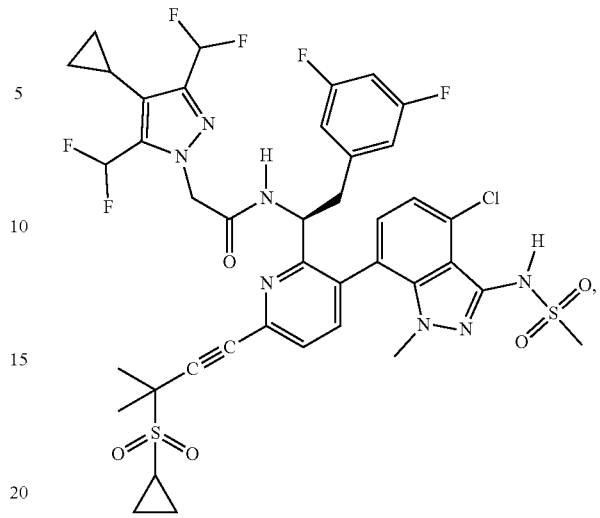
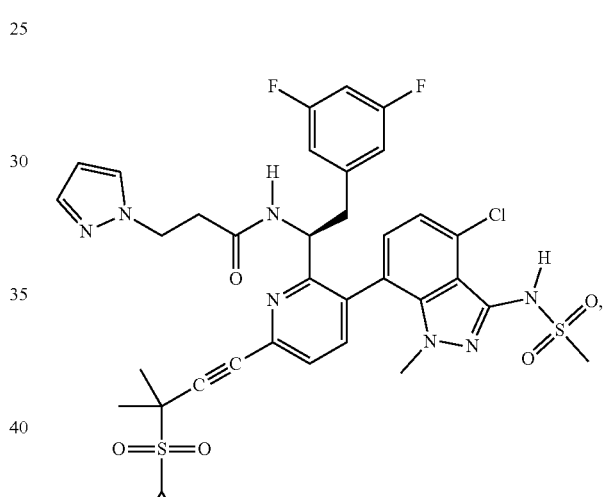
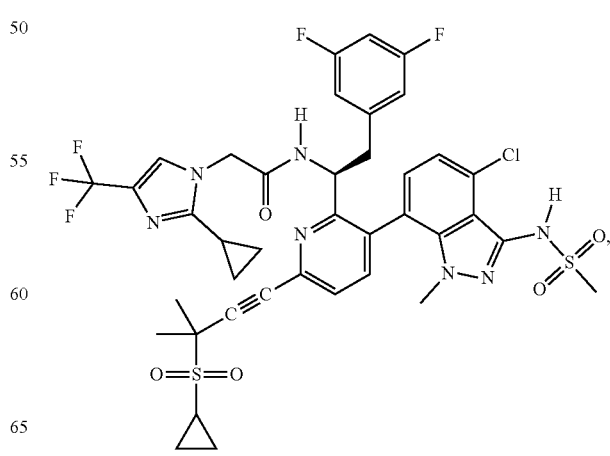

-continued

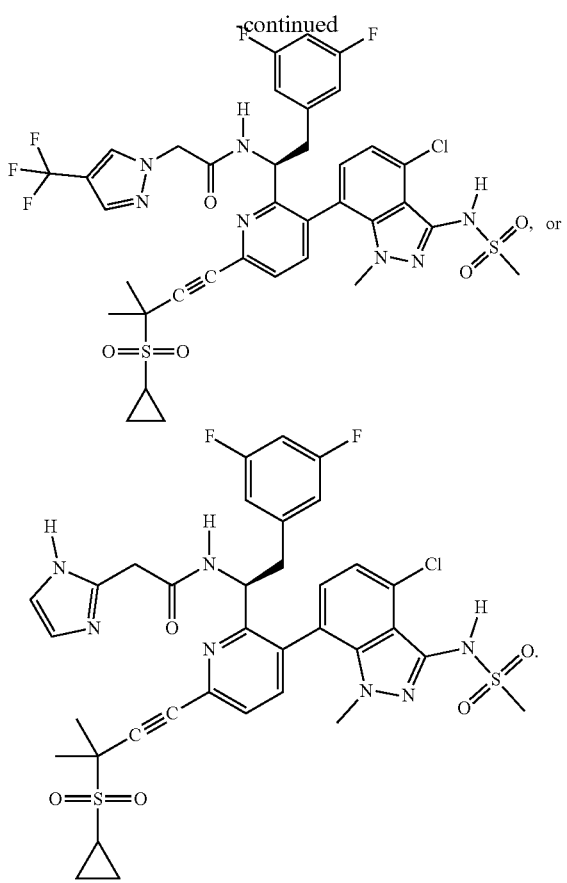

21. A pharmaceutical composition comprising a compound of claim 1, or a pharmaceutically acceptable salt thereof, and a pharmaceutically acceptable carrier.

22. A method for treating a HIV infection in a patient in need thereof comprising administering a therapeutically effective amount of a compound of claim 1, or a pharmaceutically acceptable salt thereof, to the patient.

23. A method for treating an HIV infection in a patient in need thereof comprising administering to the patient a therapeutically effective amount of a compound of claim 1, or a pharmaceutically acceptable salt thereof, in combination with a therapeutically effective amount of an additional therapeutic agent, wherein the additional therapeutic agent is a HIV protease inhibitor, a HIV non-nucleoside or non-nucleotide inhibitor of reverse transcriptase, a HIV nucleoside or nucleotide inhibitor of reverse transcriptase, a HIV integrase inhibitor, a HIV non-catalytic site integrase inhibitor, an HIV entry inhibitor, an HIV maturation inhibitor, a latency reversing agent, a compound that targets the HIV capsid, an immune-based therapy, a phosphatidylinositol 3-kinase (PI3K) inhibitor, a HIV antibody, a bispecific antibody, an antibody-like therapeutic protein, a HIV p17 matrix protein inhibitor, a IL-13 antagonist, a peptidyl-prolyl cis-trans isomerase A modulator, a protein disulfide isomerase inhibitor, a complement C5a receptor antagonist, a DNA methyltransferase inhibitor, a HIV vif gene modulator, a Vif dimerization antagonist, a HIV-1 viral infectivity factor inhibitor, a TAT protein inhibitor, a HIV-1 Nef modulator, a Hck tyrosine kinase modulator, a mixed lineage kinase-3 (MLK-3) inhibitor, a HIV-1 splicing inhibitor, a Rev protein inhibitor, an integrin antagonist, a nucleoprotein inhibitor, a splicing factor modulator, a COMM domain containing protein 1 modulator, a HIV ribonuclease H inhibitor, a retrocyclin modulator, a CDK-9 inhibitor, a dendritic ICAM-3 grabbing nonintegrin 1 inhibitor, a HIV GAG protein inhibitor, a HIV POL protein inhibitor, a Complement Factor H modulator, a ubiquitin ligase inhibitor, a deoxycytidine kinase inhibitor, a cyclin dependent kinase inhibitor, a proprotein convertase PC9 stimulator, a ATP dependent RNA helicase DDX3X inhibitor, a reverse transcriptase priming complex inhibitor, a G6PD and NADH-oxidase inhibitor, a pharmacokinetic enhancer, a HIV gene therapy, or a HIV vaccine.

* * * * *